US009428581B2

(12) United States Patent
Saito et al.

(10) Patent No.: US 9,428,581 B2
(45) Date of Patent: Aug. 30, 2016

(54) PHARMACEUTICAL COMPOSITION FOR TREATMENT AND/OR PREVENTION OF GALLBLADDER CANCER

(71) Applicant: TORAY INDUSTRIES, INC., Tokyo (JP)

(72) Inventors: Takanori Saito, Kamakura (JP); Fumiyoshi Okano, Kamakura (JP); Takayoshi Ido, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/389,078

(22) PCT Filed: Mar. 29, 2013

(86) PCT No.: PCT/JP2013/059569
§ 371 (c)(1),
(2) Date: Sep. 29, 2014

(87) PCT Pub. No.: WO2013/147176
PCT Pub. Date: Oct. 3, 2013

(65) Prior Publication Data

US 2015/0299314 A1 Oct. 22, 2015

(30) Foreign Application Priority Data

Mar. 30, 2012 (JP) ................................ 2012-080780

(51) Int. Cl.

| | |
|---|---|
| ***A61K 39/395*** | (2006.01) |
| ***C07K 16/28*** | (2006.01) |
| ***C07K 14/47*** | (2006.01) |
| ***A61K 45/06*** | (2006.01) |
| ***A61K 47/48*** | (2006.01) |
| ***C07K 16/30*** | (2006.01) |

(52) U.S. Cl.
CPC ......... *C07K 16/28* (2013.01); *A61K 39/39558* (2013.01); *A61K 45/06* (2013.01); *A61K 47/48569* (2013.01); *C07K 14/47* (2013.01); *C07K 16/30* (2013.01); *C07K 2317/23* (2013.01); *C07K 2317/24* (2013.01); *C07K 2317/34* (2013.01); *C07K 2317/732* (2013.01)

(58) Field of Classification Search
CPC ................ C07K 16/30; C07K 16/303; C07K 16/3015–16/3069; C07K 16/461–16/467; A61K 39/395; A61K 39/39558
See application file for complete search history.

(56) References Cited

U.S. PATENT DOCUMENTS

| | | | | |
|---|---|---|---|---|
| 5,698,396 | A | 12/1997 | Pfreundschuh | |
| 6,335,170 | B1 | 1/2002 | Orntoft | |
| 6,444,425 | B1 | 9/2002 | Reed et al. | |
| 7,449,184 | B2 | 11/2008 | Allison et al. | |
| 7,485,302 | B2 | 2/2009 | Adams et al. | |
| 7,745,391 | B2 | 6/2010 | Mintz et al. | |
| 8,211,634 | B2 | 7/2012 | Depinho et al. | |
| 8,709,418 | B2 | 4/2014 | Okano et al. | |
| 8,828,398 | B2 | 9/2014 | Kobayashi et al. | |
| 8,911,740 | B2 | 12/2014 | Saito et al. | |
| 2002/0006404 | A1 | 1/2002 | Hanna et al. | |
| 2003/0118599 | A1 | 6/2003 | Algate et al. | |
| 2003/0190640 | A1 | 10/2003 | Faris et al. | |
| 2004/0029114 | A1 | 2/2004 | Mack et al. | |
| 2004/0236091 | A1 | 11/2004 | Chicz et al. | |
| 2004/0258678 | A1 | 12/2004 | Bodary et al. | |
| 2005/0003390 | A1 | 1/2005 | Axenovich et al. | |
| 2005/0032113 | A1 | 2/2005 | Tanaka et al. | |
| 2005/0244413 | A1 | 11/2005 | Adolf et al. | |
| 2006/0019256 | A1 | 1/2006 | Clarke et al. | |
| 2006/0069054 | A1 | 3/2006 | Houghton et al. | |
| 2006/0275305 | A1 | 12/2006 | Bryant | |
| 2007/0048301 | A1 | 3/2007 | Bodary-Winter et al. | |
| 2007/0154931 | A1 | 7/2007 | Radich et al. | |
| 2007/0264253 | A1 | 11/2007 | Liu et al. | |
| 2008/0075722 | A1 | 3/2008 | DePinho et al. | |
| 2008/0107668 | A1 | 5/2008 | Philip et al. | |
| 2008/0306018 | A1 | 12/2008 | Croce et al. | |
| 2010/0068724 | A1 | 3/2010 | Fung et al. | |
| 2011/0123492 | A1 | 5/2011 | Okano et al. | |
| 2011/0136121 | A1 | 6/2011 | Okano et al. | |
| 2011/0189700 | A1 | 8/2011 | Moses et al. | |
| 2011/0256144 | A1* | 10/2011 | Okano et al. | 424/139.1 |
| 2012/0171699 | A1 | 7/2012 | Goodman et al. | |

(Continued)

FOREIGN PATENT DOCUMENTS

| | | | |
|---|---|---|---|
| CN | 1705676 | A | 12/2005 |
| CN | 101120252 | A | 2/2008 |

(Continued)

OTHER PUBLICATIONS

Akiyoshi, "Cancer Vaccine Therapy Using Peptides Derived from Tumor-Rejection Antigens," Jpn J Cancer Chemother., vol. 24, No. 5, Mar. 1997, pp. 511-519, with English Abstract (p. 519).
Balmaña et al., "BRCA in breast cancer: ESMO Clinical Recommendations," Annals of Oncology, vol. 20, Supplement 4, May 2009, pp. iv19-iv20.
Bodey et al., "Failure of Cancer Vaccines: The Significant Limitations of this Approach to Immunotherapy," Anticancer Research, vol. 20, 2000, pp. 2665-2676.
Brand et al., "Prospect for Anti-HER2 Receptor Therapy in Breast Cancer," Anticancer Research, vol. 26, 2006, pp. 463-470.
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.

(Continued)

*Primary Examiner* — Jessica H Roark
(74) *Attorney, Agent, or Firm* — Birch, Stewart, Kolasch & Birch, LLP

(57) ABSTRACT

Provided is an antibody effective for treatment and/or prevention of gallbladder cancer. A pharmaceutical composition for treatment and/or prevention of gallbladder cancer contains as an active ingredient an antibody or a fragment thereof having immunological reactivity with a CAPRIN-1 protein or a fragment thereof comprising at least seven consecutive amino acid residues of the amino acid sequence of the protein.

19 Claims, No Drawings

(56) References Cited

U.S. PATENT DOCUMENTS

| | | | |
|---|---|---|---|
| 2012/0214975 | A1 | 8/2012 | Sandig et al. |
| 2012/0294860 | A1 | 11/2012 | Ido et al. |
| 2012/0301471 | A1 | 11/2012 | Kobayashi et al. |
| 2012/0301476 | A1 | 11/2012 | Okano et al. |
| 2012/0321641 | A1 | 12/2012 | Okano et al. |
| 2013/0045210 | A1 | 2/2013 | Kobayashi et al. |
| 2013/0071398 | A1 | 3/2013 | Saito et al. |
| 2014/0154261 | A1 | 6/2014 | Okano et al. |
| 2014/0178373 | A1 | 6/2014 | Kobayashi et al. |
| 2014/0179558 | A1 | 6/2014 | Ido et al. |
| 2014/0186359 | A1 | 7/2014 | Okano et al. |
| 2014/0193434 | A1 | 7/2014 | Kobayashi et al. |
| 2014/0199311 | A1 | 7/2014 | Kobayashi et al. |
| 2014/0308283 | A1 | 10/2014 | Minamida et al. |
| 2015/0004171 | A1 | 1/2015 | Kobayashi et al. |
| 2015/0017172 | A1 | 1/2015 | Kobayashi et al. |
| 2015/0044221 | A1 | 2/2015 | Kobayashi et al. |
| 2015/0050283 | A1 | 2/2015 | Okano et al. |
| 2015/0218285 | A1 | 8/2015 | Saito et al. |

FOREIGN PATENT DOCUMENTS

| | | | |
|---|---|---|---|
| CN | 101189516 | A | 5/2008 |
| CN | 101836116 | A | 9/2010 |
| CN | 102170907 | A | 8/2011 |
| CN | 102171570 | A | 8/2011 |
| EP | 2 207 037 | A1 | 7/2010 |
| EP | 2 325 648 | A1 | 5/2011 |
| EP | 2322221 | A1 | 5/2011 |
| EP | 2 532 367 | A1 | 12/2012 |
| EP | 2 532 743 | A1 | 12/2012 |
| EP | 2 740 794 | A1 | 6/2014 |
| EP | 2 832 365 | A1 | 2/2015 |
| EP | 2 832 366 | A1 | 2/2015 |
| JP | 2002-540790 | A | 12/2002 |
| JP | 2003-528587 | A | 9/2003 |
| JP | 2006-316040 | A | 11/2006 |
| JP | 2013-502205 | A | 1/2013 |
| JP | 2013-505028 | A | 2/2013 |
| RU | 2234942 | C2 | 8/2004 |
| RU | 2306952 | C2 | 9/2007 |
| RU | 2006137060 | A | 4/2008 |
| WO | WO 00/04149 | A2 | 1/2000 |
| WO | WO 00/60077 | A2 | 10/2000 |
| WO | WO 01/32910 | A2 | 5/2001 |
| WO | WO 01/72295 | A2 | 10/2001 |
| WO | WO 02/078524 | A2 | 10/2002 |
| WO | WO 02/083070 | A2 | 10/2002 |
| WO | WO 02/092001 | A2 | 11/2002 |
| WO | WO 2004/076682 | A2 | 9/2004 |
| WO | WO 2004/097051 | A2 | 11/2004 |
| WO | WO 2005/007830 | A2 | 1/2005 |
| WO | WO 2005/100998 | A2 | 10/2005 |
| WO | WO 2005/116076 | A2 | 12/2005 |
| WO | WO 2006/002378 | A2 | 1/2006 |
| WO | WO 2007/150077 | A2 | 12/2007 |
| WO | WO 2008/031041 | A2 | 3/2008 |
| WO | WO 2008/059252 | A2 | 5/2008 |
| WO | WO 2008/073162 | A2 | 6/2008 |
| WO | WO 2008/088583 | A2 | 7/2008 |
| WO | WO 2009/113742 | A1 | 9/2009 |
| WO | WO 2009/117277 | A2 | 9/2009 |
| WO | WO 2010/016525 | A1 | 2/2010 |
| WO | WO 2010/016526 | A1 | 2/2010 |
| WO | WO 2010/016527 | A1 | 2/2010 |
| WO | WO 2011/096517 | A1 | 8/2011 |
| WO | WO 2011/096528 | A1 | 8/2011 |
| WO | WO 2011/096533 | A1 | 8/2011 |
| WO | WO 2011/096534 | A1 | 8/2011 |
| WO | WO 2011/096535 | A1 | 8/2011 |
| WO | WO 2012/005550 | A2 | 1/2012 |
| WO | WO 2012/013609 | A1 | 2/2012 |
| WO | WO 2013/018885 | A1 | 2/2013 |
| WO | WO 2013/018886 | A1 | 2/2013 |
| WO | WO 2013/018894 | A1 | 2/2013 |
| WO | WO 2013/147169 | A1 | 10/2013 |
| WO | WO 2013/147176 | A1 | 10/2013 |

OTHER PUBLICATIONS

Chamberlain et al., "Innovations and strategies for the development of anticancer vaccines," Expert Opinion on Pharmacotherapy, vol. 1, No. 4, 2000, pp. 603-614.

Chinese Office Action and Search Report, dated Mar. 29, 2013, for Chinese Application No. 200980139037.X.

Chinese Office Action and Search Report, dated May 9, 2013, for Chinese Application No. 201180016730.5, with an English translation.

Ellis et al., "Identification and Characterization of a Novel Protein (p137) Which Transcytoses Bidirectionally in Caco-2 Cells", The Journal of Biological Chemistry, Sep. 1, 1995, vol. 270, No. 35, pp. 20717-20723.

Evans et al., "Vaccine therapy for cancer—fact or fiction?", Q J Med, vol. 92, 1999, pp. 299-307.

Extended European Search Report, dated Aug. 13, 2013, for European Application No. 11739882.6.

Extended European Search Report, dated Aug. 26, 2011, for European Application No. 09805010.7.

Extended European Search Report, dated Jan. 30, 2013, for European Application No. 09805009.9.

Extended European Search Report, dated Nov. 6, 2013, for European Application No. 11739876.8.

GeneCards, "Cell Cycle Associated Protein 1—Biological research products for CAPRIN 1," updated Mar. 19, 2013, 10 pages.

Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.

Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.

Gure et al., "SSX: A Multigene Family with Several Members Transcribed in Normal Testis and Human Cancer," International Journal of Cancer, vol. 72, 1997, pp. 965-971.

Harlow et al., "Antibodies a Laboratory Manual", Cold Spring Harbor Laboratory, Chapter 3, 1988, pp. 23-34.

Hugo Gene Nomenclature Committee, Gene Symbol Report, CAPRIN1, Approved Name: Cell Cycle Associated Protein 1, HGNC ID: HGNC:6743, Nov. 3, 2012, 2 pages.

International Search Report and Written Opinion of the International Searching Authority (PCT/ISA/210 and PCT/ISA/237), dated Mar. 1, 2011, for International Application No. PCT/JP2011/052413, with an English translation of the International Search Report only.

International Search Report and Written Opinion of the International Searching Authority (PCT/ISA/210 and PCT/ISA/237), dated Mar. 15, 2011, for International Application No. PCT/JP2011/052384, with an English translation of the International Search Report only.

International Search Report and Written Opinion of the International Searching Authority (PCT/ISA/210 and PCT/ISA/237), dated Mar. 8, 2011, for International Application No. PCT/JP2011/052403, with an English translation of the International Search Report only.

International Search Report and Written Opinion of the International Searching Authority (PCT/ISA/210 and PCT/ISA/237), dated Mar. 8, 2011, for International Application No. PCT/JP2011/052414, with an English translation of the International Search Report only.

International Search Report and Written Opinion of the International Searching Authority (PCT/ISA/210 and PCT/ISA/237), dated Oct. 6, 2009, for International Application No. PCT/JP2009/063882, with an English translation of the International Search Report only.

(56) References Cited

OTHER PUBLICATIONS

International Search Report and Written Opinion of the International Searching Authority (PCT/ISA/210 and PCT/ISA/237), dated Sep. 8, 2009, for International Application No. PCT/JP2009/063883, with an English translation of the International Search Report only.
Itoh et al., "HUB1 is an autoantigen frequently eliciting humoral immune response in patients with adult T cell leukemia," International Journal of Oncology, vol. 14, No. 4, Apr. 1999, pp. 703-708 (Abstract only provided).
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, Feb. 27, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, One page (Abstract only provided).
Kataja et al., "Primary breast cancer: ESMO Clinical Recommendations for diagnosis, treatment and follow-up," Annals of Oncology, vol. 20, Supplement 4, May 2009, pp. iv10-iv14.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . . ," Journal of Biological Chemistry, vol. 279, No. 50, Dec. 10, 2004, pp. 52210-52217.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).
Lu et al., "Targeting serum antibody for cancer diagnosis: a focus on colorectal cancer," Expert Opinion on Therapeutic Targets, vol. 11, No. 2, 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
NCBI Reference Sequence, caprin-1 [Bos taurus], 2009, Accession No. NP_001069530, XP_615677, 1 page.
NCBI Reference Sequence, caprin-1 [Gallus gallus], 2005, Accession No. NP_001026536, XP_423820, 1 page.
NCBI Reference Sequence, caprin-1 isoform 1 [*Homo sapiens*], 1995, Accession No. NP_005889, 3 pages.
NCBI Reference Sequence, caprin-1 isoform 2 [*Homo sapiens*], 1995, Accession No. NP_976240, 3 pages.
NCBI Reference Sequence, caprin-1 isoform a [Mus musculus], 1996, Accession No. NP_058019, 3 pages.
NBCI Reference Sequence, caprin-1 isoform b [Mus musculus], 1996, Accession No. NP_001104760, 3 pages.
NCBI Reference Sequence, caprin-1 isoform c [Mus musculus], 1996, Accession No. NP_001104761, 4 pages.
NCBI Reference Sequence, Predicted: caprin-1 [Equus caballus], 2008, Accession No. XP_001492799, 1 page.
NCBI Reference Sequence, Predicted: caprin-1 isoform 2 [Canis lupus familiaris], Dec. 2, 2011, Accession No. XP_858109, 1 page.
Nelson et al., "Screening for Breast Cancer: An Update for the U.S. Preventive Services Task Force," Annals of Internal Medicine, vol. 151, No. 10, Nov. 17, 2009, pp. 727-737.
Okano et al., "Abstract 519: Identification of a novel target for antibody therapy of breast cancer", Cancer Research, vol. 72, Issue 8, Supplement 1, Apr. 15, 2012, XP-002700046, 2 pages.
Polyak et al., "Alanine-170 and proline-172 are critical determinants for extracellular CD20 epitopes; heterogeneity in the fine specificity of CD20 monoclonal antibodies is defined by additional requirements imposed by both amino acid . . . ", Blood, vol. 99, No. 9, May 1, 2002, pp. 3256-3262.
R & D Systems, "IHC Products & Protocol Guide," printed Jan. 9, 2014, pp. 1-112.
Russian Notice of Allowance, dated Jun. 7, 2013, for Russian Application No. 2011108260/10, with an English translation.
Sahin et al., "Human neoplasms elicit multiple specific immune responses in the autologous host,"Proceedings of the National Academy of Sciences USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," International Journal of Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . . ," Molecular and Cellular Biology, vol. 27, No. 6, Mar. 2007, XP_002690351, pp. 2324-2342.
Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
United States Notice of Allowance, dated Aug. 11, 2014, for U.S. Appl. No. 13/577,028.
United States Notice of Allowance, dated Dec. 2, 2013, for U.S. Appl. No. 13/576,955.
United States Notice of Allowance, dated Jul. 3, 2014, for U.S. Appl. No. 13/576,953 (Corrected Notice of Allowability).
United States Notice of Allowance, dated May 7, 2014, for U.S. Appl. No. 13/576,953.
United States Notice of Allowance, dated Sep. 12, 2014, for U.S. Appl. No. 13/577,212.
United States Office Action, dated Apr. 4, 2014, for U.S. Appl. No. 13/577,028.
United States Office Action, dated Apr. 7, 2014, for U.S. Appl. No. 13/576,950.
United States Office Action, dated Aug. 19, 2013, for U.S. Appl. No. 13/576,955.
United States Office Action, dated Aug. 26, 2013, for U.S. Appl. No. 13/576,950.
United States Office Action, dated Dec. 19, 2014, for U.S. Appl. No. 13/057,709.
United States Office Action, dated Dec. 21, 2012, for U.S. Appl. No. 13/057,515.
United States Office Action, dated Dec. 21, 2012, for U.S. Appl. No. 13/057,709.
United States Office Action, dated Dec. 29, 2014, for U.S. Appl. No. 13/576,969.
United States Office Action, dated Jan. 16, 2014, for U.S. Appl. No. 13/057,515.
United States Office Action, dated Jul. 1, 2013, for U.S. Appl. No. 13/057,515.
United States Office Action, dated Jul. 1, 2013, for U.S. Appl. No. 13/577,212.
United States Office Action, dated Jul. 16, 2013, for U.S. Appl. No. 13/057,709.

(56) References Cited

OTHER PUBLICATIONS

United States Office Action, dated Jul. 16, 2014, for U.S. Appl. No. 13/576,950.
United States Office Action, dated Jun. 14, 2013, for U.S. Appl. No. 13/576,969.
United States Office Action, dated Jun. 19, 2014, for U.S. Appl. No. 13/057,515.
United States Office Action, dated Mar. 13, 2013, for U.S. Appl. No. 13/576,955.
United States Office Action, dated Mar. 24, 2014, for U.S. Appl. No. 13/576,969.
United States Office Action, dated May 5, 2014, for U.S. Appl. No. 13/577,212.
United States Office Action, dated Nov. 15, 2013, for U.S. Appl. No. 13/576,950.
United States Office Action, dated Nov. 15, 2013, for U.S. Appl. No. 13/576,953.
United States Office Action, dated Nov. 15, 2013, for U.S. Appl. No. 13/577,028.
United States Office Action, dated Nov. 2, 2012, for U.S. Appl. No. 13/057,709.
United States Office Action, dated Nov. 9, 2012, for U.S. Appl. No. 13/057,515.
United States Office Action, dated Oct. 1, 2014, for U.S. Appl. No. 13/057,515.
United States Office Action, dated Oct. 15, 2013, for U.S. Appl. No. 13/576,969.
United States Office Action, dated Oct. 2, 2013, for U.S. Appl. No. 13/057,709.
United States Office Action, dated Oct. 21, 2013, for U.S. Appl. No. 13/577,212.
United States Office Action, dated Oct. 9, 2013, for U.S. Appl. No. 13/057,515.
United States Office Action, dated Sep. 19, 2013, for U.S. Appl. No. 13/577,028.
United States Office Action, dated Sep. 3, 2014, for U.S. Appl. No. 13/576,969.
United States Office Action, dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in Joumal of Immunology, vol. 178, 2007, pp. 2617-2621).
Wang et al., "Absence of Caprin-1 Results in Defects in Cellular Proliferation", The Journal of Immunology, vol. 175, 2005, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Published online Mar. 30, 2010), pp. 85-92.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report issued Feb. 2, 2015, in European Patent Application No. 12819473.5.
Extended European Search Report issued Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
De Pascalis et al., "Grafting of "Abbreviated" Complementary-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report issued Mar. 2, 2015, in European Patent Application No. 12819759.7.
Riechmann et al., "Reshaping Human Antibodies for Therapy," Nature (Mar. 24, 1988), vol. 332, pp. 323-327.
Russian Office Action issued Jan. 28, 2015 in Russian Patent Application No. 2012137502, with partial English translation.
Vajdos et al., "Comprehensive Functional Maps of the Antigenbining Site of an Anti-ErbB2 Antibody Obtained with Shotgun Scanning Mutagenesis," J. Mol. Biol. (2002), vol. 320, pp. 415-428.
Gong et al.,"Caprin-1 is a novel microRNA-223 target for regulating the proliferation and invasion of human breast cancer cells", Biomedicine & Pharmacotherapy, vol. 67, 2013, pp. 629-636.
Qiu et al., "Targeting a ribonucleoprotein complex containing the caprin-1 protein and the c-Myc mRNA suppresses tumor growth in mice: an identification of a novel oncotarget", Oncotarget, vol. 6, No. 4, Dec. 10, 2014, pp. 2148-2163.
Sabile et al., "Caprin-1, a novel Cyr61-interacting protein, promotes osteosarcoma tumor growth and lung metastasis in mice", Biochimica et Biophysica Acta, vol. 1832, 2013 (available online Mar. 23, 2013), pp. 1173-1182.
U.S. Office Action for U.S. Appl. No. 13/576,950, dated Mar. 30, 2015.
Extended European Search Report issued Mar. 18, 2015, in European Patent Application No. 12820225.6.
Extended European Search Report issued Mar. 23, 2005, in European Patent Application No. 12820596.0.
Non-Final Office Action issued Apr. 14, 2015, in U.S. Appl. No. 14/236,793.
GenBank Accession No. NM_005898, Feb. 11, 2008.
U.S. Office Action for U.S. Appl. No. 14/379,867, dated Jun. 24, 2015.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action issued Aug. 14, 2015, in U.S. Appl. No. 14/236,818.
Office Action issued Aug. 20, 2015, in U.S. Appl. No. 14/452,746.
Office Action issued Jul. 3, 2015, in Russian Patent Application No. 2012137503.
Office Action issued Sep. 15, 2015, in U.S. Appl. No. 14/389,266.
Padlan, E. A., "X-Ray Crystallography of Antibodies," Adv. Prot. Chem. (1996), vol. 49, pp. 57-133.
Saffari et al., "Identification of novel p53 target genes by cDNAAFLP in glioblastoma cells", Cancer Letters, 2009, No. 273, pp. 316-322.
Extended European Search Report for European Application No. 13767612.8, dated Sep. 22, 2015.
Extended European Search Report for European Application No. 13769665.4, dated Sep. 22, 2015.
Carter, Paul J., "Potent antibody therapeutics by design", Nature Reviews Immunology, vol. 6, May 2006, pp. 343-357.
GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.

(56) References Cited

OTHER PUBLICATIONS

Patent Examination Report No. 1 issued Oct. 14, 2014, in Australian Patent Application No. 2009278387.

Bodey et al., "MAGE-1, a Cancer/Testis-Antigen, Expression in Childhood Astrocytomas as an Indicator of Tumor Progression," in vivo (2002) vol. 16, pp. 583-588.

Comtesse et al., "Probing the human natural autoantibody repertoire using an immunoscreening approach," Clin. Exp. Immunol. (2000), vol. 121, pp. 430-436.

International Search Report issued Nov. 18, 2014, in PCT International Application No. PCT/JP2014/071094.

Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.

Jungbluth et al., "Immunohistochemical Analysis of NY-ESO-1 Antigen Expression in Normal and Malignant Human Tissues," Int. J. Cancer (2001), vol. 92, pp. 856-860.

Kohler et al., "Tumor antigen analysis in neuroblastoma by serological interrogation of bioinformatic data," Cancer Science (Nov. 2010), vol. 101, No. 11, pp. 2316-2324.

Nakamura et al. "Gene Expression Profile of Metastatic Human Pancratic Cancer Cells Depends on the Organ Microenvironment," Cancer Research (Jan. 1, 2007), vol. 67, No. 1, pp. 139-148.

Non-Final Office Action issued Nov. 6, 2014, in U.S. Appl. No. 13/576,950.

Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.

Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.

"*Homo sapiens* cell cycle associated protein 1, mRNA (cDNA clone MGC:1378 Image:3355481), complete cds", Genebank database, NCBI Accession No. BC001731, Sep. 11, 2007.

Extended European Search Report for Appl. No. 13820574.5 dated Jan. 11, 2016.

Huang, J. et al, "IgG Isotype Conversion of a Novel Human Anti-carcinoembryonic Antigen Antibody to Increase its Biological Activity," Anticancer Research, 2006, vol. 26, No. 2A, pp. 1057-1063.

Shibaguchi, H. et al, "New Human Antibody IgG Subclass Conversion for Enhancement of Tumor-Cytotoxic Activity," Research, 2006, vol. 11, No. 3, pp. 15-16.

* cited by examiner

PHARMACEUTICAL COMPOSITION FOR TREATMENT AND/OR PREVENTION OF GALLBLADDER CANCER

TECHNICAL FIELD

The present invention relates to a medicinal use of an antibody against a CAPRIN-1 protein or a fragment thereof, for example, as an agent for treating and/or preventing gallbladder cancer.

BACKGROUND ART

Recently, various antibody drugs for treating cancers by targeting antigen proteins on cancer cells have become up in the world. The antibody drugs show certain beneficial effects as cancer-specific therapeutic agents and have received attention. However, most of the target antigen proteins are expressed also on normal cells, and administration of such an antibody impairs not only cancer cells but also normal cells expressing the antigen, resulting in a problem of side effects therefrom. Accordingly, if a cancer antigen being specifically expressed on cancer cell surface is identified and an antibody targeting the antigen can be used as a pharmaceutical agent, treatment with an antibody drug with less side effects can be expected.

It is known to those skilled in the art as general technical knowledge that gallbladder cancer, among various cancers, is very difficult to be detected at an early stage because of its lack of symptoms and early symptoms; advanced gallbladder cancer such as lymph node metastasis, liver metastasis, lung metastasis, bone metastasis, or peritoneal metastasis is very difficult to treat, leading to a five-year survival rate of almost 0% for patients with gallbladder cancer not amenable to surgery; and gallbladder cancer is very difficult to treat and effective therapies for the cancer have not been developed.

Cytoplasmic- and proliferation-associated protein 1 (CAPRIN-1) has been known as an intracellular protein that is expressed in activation of normal cells in the resting phase or in occurrence of cell division and is involved in control of transport and translation of mRNA through formation of intracellular stress granules with RNA in cells. It was found that CAPRIN-1 is specifically expressed on the surface of cancer cells such as breast cancer cells, and CAPRIN-1 has been studied as a target of antibody drugs for cancer therapy (Patent Literature 1). However, in Patent Literature 1, expression of CAPRIN-1 protein on gallbladder cancer cells is not recognized, and it is not described or suggested that CAPRIN-1 protein can be an antigen protein of gallbladder cancer.

CITATION LIST

Patent Literature

Patent Literature 1: WO2010/016526

SUMMARY OF INVENTION

Technical Problem

It is an object of the present invention to identify a cancer antigen protein being expressed on the surface of gallbladder cancer cells and to provide a use of an antibody targeting the protein as an agent for treating and/or preventing gallbladder cancer.

Solution to Problem

The present inventors have diligently studied and, as a result, have found that a part of CAPRIN-1 protein is expressed on the cell surface of gallbladder cancer cells and also have found that an antibody against the CAPRIN-1 protein impairs the gallbladder cancer cells expressing the CAPRIN-1 protein, and have accomplished the present invention.

Accordingly, the present invention has the following characteristics.

The present invention provides a pharmaceutical composition for treating and/or preventing gallbladder cancer, comprising, as an active ingredient, an antibody or a fragment thereof having immunological reactivity with a CAPRIN-1 protein comprising an amino acid sequence set forth in any of even sequence numbers from SEQ ID NOs: 2 to 30 or an amino acid sequence having a sequence identity of 80% or more, preferably 85% or more, more preferably 90% or more, and most preferably 95% or more to the amino acid sequence, or a fragment of the CAPRIN-1 protein comprising at least seven consecutive amino acid residues of the amino acid sequence of the protein.

In another embodiment, the antibody described above is a monoclonal antibody or a polyclonal antibody.

In another embodiment, the antibody is a human antibody, a humanized antibody, a chimeric antibody, a single-chain antibody, or a multispecific antibody.

In another embodiment, the antibody is an antibody having immunological reactivity with a peptide comprising an amino acid sequence set forth in SEQ ID NO: 271, SEQ ID NO: 273, SEQ ID NO: 266, SEQ ID NO: 270, SEQ ID NO: 272, or SEQ ID NO: 269 or an amino acid sequence having a sequence identity of 80% or more, preferably 85% or more, more preferably 90% or more, and most preferably 95% or more to the amino acid sequence or a fragment of the peptide.

In another embodiment, the antibody is any one of the following antibodies (a) to (ao) having immunological reactivity with the CAPRIN-1 protein, or a pharmaceutical composition for treating and/or preventing gallbladder cancer, comprising the antibody as an active ingredient.

(a) An antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively.

(b) An antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively.

(c) An antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively.

(d) An antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively.

(e) An antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively.

(f) An antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively.

(g) An antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively.

(h) An antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively.

(i) An antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively.

(j) An antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively.

(k) An antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively.

(l) An antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively.

(m) An antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively.

(n) An antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively.

(o) An antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively.

(p) An antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively.

(q) An antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively.

(r) An antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively.

(s) An antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively.

(t) An antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively.

(u) An antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively.

(v) An antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively.

(w) An antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively.

(x) An antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively.

(y) An antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively.

(z) An antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarily determining regions (CDR1, CDR2, and CDR3) consisting of amino acid sequences set forth in SEQ ID NOs: 280, 281, and 282, respectively.

(aa) An antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively.

(ab) An antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively.

(ac) An antibody comprising a heavy chain variable domain comprising complementarily determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively.

(ad) An antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively.

(ae) An antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively.

(af) An antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively.

(ag) An antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarily determining regions (CDR1, CDR2, and CDR3) consisting of amino acid sequences set forth in SEQ ID NOs: 345, 346, and 347, respectively.

(ah) An antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively.

(ai) An antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively.

(aj) An antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively.

(ak) An antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively.

(al) An antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively.

(am) An antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively.

(an) An antibody comprising a heavy chain variable domain comprising complementarity determining regions (CDR1, CDR2, and CDR3) consisting of amino acid sequences set forth in SEQ ID NOs: 408, 409, and 410, respectively and a light chain variable domain comprising complementarity determining regions (CDR1, CDR2, and CDR3) consisting of amino acid sequences set forth in SEQ ID NOs: 412, 413, and 414, respectively.

(ao) An antibody comprising a heavy chain variable domain comprising complementarity determining regions (CDR1, CDR2; and CDR3) consisting of amino acid sequences set forth in SEQ ID NOs: 418, 419, and 420, respectively and a light chain variable domain comprising complementarity determining regions (CDR1, CDR2, and CDR3) consisting of amino acid sequences set forth in SEQ ID NOs: 422, 423, and 424, respectively.

In another embodiment, the antibody or a fragment thereof of the present invention is conjugated to an antitumor agent.

The present invention further provides a combination pharmaceutical agent comprising combination of the pharmaceutical composition of the present invention and a pharmaceutical composition containing an antitumor agent.

The present invention further provides a method of treating and/or preventing gallbladder cancer, comprising administering the pharmaceutical composition or the combination pharmaceutical agent of the present invention to a subject.

The present specification encompasses the contents in the specification and/or the drawings of Japanese Patent Application No. 2012-080780 based on which the present application claims priority.

Advantageous Effects of Invention

The antibody against the CAPRIN-1 protein used in the present invention (hereinafter, often referred to as "anti-CAPRIN-1 antibody") impairs gallbladder cancer cells. Accordingly, the antibody against the CAPRIN-1 protein is useful for treatment and prevention of gallbladder cancer.

DESCRIPTION OF EMBODIMENTS

The antitumor activity of an antibody used in the present invention against a polypeptide consisting of an amino acid sequence set forth in any of even sequence numbers from SEQ ID NOs: 2 to 30 can be evaluated by investigating the in vivo suppression of tumor growth in a tumor-bearing animal or investigating, as described below, whether or not a cytotoxicity through immune cells or a complement is observed on tumor cells expressing the polypeptide in vitro.

The nucleotide sequences of polynucleotides encoding proteins consisting of the amino acid sequences set forth in even sequence numbers from SEQ ID NOs: 2 to 30 (i.e., SEQ ID NOs: 2, 4, 6, 8, 10, 12, 14, 16, 18, 20, 22, 24, 26, 28, and 30) are set forth in odd sequence numbers from SEQ ID NOs: 1 to 29 (i.e., SEQ ID NOs: 1, 3, 5, 7, 9, 11, 13, 15, 17, 19, 21, 23, 25, 27, and 29).

The amino acid sequences set forth in SEQ ID NOs: 6, 8, 10, 12, and 14 in sequence listing are amino acid sequences of a CAPRIN-1 protein isolated as polypeptides that bind to an antibody specifically present in serum derived from tumor-bearing dogs by a SEREX method using a dog testis tissue-derived cDNA library and serum of a breast cancer dog; the amino acid sequences set forth in SEQ ID NOs: 2 and 4 are amino acid sequences isolated as human homologous factors (homologs or orthologs) of the polypeptides; the amino acid sequence set forth in SEQ ID NO: 16 is an amino acid sequence isolated as a bovine homologous factor thereof; the amino acid sequence set forth in SEQ ID NO: 18 is an amino acid sequence isolated as a horse homologous factor thereof; the amino acid sequences set forth in SEQ ID NOs: 20 to 28 are amino acid sequences isolated as mouse homologous factors thereof; and the amino acid sequence set forth in SEQ ID NO: 30 is an amino acid sequence isolated as a chicken homologous factor (see Example 1 described below) thereof. The CAPRIN-1 protein is known to be expressed in activation of normal cells in the resting phase or in occurrence of cell division.

The investigation revealed that the CAPRIN-1 protein is expressed on the cell surface of gallbladder cancer cells. In the present invention, an antibody that binds to a part of the CAPRIN-1 protein expressed on the cell surface of gallbladder cancer cells is preferably used. Examples of the partial peptide (fragment) of the CAPRIN-1 protein expressed on the cell surface of gallbladder cancer cells include peptides comprising at least seven consecutive amino acid residues in the region of amino acid residue positions (aa) 233 to (aa) 343, amino acid residue positions (aa) 512 to the C-terminal, or amino acid residue positions (aa) 50 to (aa) 98 of the amino acid sequences set forth in even sequence numbers from SEQ ID NOs: 2 to 30, excluding SEQ ID NOs: 6 and 18, in the sequence listing. Specifically, for example, the partial peptide (fragment) is a peptide comprising at least seven consecutive amino acid residues in an amino acid sequence set forth in SEQ ID NO: 429, SEQ ID NO: 428, SEQ ID NO: 273 (in the amino acid sequence set forth in SEQ ID NO: 273, the region of the amino acid sequence set forth in SEQ ID NO: 274 or SEQ ID NO: 275 is preferred), SEQ ID NO: 266 (in the amino acid sequence set forth in SEQ ID NO: 266, the region of the amino acid sequence set forth in SEQ ID NO: 267 or SEQ ID NO: 268 is preferred), SEQ ID NO: 270, SEQ ID NO: 272, SEQ ID NO: 269, SEQ ID NO: 430, SEQ ID NO: 431, or SEQ ID NO: 432, or in an amino acid sequence having a sequence identity of 80% or more, preferably 85% or more, more preferably 90% or more, and most preferably 95% or more, such as 96% or more, 97% or more, 98% or more, or 99% or more, to the amino acid sequence mentioned above. Examples of the antibody used in the present invention include all antibodies that bind to any of these peptides and show antitumor activity.

The anti-CAPRIN-1 antibody used in the present invention may be any type of antibody that shows antitumor activity, and examples thereof include monoclonal antibodies; polyclonal antibodies; recombinant antibodies such as synthetic antibodies, multispecific antibodies (e.g., diabodies and triabodies), humanized antibodies, chimeric antibodies, and single-chain antibodies (scFv); human antibodies; and antibody fragments thereof such as Fab, $F(ab')_2$, and Fv. These antibodies and fragments thereof can be prepared by those skilled in the art through a known method. In the present invention, an antibody capable of specifically binding to a CAPRIN-1 protein is desirable, and preferred is a monoclonal antibody. However, the antibody may be a polyclonal antibody that is homogeneous and can be stably produced. When the subject is a human being; a human antibody or a humanized antibody is desirable for inhibiting or suppressing rejection reaction.

Here, the term “specifically binding to a CAPRIN-1 protein” refers to binding specific to a CAPRIN-1 protein and substantially not binding other proteins.

The antitumor activity of the antibody that can be used in the present invention can be evaluated by, as described below, investigating the in vivo suppression of tumor growth in a tumor-bearing animal or investigating whether or not a cytotoxicity through immune cells or a complement is observed on tumor cells expressing the polypeptide in vitro.

The subject as an object of the treatment and/or prevention of gallbladder cancer in the present invention is a mammal such as a human being, a pet animal, a domestic animal, or an animal for competitive use; and is preferably a human being.

The production of an antigen, the production of an antibody, and a pharmaceutical composition according to the present invention will now be described.

<Production of Antigen for Producing Antibody>

The protein or a fragment thereof to be used as a sensitizing antigen for preparing an anti-CAPRIN-1 antibody used in the present invention may be derived from any animal species, such as a human being, dog, bovine, horse, mouse, rat, or chicken, and is preferably selected with consideration for compatibility with the parent cells used for cell fusion. In general, the protein is preferably a protein derived from a mammal, in particular, a human being. For example, when the CAPRIN-1 protein is a human CAPRIN-1 protein, a human CAPRIN-1 protein, a partial peptide thereof, or cells expressing a human CAPRIN-1 protein can be used.

The nucleotide sequences and the amino acid sequences of a human CAPRIN-1 protein and a homolog thereof can be obtained by, for example, accessing the GenBank (NCBI, USA) and using algorithm such as BLAST or FASTA (Karlin and Altschul, Proc. Natl. Acad. Sci. USA, 90: 5873-5877, 1993; Altschul et al., Nucleic Acids Res., 25: 3389-3402, 1997).

In the present invention, the target is a nucleic acid or protein consisting of a sequence having a sequence identity of 70% to 100%, preferably 80% to 100%, more preferably 90% to 100%, and most preferably 95% to 100%, such as 97% to 100%, 98% to 100%, 99% to 100%, or 99.5% to 100%, to the nucleotide sequence or the amino acid sequence of the ORF or the mature part of the human CAPRIN-1 gene when the nucleotide sequence and the amino acid sequence thereof are based on the sequences set forth in SEQ ID NO: 1 or 3 and SEQ ID NO: 2 or 4, respectively. Here, the term “% sequence identity” between two amino acid (or nucleotide) sequences refers to the percentage (%) of the number of amino acids (or nucleotides) in one sequence coinciding with those in the other sequence to the total number when the two sequences are aligned (alignment) with a maximum degree of similarity or coincidence by introducing a gap or not.

A fragment of the CAPRIN-1 protein has a length of from an amino acid length of an epitope (antigen determinant), which is a minimum unit recognized by an antibody, to an amino acid length shorter than the total length of the protein. The epitope refers to a polypeptide fragment having antigenicity or immunogenicity in a mammal, preferably in a human being, and its minimum unit consists of about 7 to 12 amino acids, such as 8 to 11 amino acids. Examples of the epitope include the amino acid sequences set forth in SEQ ID NO: 273, SEQ ID NO: 266, SEQ ID NO: 270, SEQ ID NO: 272, and SEQ ID NO: 269; and an amino acid sequence having a sequence identity of 80% or more, preferably 85% or more, more preferably 90% or more, and most preferably 95% or more to any of the amino acid sequences.

The polypeptide comprising a human CAPRIN-1 protein or a partial peptide thereof can be synthesized, for example, in accordance with a chemical synthesis such as a fluorenylmethyloxycarbonyl (Fmoc) method or a t-butyloxycarbonyl method (tBoc) method (Seikagaku Jikken Koza (Course of Biochemical Experiments) 1, Tanpakushitsu no Kagaku (Protein Chemistry) IV, Kagaku shushoku to peputido gosei (Chemical modification and peptide synthesis), edited by the Japanese Biochemical Society, Tokyo Kagaku Dojin (Japan), 1981). Alternatively, the peptide can be synthesized by a usual method using various commercially available peptide synthesizers. Furthermore, a target peptide can be obtained by preparing a DNA encoding the polypeptide by a known genetic engineering procedure (e.g., Sambrook, et al., Molecular Cloning, 2nd edition, Current Protocols in Molecular Biology (1989), Cold Spring Harbor Laboratory Press; Ausubel, et al., Short Protocols in Molecular Biology, 3rd edition, A compendium of Methods from Current Protocols in Molecular Biology (1995), John Wiley & Sons), incorporating the DNA into an expression vector and introducing it into a host cell, and allowing the production of the peptide in the host cell.

The DNA encoding the polypeptide can be readily prepared by a known genetic engineering procedure or by a usual method with a commercially available peptide synthesizer. For example, a DNA comprising the nucleotide sequence set forth in SEQ ID NO: 1 can be prepared by PCR using a pair of primers designed such that the nucleotide sequence set forth in SEQ ID NO: 1 can be amplified using a human chromosome or cDNA library as a template. The reaction conditions for the PCR can be appropriately determined, and non-limiting examples thereof include conditions in which a PCR buffer containing a heat stable DNA polymerase (e.g., Taq polymerase) and $Mg^{2+}$ is used, and the amplification is performed by repeating, for example, 30 cycles of a process consisting of reactions at 94° C. for 30 seconds (denaturation), at 55° C. for 30 seconds to 1 minute (annealing), and at 72° C. for 2 minutes (extension) and then performing a reaction at 72° C. for 7 minutes. The procedure, conditions, and other factors of PCR are described in, for example, Ausubel, et al., Short Protocols in Molecular Biology, 3rd edition, A compendium of Methods from Current Protocols in Molecular Biology, (1995), John Wiley & Sons (in particular, the 15th chapter).

A desired DNA can be isolated by preparing appropriate probes and primers based on the information of the nucleotide sequences and the amino acid sequences set forth in SEQ ID NOs: 1 to 30 of the sequence listing in the specification and screening, for example, a human cDNA library using the resulting probes and primers. The cDNA library is preferably constructed from cells, an organ, or tissue expressing the proteins set forth in any of even sequence numbers from SEQ ID NOs: 2 to 30. Examples of the cells and tissue include those derived from testis and cancer or tumor cells, such as leukemia, breast cancer, lymphoma, brain tumor, lung cancer, colon cancer, and gallbladder cancer. The above-described procedures such as preparation of probes or primers, construction of a cDNA library, screening of the cDNA library, and cloning of a target gene are known to those skilled in the art and can be performed, for example, in accordance with the method described in, for example, Sambrook, et, al., Molecular Cloning, 2nd edition, Current Protocols in Molecular Biology; (1989) or Ausbel, et al. (above). A DNA encoding a human CAPRIN-1 protein or a partial peptide thereof can be prepared from the thus-prepared DNA.

The host cell may be any cell that can express the above-mentioned peptide, and examples thereof include, but not limited to, prokaryotic cells such as *E. coli* cells and eukaryotic cells such as mammalian cells, e.g., monkey kidney COS1 cells and Chinese hamster ovary CHO cells, human embryonic kidney cell line HEK293, mouse embryonic fibroblast cell line NIH3T3, yeast cells, e.g., budding yeasts and fission yeast cells, silkworm cells, and *Xenopus* egg cells.

When prokaryotic cells are used as host cells, an expression vector having an origin of replicable in the prokaryotic cell, a promoter, a ribosome binding site, a multicloning site, a terminator, a drug resistance gene, an auxotrophic complementary gene, etc. is used. Examples of the expression vector for *E. coli* include pUC vector, pBluescriptII, pET expression system, and pGEX expression system. The polypeptide described above can be expressed in prokaryotic host cells by incorporating a DNA encoding the polypeptide into such an expression vector, transforming the prokaryotic host cells with the vector, and then culturing the resulting transformant. On this occasion, the polypeptide can also be expressed as a fusion protein with another protein.

When eukaryotic cells are used as host cells, an expression vector for eukaryotic cells having a promoter, a splicing region, a poly(A) addition site, etc. is used. Examples of the expression vector include pKA1, pCDM8, pSVK3, pMSG, pSVL, pBK-CMV, pBK-RSV, EBV vector, pRS, pcDNA3, and pYES2. The polypeptide described above can be expressed in eukaryotic host cells as in above by incorporating a DNA encoding the polypeptide into such an expression vector, transforming the eukaryotic host cells with the vector, and then culturing the resulting transformant. When the expression vector is, for example, pIND/V5-His, pFLAG-CMV-2, pEGFP-N1, or pEGFP-C1, the polypeptide can be expressed as a fusion protein with a tag such as His tag (e.g., $(His)_6$ to $(His)_{10}$), FLAG tag, myc tag, HA tag, or GFP.

Introduction of an expression vector into host cells can be performed by a known method such as electroporation, calcium phosphate transfection, a liposome method, a DEAE-dextran method, micro-injection, virus infection, lipofection, or binding to a cell-penetrating peptide.

A target polypeptide can be isolated and purified from the host cells by combining known separating procedures. Examples of the separating procedures include, but not limited to, treatment with a denaturant such as urea or a surfactant, ultrasonication, enzymatic digestion, salting out, solvent fractional precipitation, dialysis, centrifugation, ultrafiltration, gel filtration, SDS-PAGE, isoelectric focusing phoresis, ion exchange chromatography, hydrophobic chromatography, affinity chromatography, and reverse phase chromatography.

<Structure of Antibody>

An antibody is usually a heteromultimeric glycoprotein at least comprising two heavy chains and two light chains. Except for IgM, an antibody is a heterotetrameric glycoprotein of about 150 kDa comprising the same two light (L) chains and the same two heavy (H) chains Typically, a light chain is linked to a heavy chain through a disulfide covalent bond, and the number of disulfide bonds between the heavy chains varies depending on the isotype of immunoglobulin. The heavy chains and the light chains each have an intrachain disulfide bond. Each heavy chain has a variable domain (VH domain) at one end, followed by several constant domains. Each light chain has a variable domain (VL domain) and a constant domain at its other end. The constant domain of the light chain is aligned with the first constant domain of the heavy chain, and the light chain variable domain is aligned with the variable domain of the heavy chain. The variable domains of an antibody confer binding specificity on the antibody with specific regions displaying particular variability called complementarity determining regions (CDRs). The relatively conserved portions of the variable domains are called framework regions (FRs). The variable domains of intact heavy and light chains each comprises four FRs connected by three CDRs. The three CDRs in the heavy chain are called CDRH1, CDRH2, and CDRH3 in this order from the N-terminal side. Similarly, in the light chain, the CDRs are called CDRL1, CDRL2, and CDRL3. CDRH3 is most important in the binding specificity of an antibody to an antigen. The CDRs of each chain are held together in a contiguous state by the FRs and contribute together with CDRs of another chain to formation of the antigen binding site of the antibody. The constant domains are not directly involved in the binding of the antibody to the antigen, but exhibit various effector functions such as participation in antibody dependent cell-medicated cytotoxicity (ADCC), phagocytosis via binding to Fc γ receptor, half-life/clearance rate via neonatal Fe receptor (FcRn), and complement dependent cytotoxicity (CDC) via the C1q component of the complement cascade.

<Production of Antibody>

The anti-CAPRIN-1 antibody in the present invention is an antibody having an immunological reactivity with the full length or a fragment of a CAPRIN-1 protein.

Here, the term "immunological reactivity" refers to a property that an antibody and a CAPRIN-1 antigen bind to each other in vivo, and a function of impairing tumor (for example, death, suppression, or regression) is exhibited through such binding. That is, the antibody used in the present invention may be any antibody that binds to a CAPRIN-1 protein and thereby can impair gallbladder cancer.

Examples of the antibody include monoclonal antibodies, polyclonal antibodies, synthetic antibodies, multispecific antibodies, human antibodies, humanized antibodies, chimeric antibodies, single-chain antibodies, and antibody fragments (e.g., Fab, $F(ab')_2$, and Fv). The antibody is an appropriate class of immunoglobulin molecule, such as IgG, IgE, IgM, IgA, IgD, or IgY, or an appropriate subclass, such as $IgG_1$, $IgG_2$, $IgG_3$, $IgG_4$, $IgA_1$, or $IgA_2$.

The antibody may be further modified by, for example, acetylation, formylation, amidation, phosphorylation, or polyethylene glycolation (PEGylation), as well as glycosylation.

Examples of production of various antibodies will now be described.

In a monoclonal antibody, for example, a mouse is immunized with a CAPRIN-1 protein, gallbladder cancer cells expressing the CAPRIN-1 protein, or a cell line (e.g., TGBC14TKB) thereof; the spleen is extracted from the mouse; the spleen cells are separated and are fused with mouse myeloma cells; and clones producing antibodies having cancer cell growth-inhibitory activity are selected from the resulting fused cells (hybridomas). A hybridoma producing a monoclonal antibody having cancer cell growth-inhibitory activity is isolated and is cultured, and the antibody is purified from the culture supernatant by usual affinity purification to prepare a monoclonal antibody.

The hybridoma producing a monoclonal antibody can also be produced by, for example, as follows. First, an animal is immunized with a sensitizing antigen in accordance with a known method. In general, the sensitizing antigen is intraperitoneally or subcutaneously injected to a mammal. Specifically, the sensitizing antigen is appropriately diluted with, for example, phosphate-buffered saline (PBS) or physiological saline. The resulting suspension is optionally mixed with an appropriate amount of a normal adjuvant, such as complete Freund's adjuvant, and emulsified, and is then administered to the mammal several times at 4 to 21 days intervals. In addition, an appropriate carrier can be used in immunization with the sensitizing antigen.

After the immunization of the mammal and confirmation of an increase in the level of a desired antibody in serum, the immune cells are collected from the mammal and are subjected to cell fusion. The immune cells are preferably spleen cells.

Myeloma cells of a mammal are used as the other parent cells to be fused with the immune cells. As the myeloma cells, various known cell lines, for example, P3U1 (P3-X63Ag8U1), P3 (P3x63Ag8.653) (J. Immunol., (1979), 123, 1548-1550), P3x63Ag8U.1 (Current Topics in Microbiology and Immunology, (1978), 81, 1-7), NS-1 (Kohler, G. and Milstein, C., Eur. J. Immunol, (1976), 6, 511-519), MPC-11 (Margulies, D. H., et al., Cell, (1976), 8, 405-415), SP2/0 (Shulman, M. et al., Nature, (1978), 276, 269-270), FO (deSt. Groth, S. F., et al., J. Immunol. Methods, (1980), 35, 1-21), 5194 (Trowbridge, I. S., J. Exp. Med., (1978), 148, 313-323), or 8210 (Galfre, G. et al., Nature, (1979), 277, 131-133), can be suitably used.

The immune cells and the myeloma cells can be fundamentally fused by a known method, for example, in accordance with the method of Kohler and Milstein (Kohler, G. and Milstein, C., Methods Enzymol., (1981), 73, 3-46).

More specifically, the cell fusion is performed, for example, in a normal nutrient culture solution in the presence of a cell fusion accelerator. Examples of the cell fusion accelerator include polyethylene glycol (PEG) and Sendai virus (HVJ). Furthermore, an auxiliary agent such as dimethyl sulfoxide can be optionally used for increasing the fusion efficiency.

The number ratio between the immune cells and the myeloma cells can be arbitrarily determined. For example, the ratio of the number of the immune cells to the number of myeloma cells is preferably 1 to 10. The culture solution used in the cell fusion can be, for example, a RPMI1640 culture solution or MEM culture solution suitable for growth of the myeloma cell line or a normal culture solution that is used for such cell culture. In addition, a serum replacement such as fetal calf serum (FCS) can be added to the culture solution.

The cell fusion is performed by sufficiently mixing predetermined amounts of the immune cells and the myeloma cells in the culture solution, adding a PEG solution (average molecular weight: e.g., about 1000 to 6000) previously heated to about 37° C. to the mixture, usually, at a concentration of 30% to 60% (w/v), and mixing them to form a desired hybridoma. Successively, an appropriate culture solution is added to the mixture, and the supernatant is removed by centrifugation. This procedure is repeated to remove the components, such as the fusion promoter, that are undesirable for the growth of hybridomas.

The thus-prepared hybridoma can be selected by culturing in a usual selection culture solution, for example, a HAT culture solution (culture solution containing hypoxynthine, aminopterin, and thymidine). The culturing in the HAT culture solution is continued for a sufficient period of time (usually, several days to several weeks) for killing the cells (non-fused cells) other than the target hybridomas. Subsequently, a usual limiting dilution method is performed for screening and single cloning of the hybridoma that produces the target antibody.

Instead of the method of obtaining a hybridoma by immunizing a non-human animal with an antigen, a hybridoma that produces a human antibody having desired activity (e.g., cell growth-inhibitory activity) can be obtained by sensitizing human lymphocytes, for example, human lymphocytes infected with EB virus, with a protein, cells expressing the protein, or a lysate thereof in vitro, and fusing the sensitized lymphoxytes with myeloma cells derived from a human being and having permanent division ability, for example, U266 (Registration No. TIB196).

The thus-prepared hybridoma that produces a monoclonal antibody can be passaged in a usual culture solution and can be stored in a liquid nitrogen for a long time.

That is, a desired antigen or a cell expressing the desired antigen is used as the sensitizing antigen and is immunized in accordance with a usual method; the resulting immune cells are fused with known parent cells by a usual cell fusion; and a monoclonal antibody-producing cell (hybridoma) is screened by a usual screening method. Thus, a hybridoma can be produced.

Another example of the antibody that can be used in the present invention is a polyclonal antibody. The polyclonal antibody can be prepared, for example, as follows.

Serum is prepared by immunizing a small animal, such as a mouse, a human antibody-producing mouse, or a rabbit, with a native CAPRIN-1 protein, a recombinant CAPRIN-1 protein expressed in microorganisms, such as *E. coli*, as a fusion protein with, for example, GST, or a partial peptide thereof. The serum is purified by, for example, ammonium sulfate precipitation, protein A or protein G column chromatography, DEAE ion exchange chromatography, or an affinity column chromatography coupled with a CAPRIN-1 protein or a synthetic peptide. In examples described below, a rabbit polyclonal antibody against the CAPRIN-1 protein was produced, and an antitumor effect was confirmed.

Here, as the human antibody-producing mouse, a KM mouse (Kirin Pharma Company, Limited/Medarex Inc.) and a Xeno mouse (Amgen Inc.) are known (for example, International Publication Nos. WO02/43478 and WO02/092812). Immunization of such a mouse with a CAPRIN-1 protein or a fragment thereof can provide a complete human polyclonal antibody in the blood. Alternatively, a human-type monoclonal antibody can be produced by extracting the spleen cells from the immunized mouse and fusing the spleen cells with myeloma cells.

The antigen can be prepared in accordance with, for example, a method using animal cells (JP Patent Publication (Kohyo) No. 2007-530068) or a method using baculovirus (e.g., International Publication No. WO98/46777). An antigen having low immunogenicity may be immunized as a conjugate with a macromolecule having immunogenicity, such as albumin.

Furthermore, a transgenic antibody generated by gene recombination technology by cloning an antibody gene from a hybridoma, incorporating the gene into an appropriate vector, and introducing the vector into a host, can be used (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, a cDNA of the variable domain (V domain) of an antibody is synthesized using a reverse transcriptase from the mRNA of a hybridoma. If a DNA encoding the V domain of a target antibody is prepared, the DNA is linked to a DNA encoding a desired antibody constant domain (C domain), followed by incorporation into an expression vector. Alternatively, a DNA encoding the V domain of an antibody may be incorporated into an expression vector containing the DNA of the antibody C domain. The DNA is incorporated into the expression vector such that the DNA is expressed under the control of an expression-controlling domain, for example, an enhancer and a promoter. Subsequently, the host cell is transformed with the expression vector to express the antibody.

The anti-CAPRIN-1 antibody used in the present invention is preferably a monoclonal antibody, but may be a polyclonal antibody or a genetically altered antibody (e.g., chimeric antibody or humanized antibody).

Examples of the monoclonal antibody include human monoclonal antibodies, non-human animal monoclonal antibodies (e.g., mouse monoclonal antibodies, rat monoclonal antibodies, rabbit monoclonal antibodies, and chicken monoclonal antibodies). The monoclonal antibody can be produced by culturing hybridomas prepared by fusing myeloma cells with the spleen cells derived from a non-human mammal (e.g., mouse or human antibody-producing mouse) immunized with a CAPRIN-1 protein. In examples described below, monoclonal antibodies were produced, and the antitumor effects thereof were confirmed. These monoclonal antibodies each comprise a heavy-chain variable (VH) domain comprising the amino acid sequence set forth in SEQ ID NO: 40, SEQ ID NO: 50, SEQ ID NO: 60, SEQ ID NO: 70, SEQ ID NO: 80, SEQ ID NO: 90, SEQ ID NO: 100, SEQ ID NO: 110, SEQ ID NO: 120, SEQ ID NO: 130, SEQ ID NO: 135, SEQ ID NO: 145, SEQ ID NO: 160, SEQ ID NO: 170, SEQ ID NO: 200, SEQ ID NO: 210, SEQ ID NO: 220, SEQ ID NO: 230, SEQ ID NO: 240, SEQ ID NO: 250, SEQ ID NO: 279, SEQ ID NO: 294, SEQ ID NO: 304, SEQ ID NO: 314, SEQ ID NO: 324, SEQ ID NO: 334, SEQ ID NO: 344, SEQ ID NO: 359, SEQ ID NO: 363, SEQ ID NO: 368, SEQ ID NO: 372, SEQ ID NO: 376, SEQ ID NO: 386, SEQ ID NO: 396, SEQ ID NO: 401, SEQ ID NO: 411, or SEQ ID NO: 421 and a light-chain variable (VL) domain comprising the amino acid sequence set forth in SEQ ID NO: 44, SEQ ID NO: 54, SEQ ID NO: 64, SEQ ID NO: 74, SEQ ID NO: 84, SEQ ID NO: 94, SEQ ID NO: 104, SEQ ID NO: 114, SEQ ID NO: 124, SEQ ID NO: 139, SEQ ID NO: 149, SEQ ID NO: 155, SEQ ID NO: 164, SEQ ID NO: 174, SEQ ID NO: 180, SEQ ID NO: 185, SEQ ID NO: 190, SEQ ID NO: 195, SEQ ID NO: 204, SEQ ID NO: 214, SEQ ID NO: 224, SEQ ID NO: 234, SEQ ID NO: 244, SEQ ID NO: 254, SEQ ID NO: 283, SEQ ID NO: 289, SEQ ID NO: 298, SEQ ID NO: 308, SEQ ID NO: 318, SEQ ID NO: 328, SEQ ID NO: 338, SEQ ID NO: 348, SEQ ID NO: 361, SEQ ID NO: 365, SEQ ID NO: 370, SEQ ID NO: 380, SEQ ID NO: 390, SEQ ID NO: 405, SEQ ID NO: 415, or SEQ ID NO: 425. The VH domain comprises CDR1 represented by the amino acid sequence set forth in SEQ ID NO: 37, SEQ ID NO: 47, SEQ ID NO: 57, SEQ ID NO: 67, SEQ ID NO: 77, SEQ ID NO: 87, SEQ ID NO: 97, SEQ ID NO: 107, SEQ ID NO: 117, SEQ ID NO: 127, SEQ ID NO: 132, SEQ ID NO: 142, SEQ ID NO: 157, SEQ ID NO: 167, SEQ ID NO: 197, SEQ ID NO: 207, SEQ ID NO: 217, SEQ ID NO: 227, SEQ ID NO: 237, SEQ ID NO:247, SEQ ID NO: 276, SEQ ID NO: 291, SEQ ID NO: 301, SEQ ID NO: 311, SEQ ID NO: 321, SEQ ID NO: 331, SEQ ID NO: 341, SEQ ID NO: 351, SEQ ID NO: 373, SEQ ID NO: 383, SEQ ID NO: 393, SEQ ID NO: 398, SEQ ID NO: 408, or SEQ ID NO: 418, CDR2 represented by the amino acid sequence set forth in SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 133, SEQ ID NO: 143, SEQ ID NO: 158, SEQ ID NO: 168, SEQ ID NO: 198, SEQ ID NO: 208, SEQ ID NO: 218, SEQ ID NO: 228, SEQ ID NO: 238, SEQ ID NO: 248, SEQ ID NO 277, SEQ ID NO: 292, SEQ ID NO: 302, SEQ ID NO: 312, SEQ ID NO: 322, SEQ ID NO: 332, SEQ ID NO: 342, SEQ ID NO: 352, SEQ ID NO: 374, SEQ ID NO: 384, SEQ ID NO: 394, SEQ ID NO: 399, SEQ ID NO: 409, or SEQ ID NO: 419, and CDR3 represented by the amino acid sequence set forth in SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 134, SEQ ID NO: 144, SEQ ID NO: 159, SEQ ID NO: 169, SEQ ID NO: 199, SEQ ID NO: 209, SEQ ID NO: 219, SEQ ID NO: 229, SEQ ID NO: 239, SEQ ID NO: 249, SEQ ID NO: 278, SEQ ID NO: 293, SEQ ID NO: 303, SEQ ID NO: 313, SEQ ID NO: 323, SEQ ID NO: 333, SEQ ID NO: 343, SEQ ID NO: 353, SEQ ID NO: 357, SEQ ID NO: 375, SEQ ID NO: 385, SEQ ID NO: 395, SEQ ID NO: 400, SEQ ID NO: 410, SEQ ID NO: 420. The VL domain comprises CDR1 represented by the amino acid sequence set forth in SEQ ID NO: 41, SEQ ID NO: 51, SEQ ID NO: 61, SEQ ID NO: 71, SEQ ID NO: 81, SEQ ID NO: 91, SEQ ID NO: 101, SEQ ID NO: 111, SEQ ID NO: 121, SEQ ID NO: 136, SEQ ID NO: 146, SEQ ID NO: 152, SEQ ID NO: 161, SEQ ID NO: 171, SEQ ID NO: 177, SEQ ID NO: 182, SEQ ID NO: 187, SEQ ID NO: 192, SEQ ID NO: 201, SEQ ID NO: 211, SEQ ID NO: 221, SEQ ID NO: 231, SEQ ID NO: 241, SEQ ID NO: 251, SEQ ID NO: 280, SEQ ID NO: 286, SEQ ID NO: 295, SEQ ID NO: 305, SEQ ID NO: 315, SEQ ID NO: 325, SEQ ID NO: 335, SEQ ID NO: 345, SEQ ID NO: 354, SEQ ID NO: 377, SEQ ID NO: 387, SEQ ID NO: 402, SEQ ID NO: 412, or SEQ ID NO: 422, CDR2 represented by the amino acid sequence set forth in SEQ ID NO: 42, SEQ ID NO: 52, SEQ ID. NO: 62, SEQ ID NO: 72, SEQ ID NO: 82, SEQ ID NO: 92, SEQ ID NO: 102, SEQ ID NO: 112, SEQ ID NO: 122, SEQ ID NO: 137, SEQ ID NO: 147, SEQ ID NO: 153, SEQ ID NO: 162, SEQ ID NO: 172, SEQ ID NO: 178, SEQ ID NO: 183, SEQ ID NO: 188, SEQ ID NO: 193, SEQ ID NO: 202, SEQ ID NO: 212, SEQ ID NO: 222, SEQ ID NO: 232, SEQ ID NO: 242, SEQ ID NO: 252, SEQ ID NO: 281, SEQ ID NO: 287, SEQ ID NO: 296, SEQ ID NO: 306, SEQ ID NO: 316, SEQ ID NO: 326, SEQ ID NO: 336, SEQ ID NO: 346, SEQ ID NO: 355, SEQ ID NO: 378, SEQ ID NO: 388, SEQ ID NO: 403, SEQ ID NO: 413, or SEQ ID NO: 423, and CDR3 represented by the amino acid sequence set forth in SEQ ID NO: 43, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123, SEQ ID NO: 138, SEQ ID NO: 148, SEQ ID NO: 154, SEQ ID NO: 163, SEQ ID NO: 173, SEQ ID NO: 179, SEQ ID NO: 184, SEQ ID NO: 189, SEQ ID NO: 194, SEQ ID NO: 203, SEQ ID NO: 213, SEQ ID NO: 223, SEQ ID NO: 233, SEQ ID NO: 243, SEQ ID NO: 253, SEQ ID NO: 282, SEQ ID NO: 288, SEQ ID NO: 297, SEQ ID NO: 307, SEQ ID NO: 317, SEQ ID NO: 327, SEQ ID NO: 337, SEQ ID NO: 347, SEQ ID NO: 356, SEQ ID NO: 379, SEQ ID NO: 389, SEQ ID NO: 404, SEQ ID NO: 414, or SEQ ID NO: 424.

A chimeric antibody is produced by combining sequences derived from different animals and is, for example, an antibody consisting of the heavy and light chain variable domains of a mouse antibody and the heavy and light chain constant domains of a human antibody. The chimeric antibody can be produced by a known method, for example, by linking a DNA encoding an antibody V domain and a DNA encoding a human antibody C domain, incorporating it into an expression vector, and introducing the expression vector into a host.

Examples of the polyclonal antibody include antibodies prepared by immunizing a human antibody-producing animal (e.g., mouse) with a CAPRIN-1 protein.

The humanized antibody is an altered antibody also called reshaped human antibody. The humanized antibody is constructed by transplanting CDRs of an antibody derived from an immune animal into the complementarity determining region of a human antibody. A method by a general gene recombination technology is also known.

Specifically, a DNA sequence designed for linking the CDRs of a mouse antibody and the framework regions (FRs; including FR1 to FR4) of a human antibody in the order: FR1-CDR1-FR2-CDR2-FR3-CDR3-FR4, from the N-terminal side is synthesized by PCR from several oligonucleotides produced so as to have overlapping portions at the end regions. The resulting DNA is linked to a DNA encoding the constant domain of a human antibody and is incorporated into an expression vector, and the expression vector is introduced into a host to produce a humanized antibody (see EP Patent Application No. EP239400 and International Publication No. WO96/02576). The FRs of a human antibody linked via CDRs are selected such that the complementarity determining region forms a satisfactory antigen binding site. As needed, an amino acid in the framework region in the variable domain of the antibody may be substituted such that the complementarity determining region of the reshaped human antibody forms an appropriate antigen binding site (Sato K. et al., Cancer Research, 1993, 53: 851-856). The framework region may be substituted by a framework region derived from various human antibodies (see International Publication No. WO99/51743).

The resulting chimeric antibody or humanized antibody may be further subjected to, for example, substitution of an amino acid in the variable domain (e.g., FR) or constant domain by another amino acid.

In the amino acid substitution, for example, less than 15, less than 10, 8 or less, 7 or less, 6 or less, 5 or less, 4 or less, 3 or less, or 2 or less of amino acids, preferably one to five amino acids, and more preferably one or two amino acids are substituted. The substituted antibody should be functionally equivalent to the non-substituted antibody. The substitution is desirably conservative amino acid substitution, which is substitution between amino acids having similar properties such as charge, side chain, polarity, and aromaticity. The amino acids having similar properties can be classified into, for example, basic amino acids (arginine, lysine, and histidine), acidic amino acids (aspartic acid and glutamic acid), non-charged polar amino acids (glycine, asparagine, glutamine, serine, threonine, cysteine, and tyrosine), non-polar amino acids (leucine, isoleucine, alanine, valine, proline, phenylalanine, tryptophan, and methionine), branched chain amino acids (leucine, valine, and isoleucine), or aromatic amino acids (phenylalanine, tyrosine, tryptophan, and histidine).

Examples of modified antibodies include antibodies bound to various molecules such as polyethylene glycol (PEG). In the modified antibody used in the present invention, the antibody may be bound to any material. These modified antibodies can be prepared by chemically modifying a prepared antibody. The method for the modification has been already established in this field.

Here, the term "functionally equivalent" refers to that the objective antibody has biological or biochemical activity similar to that of an antibody used in the present invention, specifically, for example, that the objective antibody has a function of impairing tumor and does not substantially cause rejection reaction in application to a human being. Such activity is, for example, cell growth-inhibitory activity or avidity.

The method well known to those skilled in the art for preparing a polypeptide functionally equivalent to a certain polypeptide is a method of introducing a variation into the polypeptide. For example, a person skilled in the art can prepare an antibody functionally equivalent to an antibody used in the present invention by introducing an appropriate variation into the antibody through, for example, site-directed mutagenesis (Hashimoto-Gotoh, T. et al., (1995), Gene, 152, 271-275; Zoller, M. J., and Smith, M., (1983), Methods Enzymol., 100, 468-500; Kramer, W. et al., (1984), Nucleic Acids Res., 12, 9441-9456; Kramer, W. and Fritz, H. J., (1987), Methods Enzymol., 154, 350-367; Kunkel, T A., (1985), Proc. Natl. Acad. Sci. USA., 82, 488-492; Kunkel, (1988), Methods Enzymol., 85, 2763-2766).

An antibody recognizing the epitope of a CAPRIN-1 protein that is recognized by the anti-CAPRIN-1 antibody can be prepared by a method known to those skilled in the art. The antibody can be prepared by, for example, a method of producing an antibody by determining an epitope of the CAPRIN-1 protein recognized by an anti-CAPRIN-1 antibody through a usual method (e.g., epitope mapping) and using a polypeptide comprising the amino acid sequence of the epitope as the immunogen or a method of selecting an antibody having the same epitope as that of an anti-CAPRIN-1 antibody from antibodies having various epitopes produced by a usual method.

The antibody used in the present invention preferably has an affinity constant Ka ($k_{on}/k_{off}$) of $10^7$ $M^{-1}$ or more, $10^8$ $M^{-1}$ or more, $5\times10^8$ $M^{-1}$ or more, $10^9$ $M^{-1}$ or more, $5\times10^9$ $M^{-1}$ or more, $10^{10}$ $M^{-1}$ or more, $5\times10^{10}$ $M^{-1}$ or more, $10^{11}$ $M^{-1}$ or more, $5\times10^{12}$ $M^{-1}$ or more, or $10^{13}$ $M^{-1}$ or more.

The antibody used in the present invention can conjugate with an antitumor agent. The antibody and the antitumor agent can be bound to each other via a spacer having a reactive group, such as an amino group, a carboxyl group, a hydroxyl group, or a thiol group (for example, a succinic imidyl group, a formyl group, a 2-pyridyldithio group, a maleimidyl group, an alkoxycarbonyl group, or a hydroxy group).

Examples of the antitumor agent include the following antitumor agents publicly known through documents or other items, i.e., paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodonate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitemycin C, mycophenolic acid, nogalamycin, olivomycins, peplomycin, potfiromycin, puromycin, quelamycin, rodorubicin, streptonigrin, streptozoxin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifuridine, enocitabine, floxuridine, androgens such as calusterone, drostanolone propionate, epitiostanol, mepitiostane, and testolactone, aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elfornithine, elliptinium acetate, epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinodecan, topoisomerase inhibitors, difluoromethylolnitine (DMFO), retinoic acid, capecitabine, and pharmaceutically acceptable (known) salts or (known) derivatives thereof.

Whether or not a conjugate of an antibody and an antitumor agent shows antitumor activity can be evaluated by, for example, if the antibody is an anti-CAPRIN-1 antibody derived from a mouse, evaluating the antitumor effect on human cancer cells in vitro through simultaneous reaction of a conjugate of a secondary antibody that binds to a mouse antibody and a drug. For example, evaluation can be performed using an anti-human IgG antibody conjugated with saporin (Hum-ZAP (Advanced Targeting Systems, Inc.)).

In addition, combination administration of the antibody used in the present invention and an antitumor agent can provide a higher therapeutic effect. This method can be applied to a cancer patient expressing a CAPRIN-1 protein at either before or after surgery. In particular, after surgery, higher prevention of cancer recurrence and longer survival period can be obtained in a cancer expressing a CAPRIN-1 protein conventionally treated with an antitumor agent alone.

Examples of the antitumor agent used in the combination administration include the above-mentioned antitumor agents publicly known through documents or other items, and pharmaceutically acceptable (known) salts or (known) derivatives thereof. Among these agents, in particular, preferably used are cyclophosphamide, paclitaxel, docetaxel, vinorelbine, etc.

Alternatively, the antibody used in the present invention can be labeled with a radioisotope publicly known through documents or other items, such as $^{211}At$, $^{131}I$, $^{125}I$, $^{90}Y$, $^{186}Re$, $^{188}Re$, $^{153}Sm$, $^{212}Bi$, $^{32}P$, $^{175}Lu$, or $^{176}Lu$. The isotope is desirably one effective for therapy or diagnosis of tumor.

The antibody used in the present invention is an antibody having immunological reactivity with a CAPRIN-1 protein or specifically binding to a CAPRIN-1 protein and exhibiting cytotoxicity or tumor growth-inhibitory activity against gallbladder cancer. The antibody should have a structure that can almost or completely avoid rejection reaction in the objective animal to which the antibody is administered. Examples of such antibodies include, when the objective animal is a human being, human antibodies, humanized antibodies, chimeric antibodies (e.g., human-mouse chimeric antibodies), single-chain antibodies, and multispecific antibodies (e.g., diabodies and triabodies). Such an antibody is a recombinant antibody in which the variable domains of the heavy and light chains are derived from a human antibody, or in which the variable domains of the heavy and light chains consist of complementarity determining regions (CDR1, CDR2, and CDR3) derived from a non-human animal antibody and a framework region derived from a human antibody, or in which the variable domains of the heavy and light chains are derived from a non-human animal antibody and the constant domains of the heavy and light chains are derived from a human antibody. The former antibodies are preferred.

These recombinant antibodies can be produced as follows. A DNA encoding an anti-human CAPRIN-1 monoclonal antibody (e.g., human monoclonal antibody, mouse monoclonal antibody, rat monoclonal antibody, rabbit monoclonal antibody, or chicken monoclonal antibody) is cloned from antibody-producing cells such as hybridomas; a DNA encoding the light chain variable domain and the heavy chain variable domain of the antibody is produced using the resulting DNA as a template by, for example, RT-PCR; and the sequence of each variable domain of the light and heavy chains or the sequence of each of CDR1, CDR2, and CDR3 is determined based on the Kabat EU numbering system (Kabat, et al., Sequences of Proteins of Immunological Interest, 5th Ed., Public Health Service, National Institute of Health, Bethesda, Md. (1991)).

Furthermore, DNAs encoding the variable domains or DNAs encoding the CDRs are produced by gene recombination technology (Sambrook, et al., Molecular Cloning A Laboratory Manual, Cold Spring Harbor Laboratory Press, (1989)) or with a DNA synthesizer. Here, the human monoclonal antibody-producing hybridoma can be produced by immunizing a human antibody-producing animal (e.g., mouse) with a human CAPRIN-1 protein and then fusing the spleen cells excised from the immune animal with myeloma cells. Separately, as necessary, a DNA encoding the variable domain and the constant domain of a light or heavy chain derived from a human antibody is produced by gene recombination technology or with a DNA synthesizer.

In the case of a humanized antibody, the CDR-coding sequences in the DNAs encoding the variable domains of the light chain or the heavy chain derived from a human antibody are substituted with the corresponding CDR-coding sequences of an antibody derived from an animal (e.g., mouse, rat, or chicken) other than human beings to produce DNAs. The resulting DNAs are each linked to DNAs encoding the constant domains of the light chain or the heavy chain derived from a human antibody to produce a DNA encoding a humanized antibody.

In the case of a chimeric antibody, DNAs encoding the variable domains of the light chain or the heavy chain of an antibody derived from an animal (e.g., mouse, rat, or chicken) other than human beings are each linked to DNAs encoding the constant domains of the light chain or the heavy chain derived from a human antibody to produce a DNA encoding a chimeric antibody.

In the case of a single-chain antibody, the antibody is composed of a heavy chain variable domain and a light chain variable domain linearly linked to each other via a linker, and a DNA encoding the single-chain antibody can be produced by binding a DNA encoding the heavy chain variable domain, a DNA encoding the linker, and a DNA encoding the light chain variable domain Here, the heavy chain variable domain and the light chain variable domain are both derived from a human antibody or derived from a human antibody in which only the CDR is substituted with the CDR of an antibody derived from an animal (e.g., mouse, rat, chicken) other than human beings. The linker is composed of 12 to 19 amino acids, and examples thereof include $(G_4S)3$ of 15 amino acids (G.-B. Kim, et al., Protein Engineering Design and Selection, 2007, 20(9): 425-432).

In the case of a bispecific antibody (diabody), the antibody can specifically bind to two different epitopes, and a DNA encoding the bispecific antibody can be produced by, for example, binding a DNA encoding the heavy chain variable domain A, a DNA encoding the light chain variable domain B, a DNA encoding the heavy chain variable domain B, and a DNA encoding the light chain variable domain A in this order (provided that the DNA encoding the light chain variable domain B and the DNA encoding the heavy chain variable domain B are bound to each other via a DNA encoding a linker as described above). Here, the heavy chain variable domain and the light chain variable domain are both derived from a human antibody or derived from a human antibody in which only the CDR is substituted with the CDR of an antibody derived from an animal (e.g., mouse, rat, chicken) other than human beings.

A recombinant antibody can be produced by incorporating the thus-produced recombinant DNA into one or more appropriate vectors and introducing the vector or vectors into host cells (e.g., mammal cells, yeast cells, or insect cells) to (co)express the DNA (P. J. Delves., ANTIBODY PRODUCTION ESSENTIAL TECHNIQUES, 1997; WILEY, P. Shepherd, and C. Dean., Monoclonal Antibodies, 2000; OXFORD UNIVERSITY PRESS; J. W. Goding., Monoclonal Antibodies: principles and practice, 1993, ACADEMIC PRESS).

Examples of the antibodies of the present invention produced by the above-described methods include the following antibodies (a) to (ao).

(a) Antibodies each comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively, described in WO2011/096528, (for example, an antibody comprising a heavy chain variable domain set forth in SEQ ID NO: 40 and a light chain variable domain set forth in SEQ ID NO: 44).

Antibodies (b) each comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively, described in WO2011/096519, (for example, an antibody comprising a heavy chain variable domain set forth in SEQ ID NO: 50 and a light chain variable domain set forth in SEQ ID NO: 54).

(c) Antibodies each comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively, described in WO2011/096517, (for example, an antibody comprising a heavy chain variable domain set forth in SEQ ID NO: 60 and a light chain variable domain set forth in SEQ ID NO: 64).

(d) Antibodies each comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively, described in WO2011/096528, (for example, an antibody comprising a heavy chain variable domain set forth in SEQ ID NO: 70 and a light chain variable domain set forth in SEQ ID NO: 74).

(e) Antibodies each comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively, described in WO2011/096528, (for example, an antibody comprising a heavy chain variable domain set forth in SEQ ID NO: 80 and a light chain variable domain set forth in SEQ ID NO: 84).

(f) Antibodies each comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively, described in WO2011/096528, (for example, an antibody comprising a heavy chain variable domain set forth in SEQ ID NO: 90 and a light chain variable domain set forth in SEQ ID NO: 94).

(g) Antibodies each comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively, described in WO2011/096528, (for example, an antibody comprising a heavy chain variable domain set forth in SEQ ID NO: 100 and a light chain variable domain set forth in SEQ ID NO: 104).

(h) Antibodies each comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively, described in WO2011/096528, (for example, an antibody comprising a heavy chain variable domain set forth in SEQ ID NO: 110 and a light chain variable domain set forth in SEQ ID NO: 114).

(i) Antibodies each comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively, described in WO2011/096533, (for example, an antibody comprising a heavy chain variable domain set forth in SEQ ID NO: 120 and a light chain variable domain set forth in SEQ ID NO: 124).

(j) Antibodies each comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively, described in WO2011/096533, (for example, an antibody comprising a heavy chain variable domain set forth in SEQ ID NO: 130 and a light chain variable domain set forth in SEQ ID NO: 124).

(k) Antibodies each comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively, described in WO2011/096533, (for example, an antibody comprising a heavy chain variable domain set forth in SEQ ID NO: 135 and a light chain variable domain set forth in SEQ ID NO: 139).

(l) Antibodies each comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively, described in WO2011/096534, (for example, an antibody comprising a heavy chain variable domain set forth in SEQ ID NO: 145 and a light chain variable domain set forth in SEQ ID NO: 149).

(m) Antibodies each comprising a heavy chain variable domain comprising complementarity determining regions (CDR1, CDR2, and CDR3) consisting of amino acid sequences set forth in SEQ ID NOs: 142, 143; and 144, respectively and a light chain variable domain comprising complementarity determining regions (CDR1, CDR2, and CDR3) consisting of amino acid sequences set forth in SEQ ID NOs: 152, 153, and 154, respectively, described in WO2011/096534, (for example, an antibody comprising a heavy chain variable domain set forth in SEQ ID NO: 145 and a light chain variable domain set forth in SEQ ID NO: 155).

(n) Antibodies each comprising a heavy chain variable domain comprising CDRs of SEQ ID NOs: 157, 158, and 159 and a light chain variable domain comprising CDRs of SEQ ID NOs: 161, 162, and 163, described in WO2011/096534, (for example, an antibody comprising a heavy chain variable domain set forth in SEQ ID NO: 160 and a light chain variable domain set forth in SEQ ID NO: 164).

(o) Antibodies each comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively, described in WO2011/096534, (for example, an antibody comprising a heavy chain variable domain set forth in SEQ ID NO: 170 and a light chain variable domain set forth in SEQ ID NO: 174).

(p) Antibodies each comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively, described in WO2010/016526, (for example, an antibody comprising a heavy chain variable domain set forth in SEQ ID NO: 170 and a light chain variable domain set forth in SEQ ID NO: 180).

(q) Antibodies each comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively, described in WO2010/016526, (for example, an antibody comprising a heavy chain variable domain set forth in SEQ ID NO: 170 and a light chain variable domain set forth in SEQ ID NO: 185).

(r) Antibodies each comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively, described in WO2010/016526, (for example, an antibody comprising a heavy chain variable domain set forth in SEQ ID NO: 170 and a light chain variable domain set forth in SEQ ID NO: 190).

(s) Antibodies each comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively, described in WO2010/016526, (for example, an antibody comprising a heavy chain variable domain set forth in SEQ ID NO: 170 and a light chain variable domain set forth in SEQ ID NO: 195).

(t) Antibodies each comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively, described in WO2010/016526, (for example, an antibody comprising a heavy chain variable domain set forth in SEQ ID NO: 200 and a light chain variable domain set forth in SEQ ID NO: 204).

(u) Antibodies each comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively, described in WO2010/016526, (for example, an antibody comprising a heavy chain variable domain set forth in SEQ ID NO: 210 and a light chain variable domain set forth in SEQ ID NO: 214).

(v) Antibodies each comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively, described in WO2010/016526, (for example, an antibody comprising a heavy chain variable domain set forth in SEQ ID NO: 220 and a light chain variable domain set forth in SEQ ID NO: 224).

(w) Antibodies each comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively, described in WO2010/016526, (for example, an antibody comprising a heavy chain variable domain set forth in SEQ ID NO: 230 and a light chain variable domain set forth in SEQ ID NO: 234).

(x) Antibodies each comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively, described in WO2010/016526, (for example, an antibody comprising a heavy chain variable domain set forth in SEQ ID NO: 240 and a light chain variable domain set forth in SEQ ID NO: 244).

(y) Antibodies each comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively, described in WO2010/016526, (for example, an antibody comprising a heavy chain variable domain set forth in SEQ ID NO: 250 and a light chain variable domain set forth in SEQ ID NO: 254).

(z) Antibodies each comprising a heavy chain variable domain comprising complementarity determining regions (CDR1, CDR2, and CDR3) consisting of amino acid sequences set forth in SEQ ID NOs: 276, 277, and 278, respectively and complementarity determining regions (CDR1, CDR2, and CDR3) consisting of amino acid sequences set forth in SEQ ID NOs: 280, 281, and 282, respectively, described in WO2013/018894 (for example, an antibody comprising a heavy chain variable domain set forth in SEQ ID NO: 279 and a light chain variable domain set forth in SEQ ID NO: 283).

(aa) Antibodies each comprising a heavy chain variable domain comprising complementarity determining regions (CDR1, CDR2, and CDR3) consisting of amino acid sequences set forth in SEQ ID NOs: 276, 277, and 278, respectively and complementarity determining regions (CDR1, CDR2, and CDR3) consisting of amino acid sequences set forth in SEQ ID NOs: 286, 287, and 288, respectively, described in WO2013/018894 (for example, an antibody comprising a heavy chain variable domain set forth in SEQ ID NO: 279 and a light chain variable domain set forth in SEQ ID NO: 289).

(ab) Antibodies each comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively, described in WO2013/018894, (for example, an antibody comprising a heavy chain variable domain set forth in SEQ ID NO: 294 and a light chain variable domain set forth in SEQ ID NO: 298).

(ac) Antibodies each comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively, described in WO2013/018892, (for example, an antibody comprising a heavy chain variable domain set forth in SEQ ID NO: 304 and a light chain variable domain set forth in SEQ ID NO: 308).

(ad) Antibodies each comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively, described in WO2013/018891, (for example, an antibody comprising a heavy chain variable domain set forth in SEQ ID NO: 314 and a light chain variable domain set forth in SEQ ID NO: 318).

(ae) Antibodies each comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively, described in WO2013/018889, (for example, an antibody comprising a heavy chain variable domain set forth in SEQ ID NO: 324 and a light chain variable domain set forth in SEQ ID NO: 328).

(af) Antibodies each comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively, described in WO2013/018883, (for example, an antibody comprising a heavy chain variable domain set forth in SEQ ID NO: 334 and a light chain variable domain set forth in SEQ ID NO: 338).

(ag) Antibodies each comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively, or fragments of the antibodies (for example, an antibody comprising a heavy chain variable domain set forth in SEQ ID NO: 344 and a light chain variable domain set forth in SEQ ID NO: 348).

(ah) Antibodies each comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively, or fragments of the antibodies (for example, an antibody comprising a heavy chain variable domain set forth in SEQ ID NO: 359 and a light chain variable domain set forth in SEQ ID NO: 361, an antibody comprising a heavy chain variable domain set forth in SEQ ID NO: 368 and a light chain variable domain set forth in SEQ ID NO: 370, and an antibody comprising a heavy chain variable domain set forth in SEQ ID NO: 372 and a light chain variable domain set forth in SEQ ID NO: 370).

(ai) Antibodies each comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively, or fragments of the antibodies (for example, an antibody comprising a heavy chain variable domain set forth in SEQ ID NO: 363 and a light chain variable domain set forth in SEQ ID NO: 365).

(aj) Antibodies each comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively, or fragments of the antibodies (for example, an antibody comprising a heavy chain variable domain set forth in SEQ ID NO: 376 and a light chain variable domain set forth in SEQ ID NO: 380).

(ak) Antibodies each comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively, or fragments of the antibodies (for example, an antibody comprising a heavy chain variable domain set forth in SEQ ID NO: 386 and a light chain variable domain set forth in SEQ ID NO: 390).

(al) Antibodies each comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively, or fragments of the antibodies (for example, an antibody comprising a heavy chain variable domain set forth in SEQ ID NO: 396 and a light chain variable domain set forth in SEQ ID NO: 390).

(am) Antibodies each comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively, or fragments of the antibodies (for example, an antibody comprising a heavy chain variable domain set forth in SEQ ID NO: 401 and a light chain variable domain set forth in SEQ ID NO: 405).

(an) Antibodies each comprising a heavy chain variable domain comprising complementarity determining regions (CDR1, CDR2, and CDR3) set forth in SEQ ID NOs: 408, 409, and 410, respectively and a light chain variable domain comprising complementarity determining regions (CDR1, CDR2, and CDR3) set forth in SEQ ID NOs: 412, 413, and 414, respectively, or fragments of the antibodies (for example, an antibody comprising a heavy chain variable domain set forth in SEQ ID NO: 411 and a light chain variable domain set forth in SEQ ID NO: 415).

(ao) Antibodies each comprising a heavy chain variable domain comprising complementarity determining regions (CDR1, CDR2, and CDR3) set forth in SEQ ID NOs: 418, 419, and 420, respectively and a light chain variable domain comprising complementarity determining regions (CDR1, CDR2, and CDR3) set forth in SEQ ID NOs: 422, 423, and 424, respectively, or fragments of the antibodies (for example, an antibody comprising a heavy chain variable domain set forth in SEQ ID NO: 421 and a light chain variable domain set forth in SEQ ID NO: 425).

Here, the amino acid sequences set forth in SEQ ID NOs: 67, 68, and 69 are CDR1, CDR2, and CDR3, respectively of the heavy chain variable domain of a mouse antibody, similarly, sets of amino acid sequences set forth in SEQ ID NOs: 77, 78, and 79, SEQ ID NO: 87, 88, and 89, SEQ ID NO: 97, 98, and 99, SEQ ID NO: 107, 108, and 109, SEQ ID NO: 117, 118, and 119, SEQ ID NO: 127, 128, and 129, SEQ ID NO: 132, 133, and 134, SEQ ID NO: 142, 143, and 144, SEQ ID NO: 157, 158, and 159, SEQ ID NO: 167, 168, and 169, SEQ ID NO: 197, 198, and 199, SEQ ID NO: 207, 208, and 209, SEQ ID NO: 217, 218, and 219, SEQ ID NO: 227, 228, and 229, SEQ ID NO: 237, 238, and 239, SEQ ID NOs: 247, 248, and 249, SEQ ID NOs: 276, 277, and 278; 291, 292, and 293; 301, 302, and 303; 311, 312, and 313; 321, 322, and 323; 331, 332, and 333; 341, 342, and 343; 373, 374, and 375; 383, 384, and 385; 393, 394, and 395; 398, 399, and 400; 408, 409, and 410; and 418, 419, and 420 are each a set of CDR1, CDR2, and CDR3 of the heavy chain variable domain of a mouse antibody. Similarly, sets of amino acid sequences set forth in SEQ ID NO: 71, 72, and 73, SEQ ID NO: 81, 82, and 83, SEQ ID NO: 91, 92, and 93, SEQ ID NO: 101, 102, and 103, SEQ ID NO: 111, 112, and 113, SEQ ID NO: 121, 122, and 123, SEQ ID NO: 136, 137, and 138, SEQ ID NO: 146, 147, and 148, SEQ ID NO: 152, 153, and 154, SEQ ID NO: 161, 162, and 163, SEQ ID. NO: 171, 172, and 173, SEQ ID NO: 177, 178, and 179, SEQ ID NO: 182, 183, and 184, SEQ ID NO: 187, 188, and 189, SEQ ID NO: 192, 193, and 194, SEQ ID NO: 201, 202, and 203, SEQ ID NO: 211, 212, and 213, SEQ ID NO: 221, 222, and 223, SEQ ID NO: 231, 232, and 233, SEQ ID NO: 241, 242, and 243, SEQ ID NO: 251, 252, and 253, SEQ ID NO: 280, 281, and 282, SEQ ID NO: 286, 287, and 288, SEQ ID NO: 295, 296, and 297, SEQ ID NO: 305, 306, and 307, SEQ ID NO: 315, 316, and 317, SEQ ID NO: 325, 326, and 327, SEQ ID NO: 335, 336, and 337, SEQ ID NO: 345, 346, and 347, SEQ ID NO: 377, 378, and 379, SEQ ID NO: 387, 388, and 389, SEQ ID NO: 402, 403, and 404, SEQ ID NO: 412, 413, and 414, SEQ ID NO: 422, 423, and 424 are each a set of CDR1, CDR2, and CDR3 of the light chain variable domain of a mouse antibody.

Similarly, the amino acid sequences set forth in SEQ ID NOs: 37, 38, and 39, SEQ ID NOs: 47, 48, and 49, or SEQ ID NOs: 57, 58, and 59 are each CDR1, CDR2, and CDR3, respectively of the heavy chain variable domain of a chicken antibody; and the amino acid sequences set forth in SEQ ID NOs: 41, 42, and 43, SEQ ID NOs: 51, 52, and 53, or SEQ ID NOs: 61, 62, and 63 are each CDR1, CDR2, and CDR3, respectively of the light chain variable domain of a chicken antibody.

Similarly, the amino acid sequences set forth in SEQ ID NOs: 351, 352, and 353 are CDR1, CDR2, and CDR3, respectively of the heavy chain variable domain of a rabbit antibody; and the amino acid sequences set forth in SEQ ID NOs: 354, 355, and 356 are CDR1, CDR2, and CDR3, respectively of the light chain variable domain of a rabbit antibody.

Examples of the humanized antibody, chimeric antibody, single-chain antibody, and multispecific antibody used in the present invention include the following antibodies (those exemplified as antibodies (ah)).

(i) Antibodies each comprising a heavy chain variable domain comprising the amino acid sequences set forth in SEQ ID NOs: 351, 352, and 353 and the amino acid sequence of the framework region derived from a human antibody; and a light chain variable domain comprising the amino acid sequences set forth in SEQ ID NOs: 354, 355, and 356 and the amino acid sequence of the framework region derived from a human antibody.

(ii) Antibodies each comprising a heavy chain variable domain comprising the amino acid sequences set forth in SEQ ID NOs: 351, 352, and 353 and the amino acid sequence of the framework region derived from a human antibody; a heavy chain constant domain comprising the amino acid sequence derived from a human antibody; a light chain variable domain comprising the amino acid sequences set forth in SEQ ID NOs: 354, 355, and 356 and the amino acid sequence of the framework region derived from a human antibody; and a light chain constant domain comprising the amino acid sequence derived from a human antibody.

(iii) Antibodies each comprising a heavy chain variable domain comprising the amino acid sequence set forth in SEQ ID NO: 368, a heavy chain constant domain comprising the amino acid sequence derived from a human antibody, a light chain variable domain comprising the amino acid sequences set forth in SEQ ID NO: 370, and a light chain constant domain comprising the amino acid sequence derived from a human antibody.

The sequences of the constant domains and the variable domains of human antibody heavy and light chains are available from, for example, NCBI (e.g., GenBank or UniGene, USA). For example, the sequence of the human $IgG_1$ heavy chain constant domain can be referred to as Registration No. J00228, the sequence of the human $IgG_2$ heavy chain constant domain can be referred to as Registration No. J00230, the sequence of the human $IgG_3$ heavy chain constant domain can be referred to as Registration No. X03604, the sequence of the human $IgG_4$ heavy chain constant domain can be referred to as Registration No. K01316, the sequence of the human light chain κ constant domain can be referred to as, for example, Registration No. V00557, X64135, or X64133, and the sequence of the human light chain λ constant domain can be referred to as, for example, Registration No. X64132 or X64134.

Examples of the humanized antibodies exemplified as the antibodies (ah) include the antibodies (ai), antibodies comprising the heavy chain variable domain set forth in SEQ ID NO: 368 and the light chain variable domain set forth in SEQ ID NO: 370, and antibodies comprising the heavy chain variable domain set forth in SEQ ID NO: 372 and the light chain variable domain set forth in SEQ ID NO: 370.

These antibodies preferably have cytotoxicity and can thereby show antitumor effects.

It is obvious that the specific sequences of the variable domains and CDRs of heavy chains and light chains of the above-mentioned antibodies are intended to merely show examples and are not limited to specific sequences. A hybridoma producing another human antibody or a non-human animal antibody (e.g., mouse antibody) against a human CAPRIN-1 protein is produced, and the monoclonal antibody produced by the hybridoma is collected and is determined whether or not the antibody is a target antibody using the immunological affinity to the human CAPRIN-1 protein and cytotoxicity as indices. After the identification of the hybridoma producing a target monoclonal antibody, the DNA encoding the variable domains of the heavy and light chains of the target antibody is produced from the hybridoma as described above, and the DNA is sequenced. The DNA is used for producing another antibody.

Furthermore, the antibody used in the present invention may have substitution, deletion, or addition of one to several (preferably one or two) amino acids of each of the antibodies (i) to (iv), in particular, in the sequence of the framework region and/or the sequence constant domain, as long as the specificity, i.e., the specific recognition of the CAPRIN-1 protein, is maintained. Herein, the term "several" refers to two to five, preferably two or three.

The antitumor effect by the anti-CAPRIN-1 antibody used in the present invention on gallbladder cancer cells expressing CAPRIN-1 protein is believed to be caused by the following mechanism.

The mechanism involves the effector-cell antibody-dependent cellular cytotoxicity (ADCC) of CAPRIN-1-protein-expressing cells and complement-dependent cellular cytotoxicity (CDC) of CAPRIN-1-protein-expressing cells.

Accordingly, the activity of the anti-CAPRIN-1 antibody used in the present invention can be evaluated by measuring the ADCC activity or CDC activity on gallbladder cancer cells expressing the CAPRIN-1 protein in vitro, as specifically shown in the following examples.

The anti-CAPRIN-1 antibody used in the present invention binds to CAPRIN-1 protein on gallbladder cancer cells and shows antitumor action by the above-mentioned activity, and it is therefore believed that the antibody is useful for therapy or prevention of gallbladder cancer. That is, the present invention provides a pharmaceutical composition, of which the active ingredient is the anti-CAPRIN-1 antibody, for treating and/or preventing gallbladder cancer. In the case of administering the anti-CAPRIN-1 antibody to a human being (antibody therapy), the antibody is preferably human antibody or a humanized antibody for reducing immunogenicity.

A higher binding affinity of the anti-CAPRIN-1 antibody to the CAPRIN-1 protein on gallbladder cancer cell surface provides stronger antitumor activity by the anti-CAPRIN-1 antibody. Accordingly, an anti-CAPRIN-1 antibody having high binding affinity to a CAPRIN-1 protein is expected to show a stronger antitumor effect and can be applied to a pharmaceutical composition for treating and/or preventing gallbladder cancer. As the high binding affinity, as described above, the binding constant (affinity constant) Ka ($k_{on}/k_{off}$) is preferably $10^7$ $M^{-1}$ or more, $10^8$ $M^{-1}$ or more, $5\times10^8$ $M^{-1}$ or more, $10^9$ $M^{-1}$ or more, $5\times10^9$ $M^{-1}$ or more, $10^{10}$ $M^{-1}$ or more, $5\times10^{10}$ $M^{-1}$, or more, $10^{11}$ $M^{-1}$ or more, $5\times10^{11}$ $M^{-1}$ or more, $10^{12}$ $M^{-1}$ or more, or $10^{13}$ $M^{-1}$ or more.

<Binding to Antigen-Expressing Cell>

The ability of an antibody to bind to a CAPRIN-1 protein can be specified through binding assay by, for example, ELISA, Western blotting, immunofluorescence, or flow cytometry, as described in Examples.

<Immunohistochemical Staining>

The antibody recognizing a CAPRIN-1 protein can be tested for reactivity with the CAPRIN-1 protein by an immunohistochemical method well known to those skilled in the art using paraformaldehyde or acetone fixed frozen sections or paraformaldehyde fixed paraffin-embedded tissue sections from tissue derived from a patient during surgery or tissue derived from an animal carrying heterotransplant inoculated with a cell line expressing a CAPRIN-1 protein naturally or after transfection.

An antibody reactive with a CAPRIN-1 protein can be stained by various methods for immunohistochemical staining. For example, the antibody can be visualized by reacting a horseradish peroxidase-conjugated goat anti-mouse or anti-rabbit antibody.

<Pharmaceutical Composition>

The target of the pharmaceutical composition for treating and/or preventing gallbladder cancer of the present invention may be any gallbladder cancer (cells) expressing a CAPRIN-1 gene.

The terms "tumor" and "cancer" used throughout the present specification refer to a malignant neoplasm and are used interchangeably.

The gallbladder cancer as a target in the present invention expresses a gene encoding an amino acid sequence set forth in any of even sequence numbers from SEQ ID NOs: 2 to 30, an amino acid sequence having a sequence identity of 80% or more, preferably 90% or more, more preferably 95% or more, and most preferably 97% or more to the amino acid sequence, or a partial sequence comprising at least seven, preferably at least eight consecutive amino acid residues of any of these amino acid sequences. Examples of the gallbladder cancer include, but not limited to, carcinoma arising in gallbladder (primary cancer) and metastatic cancer.

The objective animal is mammals such as a primate, a pet animal, a domestic animal, and an animal for competitive use, and is preferably a human being, a dog, or a cat.

The pharmaceutical composition of the antibody used in the present invention can be readily formulated by a method known to those skilled in the art. The pharmaceutical composition can be used, for example, parenterally in a form of an aseptic solution with water or another pharmaceutically acceptable liquid or an injection of a suspension preparation. For example, it is proposed to formulate by appropriately combining the pharmaceutical composition with a pharmacologically acceptable carrier or medium, specifically, sterilized water, physiological saline, vegetable oil, an emulsifier, a suspending agent, a surfactant, a stabilizer, a flavoring agent, an excipient, a vehicle, an antiseptic, or a binder, and mixing them at a unit dosage form desired in enforcement of generally recognized drug manufacture. The amount of the active ingredient in such a drug is controlled so as to provide an appropriate dose within an indicated range.

The aseptic composition for injection can be prescribed in accordance with the enforcement of usual pharmaceutical preparation using a vehicle such as distilled water for injection.

Examples of aqueous solutions for injection include physiological saline and isotonic solutions containing glucose or other adjuvants, such as D-sorbitol, D-mannose, D-mannitol, or sodium chloride. The aqueous solution may be used together with an appropriate solubilizer, for example, alcohol, specifically, ethanol or polyalcohol; propylene glycol, polyethylene glycol, or a nonionic detergent; or polysorbate 80™ or HCO-60.

Examples of oily liquids include sesame oil and soybean oil, and the oily liquid may be used together with benzyl benzoate or benzyl alcohol as a solubilizer. In addition, a buffer such as a phosphate buffer or a sodium acetate buffer, a soothing agent such as procaine hydrochloride, a stabilizer such as benzyl alcohol or phenol, or an antioxidant may be blended. The prepared injection is usually packed in an appropriate ampoule.

The administration is oral or parenteral and is preferably parenteral, and examples thereof include injection, transnasal, pulmonary, and transdermal dosage forms. In the injection dosage form, for example, systemic or local administration can be performed by intravenous, intramuscular, intraperitoneal, or subcutaneous injection.

The administration method can be appropriately selected based on the age, weight, sex, symptoms, etc. of a patient. The dose of the pharmaceutical composition containing an antibody or a polynucleotide encoding the antibody can be selected, for example, within a range of 0.0001 to 1000 mg/kg body weight per once or, for example, within a range of 0.001 to 100000 mg/body per patient. These numerical values are not necessarily restrictive. The dose and administration method vary depending on the weight, age, sex, symptoms, etc. of a patient, but can be appropriately selected by those skilled in the art.

Gallbladder cancer can be treated and/or prevented by administering the pharmaceutical composition of the present invention to a subject.

The present invention further encompasses a method of treating and/or preventing gallbladder cancer comprising administering the pharmaceutical composition of the present invention together with an antitumor agent as exemplified above or a pharmaceutical composition containing such an antitumor agent to a subject. The antibody or a fragment thereof of the present invention and the antitumor agent can be simultaneously or separately administered to a subject. In the case of separate administration, either pharmaceutical composition may be administered earlier or later, and the administration interval, doses, administration routes, and the frequency of administration thereof can be appropriately selected by a medical specialist. Examples of the other medicinal dosage form to be simultaneously administered also include pharmaceutical compositions prepared by mixing the antibody or a fragment thereof of the present invention and an antitumor agent in a pharmacologically acceptable carrier (or medium) and formulating the mixture. The description for the prescription, formulation, administration route, dose, cancer, etc. relating to the pharmaceutical composition containing the antibody of the present invention and the dosage form can be applied to any of the pharmaceutical compositions containing antitumor agents and the dosage forms. Therefore, the present invention also provides a combination pharmaceutical agent (also referred to as "pharmaceutical kit") for treatment and/or prevention of gallbladder cancer, comprising the pharmaceutical composition of the present invention and a pharmaceutical composition containing an antitumor agent as exemplified above.

The present invention also provides a pharmaceutical composition for treating and/or preventing gallbladder cancer, comprising the antibody or a fragment thereof of the present invention and an antitumor agent together with a pharmacologically acceptable carrier.

Alternatively, the antitumor agent may be conjugated with the antibody or a fragment thereof of the present invention. The conjugate can be mixed with a pharmacologically acceptable carrier (or medium) and formulated into a pharmaceutical composition as in above.

EXAMPLES

The present invention will now be more specifically described based on examples, but the scope of the present invention is not limited by these examples.

Example 1

Identification of Cancer Antigen Protein by SEREX Method (1) Preparation of cDNA Library Total RNA was extracted from the testis tissue of a healthy dog by an acid guanidium-phenol-chloroform method, and poly(A) RNA was purified using Oligotex-dT30 mRNA purification Kit (manufactured by Takara Shuzo Co., Ltd.) in accordance with the protocol attached to the kit.

A cDNA phage library derived from dog testis was synthesized using the obtained mRNA (5 μg). The cDNA phage library was prepared using cDNA Synthesis Kit, ZAP-cDNA Synthesis Kit, and ZAP-cDNA Gigapack III Gold Cloning Kit (manufactured by Stratagene Corporation) in accordance with the protocols attached to the kits. The size of the produced cDNA phage library was $7.73\times10^5$ pfu/mL.

(2) Screening of cDNA Library with Serum

The cDNA phage library derived from dog testis was used for immunoscreening. Specifically, host *E. coli* (XL1-Blue MRF) cells were infected with the library such that 2210 clones were formed on a Φ90×15 mm NZY agarose plate. Then, the host *E. coli* cells were cultured at 42° C. for 3 to 4 hours to produce plaques. The plate was covered with a nitrocellulose membrane (Hybond C Extra: manufactured by GE Healthcare Bio-Sciences), impregnated with isopropyl-β-D-thiogalactoside (IPTG), at 37° C. for 4 hours to introduce and express proteins, and the proteins were transferred to the membrane. Subsequently, the membrane was collected and immersed in TBS (10 mM Tris-HCl, 150 mM NaCl, pH 7.5) containing 0.5% skimmed milk and was shaken overnight at 4° C. to prevent non-specific reaction. This filter was reacted with 500-fold diluted ill dog serum at room temperature for 2 to 3 hours.

The ill dog serum collected from breast cancer dogs was used. The serum was stored at −80° C. and was pretreated immediately before the use. The pretreatment of the serum was performed as follows: host *E. coli* (XL1-Blure MRF) cells were infected with λZAP Express phage into which no foreign genes were inserted and were cultured on NZY plate medium at 37° C. overnight. Subsequently, a 0.2 M $NaHCO_3$ buffer, pH 8.3, containing 0.5 M NaCl was added to the plate, followed by being left to stand at 4° C. for 15 hours. Then, the supernatant was collected as an *E. coli*/phage extract. Subsequently, the collected *E. coli*/phage extract was allowed to pass through NHS-column (manufactured by GE Healthcare Bio-Sciences) to immobilize the proteins derived from the *E. coli* and the phage. Serum from the ill dogs was allowed to pass through the protein-immobilized column for removing, from the serum, antibodies adsorbing to *E. coli* or the phage. The serum fraction passed through the column was 500-fold diluted with TBS containing 0.5% skimmed milk to provide an immunoscreening material.

The membrane blotted with the thus-treated serum and the fusion protein was washed with TBS-T (0.05% Tween 20/TBS) four times and was then subjected to reaction with a secondary antibody, goat anti-dog IgG diluted by 5000-fold with TBS containing 0.5% skimmed milk (Goat anti Dog IgG-h+I HRP conjugated: manufactured by BETHYL Laboratories, Inc.), at room temperature for 1 hour. Detection by enzymatic color reaction using a NBT/BCIP reaction solution (manufactured by Roche Diagnostics K.K.) was performed, and colonies corresponding to the color reaction positive positions on the Φ90×15 mm NZY agarose plate were collected and were each dissolved in 500 μL of an SM buffer (100 mM NaCl, 10 mM $MgClSO_4$, 50 mM Tris-HCl, 0.01% gelatin, pH 7.5). Second, third, or more screenings were performed by the same procedure as above until the color reaction positive colony was unified. As a result, five positive clones were isolated by screening of 30940 phage clones that react with IgG in serum.

(3) Homology Search of Isolated Antigen Gene

In order to use the five positive clones isolated by the above-described method for nucleotide sequence analysis, the phage vector was converted to a plasmid vector. Specifically, 200 μL of a solution of host *E. coli* (XL1-Blue MRF) adjusted to an absorbance OD600 of 1.0 was mixed with 250 μL of purified phage solution and 1 μL of ExAssist helper phage (manufactured by Stratagene Corporation). After reaction at 37° C. for 15 minutes, 3 mL of an LB medium was added to the mixture, followed by culturing at 37° C. for 2.5 to 3 hours. Immediately after the culturing, the culture medium was warmed in a water bath of 70° C. for 20 minutes, followed by centrifugation at 4° C., 1000×g, for 15 minutes. The supernatant was collected as a phagemid solution. Subsequently, 200 μL of a solution of phagemid host *E. coli* (SOLR) adjusted to an absorbance OD600 of 1.0 was mixed with 10 μL of a purified phage solution. After reaction at 37° C. for 15 minutes, 50 μL of the reaction mixture was seeded on an LB agar medium containing ampicillin (final concentration: 50 μg/mL), followed by culturing at 37° C. overnight. Single colonies of transformed SOLR were collected and were cultured in an LB medium containing ampicillin (final concentration: 50 μg/mL) at 37° C., and a plasmid DNA having an intended insertion was purified with QIAGEN plasmid Miniprep Kit (manufactured by Qiagen).

The purified plasmid was subjected to analysis of the full-length insert sequence by a primer walking method using the T3 primer set forth in SEQ ID NO: 31 and the T7 primer set forth in SEQ ID NO: 32. As a result of this sequence analysis, gene sequences set forth in SEQ ID NOs: 5, 7, 9, 11, and 13 were obtained. Homology search of the nucleotide sequences and the amino acid sequences (SEQ ID NOs: 6, 8, 10, 12, and 14) of the genes for known genes using a homology search program, BLAST search (www.ncbi.nlm.nih.gov/BLAST/) revealed that all of the resulting five genes each encode a CAPRIN-1 protein. The sequence identity among the five genes was 100% in nucleotide sequence, in the region to be translated into a protein, and 99% in amino acid sequence. The sequence identity of the genes with a gene encoding a human homologous factor was 94% in nucleotide sequence, in the region to be translated into a protein, and 98% in amino acid sequence. The nucleotide sequences of the human homologous factor are set forth in SEQ ID NOs: 1 and 3, and the amino acid sequences are set forth in SEQ ID NOs: 2 and 4. The sequence identity of the obtained dog genes with a gene encoding a bovine homologous factor was 94% in nucleotide sequence, in the region to be translated into a protein, and 97% in amino acid sequence. The nucleotide sequence of the bovine homologous factor is set forth in SEQ ID NO: 15, and the amino acid sequence is set forth in SEQ ID NO: 16. The sequence identity between the gene encoding the human homologous factor and the gene encoding the bovine homologous factor was 94% in nucleotide sequence, in the region to be translated into a protein, and 93% to 97% in amino acid sequence. The sequence identity of the obtained dog genes with a gene encoding a horse homologous factor was 93% in nucleotide sequence, in the region to be translated into a protein, and 97% in amino acid sequence. The nucleotide sequence of the horse homologous factor is set forth in SEQ ID NO: 17, and the amino acid sequence is set forth in SEQ ID NO: 18. The sequence identity between the gene encoding the human homologous factor and the gene encoding the horse homologous factor was 93% in nucleotide sequence, in the region to be translated into a protein, and 96% in amino acid sequence. The sequence identity of the obtained dog genes with a gene encoding a mouse homologous factor was 87% to 89% in nucleotide sequence, in the region to be translated into a protein, and 95% to 97% in amino acid sequence. The nucleotide sequences of the mouse homologous factor are set forth in SEQ ID NOs: 19, 21, 23, 25, and 27, and the amino acid sequences are set forth in SEQ ID NOs: 20, 22, 24, 26, and 28. The sequence identity between the gene encoding the human homologous factor and the gene encoding the mouse homologous factor was 89% to 91% in nucleotide sequence, in the region to be translated into a protein, and 95% to 96% in amino acid sequence. The sequence identity of the obtained dog genes with a gene encoding a chicken homologous factor was 82% in nucleotide sequence, in the region to be translated into a protein, and 87% in amino acid sequence. The nucleotide sequence of the chicken homologous factor is set forth in SEQ ID NO: 29, and the amino acid sequence is set forth in SEQ ID NO: 30. The sequence identity between the gene encoding the human homologous factor and the gene encoding the chicken homologous factor was 81% to 82% in nucleotide sequence, in the region to be translated into a protein, and 86% in amino acid sequence.

(4) CAPRIN-1 Gene Expression Analysis with Human Gallbladder Cancer Cells

The genes obtained by the above-described method were investigated for expression in a cell line of human gallbladder cancer TGBC14TKB (obtained from The Institute of Physical and Chemical Research) by RT-PCR. Reverse transcription was performed as follows: Total RNA was extracted from 50 to 100 mg of each tissue and 5 to $10\times10^6$ cells of each cell line with TRIZOL reagent (manufactured by invitrogen) in accordance with the protocol attached to the reagent. Using this total RNA, cDNA was synthesized with Superscript First-Strand Synthesis System for RT-PCR (manufactured by invitrogen) in accordance with the protocol attached to the system. The PCR was performed using primers (set forth in SEQ ID NOs: 33 and 34) specific to the resulting gene as follows: The total volume of a mixture containing 0.25 μL of the sample prepared by the reverse transcription, 2 μM of each of the primers, 0.2 mM of each dNTP, and 0.65 U of ExTaq polymerase (manufactured by Takara Shuzo Co., Ltd.) was adjusted to 25 μL with the buffer attached to the reagent, and a process consisting of reactions at 94° C. for 30 seconds, at 60° C. for 30 seconds, and at 72° C. for 30 seconds was repeated 30 cycles with Thermal Cycler (manufactured by BIO-RAD Laboratories, Inc.). The gene-specific primers amplified the region of 698 to 1124 nucleotides of the nucleotide sequence (human CAPRIN-1 gene) set forth in SEQ ID NO: 1. For comparison, GAPDH-specific primers (set forth in SEQ ID NOs: 35 and 36) were simultaneously used. As a result, expression was observed in the cell line TGBC14TKB.

Example 2

Production of Anti-Human CAPRIN-1 Polyclonal Antibody

A mixture of 1 mg of a human CAPRIN-1 recombinant protein produced in accordance with example 3 of WO2010/016526 and an equivalent volume of an incomplete Freund's adjuvant (IFA) solution was subcutaneously injected to a rabbit four times with 2 weeks intervals. The blood was then collected to obtain antiserum containing a polyclonal antibody. The antiserum was further purified using a protein G carrier (manufactured by GE Healthcare Bioscience) to obtain an anti-CAPRIN-1 polyclonal antibody. Serum of a rabbit not administered with the antigen was similarly purified with a protein G carrier and was used as a control antibody.

Example 3

Expression Analysis of CAPRIN-1 Protein in Human Gallbladder Cancer (1) Expression Analysis of CAPRIN-1 Protein on Human Gallbladder Cancer Cells A human gallbladder cancer cell line TGBC14TKB, which was confirmed to express the CAPRIN-1 gene, was investigated for whether or not a CAPRIN-1 protein is expressed on the cell surface. $1\times10^6$ cells of TGBC14TKB of which gene expression was confirmed in above were centrifuged with a 1.5-mL micro centrifugation tube. To the cells was added 2 μg (5 μL) of the anti-CAPRIN-1 polyclonal antibody prepared in Example 2. The mixture was suspended in 95 μL of PBS containing 0.1% fetal bovine serum, and the suspension was left to stand on ice for 1 hour. After washing with PBS, the cells were suspended in 5 μL of a FITC-labeled goat anti-rabbit IgG antibody (manufactured by Santa Cruz Biotechnology, Inc.) and 95 μL of PBS containing 0.1% fetal bovine serum (FBS), and the suspension was left to stand on ice for 1 hour. After washing with PBS, the fluorescence intensity was measured with FACS Calibur available from Becton, Dickinson and Company. Separately, as a control, the same procedure as in above was performed using the control antibody prepared in Example 2, instead of the anti-CAPRIN-1 polyclonal antibody. As a result, the fluorescence intensity in TGBC14TKB to which the anti-human CAPRIN-1 polyclonal antibody was added was 20% or more higher than that in the control in every case. This demonstrates that the CAPRIN-1 protein was expressed on the cell surface of the human gallbladder cancer cell line. The rate of increase in the fluorescence intensity is represented by the rate of increase in the mean fluorescence intensity (MFI value) in each cell and is calculated by the following calculation formula:

Rate of increase in mean fluorescence intensity(rate of increase in fluorescence intensity)(%)=((MFI value of cells reacted with anti-human CAPRIN-1 antibody)−(MFI value of control))/(MFI value of control)×100.

(2) Expression Analysis of CAPRIN-1 Protein in Human Gallbladder Cancer Tissue

Twenty-six gallbladder cancer tissue samples of a paraffin embedded human gallbladder cancer tissue array (manufactured by BIOMAX, Inc.) were subjected to immunohistochemical staining. The human gallbladder cancer tissue array was treated at 60° C. for 3 hours and was then put in a staining bottle filled with xylene. The xylene in the bottle was replaced by fresh one three times at every 5 minutes. Subsequently, the same procedure was performed using ethanol and PBS-T instead of xylene. The human gallbladder cancer tissue array was put in a staining bottle filled with a 10 mM citric acid buffer (pH 6.0) containing 0.05% Tween 20 and was treated at 125° C. for 5 minutes, followed by being left to stand at room temperature for 40 minutes or more. Excess water around the section was wiped away with a Kimwipe, the section was encircled with Dako pen, and an appropriate amount of Peroxidase Block (manufactured by DAKO) was dropwise added thereto. After being left to stand at room temperature for 5 minutes, the section was put in a staining bottle filled with PBS-T, and PBS-T was replaced by fresh one three times at every 5 minutes. As a blocking solution, a PBS-T solution containing 10% FBS was placed onto the section, followed by being left to stand in a moisture chamber at room temperature for 1 hour. A solution in which the concentration of the anti-CAPRIN-1 polyclonal antibody prepared in Example 2 was adjusted to 10 μg/mL with a PBS-T solution containing 5% FBS was further placed onto the section, and the section was left to stand in a moist chamber at 4° C. overnight and was then washed in PBS-T for 10 minutes three times. An appropriate amount of Peroxidase Labelled Polymer Conjugate (manufactured by DAKO) was dropwise placed onto the section, followed by being left to stand in a moisture chamber at room temperature for 30 minutes. After washing in PBS-T for 10 minutes three times, DAB color-developing solution (manufactured by DAKO) was placed onto the section, followed by being left to stand at room temperature for about 10 minutes. The color-developing solution was removed, and the section was washed in PBS-T for 10 minutes three times, was then rinsed with distilled water, was put in 70%, 80%, 90%, 95%, and 100% ethanol solutions in this order for 1 minute in each ethanol solution, and was left to stand in xylene overnight. The slide glass was taken out and was enclosed in Glycergel Mounting Medium (manufactured by DAKO) for observation. The results demonstrated that the CAPRIN-1 protein was highly expressed in 19 samples (73%) of 26 samples of gallbladder cancer tissue in total.

Example 4

Antitumor Effect (ADCC Activity) of Anti-CAPRIN-1 Polyclonal Antibody on Gallbladder Cancer Cells Whether or not an anti-CAPRIN-1 antibody can impair the gallbladder cancer cells expressing a CAPRIN-1 protein was investigated. Evaluation was performed using the anti-human CAPRIN-1 polyclonal antibody prepared in Example 2. $1\times10^6$ cells of a human gallbladder cancer cell line TGBC14TKB, which were confirmed to express the CAPRIN-1 protein, were collected in a 50-mL centrifugation tube, and 100 μCi of $^{51}$chromium was added thereto, followed by incubation at 37° C. for 2 hours. Subsequently, the cells were washed with RPMI1640 medium containing 10% fetal calf serum three times and were then added to a 96-well V-bottom plate at $1\times10^3$ cells per well. To each well was added 1 μg of the anti-human CAPRIN-1 polyclonal antibody and further added $2\times10^5$ lymphocytes isolated from human peripheral blood, followed by culturing at 37° C. in 5% $CO_2$ for 4 hours. After the culturing, the amount of $^{51}$chromium (Cr) secreted from the impaired tumor cells into the culture supernatant was measured to calculate the ADCC activity on the gallbladder cancer cells by the anti-human CAPRIN-1 polyclonal antibody. The results demonstrated that in the case of the anti-human CAPRIN-1 polyclonal antibody, the ADCC activity on TGBC14TKB was 14% or more, whereas the ADCC activity on TGBC14TKB was less than 5% in the case of using the control antibody prepared from the peripheral blood of a rabbit not immunized with the antigen and was also less than 5% in the case of not using any antibodies. Accordingly, it was revealed that the ADCC activity in the use of an anti-CAPRIN-1 antibody can impair gallbladder cancer cells expressing the CAPRIN-1 protein. The cytotoxicity is the results, as described above, when the anti-CAPRIN-1 antibody used in the present invention, lymphocytes, and $1\times10^3$ tumor cells with $^{51}$chromium were mixed and cultured for 4 hours, and is shown as the cytotoxicity on the tumor cells calculated by the following calculation formula * by measuring the amount of $^{51}$chromium released into the medium after the culturing.

cytotoxicity (%)=(amount of $^{51}$chromium released from tumor cells in the presence of anti-CAPRIN-1 antibody and lymphocytes)/(amount of $^{51}$chromium released from tumor cells in the presence of 1 N hydrochloric acid)×100. Formula *

Example 5

Production of Anti-CAPRIN-1 Mouse and Chicken Monoclonal Antibodies

The human CAPRIN-1 recombinant protein (100 μg) produced in Example 2 was mixed with the same quantity of MPL/TDM adjuvant (manufactured by Sigma-Aldrich Co., LLC.), and the mixture was used as an antigen solution for one mouse. The antigen solution was intraperitoneally administered to 6-week old Balb/c mice (manufactured by Japan SLC, Inc.) and further administered three times or 24 times with one week intervals to complete the immunization. The spleen was extracted on the third day from the last immunization and was ground between sterilized two slide glasses and was washed with PBS (−) (manufactured by Nissui Pharmaceutical Co., Ltd.), followed by centrifugation at 1500 rpm for 10 minutes to remove the supernatant. This procedure was repeated three times to obtain spleen cells. The resulting spleen cells and mouse myeloma cells SP2/0 (purchased from ATCC) were mixed at a ratio of 10:1, and a PEG solution prepared by mixing 200 μL of RPMI1640 medium containing 10% FBS and 800 μL of PEG 1500 (manufactured by Boehringer Ingelheim GmbH) and heated to 37° C. was added to the resulting mixture, followed by being left to stand for 5 minutes for cell fusion. Centrifugation at 1700 rpm for 5 minutes was performed, and the supernatant was removed. The cells were suspended in a mixture of 150 mL of RPMI1640 medium (HAT selection medium) containing 15% FBS and 2% equivalents of a HAT solution manufactured by Gibco, and the suspension was seeded to 15 plates, which were 96-well plates (manufactured by Nunc), at 100 μL per well. Culturing at 37° C. in 5% $CO_2$ for 7 days gave hybridomas of the spleen cells and the myeloma cells.

Hybridomas were selected using, as an index the binding affinity of the antibodies produced by the hybridomas to a CAPRIN-1 protein. A 1 μg/mL solution of CAPRIN-1 protein prepared in Example 2 was added to a 96-well plate at 100 μL per well, followed by being left to stand at 4° C. for 18 hours. Each well was washed with PBS-T three times, and 400 μL of a 0.5% bovine serum albumin (BSA) solution (manufactured by Sigma-Aldrich Co., LLC.) was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing antibodies showing high absorbance values were selected.

The selected hybridomas were seeded to a 96-well plate at 0.5 cells per well and were cultured. After one week, hybridomas forming single colonies were observed in the wells. The cells in the wells were further cultured, and hybridomas were selected using, as an index, the binding affinity of the antibodies produced by the cloned hybridomas to a CAPRIN-1 protein. A 1 μg/mL solution of CAPRIN-1 protein prepared in Example 2 was added to a 96-well plate at 100 μL per well, followed by being left to stand at 4° C. for 18 hours. Each well was washed with PBS-T three times, and 400 μL of a 0.5% BSA solution was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, 150 hybridoma strains producing mouse monoclonal antibodies reactive to a CAPRIN-1 protein were obtained.

Subsequently, from these mouse monoclonal antibodies, antibodies reactive to the cell surface of cancer cells expressing the CAPRIN-1 protein were selected. Specifically, $1\times10^6$ cells of human breast cancer cell line MDA-MB-231V were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled goat anti-mouse IgG antibody (manufactured by life technologies) diluted by 500-fold with PBS containing 0.1% FBS, followed by being left to stand on ice for 1 hour. After washing with PBS, the fluorescence intensity was measured with FACS Calibur available from Becton, Dickinson and Company. Separately, as a control, the same procedure as in above was performed using non-treated serum of a 6-week old Balb/c mouse diluted by 500-fold with a hybridoma culturing medium, instead of the antibody. As a result, 22 mouse monoclonal antibodies (mouse monoclonal antibodies #1 to #22) that showed higher fluorescence intensities compared to the control, i.e., reacted with the cell surface of breast cancer cells were selected.

In order to produce a chicken monoclonal antibody, 300 μg of an antigen protein (human CAPRIN-1 protein) set forth in SEQ ID NO: 2 prepared in Example 2 was mixed with the same quantity of complete Freund's adjuvant, and the mixture was used as an antigen solution for one chicken. The antigen solution was intraperitoneally administered to 7-week old chickens and further administered seven times with four weeks intervals to complete the immunization. The spleen was extracted on the fourth day from the last immunization and was ground between sterilized two slide glasses and was washed with PBS (−) (manufactured by Nissui Pharmaceutical Co., Ltd.), followed by centrifugation at 1500 rpm for 10 minutes to remove the supernatant. This procedure was repeated three times to obtain spleen cells. The resulting spleen cells and light chain-deficient chicken myeloma cells established by transformation from chicken using bird reticuloendotheliosis virus were mixed at a ratio of 5:1, and a PEG solution prepared by mixing 200 μL of IMDM medium containing 10% FBS and 800 μL of PEG 1500 (manufactured by Boehringer Ingelheim GmbH) and heated to 37 μC was added to the resulting mixture, followed by being left to stand for 5 minutes for cell fusion. Centrifugation at 1700 rpm for 5 minutes was performed, and the supernatant was removed. The cells were suspended in a mixture of 300 mL of IMDM medium (HAT selection medium) containing 10% FBS and 2% equivalents of a HAT solution manufactured by Gibco, and the suspension was seeded to 30 plates, which were 96-well plates (manufactured by Nunc), at 100 L per well. Culturing at 37° C. in 5% $CO_2$ for 7 days gave hybridomas by fusion of the spleen cells and the myeloma cells.

Hybridomas were selected using, as an index, the binding affinity of the antibodies produced by the hybridomas to a CAPRIN-1 protein. A 1 μg/mL solution of CAPRIN-1 protein prepared in Example 2 was added to a 96-well plate at 100 μL per well, followed by being left to stand at 4° C. for 18 hours. Each well was washed with PBS-T three times, and 400 μL of a 0.5% bovine serum albumin (BSA) solution (manufactured by Sigma-Aldrich Co., LLC.) was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-chicken IgY antibody (manufactured by Sigma-Aldrich Co., LLC.) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing antibodies showing high absorbance values were selected.

The selected hybridomas were seeded to a 96-well plate at 0.5 cells per well and were cultured. After one week, hybridomas forming single colonies were observed in the wells. The cells in the wells were further cultured, and hybridomas were selected using, as an index, the binding affinity of the antibodies produced by the cloned hybridomas to a CAPRIN-1 protein. A 1 μg/mL solution of human CAPRIN-1 protein was added to a 96-well plate at 100 μL per well, followed by being left to stand at 4° C. for 18 hours. Each well was washed with PBS-T three times, and 400 μL of a 0.5% BSA solution was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-chicken IgY antibody (manufactured by Sigma-Aldrich Co., LLC.) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridoma strains producing monoclonal antibodies showing reactivity with the CAPRIN-1 protein were obtained.

Subsequently, from these monoclonal antibodies, antibodies reactive to the cell surface of cancer cells expressing the CAPRIN-1 protein were selected. Specifically, $5\times10^5$ cells of human breast cancer cell line MDA-MB-231V were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled goat anti-chicken IgG (H+L) antibody (manufactured by SouthernBiotech) diluted by 30-fold with PBS containing 0.1% FBS, followed by being left to stand on ice for 1 hour. After washing with PBS, the fluorescence intensity was measured with FACS Calibur available from Becton, Dickinson and Company. Separately, the same procedure as in above was performed using a hybridoma culturing medium to prepare a control sample. As a result, three monoclonal antibodies (chicken monoclonal antibodies #1, #2, and #3) that showed higher fluorescence intensities compared to the control, i.e., reacted with the cell surface of breast cancer cells expressing the CAPRIN-1 protein were selected.

Example 6

Characterization of Selected Antibody (1) Cloning of Gene of Variable Domain of Anti-CAPRIN-1 Monoclonal Antibody mRNA was extracted from each of hybridoma strains producing 22 mouse monoclonal antibodies and 3 chicken monoclonal antibodies selected in Example 5. Genes of the heavy-chain variable (VH) domains and the light-chain variable (VL) domains of all anti-CAPRIN-1 monoclonal antibodies were prepared by RT-PCR using primers specific for mouse FR1-derived sequence and mouse FR4-derived sequence in the hybridomas producing mouse monoclonal antibodies and primers specific for chicken FR1-derived sequence and chicken FR4-derived sequence in the hybridomas producing chicken monoclonal antibodies. These genes were cloned into a pCR2.1 vector (manufactured by life technologies) for sequencing.

(1)-1 RT-PCR mRNA was prepared from $1\times10^6$ hybridomas of each strain producing a mouse monoclonal antibody with mRNA micro purification kit (manufactured by GE Healthcare Bio-Sciences), and the resulting mRNA was reverse-transcribed with SuperScriptII 1st strand synthesis kit (manufactured by life technologies) to synthesize cDNA. These procedures were performed in accordance with the protocol attached to each kit. The gene of the antibody was amplified by PCR using the resulting cDNA. In order to obtain a gene of the VH domain, a primer (SEQ ID NO: 257) specific to the mouse heavy chain FR1 sequence and a primer (SEQ ID NO: 258) specific to the mouse heavy chain FR4 sequence were used. In order to obtain a gene of the VL domain, a primer (SEQ ID NO: 259) specific to the mouse light chain FR1 sequence and a primer (SEQ ID NO: 260) specific to the mouse light chain FR4 were used. These primers were designed by referring to Jones, S. T. and Bending, M. M., Bio/Technology, 9, 88-89 (1991). In the PCR, Ex-taq (manufactured by Takara Bio Inc.) was used. A cDNA sample was added to 5 μL of 10×EX Taq Buffer, 4 μL (2.5 mM) of dNTP Mixture, 2 μL (1.0 μM) of each primer, and 0.25 μL (5 U/nL) of Ex Taq, and the total volume was adjusted to 50 μL with sterilized water. After treatment at 94° C. for 2 minutes, a cycle consisting of denaturation at 94° C. for 1 minute, annealing at 58° C. for 30 seconds, and extension at 72° C. for 1 minute was repeated for 30 cycles.

Total RNA was extracted from $1\times10^6$ hybridomas of each strain producing a chicken monoclonal antibody using High Pure RNA Isolation Kit (manufactured by Roche Diagnostics K.K.), and cDNA was synthesized using PrimeScript II 1st strand cDNA Synthesis Kit (manufactured by Takara Bio Inc.). These procedures were performed in accordance with the protocol attached to each kit. The chicken antibody heavy chain variable domain gene and the chicken antibody light chain variable domain gene were each amplified using the synthesized cDNA as a template and KOD-Plus-DNA Polymerase (manufactured by Toyobo Co., Ltd.) by PCR according to a usual method. In order to obtain a gene of the VH domain of a chicken antibody, a primer specific to the chicken heavy chain FR1 sequence and a primer specific to the chicken heavy chain FR4 sequence were used. In order to obtain a gene of the VL domain, a primer specific to the chicken light chain FR1 sequence and a primer specific to the chicken light chain FR4 were used.

(1)-2 Cloning

Each PCR product prepared above was subjected to agarose gel electrophoresis, and the DNA bands of the VH domain and the VL domain were cut out. DNA fragments were purified with QIAquick Gel purification kit (manufactured by Qiagen) in accordance with the protocol attached to the kit. Each purified DNA was cloned into a pCR2.1 vector using a TA cloning kit (manufactured by life technologies). The linked vector was transformed into DH5a competent cells (manufactured by Toyobo Co., Ltd.) in accordance with a usual method. Ten clones of each transformant was cultured in a medium (100 μg/mL ampicillin) at 37° C. overnight, and each plasmid DNA was purified using Qiaspin Miniprep kit (manufactured by Qiagen).

(1)-3 Sequencing

The VH domain and VL domain genes in each of the plasmids prepared above were sequenced using M13 forward primer (SEQ ID NO: 261) and M13 reverse primer (SEQ ID NO: 262) with a fluorescence sequencer (DNA sequencer 3130XL, manufactured by ABI) using BigDye terminator Ver 3.1 cycle sequencing kit manufactured by ABI in accordance with the protocol attached to the kit. As a result, each gene sequence and amino acid sequence were determined.

That is, these monoclonal antibodies each comprise a heavy-chain variable (VH) domain (sequence number of the gene sequence is shown in parentheses) comprising the amino acid sequence set forth in SEQ ID NO: 40 (SEQ ID NO: 45), SEQ ID NO: 50 (SEQ ID NO: 55), SEQ ID NO: 60 (SEQ ID NO: 65), SEQ ID NO: 70 (SEQ ID NO: 75), SEQ ID NO: 80 (SEQ ID NO: 85), SEQ ID NO: 90 (SEQ ID NO: 95), SEQ ID NO: 100 (SEQ ID NO: 105), SEQ ID NO: 110 (SEQ ID NO: 115), SEQ ID NO: 120 (SEQ ID NO: 125), SEQ ID NO: 130 (SEQ ID NO: 131), SEQ ID NO: 135 (SEQ ID NO: 140), SEQ ID NO: 145 (SEQ ID NO: 150), SEQ ID NO: 160 (SEQ ID NO: 165), SEQ ID NO: 170 (SEQ ID NO: 175), SEQ ID NO: 200 (SEQ ID NO: 205), SEQ ID NO: 210 (SEQ ID NO: 215), SEQ ID NO: 220 (SEQ ID NO: 225), SEQ ID NO: 230 (SEQ ID NO: 235), SEQ ID NO: 240 (SEQ ID NO: 245), or SEQ ID NO: 250 (SEQ ID NO: 255) and a light-chain variable (VL) domain (sequence number of the gene sequence is shown in parentheses) comprising the amino acid sequence set forth in SEQ ID NO: 44 (SEQ ID NO: 46), SEQ ID NO: 54 (SEQ ID NO: 56), SEQ ID NO: 64 (SEQ ID NO: 66), SEQ ID NO: 74 (SEQ ID NO: 76), SEQ ID NO: 84 (SEQ ID NO: 86), SEQ ID NO: 94 (SEQ ID NO: 96), SEQ ID NO: 104 (SEQ ID NO: 106), SEQ ID NO: 114 (SEQ ID NO: 116), SEQ ID NO: 124 (SEQ ID NO: 126), SEQ ID NO: 139 (SEQ ID NO: 141), SEQ ID NO: 149 (SEQ ID NO: 151), SEQ ID NO: 155 (SEQ ID NO: 156), SEQ ID NO: 164 (SEQ ID NO: 166), SEQ ID NO: 174 (SEQ ID NO: 176), SEQ ID NO: 180 (SEQ ID NO: 181), SEQ ID NO: 185 (SEQ ID NO: 186), SEQ ID NO: 190 (SEQ ID NO: 191), SEQ ID NO: 195 (SEQ ID NO: 196), SEQ ID NO: 204 (SEQ ID NO: 206), SEQ ID NO: 214 (SEQ ID NO: 216), SEQ ID NO: 224 (SEQ ID NO: 226), SEQ ID NO: 234 (SEQ ID NO: 236), SEQ ID NO: 244 (SEQ ID NO: 246), or SEQ ID NO: 254 (SEQ ID NO: 256). The VH domain comprises CDR1 represented by the amino acid sequence set forth in SEQ ID NO: 37, SEQ ID NO: 47, SEQ ID NO: 57, SEQ ID NO: 67, SEQ ID NO: 77, SEQ ID NO: 87, SEQ ID NO: 97, SEQ ID NO: 107, SEQ ID NO: 117, SEQ ID NO: 127, SEQ ID NO: 132, SEQ ID NO: 142, SEQ ID NO: 157, SEQ ID NO: 167, SEQ ID NO: 197, SEQ ID NO: 207, SEQ ID NO: 217, SEQ ID NO: 227, SEQ ID NO: 237, or SEQ ID NO: 247, CDR2 represented by the amino acid sequence set forth in SEQ ID NO: 38, SEQ ID NO: 48, SEQ ID NO: 58, SEQ ID NO: 68, SEQ ID NO: 78, SEQ ID NO: 88, SEQ ID NO: 98, SEQ ID NO: 108, SEQ ID NO: 118, SEQ ID NO: 128, SEQ ID NO: 133, SEQ ID NO: 143, SEQ ID NO: 158, SEQ ID NO: 168, SEQ ID NO: 198, SEQ ID NO: 208, SEQ ID NO: 218, SEQ ID NO: 228, SEQ ID NO: 238, or SEQ ID NO: 248; and CDR3 represented by the amino acid sequence set forth in SEQ ID NO: 39, SEQ ID NO: 49, SEQ ID NO: 59, SEQ ID NO: 69, SEQ ID NO: 79, SEQ ID NO: 89, SEQ ID NO: 99, SEQ ID NO: 109, SEQ ID NO: 119, SEQ ID NO: 129, SEQ ID NO: 134, SEQ ID NO: 144, SEQ ID NO: 159, SEQ ID NO: 169, SEQ ID NO: 199, SEQ ID NO: 209, SEQ ID NO: 219, SEQ ID NO: 229, SEQ ID NO: 239, or SEQ ID NO: 249. The VL domain comprises CDR1 represented by the amino acid sequence set forth in SEQ ID NO: 41, SEQ ID NO: 51, SEQ ID NO: 61, SEQ ID NO: 71, SEQ ID NO: 81, SEQ ID NO: 91, SEQ ID NO: 101, SEQ ID NO: 111, SEQ ID NO: 121, SEQ ID NO: 136, SEQ ID NO: 146, SEQ ID NO: 152, SEQ ID NO: 161, SEQ ID NO: 171, SEQ ID NO: 177, SEQ ID NO: 182, SEQ ID NO: 187, SEQ ID NO: 192, SEQ ID NO: 201, SEQ ID NO: 211, SEQ ID NO: 221, SEQ ID NO: 231, SEQ ID NO: 241, or SEQ ID NO: 251, CDR2 represented by the amino acid sequence set forth in SEQ ID NO: 42, SEQ ID NO: 52, SEQ ID NO: 62, SEQ ID NO: 72, SEQ ID NO: 82, SEQ ID NO: 92, SEQ ID NO: 102, SEQ ID NO: 112, SEQ ID NO: 122, SEQ ID NO: 137, SEQ ID NO: 147, SEQ ID NO: 153, SEQ ID NO: 162, SEQ ID NO: 172, SEQ ID NO: 178, SEQ ID NO: 183, SEQ ID NO: 188, SEQ ID NO: 193, SEQ ID NO: 202, SEQ ID NO: 212, SEQ ID NO: 222, SEQ ID NO: 232, SEQ ID NO: 242, or SEQ ID NO: 252, and CDR3 represented by the amino acid sequence set forth in SEQ ID NO: 43, SEQ ID NO: 53, SEQ ID NO: 63, SEQ ID NO: 73, SEQ ID NO: 83, SEQ ID NO: 93, SEQ ID NO: 103, SEQ ID NO: 113, SEQ ID NO: 123, SEQ ID NO: 138, SEQ ID NO: 148, SEQ ID NO: 154, SEQ ID NO: 163, SEQ ID NO: 173, SEQ ID NO: 179, SEQ ID NO: 184, SEQ ID NO: 189, SEQ ID NO: 194, SEQ ID NO: 203, SEQ ID NO: 213, SEQ ID NO: 223, SEQ ID NO: 233, SEQ ID NO: 243, or SEQ ID NO: 253.

The amino acid sequence of the heavy chain variable domain of each of the resulting monoclonal antibodies is set forth in SEQ ID NO: 40, SEQ ID NO: 50, SEQ ID NO: 60, SEQ ID NO: 70, SEQ ID NO: 80, SEQ ID NO: 90, SEQ ID NO: 100, SEQ ID NO: 110, SEQ ID NO: 120, SEQ ID NO: 130, SEQ ID NO: 135, SEQ ID NO: 145, SEQ ID NO: 160, SEQ ID NO: 170, SEQ ID NO: 200, SEQ ID NO: 210, SEQ ID NO: 220, SEQ ID NO: 230, SEQ ID NO: 240, and SEQ ID NO: 250, and the amino acid sequence of the light chain variable domain is set forth in SEQ ID NO: 44, SEQ ID NO: 54, SEQ ID. NO: 64, SEQ ID NO: 74, SEQ ID NO: 84, SEQ ID NO: 94, SEQ ID NO: 104, SEQ ID NO: 114, SEQ ID NO: 124, SEQ ID NO: 139, SEQ ID NO: 149, SEQ ID NO: 155, SEQ ID NO: 164, SEQ ID NO: 174, SEQ ID NO: 180, SEQ ID NO: 185, SEQ ID NO: 190, SEQ ID NO: 195, SEQ ID NO: 204, SEQ ID NO: 214, SEQ ID NO: 224, SEQ ID NO: 234, SEQ ID NO: 244, and SEQ ID NO: 254.

That is, mouse monoclonal antibody #1 comprises a heavy chain variable domain set forth in SEQ ID NO: 70 and a light chain variable domain set forth in SEQ ID NO: 74; mouse monoclonal antibody #2 comprises a heavy chain variable domain set forth in SEQ ID NO: 80 and a light chain variable domain set forth in SEQ ID NO: 84; mouse monoclonal antibody #3 comprises a heavy chain variable domain set forth in SEQ ID NO: 90 and a light chain variable domain set forth in SEQ ID NO: 94; mouse monoclonal antibody #4 comprises a heavy chain variable domain set forth in SEQ ID NO: 100 and a light chain variable domain set forth in SEQ ID NO: 104; mouse monoclonal antibody #5 comprises a heavy chain variable domain set forth in SEQ ID NO: 110 and a light chain variable domain set forth in SEQ ID NO: 114; mouse monoclonal antibody #6 comprises a heavy chain variable domain set forth in SEQ ID NO: 120 and a light chain variable domain set forth in SEQ ID NO: 124; mouse monoclonal antibody #7 comprises a heavy chain variable domain set forth in SEQ ID NO: 130 and a light chain variable domain set forth in SEQ ID NO: 124; mouse monoclonal antibody #8 comprises a heavy chain variable domain set forth in SEQ ID NO: 135 and a light chain variable domain set forth in SEQ ID NO: 139; mouse monoclonal antibody #9 comprises a heavy chain variable domain set forth in SEQ ID NO: 145 and a light chain variable domain set forth in SEQ ID NO: 149; mouse monoclonal antibody #10 comprises a heavy chain variable domain set forth in SEQ ID NO: 145 and a light chain variable domain set forth in SEQ ID NO: 155; mouse monoclonal antibody #11 comprises a heavy chain variable domain set forth in SEQ ID NO: 160 and a light chain variable domain set forth in SEQ ID NO: 164; mouse monoclonal antibody #12 comprises a heavy chain variable domain set forth in SEQ ID NO: 170 and a light chain variable domain set forth in SEQ ID NO: 174; mouse monoclonal antibody #13 comprises a heavy chain variable domain set forth in SEQ ID NO: 170 and a light chain variable domain set forth in SEQ ID NO: 180; mouse monoclonal antibody #14 comprises a heavy chain variable domain set forth in SEQ ID NO: 170 and a light chain variable domain set forth in SEQ ID NO: 185; mouse monoclonal antibody #15 comprises a heavy chain variable domain set forth in SEQ ID NO: 170 and a light chain variable domain set forth in SEQ ID NO: 190; mouse monoclonal antibody #16 comprises a heavy chain variable domain set forth in SEQ ID NO: 170 and a light chain variable domain set forth in SEQ ID NO: 195; mouse monoclonal antibody #17 comprises a heavy chain variable domain set, forth in SEQ ID NO: 200 and a light chain variable domain set forth in SEQ ID NO: 204; mouse monoclonal antibody #18 comprises a heavy chain variable domain set forth in SEQ ID NO: 210 and a light chain variable domain set forth in SEQ ID NO: 214; mouse monoclonal antibody #19 comprises a heavy chain variable domain set forth in SEQ ID NO: 220 and a light chain variable domain set forth in SEQ ID NO: 224; mouse monoclonal antibody #20 comprises a heavy chain variable domain set forth in SEQ ID NO: 230 and a light chain variable domain set forth in SEQ ID NO: 234; mouse monoclonal antibody #21 comprises a heavy chain variable domain set forth in SEQ ID NO: 240 and a light chain variable domain set forth in SEQ ID NO: 244; and mouse monoclonal antibody #22 comprises a heavy chain variable domain set forth in SEQ ID NO: 250 and a light chain variable domain set forth in SEQ ID NO: 254.

The amino acid sequences of the heavy chain variable domains of the resulting chicken monoclonal antibodies are set forth in SEQ ID NOs: 40, 50, and 60; and the amino acid sequences of the light chain variable domains are set forth in SEQ ID NOs: 44, 54, and 64.

That is, the chicken monoclonal antibody #1 comprises a heavy chain variable domain set forth in SEQ ID NO: 40 and a light chain variable domain set forth in SEQ ID NO: 44, wherein the CDRs 1 to 3 in the heavy chain variable domain consist of the amino acid sequences set forth in SEQ ID NOs: 37, 38, and 39, respectively; and the CDRs 1 to 3 in the light chain variable domain consist of the amino acid sequences set forth in SEQ ID NOs: 41, 42, and 43, respectively. The chicken monoclonal antibody #2 comprises a heavy chain variable domain set forth in SEQ ID NO: 50 and a light chain variable domain set forth in SEQ ID NO: 54, wherein the CDRs 1 to 3 in the heavy chain variable domain consist of the amino acid sequences set forth in SEQ ID NOs: 47, 48, and 49, respectively; and the CDRs 1 to 3 in the light chain variable domain consist of the amino acid sequences set forth in SEQ ID NOs: 51, 52, and 53, respectively. The chicken monoclonal antibody #3 comprises a heavy chain variable domain set forth in SEQ ID NO: 60 and a light chain variable domain set forth in SEQ ID NO: 64, wherein the CDRs 1 to 3 in the heavy chain variable domain consist of the amino acid sequences set forth in SEQ ID NOs: 57, 58, and 59, respectively; and the CDRs 1 to 3 in the light chain variable domain consist of the amino acid sequences set forth in SEQ ID NOs: 61, 62, and 63, respectively.

(2) Production of Human-Chicken Chimeric Recombinant Antibody and Mouse-Chicken Chimeric Antibody Both terminals of an amplified fragment of the gene of the heavy chain variable domain set forth in SEQ ID NO: 40 of the chicken monoclonal antibody #1 prepared in the above (1) were treated with restriction enzymes, and the fragment was purified and was inserted into pcDNA4/myc-His vector (manufactured by life technologies) containing a leader sequence derived from a chicken antibody comprising the sequence set forth in SEQ ID NO: 263 and the H-chain constant domain of human $IgG_1$ comprising the sequence set forth in SEQ ID NO: 264 in accordance with a usual method. Separately, both terminals of an amplified fragment of the gene of the light chain variable domain set forth in SEQ ID NO: 44 of the chicken monoclonal antibody #1 were treated with restriction enzymes, and the fragment was purified and was inserted into pcDNA3.1/myc-His vector (manufactured by life technologies) containing a leader sequence derived from a chicken antibody comprising the sequence set forth in SEQ ID NO: 263 and the L-chain constant domain of human $IgG_1$ comprising the sequence set forth in SEQ ID NO: 265 in accordance with a usual method.

Subsequently, the recombinant vector containing the heavy chain variable domain set forth in SEQ ID NO: 40 of the chicken monoclonal antibody #1 and the recombinant vector containing the light chain variable domain set forth in SEQ ID NO: 44 of the chicken monoclonal antibody #1 were introduced into CHO-K1 cells (obtained from Riken Cell Bank). Specifically, $2\times10^5$ CHO-K1 cells cultured in each well, of a 12-well culture plate, containing 1 mL of Ham's F12 medium (manufactured by life technologies) containing 10% FBS were washed with PBS (−). To each well were added 1 mL of fresh Ham's F12 medium containing 10% FBS and a mixture of 30 μL at of OptiMEM (manufactured by life technologies) containing 250 ng of each of the above-mentioned vectors and 30 μL of Polyfect transfection reagent (manufactured by Qiagen). The CHO-K1 cells introduced with the recombinant vectors were cultured in Ham's F12 medium containing 10% FBS, 200 μg/mL Zeocin (manufactured by life technologies), and 200 μg/mL Geneticin (manufactured by Roche) and were then seeded to a 96-well plate at 0.5 cells per well to produce a cell line stably producing human-chicken chimeric antibody #1 (#1) comprising the variable domain of the chicken monoclonal antibody #1. Similarly, cell lines stably producing human-chicken chimeric antibody #2 (#2) and human-chicken chimeric antibody #3 (#3) were produced from chicken monoclonal antibodies #2 and #3, respectively.

The produced cell lines were each cultured at $5\times10^5$ cells/mL in a 150-$cm^2$ flask containing 30 mL of serum-free OptiCHO medium (manufactured by life technologies) for 5 days to obtain a culture supernatant containing #1, #2, or #3.

Similarly, both terminals of an amplified fragment of the gene of the heavy chain variable domain set forth in SEQ ID NO: 40 of the chicken monoclonal antibody #1 were treated with restriction enzymes, and the fragment was purified and was inserted into pcDNA4/myc-His vector (manufactured by life technologies) containing a leader sequence derived from a chicken antibody and the H-chain constant domain of mouse $IgG_1$ in accordance with a usual method. Separately, both terminals of an amplified fragment of the gene of the light chain variable domain set forth in SEQ ID NO: 44 of the chicken monoclonal antibody #1 were treated with restriction enzymes, and the fragment was purified and was inserted into pcDNA3.1/myc-His vector (manufactured by life technologies) containing a leader sequence derived from a chicken antibody and the L-chain constant domain of mouse $IgG_1$ in accordance with a usual method. These vectors were introduced into CHO-K1 cells as in above to produce a cell line stably producing mouse-chicken chimeric antibody #1 comprising the variable domain of chicken monoclonal antibody #1. Similarly, cell lines stably producing mouse-chicken chimeric antibody #2 (#2) and mouse-chicken chimeric antibody #3 (#3) were produced from chicken monoclonal antibodies #2 and #3, respectively.

The produced cell lines were each cultured at $5\times10^5$ cells/mL in a 150-$cm^2$ flask containing 30 mL of serum-free OptiCHO medium (manufactured by life technologies) for 5 days to obtain a culture supernatant containing mouse-chicken chimeric antibody #1, mouse-chicken chimeric antibody #2, and mouse-chicken chimeric antibody #3.

(3) Expression of CAPRIN-1 Protein on Gallbladder Cancer Cell Surface Using Prepared Monoclonal Antibody Subsequently, a gallbladder cell line TGBC14TKB, which was confirmed to express a CAPRIN-1 gene, was investigated for whether or not a CAPRIN-1 protein is expressed on the surfaces of these cells. $1\times10^6$ cells of TGBC14TKB were centrifuged with a 1.5-mL micro centrifugation tube. To the cells was added the culture supernatant (100 μL) containing any of anti-CAPRIN-1 mouse monoclonal antibodies #1 to #22 reacting to cancer cell surface produced in Example 4 and anti-CAPRIN-1 mouse-chicken chimeric antibodies #1 to #3 produced in the above (2), followed by being left to stand on ice for 1 hour. After washing with PBS, the cells were suspended in a FITC-labeled goat anti-mouse IgG antibody (manufactured by life technologies) diluted by 500-fold with PBS containing 0.1% FBS, followed by being left to stand on ice for 1 hour. After washing with PBS, the fluorescence intensity was measured with FACS Calibur available from Becton, Dickinson and Company. Separately, as a control, the same procedure as in above was performed using an iso-type control antibody, instead of the culture supernatants containing the anti-CAPRIN-1 mouse monoclonal antibodies #1 to #22 and the mouse-chicken chimeric antibodies #1 to #3. As a result, the fluorescence intensity in the cells to which any of the monoclonal antibodies #1 to #22 and the mouse-chicken chimeric antibodies #1 to #3 was added was 20% or more higher than that in the control in every case. Specifically, in the case of using mouse-chicken chimeric antibody #1, the fluorescence intensity was enhanced by 200% or more. This demonstrates that the CAPRIN-1 protein was expressed on the cell surface of the human gallbladder cancer cell lines. The rate of increase in the fluorescence intensity is represented by the rate of increase in the mean fluorescence intensity (MFI value) in each cell and is calculated by the following calculation formula:

Rate of increase in mean fluorescence intensity(rate of increase in fluorescence intensity)(%)=((MFI value of cells reacted with anti-human CAPRIN-1 antibody)−(MFI value of control))/(MFI value of control)×100.

(4) Antitumor Effect (ADCC Activity) of Anti-CAPRIN-1 Antibody on Human Gallbladder Cancer Cells Among the antibodies prepared above, human-chicken chimeric antibody #1 was used for evaluation of cytotoxicity (ADCC activity) on human gallbladder cancer cells. Human-chicken chimeric antibody #1 contained in the culture supernatant prepared in the above (2) was purified using Hitrap Protein A Sepharose FF (manufactured by GE Healthcare Bio-Sciences), substituted with PBS (−), and filtered through a filter of 0.22 μm (manufactured by Millipore Corporation), and was used as the antibody for measuring activity. $1\times10^6$ cells of a human gallbladder cancer cell line TGBC14TKB were collected in a 50-mL, centrifugation tube, and 100 μCi of $^{51}$chromium was added thereto, followed by incubation at 37° C. for 2 hours. Subsequently, the cells were washed with RPMI1640 medium containing 10% FBS three times and were then added to a 96-well V-bottom plate at $2\times10^3$ cells per well as target cells. To each well was added 1.2 μg of the antibody purified above. Separately, a cell population containing human NK cells was isolated from human peripheral blood lymphocytes by the following procedure: Human peripheral mononuclear cells were subjected to reaction with FITC fluorescent dye-labeled antibodies (anti-human CD3 antibody, anti-human CD20 antibody, anti-human CD19 antibody, anti-human CD11c antibody, and anti-HLA-DR antibody (Becton, Dickinson and Company)), and a cell population containing NK cells not stained with these antibodies was isolated using a cell sorter (FACS Vantage SE (Becton, Dickinson and Company)) or a human NK cell separation kit (NK Cell Isolation Kit (manufactured by Miltenyi Biotec GmbH)). The cell population containing NK cells were further added to the plate at $2\times10^5$ cells per well, followed by culturing at 37° C. in 5% $CO_2$ for 4 hours. After the culturing, the amount of $^{51}$chromium secreted from the impaired tumor cells into the culture supernatant was measured to calculate the ADCC activity on the gallbladder cancer cells by the anti-CAPRIN-1 antibody. As a result, the cytotoxicities of human-chicken chimeric antibody #1 on TGBC14TKB were 20%, whereas the cytotoxicities on TGBC14TKB were both less than 5% in the case of using the monoclonal antibody that reacts with the CAPRIN-1 protein itself but does not react with the cell surface of cancer cells and in the case of not using antibodies. Similarly, the cytotoxicities on TGBC14TKB of anti-CAPRIN-1 mouse monoclonal antibodies #1 to #22, human-chicken chimeric antibodies #2 and #3 were also investigated and were all 15% or more, whereas the cytotoxicities were less than 5% in the case of using the monoclonal antibody that reacts with the CAPRIN-1 protein itself but does not react with the cell surface of cancer cells and in the case of not using antibodies. The results above demonstrated that the prepared anti-CAPRIN-1 monoclonal antibodies impair cancer cells expressing the CAPRIN-1 protein through ADCC activity. The cytotoxicity is the results, as described above, when the anti-CAPRIN-1 antibody used in the present invention, the cell population containing human NK cells, and $2\times10^3$ tumor cells with $^{51}$chromium were mixed and cultured for 4 hours, and is shown as the cytotoxicity on the tumor cells calculated by the following calculation formula * by measuring the amount of $^{51}$chromium released into the medium after the culturing.

cytotoxicity (%)=(amount of $^{51}$chromium released from tumor cells in the presence of cell population containing anti-CAPRIN-1 antibody and NK cells)/(amount of $^{51}$chromium released from tumor cells in the presence of 1 N hydrochloric acid)×100. Formula *

Example 7

Identification of Peptide of CAPRIN-1 Protein Binding to Anti-CAPRIN-1 Antibody Reacting to Cell Surface of Cancer Cells Partial sequences of the CAPRIN-1 protein recognized by anti-CAPRIN-1 antibodies were identified using anti-CAPRIN-1 monoclonal antibodies #12 to #22, which react to cell surface of cancer cells, prepared above.

First, DTT (manufactured by Fluka) was added at a final concentration of 10 mM to 100 μL of a 1 μg/μL solution of recombinant CAPRIN-1 protein in PBS, followed by reaction at 95° C. for 5 minutes to reduce the disulfide bond in the CAPRIN-1 protein. Next, iodoacetamide (manufactured by Wako Pure Chemical Industries, Ltd.) was added thereto at a final concentration of 20 mM, followed by alkylation of the thiol group at 37° C. under a light-shielded condition for 30 minutes. To 40 pig of the resulting reduced alkylated CAPRIN-1 protein was added 50 μg of any of anti-CAPRIN-1 monoclonal antibodies #12 to #22. The total amount of each mixture was adjusted to 1 mL with a 20 mM phosphate buffer (pH 7.0), followed by reaction at 4° C. overnight with stirring.

Subsequently, trypsin (manufactured by Promega K.K.) was added at a final concentration of 0.2 μg to each reaction mixture, followed by reaction at 37° C. for 1, 2, 4, or 12 hours. The reaction mixture was mixed with protein A-glass beads (manufactured by GE Healthcare Bio-Sciences) blocked with PBS containing 1% BSA (manufactured by Sigma-Aldrich Co., LLC.) and washed with PBS in advance and 1 mM calcium carbonate in a NP-40 buffer (20 mM phosphate buffer (pH 7.4), 5 mM EDTA, 150 mM NaCl, 1% NP-40), followed by reaction for 30 minutes.

Each reaction solution was washed with a 25 mM ammonium carbonate buffer (pH 8.0), followed by elution of antigen-antibody complexes with 100 μL of 0.1% formic acid. The eluate was analyzed by LC-MS using Q-TOF Premier (manufactured by Waters-MicroMass) in accordance with the protocol attached to the instrument.

As a result, a polypeptide set forth in SEQ ID NO: 273 was identified as a partial sequence of the CAPRIN-1 protein recognized by all of anti-CAPRIN-1 monoclonal antibodies #12 to #22. Furthermore, a peptide set forth in SEQ ID NO: 274 was identified as a partial sequence of the polypeptide set forth in above SEQ ID NO: 273 recognized by the monoclonal antibodies #13 to #16, #17 to #19, and #21; and a partial sequence peptide set forth in SEQ ID NO: 275 was found to be recognized by the monoclonal antibodies #13 to #16.

Epitope peptides in the CAPRIN-1 protein recognized by antibodies were identified using human-chicken chimeric monoclonal antibody #1, human-chicken chimeric monoclonal antibody #3, and mouse monoclonal antibodies #1 to #11. Candidate peptides (93 peptides) each consisting of 12 to 16 amino acids of the amino acid sequence of the human CAPRIN-1 protein were synthesized and were each dissolved at a concentration of 1 mg/mL in DMSO.

Each peptide was dissolved at a concentration of 30 μg/mL in a 0.1 M sodium carbonate buffer (pH 9.6). The solution was added to a 96-well plate (manufactured by Nunc, Product No. 436006) at 100 μL per well, followed by being left to stand at 4° C. overnight. The solution was removed, and 200 μL of 10 mM ethanolamine/0.1 M sodium carbonate buffer (pH 9.6) was added to each well, followed by being left to stand at room temperature for 1 hour. The solution was removed, and each well was washed with PBS containing 0.5% Tween 20 (PBST) twice to prepare a peptide-immobilized plate.

The cell culture supernatant containing human-chicken chimeric monoclonal antibody #1 (#1), human-chicken chimeric monoclonal antibody #3 (#3), or a mouse monoclonal antibody (#1, #2, #3, #4, #5, #6, #7, #8, #9, #10, or #11) was added to each plate at an amount of 50 μL per well, followed by shaking at room temperature for 1 hour. The solution was removed, and each well was washed with PBST three times. Subsequently, a secondary antibody solution containing a HRP-labeled anti-human IgG antibody (manufactured by life technologies) diluted by 3000- to 4000-fold with PBST was added to the human-chicken chimeric monoclonal antibody wells at 50 μL per well, while a secondary antibody solution containing a HRP-labeled anti-mouse IgG antibody (manufactured by life technologies) diluted by 3000- to 4000-fold with PBST was added to the mouse monoclonal antibody wells at a 50 μL per well. The solution was removed, and each well was washed with PBST six times.

Color reaction was performed by adding 100 μL of a TMB substrate solution (manufactured by Thermo Fisher Scientific K.K.) to each well and leaving the mixture to stand for 15 to 30 minutes. After the coloring, 100 μL of 1 N sulfuric acid was added to each well to stop the reaction. The absorbance was measured at 450 nm and 595 nm with an absorption spectrometer. As a result, a polypeptide set forth in SEQ ID NO: 266 was identified as a partial sequence of the CAPRIN-1 recognized by all of the anti-CAPRIN-1 antibodies: human-chicken chimeric monoclonal antibody #1 and anti-CAPRIN-1 monoclonal antibodies #1 to #5. In addition, a peptide set forth in SEQ ID NO: 267 was identified as a partial peptide of the polypeptide set forth in SEQ ID NO: 266 recognized by human-chicken chimeric monoclonal antibody #1 and mouse monoclonal antibodies #3 and #4; and a peptide set forth in SEQ ID NO: 268 was identified as a partial peptide of the polypeptide set forth in SEQ ID NO: 266 recognized by mouse monoclonal antibodies #1, #2, and #5. It was therefore demonstrated that the polypeptide set forth in SEQ ID NO: 266 contains an epitope region for the anti-CAPRIN-1 antibodies: human-chicken chimeric monoclonal antibody #1 and mouse monoclonal antibodies #1 to #5. Furthermore, a polypeptide comprising the amino acid sequence set forth in SEQ ID NO: 270 was identified as a partial sequence of the CAPRIN-1 protein recognized by all of anti-CAPRIN-1 monoclonal antibodies

#6, #7, and #8. It was therefore demonstrated that the polypeptide set forth in SEQ ID NO: 270 contains an epitope region for anti-CAPRIN-1 antibodies #6, #7, and #8. In addition, a polypeptide comprising the amino acid sequence set forth in SEQ ID NO: 272 was identified as a partial sequence of the CAPRIN-1 protein recognized by all of anti-CAPRIN-1 monoclonal antibodies #9, #10, and #11. It was therefore demonstrated that the polypeptide set forth in SEQ ID NO: 272 contains an epitope region for anti-CAPRIN-1 antibodies #9, #10, and #11. In addition, a polypeptide comprising the amino acid sequence set forth in SEQ ID NO: 269 was identified as a partial sequence of the CAPRIN-1 protein recognized by human-chicken chimeric monoclonal antibody #3. It was therefore demonstrated that the polypeptide set forth in SEQ ID NO: 269 contains an epitope region for human-chicken chimeric monoclonal antibody #3.

Example 8

Production of Mouse Monoclonal Antibodies #30 and #34 to #36 Against CAPRIN-1 Protein (1) Production of Mouse Anti-CAPRIN-1 Monoclonal Antibodies #30 and #34 to #36

A mixture of 100 μg of a human CAPRIN-1 protein comprising the amino acid sequence set forth in SEQ ID NO: 2 prepared in accordance with example 3 of WO2010/016526 mixed with the same quantity of MPL+TDM adjuvant (manufactured by Sigma-Aldrich Co., LLC.) was used as an antigen solution for one mouse. The antigen solution was intraperitoneally administered to 6-week old Balb/c mice (manufactured by Japan SLC, Inc.) and further administered seven times with one week intervals to complete the immunization. The spleen was extracted on the third day from the last immunization and was ground between sterilized two slide glasses and was washed with PBS (−) (manufactured by Nissui Pharmaceutical Co., Ltd.), followed by centrifugation at 1500 rpm for 10 minutes to remove the supernatant. This procedure was repeated three times to obtain spleen cells. The resulting spleen cells and mouse myeloma cells SP2/0 (purchased from ATCC) were mixed at a ratio of 10:1, and a PEG solution prepared by mixing 200 μL of RPMI1640 medium containing 10% FBS and 800 μL of PEG 1500 (manufactured by Boehringer Ingelheim GmbH) and heated to 37° C. was added to the resulting mixture, followed by being left to stand for 5 minutes for cell fusion. Centrifugation at 1700 rpm for 5 minutes was performed, and the supernatant was removed. The cells were suspended in a mixture of 150 mL of RPMI1640 medium (HAT selection medium) containing 15% FBS and 2% equivalents of a HAT solution manufactured by Gibco, and the suspension was seeded to 15 plates, which were 96-well plates (manufactured by Nunc), at 100 μL per well. Culturing at 37° C. in 5% $CO_2$ for 7 days gave hybridomas by fusion of the spleen cells and the myeloma cells.

Hybridomas were selected using, as an index, the binding affinity of the antibodies produced by the hybridomas to a CAPRIN-1 protein. A 1 μg/mL solution of CAPRIN-1 protein prepared by the method described in example 3 of WO2010/016526 was added to a 96-well plate at 100 μL per well, followed by being left to stand at 4° C. for 18 hours. Each well was washed with PBS-T three times, and 400 μL of a 0.5% bovine serum albumin (BSA) solution (manufactured by Sigma-Aldrich Co., LLC.) was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing antibodies showing high absorbance values were selected.

The selected hybridomas were seeded to a 96-well plate at 0.5 cells per well and were cultured. After one week, hybridomas forming single colonies were observed in the wells. The cells in the wells were further cultured, and hybridomas were selected using, as an index, the binding affinity of the antibodies produced by the cloned hybridomas to a CAPRIN-1 protein. A 1 μg/mL solution of CAPRIN-1 protein prepared by the method described in example 3 of WO2010/016526 was added to a 96-well plate at 100 μL per well, followed by being left to stand at 4° C. for 18 hours. Each well was washed with PBS-T three times, and 400 μL of a 0.5% BSA solution was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridoma cell lines producing monoclonal antibodies reactive to the CAPRIN-1 protein were obtained.

Subsequently, from the resulting monoclonal antibodies, antibodies reactive to the cell surface of breast cancer cells expressing the CAPRIN-1 were selected. Specifically, $1\times10^6$ cells of human breast cancer cell line MDA-MB-231V were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled goat anti-mouse IgG antibody (manufactured by life technologies) diluted by 500-fold with PBS containing 0.1% FBS, followed by being left to stand on ice for 1 hour. After washing with PBS, the fluorescence intensity was measured with FACS Calibur available from Becton, Dickinson and Company. Separately, the same procedure as in above was performed as a control using non-treated serum of a 6-week old Balb/c mouse diluted by 500-fold with a hybridoma culturing medium, instead of the antibody. As a result, four monoclonal antibodies (mouse anti-CAPRIN-1 antibodies #30 and #34 to #36) that showed higher fluorescence intensities compared to the control, i.e., reacted with the cell surface of breast cancer cells were selected.

(2) Identification of CAPRIN-1 Epitope Recognized by Each Mouse Anti-CAPRIN-1 Monoclonal Antibody The CAPRIN-1 epitope regions recognized by the resulting four monoclonal antibodies were identified. Candidate peptides (93 peptides) each consisting of 12 to 16 amino acids of the amino acid sequence of the human CAPRIN-1 protein were synthesized and were each dissolved at a concentration of 1 mg/mL in DMSO.

Each peptide was dissolved at a concentration of 30 μg/mL in a 0.1 M sodium carbonate buffer (pH 9.6). The solution was added to a 96-well plate (manufactured by Nunc, Product No. 436006) at 100 μL per well, followed by being left to stand at 4° C. overnight. The solution was removed, and 200 μL of 10 mM ethanolamine/0.1 M sodium carbonate buffer (pH 9.6) was added to each well, followed by being left to stand at room temperature for 1 hour. The solution was removed, and each well was washed with PBS containing 0.5% Tween 20 (PBST) twice to prepare a peptide-immobilized plate.

The cell culture supernatant containing anti-CAPRIN-1 antibody #1 was added to the plate at an amount of 50 μL per well, followed by shaking at room temperature for 1 hour. The solution was removed, and each well was washed with PBST three times. Subsequently, 50 μL of a secondary antibody solution containing a HRP-labeled anti-mouse IgG antibody (manufactured by life technologies) diluted by 3000- to 4000-fold with PBST was added to each well. The solution was removed, and each well was washed with PBST six times.

Color reaction was performed by adding 100 μL of a TMB substrate solution (manufactured by Thermo Fisher Scientific K.K.) to each well and leaving the mixture to stand for 15 to 30 minutes. After the coloring, 100 μL of 1 N sulfuric acid was added to each well to stop the reaction. The absorbance was measured at 450 nm and 595 tam with an absorption spectrometer.

As a result, a polypeptide set forth in SEQ ID NO: 429 was identified as a partial sequence of CAPRIN-1 recognized by mouse anti-CAPRIN-1 antibody #30; a polypeptide set forth in SEQ ID NO: 431 was identified as a partial sequence of CAPRIN-1 recognized by mouse anti-CAPRIN-1 antibody #34; and a polypeptide set forth in SEQ ID NO: 432 was identified as a partial sequence of CAPRIN-1 recognized by mouse anti-CAPRIN-1 antibodies #35 and #36.

(3) Cloning of Gene of Variable Domain of Each Mouse Anti-CAPRIN-1 Monoclonal Antibody The resulting monoclonal antibodies were analyzed for the gene sequence encoding the variable domains and their amino acid sequences in accordance with the method described in example 5 of WO2010/016526.

The results demonstrated that mouse anti-CAPRIN-1 antibody #30 comprises a heavy chain variable domain consisting of the amino acid sequence set forth in SEQ ID NO: 344 and a light chain variable domain consisting of the amino acid sequence set forth in SEQ ID NO: 348. The gene sequence encoding the heavy chain variable domain is set forth in SEQ ID NO: 349; and the gene sequence encoding the light chain variable domain is set forth in SEQ ID NO: 350. CDRs 1 to 3 in the heavy chain variable domain consist of the amino acid sequences set forth in SEQ ID NOs: 341, 342, and 343, respectively. CDRs 1 to 3 in the light chain variable domain consist of the amino acid sequences set forth in SEQ ID NOs: 345, 346, and 347, respectively.

Furthermore, the results demonstrated that mouse anti-CAPRN-1 antibody #34 comprises a heavy chain variable domain consisting of the amino acid sequence set forth in SEQ ID NO: 401 and a light chain variable domain consisting of the amino acid sequence set forth in SEQ ID NO: 405. The gene sequence encoding the heavy chain variable domain is set forth in SEQ ID NO: 406; and the gene sequence encoding the light chain variable domain is set forth in SEQ ID NO: 407. CDRs 1 to 3 in the heavy chain variable domain consist of the amino acid sequences set forth in SEQ ID NOs: 398, 399, and 400, respectively. CDRs 1 to 3 in the light chain variable domain consist of the amino acid sequences set forth in SEQ ID NOs: 402, 403, and 404, respectively.

The results demonstrated that mouse anti-CAPRN-1 antibody #35 comprises a heavy chain variable domain consisting of the amino acid sequence set forth in SEQ ID NO: 411 and a light chain variable domain consisting of the amino acid sequence set forth in SEQ ID NO: 415. The gene sequence encoding the heavy chain variable domain is set forth in SEQ ID NO: 416; and the gene sequence encoding the light chain variable domain is set forth in SEQ ID NO: 417. CDRs 1 to 3 in the heavy chain variable domain consist of the amino acid sequences set forth in SEQ ID NOs: 408, 409, and 410, respectively. CDRs 1 to 3 in the light chain variable domain consist of the amino acid sequences set forth in SEQ ID NOs: 412, 413, and 414, respectively.

The results demonstrated that mouse anti-CAPRIN-1 antibody #36 comprises a heavy chain variable domain consisting of the amino acid sequence set forth in SEQ ID NO: 421 and a light chain variable domain consisting of the amino acid sequence set forth in SEQ ID NO: 425. The gene sequence encoding the heavy chain variable domain is set forth in SEQ ID NO: 426; and the gene sequence encoding the light chain variable domain is set forth in SEQ ID NO: 427. CDRs 1 to 3 in the heavy chain variable domain consist of the amino acid sequences set forth in SEQ ID NOs: 418, 419, and 420, respectively. CDRs 1 to 3 in the light chain variable domain consist of the amino acid sequences set forth in SEQ ID NOs: 422, 423, and 424, respectively.

(4) Expression Analysis of CAPRIN-1 Protein on Gallbladder Cancer Cell Surface Using Each Mouse Anti-CAPRIN-1 Monoclonal Antibody A human gallbladder cancer cell line TGBC14TKB was investigated whether or not a CAPRIN-1 protein is expressed on the cell surface. $5\times10^5$ cells of the gallbladder cancer cell line were centrifuged with a 1.5-mL micro centrifugation tube. The cells were subjected to reaction with each mouse anti-CAPRIN-1 antibody at a final concentration of 20 μg/mL, followed by being left to stand on ice for 1 hour. After washing with PBS, the cells were reacted with a 100-fold diluted Alexa488-labeled goat anti-mouse IgG antibody (manufactured by life technologies), followed by being left to stand on ice for 30 hours. After washing with PBS, the fluorescence intensity was measured with FACS Calibur available from Becton, Dickinson and Company. As a negative control, only the secondary antibody was used in the reaction. As a result, the fluorescence intensities in the cells to which the anti-CAPRIN-1 antibody was added were 35% or more higher than that in the control in the gallbladder cancer cell line. This demonstrates that the CAPRIN-1 protein is expressed on the cell surface of the gallbladder cancer cell line.

Example 9

Production of Mouse Monoclonal Antibodies #31 to #33 Against CAPRIN-1 Protein (1) Production of Mouse Anti-CAPRIN-1 Antibody #31

A mixture of 100 μg of a human CAPRIN-1 protein comprising the amino acid sequence set forth in SEQ ID NO: 2 prepared in accordance with example 3 of WO2010/016526 mixed with the same quantity of MPL+TDM adjuvant (manufactured by Sigma-Aldrich Co., LLC.) was used as an antigen solution for one mouse. The antigen solution was intraperitoneally administered to 6-week old Balb/c mice (manufactured by Japan SLC, Inc.) and further administered seven times with one week intervals to complete the immunization. The spleen was extracted on the third day from the last immunization and was ground between sterilized two slide glasses and was washed with PBS (−) (manufactured by Nissui Pharmaceutical Co., Ltd.), followed by centrifugation at 1500 rpm for 10 minutes to remove the supernatant. This procedure was repeated three times to obtain spleen cells. The resulting spleen cells and mouse myeloma cells SP2/0 (purchased from ATCC) were mixed at a ratio of 10:1, and a PEG solution prepared by mixing 200 μL of RPMI1640 medium containing 10% FBS and 800 μL of PEG 1500 (manufactured by Boehringer Ingelheim GmbH) and heated to 37° C. was added to the resulting mixture, followed by being left to stand for 5 minutes for cell fusion. Centrifugation at 1700 rpm for 5 minutes was performed, and the supernatant was removed. The cells were suspended in a mixture of 150 mL of RPMI1640 medium (HAT selection medium) containing 15% FBS and 2% equivalents of a HAT solution manufactured by Gibco, and the suspension was seeded to 15 plates, which were 96-well plates (manufactured by Nunc), at 100 μL per well. Culturing at 37° C. in 5% $CO_2$ for 7 days gave hybridomas by fusion of the spleen cells and the myeloma cells.

Hybridomas were selected using, as an index, the binding affinity of the antibodies produced by the hybridomas to a CAPRIN-1 protein. A 1 μg/mL solution of CAPRIN-1 protein prepared by the method described in example 3 of WO2010/016526 was added to a 96-well plate at 100 μL per well, followed by being left to stand at 4° C. for 18 hours. Each well was washed with PBS-T three times, and 400 μL of a 0.5% bovine serum albumin (BSA) solution (manufactured by Sigma-Aldrich Co., LLC.) was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing antibodies showing high absorbance values were selected.

The selected hybridomas were seeded to a 96-well plate at 0.5 cells per well and were cultured. After one week, hybridomas forming single colonies were observed in the wells. The cells in the wells were further cultured, and hybridomas were selected using, as an index, the binding affinity of the antibodies produced by the cloned hybridomas to a CAPRIN-1 protein. A 1 μg/mL solution of the CAPRIN-1 protein prepared by the method described in example 3 of WO2010/016526 was added to a 96-well plate at 100 μL per well, followed by being left to stand at 4° C. for 18 hours. Each well was washed with PBS-T three times, and 400 μL of a 0.5% BSA solution was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T three times, and 100 μL of a TMS substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, 61 hybridomas producing monoclonal antibodies reactive to the CAPRIN-1 protein were obtained.

Subsequently, from the resulting monoclonal antibodies, antibodies reactive to the cell surface of breast cancer cells expressing CAPRIN-1 were selected. Specifically, $1\times10^6$ cells of human breast cancer cell line MDA-MB-231V were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled goat anti-mouse IgG antibody (manufactured by life technologies) diluted by 500-fold with PBS containing 0.1% FBS, followed by being left to stand on ice for 1 hour. After washing with PBS, the fluorescence intensity was measured with FACS Calibur available from Becton, Dickinson and Company. Separately, the same procedure as in above was performed as a control using non-treated serum of a 6-week old Balb/c mouse diluted by 500-fold with a hybridoma culturing medium, instead of the antibody. As a result, one mouse monoclonal antibody (mouse anti-CAPRIN-1 antibody #31) showing higher fluorescence intensity compared to the control, i.e., reacting with the cell surface of breast cancer cells was selected.

(2) Identification of CAPRIN-1 Epitope Recognized by Mouse Anti-CAPRIN-1 Antibody #31

The CAPRIN-1 epitope region recognized was identified using monoclonal antibody (mouse anti-CAPRIN-1 antibody #31) against CAPRIN-1 reactive to the cell surface of cancer cells obtained in the above (1). Candidate peptides (93 peptides) each consisting of 12 to 16 amino acids of the amino acid sequence of the human CAPRIN-1 protein were synthesized and were each dissolved at a concentration of 1 mg/mL in DMSO.

Each peptide was dissolved at a concentration of 30 μg/mL in a 0.1 M sodium carbonate buffer (pH 9.6). The solution was added to a 96-well plate (manufactured by Nunc, Product No. 436006) at 100 μL per well, followed by being left to stand at 4° C. overnight. The solution was removed, and 200 μL of 10 mM ethanolamine/0.1 M sodium carbonate buffer (pH 9.6) was added to each well, followed by being left to stand at room temperature for 1 hour. The solution was removed, and each well was washed with PBS containing 0.5% Tween 20 (PBST) twice to prepare a peptide-immobilized plate.

The cell culture supernatant containing anti-CAPRIN-1 antibody #31 was added to the plate at an amount of 50 μL per well, followed by shaking at room temperature for 1 hour. The solution was removed, and each well was washed with PBST three times. Subsequently, 50 μL of a secondary antibody solution containing a HRP-labeled anti-mouse IgG antibody (manufactured by life technologies) diluted by 3000- to 4000-fold with PBST was added to each well. The solution was removed, and each well was washed with PBST six times.

Color reaction was performed by adding 100 μL of a TMB substrate solution (manufactured by Thermo Fisher Scientific K.K.) to each well and leaving the mixture to stand for 15 to 30 minutes. After the coloring, 100 μL of 1 N sulfuric acid was added to each well to stop the reaction. The absorbance was measured at 450 nm and 595 nm with an absorption spectrometer.

As a result, a polypeptide set forth in SEQ ID NO: 430 was identified as a partial sequence of CAPRIN-1 recognized by mouse anti-CAPRIN-1 antibody #31 prepared in the above (1).

(3) Production of Mouse Anti-CAPRIN-1 Antibodies #32 and #33

As in the method of the above (1), a fusion protein of a polypeptide comprising the amino acid sequence set forth in SEQ ID NO: 430 identified in the above (2) and a carrier protein, Keyhole limpet haemocyanin (KLH), was used as an immunogen; the immunogen was mixed with the same quantity of an adjuvant, TiterMax Gold (registered trademark) (CytRx Corp.); and the mixture was intraperitoneally administered to each mouse four times at 7 days intervals at 100 μg per once. The spleen cells were extracted on the third day from the last immunization. As in the method of the above (1), the spleen cells were fused with mouse myeloma cells to produce hybridomas. Subsequently, antibodies were selected using, as an index, the reactivity of the antibodies contained in the culture supernatants of the resulting hybridomas with a 1 μg/mL solution of CAPRIN-1 protein prepared in example 3 of WO2010/016526 and with a fusion protein of the amino acid sequence set forth in SEQ ID NO: 5 used as the immunogen and a carrier protein, BSA. Specifically, 100 μL of a 1 μg/mL solution of CAPRIN-1 protein prepared in example 3 of WO2010/016526 and 100 μL of a 30 μg/mL solution of the fusion protein of the amino acid sequence set forth in SEQ ID NO: 5 and the carrier protein, BSA, were added to each well of a 96-well plate, followed by being left to stand at 4° C. for 18 hours. Each well was washed with PBS-T, and 400 μL of a solution of Block Ace (DS Pharma Biomedical Co., Ltd.) was added to each well, followed by being left to stand at room temperature for 3 hours. The solution was removed, and each well was washed with PBS-T, and 100 μL of the hybridoma culture supernatant prepared above was added to each well, followed by being left to stand at room temperature for 2 hours. Each well was washed with PBS-T, and 100 μL of a HRP-labeled anti-mouse IgG (H+L) antibody (manufactured by life technologies) diluted by 5000-fold with PBS was added to each well, followed by being left to stand at room temperature for 1 hour. Each well was washed with PBS-T, and 100 μL of a TMB substrate solution (manufactured by Thermo Fisher Scientific K.K.) was added to each well, followed by being left to stand for 5 to 30 minutes for color reaction. After the coloring, 100 μL of 1 N sulfuric acid was added to each well to stop the reaction. The absorbance was measured at 450 nm and 595 nm with an absorption spectrometer. As a result, hybridomas producing antibodies showing high absorbance values were selected.

The selected hybridomas were seeded to a 96-well plate at 0.3 cells per well and were cultured. After one week, hybridomas forming single colonies were observed in the wells. The cells in the wells were further cultured, and hybridomas producing antibodies against a partial sequence of the CAPRIN-1 protein, the amino acid sequence set forth in SEQ ID NO: 430, were selected using, as an index, the binding affinity of the antibodies produced by the cloned hybridomas to the amino acid sequence set forth in SEQ ID NO: 430.

Monoclonal antibodies reactive to the cell surface of breast cancer cells expressing CAPRIN-1 were selected from the monoclonal antibodies produced by the resulting hybridomas. Specifically, $1\times10^6$ cells of human breast cancer cell line MDA-MB-231V were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled goat anti-mouse IgG antibody (manufactured by life technologies) diluted by 500-fold with PBS containing 0.1% FBS, followed by being left to stand on ice for 1 hour. After washing with PBS, the fluorescence intensity was measured with FACS Calibur available from Becton, Dickinson and Company. Separately, the same procedure as in above was performed as a negative control using non-treated serum of a 6-week old Balb/c mouse diluted by 500-fold with a hybridoma culturing medium instead of the antibody and using only the secondary antibody in the reaction. As a result, two mouse monoclonal antibodies (mouse anti-CAPRIN-1 antibody #32 and mouse anti-CAPRIN-1 antibody #33) showing higher fluorescence intensity compared to the negative control, i.e., reacting with the cell surface of breast cancer cells were obtained.

It was investigated whether or not the resulting mouse anti-CAPRIN-1 antibodies #32 and #33 specifically react with a polypeptide having the amino acid sequence set forth in SEQ ID NO: 430, a partial sequence of CAPRIN-1, used as the immunogen. A solution of 30 μg/mL of the amino acid sequence set forth in SEQ ID NO: 430 or of a partial sequence other than the amino acid sequence set forth in SEQ ID NO: 430 of CAPRIN-1 in an aqueous solution of 0.1 M sodium carbonate was added to a 96-well plate for ELISA, Immobilizer Amino (Nunc), at an amount of 100 μg/mL, followed by reaction at 4° C. overnight to immobilize the peptide to the well. An aqueous solution of 0.1 M sodium carbonate containing 10 mM ethanolamine was added to the peptide-immobilized wells, followed by being left to stand at room temperature for 1 hour. The solution in the wells was removed. After washing with PBS-T, 400 μL of a Block Ace solution was added to each well, followed by being left to stand at room temperature for 3 hours. The solution in the wells was removed. After washing with PBS-T, 50 μL of the culture supernatant containing mouse anti-CAPRIN-31 #32 or #33 was added to each well, followed by reaction at room temperature for 1 hour. After washing with PBS-T, 50 μL of a HRP-labeled anti-mouse IgG (H+L) antibody (manufactured by life technologies) diluted by 5000-fold with the Block Ace solution was added to each well, followed by being left to stand at room temperature for 1 hour. Each well was sufficiently washed with PBS-T, and 100 μL of a TMB substrate solution (manufactured by Thermo Fisher Scientific K.K.) was added to each well, followed by being left to stand for 5 to 30 minutes for color reaction. After the coloring, 100 μL of 1 N sulfuric acid was added to each well to stop the reaction. The absorbance was measured at 450 nm and 595 nm with an absorption spectrometer. As a result, mouse anti-CAPRIN-1 antibodies #32 and #33 did not react with the partial sequence of CAPRIN-1 not containing the amino acid sequence set forth in SEQ ID NO: 430 and specifically reacted with only the polypeptides comprising the amino acid sequence set forth in SEQ ID NO: 430. This therefore demonstrated that the polypeptide set forth in SEQ ID NO: 430 comprises an epitope region for the mouse monoclonal antibodies #32 and #33.

(4) Characterization of Mouse Anti-CAPRIN-1 Antibodies #31 to #33

From the mouse anti-CAPRIN-1 antibodies #31 to #33 prepared in the above (1) and (3), amplified fragments of the genes encoding variable domains were obtained in accordance with the method described in example 5 of WO2010/016526, and the gene sequences and the amino acid sequences were analyzed. The resulting gene sequence encoding the heavy chain variable domain of the mouse anti-CAPRIN-1 antibody #31 is set forth in SEQ ID NO: 381, and its amino acid sequence is set forth in SEQ ID NO: 376. The gene sequence encoding the light chain variable domain is set forth in SEQ ID NO: 382, and its amino acid sequence is set forth in SEQ ID NO: 380. Similarly, the resulting gene sequence encoding the heavy chain variable domain of the mouse anti-CAPRIN-1 antibody #32 is set forth in SEQ ID NO: 391, and its amino acid sequence is set forth in SEQ ID NO: 386. The gene sequence encoding the light chain variable domain is set forth in SEQ ID NO: 392, and its amino acid sequence is set forth in SEQ ID NO: 390. The resulting gene sequence encoding the heavy chain variable domain of the mouse anti-CAPRIN-1 antibody #33 is set forth in SEQ ID NO: 397, and its amino acid sequence is set forth in SEQ ID NO: 396. The gene sequence encoding the light chain variable domain is set forth in SEQ ID NO: 392, and its amino acid sequence is set forth in SEQ ID NO: 390.

In addition, it was confirmed that CDRs 1 to 3 in the heavy chain variable domain of mouse anti-CAPRIN-1 antibody #31 consist of the amino acid sequences set forth in SEQ ID NOs: 373, 374, and 375, respectively, and that CDRs 1 to 3 in the light chain variable domain consist of the amino acid sequences set forth in SEQ ID NOs: 377, 378, and 379, respectively. Similarly, it was confirmed that CDRs 1 to 3 in the heavy chain variable domain of mouse anti-CAPRIN-1 antibody #32 consist of the amino acid sequences set forth in SEQ ID NOs: 383, 384, and 385, respectively, and that CDRs 1 to 3 in the light chain variable domain consist of the amino acid sequences set forth in SEQ ID NOs: 387, 388, and 389, respectively. It was also confirmed that CDRs 1 to 3 in the heavy chain variable domain of mouse anti-CAPRIN-1 antibody #33 consist of the amino acid sequences set forth in SEQ ID NOs: 393, 394, and 395, respectively, and that CDRs 1 to 3 in the light chain variable domain consist of the amino acid sequences set forth in SEQ ID NOs: 387, 388, and 389, respectively.

Example 10

Expression Analysis of CAPRIN-1 Protein on Gallbladder Cancer Cell Surface Using Mouse Anti-CAPRIN-1 Monoclonal Antibodies #30 to #36

A human gallbladder cancer cell line TGBC14TKB was investigated whether or not a CAPRIN-1 protein is expressed on the cell surface using mouse anti-CAPRIN-1 monoclonal antibodies #30 to #36. $5\times10^5$ cells of TGBC14TKB were centrifuged with a 1.5-mL micro centrifugation tube. The cells were subjected to reaction with each of mouse anti-CAPRIN-1 antibodies #30 to #36 at a final concentration of 20 μg/mL, followed by being left to stand on ice for 1 hour. After washing with PBS, the cells were reacted with a 100-fold diluted Alexa488-labeled goat anti-mouse IgG antibody (manufactured by life technologies), followed by being left to stand on ice for 30 hours. After washing with PBS, the fluorescence intensity was measured with FACS Calibur available from Becton, Dickinson and Company. Separately, the cells were subjected to reaction with only the secondary antibody as a negative control. As a result, the fluorescence intensities in TGBC14TKB to which mouse anti-CAPRIN-1 monoclonal antibodies #30 to #36 were added were 35% or more higher than that in the control. This demonstrates that the CAPRIN-1 protein is expressed on the cell membrane surface of the gallbladder cancer cell line.

Example 11

Production of Human-Mouse Chimeric Anti-CAPRIN-1 Antibody

Both terminals of an amplified fragment of the gene comprising the heavy chain variable domain of each of mouse anti-CAPRIN-1 antibodies #30 to #36 were treated with restriction enzymes, and the fragment was purified and was inserted into pcDNA4/myc-His vector (manufactured by life technologies) containing a leader sequence derived from a mouse antibody and the H-chain constant domain of human $IgG_1$ comprising the amino acid sequence set forth in SEQ ID NO: 264, in accordance with a usual method. Both terminals of an amplified fragment of the gene comprising the light chain variable domain of each of mouse anti-CAPRIN-1 antibodies #30 to #36 were treated with restriction enzymes, and the fragment was purified and was inserted into pcDNA4/myc-His vector (manufactured by life technologies) containing a leader sequence derived from a mouse antibody and the L-chain constant domain of human $IgG_1$ comprising the amino acid sequence set forth in SEQ ID NO: 265, in accordance with a usual method.

Subsequently, the recombinant vector containing the heavy chain variable domain of any of mouse anti-CAPRIN-1 antibodies #30 to #36 and the recombinant vector containing the light chain variable domain of the mouse anti-CAPRIN-1 antibody were introduced into CHO-K1 cells (obtained from Riken Cell Bank). Specifically, $2\times10^5$ CHO-K1 cells cultured in each well, of a 12-well culture plate, containing 1 mL of Ham's F12 medium (manufactured by life technologies) containing 10% FBS were washed with PBS (−). To each well were added 1 mL of fresh Ham's F12 medium containing 10% FBS and a mixture of 30 μL of OptiMEM (manufactured by life technologies) containing 250 ng of each of the above-mentioned vectors and 30 μL of Polyfect transfection reagent (manufactured by Qiagen). The CHO-K1 cells introduced with the recombinant vectors were cultured in Ham's F, 12 medium containing 10% FBS, 200 μg/mL Zeocin (manufactured by life technologies), and 200 μg/mL Geneticin (manufactured by Roche) and were then seeded to a 96-well plate at 0.5 cells per well to produce cell lines stably producing human-mouse chimeric anti-CAPRIN-1 antibodies #30 to #36 comprising the variable domains of the mouse anti-CAPRIN-1 antibodies #30 to #36.

The produced cell lines were each cultured at $5\times10^5$ cells/mL in a 150-$cm^2$ flask containing 30 mL of serum-free OptiCHO medium (manufactured by life technologies) for 5 days to obtain culture supernatants containing human-mouse chimeric anti-CAPRIN-1 antibody #30 to #36, respectively.

Example 12

Antitumor Activity (ADCC Activity) of Anti-CAPRIN-1 Antibodies on Gallbladder Cancer Cells In order to evaluate the intensity of the cytotoxicity, on gallbladder cancer cells expressing CAPRIN-1, of antibodies against peptides derived from CAPRIN-1 set forth in SEQ ID NOs: 429 to 432, ADCC activity was measured using human-mouse chimeric anti-CAPRIN-1 antibodies #30 to #36. $1\times10^5$ cells of each of the gallbladder cancer cell line TGBC14TKB were collected in a 50-mL micro centrifugation tube and were incubated with 100 μCi of $^{51}$chromium at 37° C. for 2 hours. Subsequently, the cells were washed with RPMI1640 medium containing 10% fetal bovine serum three times. Separately, any of human-mouse chimeric anti-CAPRIN-1 antibodies #30 to #36 was added to each well of a 96-well V-bottom plate at a final concentration of 5 μg/mL, and $2\times10^5$ human NK cells separated from human peripheral blood lympocytes as effector cells by a usual method were added to each well. To each well were added $2\times10^3$ gallbladder cancer cells with $^{51}$chromium prepared above, and the mixture was cultured for 4 hours. The amount of $^{51}$chromium released into the medium after the culturing, and the cytotoxicity on gallbladder cancer cells was calculated by the following calculation formula *:

cytotoxicity (%)=(amount of $^{51}$chromium released from target cells in the presence of antibody against CAPRIN-1 and lymphocytes)/(amount of $^{51}$chromium released from target cells in the presence of 1 N hydrochloric acid)×100. Formula *

As a result, every human-mouse chimeric anti-CAPRIN-1 antibody showed 20% or more activity on gallbladder cancer cells, whereas the activity of a human $IgG_1$ antibody used as the negative control was less than 7% on gallbladder cancer cells.

Example 13

Production of Anti-CAPRIN-1 Monoclonal Antibody Using Rabbit (1) Production of Rabbit Anti-CAPRIN-1 Monoclonal Antibody #1

A mixture of 300 μg of an antigen protein (human CAPRIN-1) mixed with the same quantity of a complete Freund's adjuvant was used as an antigen solution for one rabbit. In the second and subsequent immunization, a mixture with an incomplete Freund's adjuvant was used. The antigen solution was intraperitoneally administered to 7-week old rabbits and further administered seven times with four weeks intervals to complete the immunization. The spleen was extracted on the fourth day from the last immunization and was ground between sterilized two slide glasses and was washed with PBS (−) (manufactured by Nissui Pharmaceutical Co., Ltd.), followed by centrifugation at 1500 rpm for 10 minutes to remove the supernatant. This procedure was repeated three times to obtain spleen cells. The resulting spleen cells and rabbit myeloma cells were mixed at a ratio of 5:1, and a PEG solution prepared by mixing 200 μL of IMDM medium containing 10% FBS and 800 μL of PEG 1500 (manufactured by Boehringer Ingelheim GmbH) and heated to 37° C. was added to the resulting mixture, followed by being left to stand for 5 minutes for cell fusion. Centrifugation at 1700 rpm for 5 minutes was performed, and the supernatant was removed. The cells were suspended in a mixture of 300 mL of IMDM medium (HAT selection medium) containing 10% FBS and 2% equivalents of a HAT solution manufactured by Gibco, and the suspension was seeded to 30 plates, which were 96-well plates (manufactured by Nunc), at 100 μL per well. Culturing at 37° C. in 5% $CO_2$ for 7 days gave hybridomas of the spleen cells and the rabbit myeloma cells.

Hybridomas were selected using, as an index, the reactivity of the antibodies produced by the hybridomas to a CAPRIN-1 protein. A 1 μg/mL solution of CAPRIN-1 protein was added to a 96-well plate at 100 μL per well, followed by being left to stand at 4° C. for 18 hours. Each well was washed with PBS-T three times, and 400 μL of a 0.5% bovine serum albumin (BSA) solution (manufactured by Sigma-Aldrich Co., LLC.) was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-rabbit antibody diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing antibodies showing high absorbance values were selected.

The selected hybridomas were seeded to a 96-well plate at 0.5 cells per well and were cultured. After one week, hybridomas forming single colonies were observed in the wells. The cells in the wells were further cultured, and hybridomas were selected using, as an index, the reactivity of the antibodies produced by the cloned hybridomas to a CAPRIN-1 protein. A 1 μg/mL solution of the CAPRIN-1 protein was added to a 96-well plate at 100 μL per well, followed by being left to stand at 4° C. for 18 hours. Each well was washed with PBS-T three times, and 400 μL of a 0.5% BSA solution was added to each well, followed by being left to stand at room temperature for 3 hours. The solution was removed, and each well was washed with 400 μL of PBS-T three times, and 100 μL of the hybridoma culture supernatant prepared above was added to each well, followed by being left to stand at room temperature for 2 hours. Each well was washed with PBS-T three times, and 100 μL of a HRP-labeled anti-rabbit IgG antibody diluted by 5000-fold with PBS was added to each well, followed by being left to stand at room temperature for 1 hour. Each well was washed with PBS-T three times, and 100 μL of a TMB substrate solution (manufactured by Thermo Fisher Scientific K.K.) was added to each well, followed by being left to stand for 15 to 30 minutes for color reaction. After the coloring, 100 μL of 1 N sulfuric acid was added to each well to stop the reaction. The absorbance was measured at 450 nm and 595 nm with an absorption spectrometer. As a result, several hybridomas producing monoclonal antibodies reactive to the CAPRIN-1 protein were obtained.

Subsequently, monoclonal antibodies reactive to the cell surface of cancer cells expressing CAPRIN-1 were selected from the rabbit monoclonal antibodies reactive to the CAPRIN-1 protein. Specifically, $2\times10^5$ cells of human breast cancer cell line MDA-MB-231V and of human lung cancer cell line QG56 were centrifuged with a 1.5-mL micro centrifugation tube. To the cells was added 100 μL of the culture supernatant of the above-described hybridomas, followed by being left to stand on ice for 1 hour. After washing with PBS, to the cells was added a FITC-labeled anti-rabbit IgG (H+L) antibody or Alexa488-labeled anti-rabbit IgG (H+L) diluted by 100-fold with PBS (−) containing 0.05% FBS, followed by being left to stand on ice for 1 hour. After washing with PBS, the fluorescence intensity was measured with FACS Calibur available from Becton, Dickinson and Company. Separately, the same procedure as in above was performed using a hybridoma culturing medium to prepare a negative control sample. As a result, one rabbit anti-CAPRIN-1 monoclonal antibody (rabbit anti-CAPRIN-1 monoclonal antibody #1) showing higher fluorescence intensity compared to the negative control, i.e., reacting with the cell surface of cancer cell lines MDA-MB-231 and QG56 expressing CAPRIN-1 was selected.

Subsequently, the CAPRIN-1 epitope recognized by the selected rabbit anti-CAPRIN-1 monoclonal antibody #1 was identified. Candidate peptides (93 peptides) each consisting of 12 to 16 amino acids of the amino acid sequence of the human CAPRIN-1 protein were synthesized and were each dissolved at a concentration of 1 mg/mL in DMSO. Each peptide was dissolved at a concentration of 30 μg/mL in a 0.1 M sodium carbonate buffer (pH 9.6). The solution was added to a 96-well plate (manufactured by Nunc, Product No. 436006) at 100 μL per well, followed by being left to stand at 4° C. overnight. The solution was removed, and 200 μL of 10 mM ethanolamine/0.1 M sodium carbonate buffer (pH 9.6) was added to each well, followed by being left to stand at room temperature for 1 hour. The solution was removed, and each well was washed with PBS containing 0.5% Tween 20 (PBST) twice to prepare a peptide-immobilized plate. For confirmation, this plate was also provided with a well to which the CAPRIN-1 protein was immobilized in accordance with the method described above. Rabbit anti-CAPRIN-1 monoclonal antibody #1 purified to a concentration of 0.1 ug/mL by a usual method was added to the plate at an amount of 50 μL per well, followed by shaking at room temperature for 1 hour. The solution was removed, and each well was washed with PBST three times. Subsequently, 50 μL of a secondary antibody solution containing a HRP-labeled anti-rabbit IgG antibody diluted by 3000- to 4000-fold with PBST was added to each well. The solution was removed, and each well was washed with PBST six times. Color reaction was performed by adding 100 μL of a TMB substrate solution (manufactured by Thermo Fisher Scientific K.K.) to each well and leaving the mixture to stand for 15 to 30 minutes. After the coloring, 100 μL of 1 N sulfuric acid was added to each well to stop the reaction. The absorbance was measured at 450 nm and 595 nm with an absorption spectrometer. As a result, rabbit anti-CAPRIN-1 monoclonal antibody, rabbit anti-CAPRIN-1 monoclonal antibody #1 was reactive to only the polypeptides comprising the amino acid sequence set forth in SEQ ID NO: 430 in 93 peptides synthesized as partial peptides of CAPRIN-1 and was not reactive to other polypeptides. In addition, rabbit anti-CAPRIN-1 monoclonal antibody #1 was specifically reactive to the CAPRIN-1 protein. This result remonstrated that an epitope for rabbit anti-CAPRIN-1 monoclonal antibody #1 is contained in the polypeptide set forth in SEQ ID NO: 430.

Subsequently, from rabbit anti-CAPRIN-1 monoclonal antibody #1 prepared above, an amplified fragment of the gene encoding the variable domain was obtained in accordance with the method described in example 5 of WO2010/016526, and the gene sequence and the amino acid sequence were analyzed. Specifically, mRNA was extracted from the hybridoma producing rabbit anti-CAPRIN-1 monoclonal antibody #1, and the genes of the heavy-chain variable (VH) domain and the light-chain variable (VL) domain of the antibody were obtained by RT-PCR using primers specific to the rabbit variable domain sequences. In order to determine the sequence, the genes were cloned into pCR2.1 vectors (manufactured by life technologies). The gene sequences of the VH domain and the VL domain in each plasmid prepared by cloning were determined using M13 forward primer and M13 reverse primer with a fluorescence sequencer.

The results demonstrated that the resulting rabbit anti-CAPRIN-1 monoclonal antibody #1 comprises a heavy chain variable domain set forth in SEQ ID NO: 359 in which CDRs 1 to 3 consist of amino acid sequences set forth in SEQ ID NOs: 351, 352, and 353, respectively, and a light chain variable domain set forth in SEQ ID NO: 361 in which CDRs 1 to 3 consist of amino acid sequences set forth in SEQ ID NOs: 354, 355, and 356, respectively.

(2) Production of Human-Rabbit Chimeric Anti-CAPRIN-1 Antibody #1

The gene set forth in SEQ ID NO: 358 for expressing the heavy chain variable domain of the rabbit anti-CAPRIN-1 monoclonal antibody #1 prepared above and the gene set forth in SEQ ID NO: 360 for expressing the light chain variable domain were respectively inserted into a mammalian cell expression vector containing human $IgG_1$ heavy chain constant domain and a mammalian cell expression vector containing human $IgG_1$ light chain constant domain. A culture supernatant containing human-rabbit chimeric anti-CAPRIN-1 antibody #1 humanized by introducing the produced two recombinant expression vectors into mammalian cells in accordance with a usual method was obtained.

(3) Antigen Specificity, Reactivity with Cancer Cells, and Antitumor Activity of Human-Rabbit Chimeric Anti-CAPRIN-1 Antibody #1

Human-rabbit chimeric anti-CAPRIN-1 antibody #1 contained in the culture supernatant prepared in the above (2) was purified using Hitrap Protein A Sepharose FF (manufactured by GE Healthcare Bio-Sciences) in accordance with a usual method, substituted with PBS (−), and filtered through a filter of 0.22 μm (manufactured by Millipore Corporation), and was used for investigation of the antigen specificity, reactivity with cancer cells, and antitumor effect.

First, as in the above (1), the reaction specificity of human-rabbit chimeric anti-CAPRIN-1 antibody #1 on the CAPRIN-1 protein and a polypeptide comprising the amino acid sequence set forth in SEQ ID NO: 430, which is the epitope for rabbit anti-CAPRIN-1 monoclonal antibody #1, was investigated. The results demonstrated that human-rabbit chimeric anti-CAPRIN-1 antibody #1 had reaction specificity on the CAPRIN-1 protein and the polypeptide comprising the amino acid sequence set forth in SEQ ID NO: 430, as in rabbit anti-CAPRIN-1 monoclonal antibody #1.

Next, the reactivity of human-rabbit chimeric anti-CAPRIN-1 antibody #1 to the CAPRIN-1 protein on the cell surface of a gallbladder cancer cell line TGBC14TKB was investigated. $1\times10^6$ cells of each cell line were centrifuged with a. 1.5-mL micro centrifugation tube. To the cells was added the cell culture supernatant (100 μL) containing the antibody, followed by being left to stand on ice for 1 hour. After washing with PBS, to the cells was added an Alexa488-labeled goat anti-human IgG (H+L) antibody (manufactured by life technologies) diluted by 100-fold with PBS containing 0.1% FBS, followed by being left to stand at 4° C. for 60 minutes. After washing with PBS (−), the fluorescence intensity was measured with FACS Calibur available from Becton, Dickinson and Company. Separately, the cells were reacted with only the secondary antibody as a negative control. As a result, human-rabbit chimeric anti-CAPRIN-1 antibody #1 showed higher reactivity by 30% or more higher fluorescence intensity compared to the negative control. This demonstrated that a part of the CAPRIN-1 protein set forth in SEQ ID NO: 430 was expressed on the cell surface of the human cancer cell lines. The rate of increase in the fluorescence intensity is represented by the rate of increase in the mean fluorescence intensity (MFI value) in each cell and is calculated by the following calculation formula:

Rate of increase in mean fluorescence intensity(rate of increase in fluorescence intensity)(%)=((MFI value of cells reacted with anti-human CAPRIN-1 antibody)−(MFI value of control))/(MFI value of control)×100.

Furthermore, the antitumor activity of human-rabbit chimeric anti-CAPRIN-1 antibody #1 on a gallbladder cancer cell line TGBC14TKB was evaluated. $1\times10^6$ cells of the gallbladder cancer cell line were collected in a 50-mL micro centrifugation tube and were incubated with 100 μCi of $^{51}$chromium at 37° C. for 2 hours. Subsequently, the cells were washed with RPMI1640 medium containing 10% FBS three times to prepare target cells. Purified human-rabbit chimeric anti-CAPRIN-1 antibody #1 was added to a 96-well V-bottom plate at a final concentration of 5 μg/mL. Subsequently, $2\times10^5$ human NK cells separated from human peripheral blood lympocytes prepared in accordance with a usual method were added to each well. $2\times10^3$ target cells were mixed with the antibody in each well of the 96-well V-bottom plate, followed by culturing at 37° C. in 5% $CO_2$ for 4 hours. After the culturing, the amount of $^{51}$chromium secreted from the impaired tumor cells into the culture supernatant was measured to calculate the cytotoxicity on the gallbladder cancer cells by the anti-CAPRIN-1 antibody. Separately, the reaction was performed using an iso-type control antibody as a negative control. As a result, human-rabbit chimeric anti-CAPRIN-1 antibody #1 showed antitumor activity of 25% or more on gallbladder cancer cells, whereas the cytotoxicity in the case of using the iso-type control antibody was less than 5% on gallbladder cancer cells. These results revealed that the antibody against the peptide derived from CAPRIN-1 set forth in SEQ ID NO: 430, human-rabbit chimeric anti-CAPRIN-1 antibody #1, shows antitumor activity on the gallbladder cancer cells expressing CAPRIN-1 through ADCC activity.

Example 14

Production of Humanized Anti-CAPRIN-1 Antibodies #1 to #3

A humanized antibody of rabbit anti-CAPRIN-1 antibody was produced. Based on the information of the amino acid sequence of the heavy chain variable domain of rabbit anti-CAPRIN-1 monoclonal antibody #1, the nucleotide sequence set forth in SEQ ID NO: 362 was designed such that CDRs 1 to 3 in the heavy chain variable domain consist of the amino acid sequences set forth in SEQ ID NOs: 351, 352, and 357, respectively, and that the framework region can express a heavy chain variable domain (SEQ ID NO: 363) comprising the sequence of a human antibody. The nucleotide sequence was inserted into a mammalian cell expression vector containing the heavy chain constant domain of human $IgG_1$. Similarly, the nucleotide sequence set forth in SEQ ID NO: 364 was designed such that CDRs 1 to 3 in the light chain variable domain consist of the amino acid sequences set forth in SEQ ID NOs: 354, 355, and 356, respectively, and that the framework region can express a light chain variable domain (SEQ ID NO: 365) comprising the sequence of a human antibody. The nucleotide sequence was inserted into a mammalian cell expression vector containing the light chain constant domain of human $IgG_1$. The two recombinant expression vectors were introduced into mammalian cells in accordance with a usual method to obtain a culture supernatant containing humanized anti-CAPRIN-1 antibody #1.

In addition, based on the information of the amino acid sequence of the heavy chain variable domain of rabbit anti-CAPRIN-1 monoclonal antibody #1, the nucleotide sequence set forth in SEQ ID NO: 367 was designed such that CDRs 1 to 3 consist of the amino acid sequences set forth in SEQ ID NOs: 351, 352, and 353, respectively, and that the framework region can express a heavy chain variable domain (SEQ ID NO: 368) comprising the sequence of a human antibody. The nucleotide sequence was inserted into a mammalian cell expression vector containing the heavy chain constant domain of human $IgG_1$. Similarly, the nucleotide sequence set forth in SEQ ID NO: 369 was designed such that CDRs 1 to 3 in the light chain variable domain consist of the amino acid sequences set forth in SEQ ID NOs: 354, 355, and 356, respectively, and that the framework region can express a light chain variable domain (SEQ ID NO: 370) comprising the sequence of a human antibody. The nucleotide sequence was inserted into a mammalian cell expression vector containing the light chain constant domain of human $IgG_1$. The two recombinant expression vectors were introduced into mammalian cells in accordance with a usual method to obtain a culture supernatant containing humanized anti-CAPRIN-1 antibody #2.

In addition, based on the information of the amino acid sequence of the heavy chain variable domain of rabbit anti-CAPRIN-1 monoclonal antibody #1, the nucleotide sequence set forth in SEQ ID NO: 371 was designed such that CDRs 1 to 3 consist of the amino acid sequences set forth in SEQ ID NOs: 351, 352, and 353, respectively, and that the framework region can express a heavy chain variable domain (SEQ ID NO: 372) comprising the sequence of a human antibody. The nucleotide sequence was inserted into a mammalian cell expression vector containing the heavy chain constant domain of human $IgG_1$. Similarly, the nucleotide sequence set forth in SEQ ID NO: 369 was designed such that CDRs 1 to 3 in the light chain variable domain consist of the amino acid sequences set forth in SEQ ID NOs: 354, 355, and 356, respectively, and that the framework region can express a light chain variable domain (SEQ ID NO: 370) comprising the sequence of a human antibody. The nucleotide sequence was inserted into a mammalian cell expression vector containing the light chain constant domain of human $IgG_1$. The two recombinant expression vectors were introduced into mammalian cells in accordance with a usual method to obtain a culture supernatant containing humanized anti-CAPRIN-1 antibody #3.

Antigen Specificity, Reactivity with Cancer Cells, and Antitumor Activity of Humanized Anti-CAPRIN-1 Antibody The reactivity with CAPRIN-1 of the three humanized anti-CAPRIN-1 antibodies #1 to #3 prepared above was evaluated. As a result, the reactivity of these antibodies with the CAPRIN-1 protein, the epitope peptide set forth in SEQ ID NO: 430, and gallbladder cancer cell lines was equivalent to that of human-rabbit chimeric anti-CAPRIN-1 monoclonal antibody #1. The antitumor activity on gallbladder cancer cell lines of these three humanized anti-CAPRIN-1 antibodies was also evaluated. The results demonstrated that the antitumor activity of every antibody was equivalent to that of the human-rabbit chimeric anti-CAPRIN-1 monoclonal antibody #1.

Example 15

Expression Analysis of CAPRIN-1 Protein on Gallbladder Cancer Cell Surface Using Mouse Anti-CAPRIN-1 Monoclonal Antibodies #23 to #29

As in Example 10, a human gallbladder cancer cell line TGBC14TKB was investigated whether or not a CAPRIN-1 protein is expressed on the cell surface using anti-CAPRIN-1 monoclonal antibody #23 comprising a heavy chain variable domain set forth in SEQ ID NO: 279 comprising complementarity determining regions (CDR1, CDR2, and CDR3) consisting of amino acid sequences set forth in SEQ ID NOs: 276, 277, and 278, respectively and a light chain variable domain set forth in SEQ ID NO: 283 comprising complementarity determining regions (CDR1, CDR2, and CDR3) consisting of amino acid sequences set forth in SEQ ID NOs: 280, 281, and 282, respectively prepared in WO/2013/018894; anti-CAPRIN-1 monoclonal antibody #24 comprising a heavy chain variable domain set forth in SEQ ID NO: 279 comprising complementarity determining regions (CDR1, CDR2, and CDR3) consisting of amino acid sequences set forth in SEQ ID NOs: 276, 277, and 278, respectively and a light chain variable domain set forth in SEQ ID NO: 289 comprising complementarity determining regions (CDR1, CDR2, and CDR3) consisting of amino acid sequences set forth in SEQ ID NOs: 286, 287, and 288, respectively; anti-CAPRIN-1 monoclonal antibody #25 comprising a heavy chain variable domain set forth in SEQ ID NO: 294 comprising complementarity determining regions (CDR1, CDR2, and CDR3) consisting of amino acid sequences set forth in SEQ ID NOs: 291, 292, and 293, respectively and a light chain variable domain set forth in SEQ ID NO: 298 comprising complementarity determining regions (CDR1, CDR2, and CDR3) consisting of amino acid sequences set forth in SEQ ID NOs: 295, 296, and 297, respectively; anti-CAPRIN-1 monoclonal antibody #26 comprising a heavy chain variable domain set forth in SEQ ID NO: 304 comprising complementarity determining regions (CDR1, CDR2, and CDR3) consisting of amino acid sequences set forth in SEQ ID NOs: 301, 302, and 303, respectively and a light chain variable domain set forth in SEQ ID NO: 308 comprising complementarity determining regions (CDR1, CDR2, and CDR3) consisting of amino acid sequences set forth in SEQ ID NOs: 305, 306, and 307, respectively prepared in WO/2013/018894; anti-CAPRIN-1 monoclonal antibody #27 comprising a heavy chain variable domain set forth in SEQ ID NO: 314 comprising complementarity determining regions (CDR1, CDR2, and CDR3) consisting of amino acid sequences set forth in SEQ ID NOs: 311, 312, and 313, respectively and a light chain variable domain set forth in SEQ ID NO: 318 comprising complementarity determining regions (CDR1, CDR2, and CDR3) consisting of amino acid sequences set forth in SEQ ID NOs: 315, 316, and 317, respectively prepared in WO/2013/018891; anti-CAPRIN-1 monoclonal antibody #28 comprising a heavy chain variable domain set forth in SEQ ID NO: 324 comprising complementarity determining regions (CDR1, CDR2, and CDR3) consisting of amino acid sequences set forth in SEQ ID NOs: 321, 322, and 323, respectively and a light chain variable domain set forth in SEQ ID NO: 328 comprising complementarity determining regions (CDR1, CDR2, and CDR3) consisting of amino acid sequences set forth in SEQ ID NOs: 325, 326, and 327, respectively prepared in WO/2013/018889; and anti-CAPRIN-1 monoclonal antibody #29 comprising a heavy chain variable domain set forth in SEQ ID NO: 334 comprising complementarity determining regions (CDR1, CDR2, and CDR3) consisting of amino acid sequences set forth in SEQ ID NOs: 331, 332, and 333, respectively and a light chain variable domain set forth in SEQ ID NO: 338 comprising complementarity determining regions (CDR1, CDR2, and CDR3) consisting of amino acid sequences set forth in SEQ ID NOs: 335, 336, and 337, respectively prepared in WO/2013/018883. As a result, reactivity with gallbladder cancer cell lines equivalent to those of mouse anti-CAPRIN-1 monoclonal antibodies #30 to #36 in Example 10 was observed.

Example 16

Antitumor Activity on Gallbladder Cancer Cells of Human-Mouse Chimeric Anti-CAPRIN-1 Antibodies #23 to #29

Cell lines stably producing human-mouse chimeric anti-CAPRIN-1 antibodies #23 to #29 respectively having the variable domains of mouse anti-CAPRIN-1 antibodies #23 to #29 described in Example 15 were produced by a method similar to that in Example 11 to obtain culture supernatants containing human-mouse chimeric anti-CAPRIN-1 antibodies #23 to #29. The antibodies purified from the supernatants by a usual method were used for investigation of antitumor activity on gallbladder cancer cells. In order to evaluate the intensity of cytotoxicity on gallbladder cancer cells expressing CAPRIN-1, ADCC activity was measured using human-mouse chimeric anti-CAPRIN-1 antibodies #23 to #29. The ADCC activity on a gallbladder cancer cell line TGBC14TKB was evaluated by a method similar to that in Example 12. As a result, every human-mouse chimeric anti-CAPRIN-1 antibody showed 20% or more activity on the gallbladder cancer cell line TGBC14TKB, whereas the activity of a human $IgG_1$ antibody used as the negative control was less than 5% on gallbladder cancer cells.

INDUSTRIAL APPLICABILITY

The antibody of the present invention is useful for treatment and/or prevention of gallbladder cancer.

All publications, patents, and patent applications cited in the present specification are hereby incorporated by reference in their entirety.

The invention claimed is:

1. A method of treating CAPRIN-1 expressing gallbladder cancer, comprising:

administering a pharmaceutical composition to a subject having CAPRIN-1 expressing gallbladder cancer, said pharmaceutical composition comprising, as an active ingredient, an antibody or a fragment thereof having immunological reactivity with a CAPRIN-1 protein expressed on the surface of a gallbladder tumor cell that comprises the amino acid sequence set forth in any of even sequence numbers from SEQ ID NOs: 2 to 30.

2. The method according to claim 1, wherein the antibody or fragment thereof binds a fragment of the CAPRIN-1 protein that comprises at least seven consecutive amino acid residues in the region of amino acid residue positions from 233 to 343, amino acid residue positions from 512 to the C-terminal, or amino acid residue positions from 50 to 98 of the amino acid sequence set forth in any of even sequence numbers from SEQ ID NOs: 2 to 30 excluding SEQ ID NOs: 6 and 18.

3. The method according to claim 1, wherein the antibody or fragment thereof binds a fragment of the CAPRIN-1 protein that comprises at least seven consecutive amino acid residues in an amino acid sequence set forth in SEQ ID NO: 267, SEQ ID NO: 429, SEQ ID NO: 428, SEQ ID NO: 273, SEQ ID NO: 266, SEQ ID NO: 270, SEQ ID NO: 272, SEQ ID NO: 269, SEQ ID NO: 430, SEQ ID NO: 431, or SEQ ID NO: 432.

4. The method according to claim 1, wherein the antibody is a monoclonal antibody or a polyclonal antibody.

5. The method according to claim 1, wherein the antibody is a human antibody, a humanized antibody, a chimeric antibody, a single-chain antibody, or a multispecific antibody.

6. The method according to claim 1, wherein the antibody or a fragment thereof is a monoclonal antibody or fragment thereof that binds CAPRIN-1 and is selected from the group consisting of (a) to (ao):

(a) an antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively;

(b) an antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively;

(c) an antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively;

(d) an antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively;

(e) an antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively;

(f) an antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively;

(g) an antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively;

(h) an antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively;

(i) an antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively;

(j) an antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively;

(k) an antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively;

(l) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively;

(m) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively;

(n) an antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively;

(o) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively;

(p) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively;

(q) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively;

(r) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively;

(s) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively;

(t) an antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively;

(u) an antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively;

(v) an antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively;

(w) an antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively;

(x) an antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively;

(y) an antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively;

(z) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 280, 281, and 282, respectively;

(aa) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively;

(ab) an antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively;

(ac) an antibody comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively;

(ad) an antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively;

(ae) an antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively;

(af) an antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively;

(ag) an antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively;

(ah) an antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively;

(ai) an antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively;

(aj) an antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively;

(ak) an antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively;

(al) an antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively;

(am) an antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively;

(an) an antibody comprising a heavy chain variable domain comprising complementarity determining regions (CDR1, CDR2, and CDR3) consisting of amino acid sequences set forth in SEQ ID NOs: 408, 409, respectively and 410 and a light chain variable domain comprising a light chain variable domain comprising complementarity determining regions (CDR1, CDR2, and CDR3) consisting of amino acid sequences set forth in SEQ ID NOs: 412, 413, and 414, respectively; and (ao) an antibody comprising a heavy chain variable domain comprising complementarity determining regions (CDR1, CDR2, and CDR3) consisting of amino acid sequences set forth in SEQ ID NOs: 418, 419, and 420, respectively and a light chain variable domain comprising a light chain variable domain comprising complementarity determining regions (CDR1, CDR2, and CDR3) consisting of amino acid sequences set forth in SEQ ID NOs: 422, 423, and 424, respectively.

7. The method according to claim 1, wherein the antibody or a fragment thereof is conjugated to an antitumor agent.

8. The method according to claim 1, wherein the pharmaceutical composition is a combination pharmaceutical agent further comprising a pharmaceutical composition comprising an antitumor agent.

9. The method according to claim 2, wherein the antibody or fragment thereof binds a fragment of the CAPRIN-1 protein that comprises at least seven consecutive amino acid residues in an amino acid sequence set forth in SEQ ID NO: 267, SEQ ID NO: 429, SEQ ID NO: 428, SEQ ID NO: 273, SEQ ID NO: 266, SEQ ID NO: 270, SEQ ID NO: 272, SEQ ID NO: 269, SEQ ID NO: 430, SEQ ID NO: 431, or SEQ ID NO: 432.

10. The method according to claim 2, wherein the antibody is a monoclonal antibody or a polyclonal antibody.

11. The method according to claim 3, wherein the antibody is a monoclonal antibody or a polyclonal antibody.

12. The method according to claim 2, wherein the antibody is a human antibody, a humanized antibody, a chimeric antibody, a single-chain antibody, or a multispecific antibody.

13. The method according to claim 3, wherein the antibody is a human antibody, a humanized antibody, a chimeric antibody, a single-chain antibody, or a multispecific antibody.

14. The method according to claim 4, wherein the antibody is a human antibody, a humanized antibody, a chimeric antibody, a single-chain antibody, or a multispecific antibody.

15. The method according claim 2, wherein the antibody or a fragment thereof is a monoclonal antibody or fragment thereof that binds CAPRIN-1 and is selected from the group consisting of (a) to (ao):

(a) an antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively;

(b) an antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively;

(c) an antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively;

(d) an antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively;

(e) an antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively;

(f) an antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively;

(g) an antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively;

(h) an antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively;

(i) an antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively;

(j) an antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively;

(k) an antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively;

(l) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively;

(m) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively;

(n) an antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively;

(o) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively;

(p) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively;

(q) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively;

(r) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively;

(s) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively;

(t) an antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively;

(u) an antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively;

(v) an antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively;

(w) an antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively;

(x) an antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively;

(y) an antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively;

(z) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 280, 281, and 282, respectively;

(aa) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively;

(ab) an antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively;

(ac) an antibody comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively;

(ad) an antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively;

(ae) an antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively;

(af) an antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively;

(ag) an antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively;

(ah) an antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively;

(ai) an antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively;

(aj) an antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively;

(ak) an antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively;

(al) an antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively;

(am) an antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively;

(an) an antibody comprising a heavy chain variable domain comprising complementarity determining regions (CDR1, CDR2, and CDR3) consisting of amino acid sequences set forth in SEQ ID NOs: 408, 409, respectively and 410 and a light chain variable domain comprising a light chain variable domain comprising complementarity determining regions (CDR1, CDR2, and CDR3) consisting of amino acid sequences set forth in SEQ ID NOs: 412, 413, and 414, respectively; and (ao) an antibody comprising a heavy chain variable domain comprising complementarity determining regions (CDR1, CDR2, and CDR3) consisting of amino acid sequences set forth in SEQ ID NOs: 418, 419, and 420, respectively and a light chain variable domain comprising a light chain variable domain comprising complementarity determining regions (CDR1, CDR2, and CDR3) consisting of amino acid sequences set forth in SEQ ID NOs: 422, 423, and 424, respectively.

16. The method according claim 3, wherein the antibody or a fragment thereof is a monoclonal antibody or fragment thereof that binds CAPRIN-1 and is selected from the group consisting of (a) to (ao):

(a) an antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively;

(b) an antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively;

(c) an antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively;

(d) an antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively;

(e) an antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively;

(f) an antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively;

(g) an antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively;

(h) an antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively;

(i) an antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively;

(j) an antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively;

(k) an antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively;

(l) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively;

(m) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively;

(n) an antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively;

(o) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively;

(p) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively;

(q) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively;

(r) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively;

(s) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively;

(t) an antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively;

(u) an antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively;

(v) an antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively;

(w) an antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively;

(x) an antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively;

(y) an antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively;

(z) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 280, 281, and 282, respectively;

(aa) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively;

(ab) an antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively;

(ac) an antibody comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively;

(ad) an antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively;

(ae) an antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively;

(af) an antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively;

(ag) an antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively;

(ah) an antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively;

(ai) an antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively;

(aj) an antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively;

(ak) an antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389;

(al) an antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively;

(am) an antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively;

(an) an antibody comprising a heavy chain variable domain comprising complementarity determining regions (CDR1, CDR2, and CDR3) consisting of amino acid sequences set forth in SEQ ID NOs: 408, 409, respectively and 410 and a light chain variable domain comprising a light chain variable domain comprising complementarity determining regions (CDR1, CDR2, and CDR3) consisting of amino acid sequences set forth in SEQ ID NOs: 412, 413, and 414, respectively; and (ao) an antibody comprising a heavy chain variable domain comprising complementarity determining regions (CDR1, CDR2, and CDR3) consisting of amino acid sequences set forth in SEQ ID NOs: 418, 419, and 420, respectively and a light chain variable domain comprising a light chain variable domain comprising complementarity determining regions (CDR1, CDR2, and CDR3) consisting of amino acid sequences set forth in SEQ ID NOs: 422, 423, and 424, respectively.

17. The method according claim 4, wherein the antibody or a fragment thereof is a monoclonal antibody or fragment thereof that binds CAPRIN-1 and is selected from the group consisting of (a) to (ao):

(a) an antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively;

(b) an antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively;

(c) an antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively;

(d) an antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively;

(e) an antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively;

(f) an antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively;

(g) an antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively;

(h) an antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively;

(i) an antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively;

(j) an antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively;

(k) an antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively;

(l) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively;

(m) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively;

(n) an antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively;

(o) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively;

(p) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively;

(q) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively;

(r) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively;

(s) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively;

(t) an antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively;

(u) an antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively;

(v) an antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively;

(w) an antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively;

(x) an antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively;

(y) an antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively;

(z) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 280, 281, and 282, respectively;

(aa) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively;

(ab) an antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively;

(ac) an antibody comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively;

(ad) an antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively;

(ae) an antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively;

(af) an antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively;

(ag) an antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively;

(ah) an antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively;

(ai) an antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively;

(aj) an antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively;

(ak) an antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively;

(al) an antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively;

(am) an antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively;

(an) an antibody comprising a heavy chain variable domain comprising complementarity determining regions (CDR1, CDR2, and CDR3) consisting of amino acid sequences set forth in SEQ ID NOs: 408, 409, respectively and 410 and a light chain variable domain comprising a light chain variable domain comprising complementarity determining regions (CDR1, CDR2, and CDR3) consisting of amino acid sequences set forth in SEQ ID NOs: 412, 413, and 414, respectively; and (ao) an antibody comprising a heavy chain variable domain comprising complementarity determining regions (CDR1, CDR2, and CDR3) consisting of amino acid sequences set forth in SEQ ID NOs: 418, 419, and 420, respectively and a light chain variable domain comprising a light chain variable domain comprising complementarity determining regions (CDR1, CDR2, and CDR3) consisting of amino acid sequences set forth in SEQ ID NOs: 422, 423, and 424, respectively.

18. The method according claim 5, wherein the antibody or a fragment thereof is a monoclonal antibody or fragment thereof that binds CAPRIN-1 and is selected from the group consisting of (a) to (ao):

(a) an antibody comprising a heavy chain variable domain comprising complementarity determining regions (CDR1, CDR2, and CDR3) consisting of amino acid sequences set forth in SEQ ID NOs: 37, 38, and 39, respectively and a light chain variable domain comprising complementarity determining regions (CDR1, CDR2, and CDR3) consisting of amino acid sequences set forth in SEQ ID NOs: 41, 42, and 43, respectively;

(b) an antibody comprising a heavy chain variable domain comprising complementarity determining regions (CDR1, CDR2, and CDR3) consisting of amino acid sequences set forth in SEQ ID NOs: 47, 48, and 49, respectively and a light chain variable domain comprising complementarity determining regions (CDR1, CDR2, and CDR3) consisting of amino acid sequences set forth in SEQ ID NOs: 51, 52, and 53, respectively;

(c) an antibody comprising a heavy chain variable domain comprising complementarity determining regions (CDR1, CDR2, and CDR3) consisting of amino acid sequences set forth in SEQ ID NOs: 57, 58, and 59, respectively and a light chain variable domain comprising complementarity determining regions (CDR1, CDR2, and CDR3) consisting of amino acid sequences set forth in SEQ ID NOs: 61, 62, and 63, respectively;

(d) an antibody comprising a heavy chain variable domain comprising complementarity determining regions (CDR1, CDR2, and CDR3) consisting of amino acid sequences set forth in SEQ ID NOs: 67, 68, and 69, respectively and a light chain variable domain comprising complementarity determining regions (CDR1, CDR2, and CDR3) consisting of amino acid sequences set forth in SEQ ID NOs: 71, 72, and 73, respectively;

(e) an antibody comprising a heavy chain variable domain comprising complementarity determining regions (CDR1, CDR2, and CDR3) consisting of amino acid sequences set forth in SEQ ID NOs: 77, 78, and 79, respectively and a light chain variable domain comprising complementarity determining regions (CDR1, CDR2, and CDR3) consisting of amino acid sequences set forth in SEQ ID NOs: 81, 82, and 83, respectively;

(f) an antibody comprising a heavy chain variable domain comprising complementarity determining regions (CDR1, CDR2, and CDR3) consisting of amino acid sequences set forth in SEQ ID NOs: 87, 88, and 89, respectively and a light chain variable domain comprising complementarity determining regions (CDR1, CDR2, and CDR3) consisting of amino acid sequences set forth in SEQ ID NOs: 91, 92, and 93, respectively;

(g) an antibody comprising a heavy chain variable domain comprising complementarity determining regions (CDR1, CDR2, and CDR3) consisting of amino acid sequences set forth in SEQ ID NOs: 97, 98, and 99, respectively and a light chain variable domain comprising complementarity determining regions (CDR1, CDR2, and CDR3) consisting of amino acid sequences set forth in SEQ ID NOs: 101, 102, and 103, respectively;

(h) an antibody comprising a heavy chain variable domain comprising complementarity determining regions (CDR1, CDR2, and CDR3) consisting of amino acid sequences set forth in SEQ ID NOs: 107, 108, and 109, respectively and a light chain variable domain comprising complementarity determining regions (CDR1, CDR2, and CDR3) consisting of amino acid sequences set forth in SEQ ID NOs: 111, 112, and 113, respectively;

(i) an antibody comprising a heavy chain variable domain comprising complementarity determining regions (CDR1, CDR2, and CDR3) consisting of amino acid sequences set forth in SEQ ID NOs: 117, 118, and 119, respectively and a light chain variable domain comprising complementarity determining regions (CDR1, CDR2, and CDR3) consisting of amino acid sequences set forth in SEQ ID NOs: 121, 122, and 123, respectively;

(j) an antibody comprising a heavy chain variable domain comprising complementarity determining regions (CDR1, CDR2, and CDR3) consisting of amino acid sequences set forth in SEQ ID NOs: 127, 128, and 129, respectively and a light chain variable domain comprising complementarity determining regions (CDR1, CDR2, and CDR3) consisting of amino acid sequences set forth in SEQ ID NOs: 121, 122, and 123, respectively;

(k) an antibody comprising a heavy chain variable domain comprising complementarity determining regions (CDR1, CDR2, and CDR3) consisting of amino acid sequences set forth in SEQ ID NOs: 132, 133, and 134, respectively and a light chain variable domain comprising complementarity determining regions (CDR1, CDR2, and CDR3) consisting of amino acid sequences set forth in SEQ ID NOs: 136, 137, and 138, respectively;

(l) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 146, 147, and 148, respectively;

(m) an antibody comprising a heavy chain variable domain comprising complementarity determining regions (CDR1, CDR2, and CDR3) consisting of amino acid sequences set forth in SEQ ID NOs: 142, 143, and 144, respectively and a light chain variable domain comprising complementarity determining regions (CDR1, CDR2, and CDR3) consisting of amino acid sequences set forth in SEQ ID NOs: 152, 153, and 154, respectively;

(n) an antibody comprising a heavy chain variable domain comprising complementarity determining regions (CDR1, CDR2, and CDR3) consisting of amino acid sequences set forth in SEQ ID NOs: 157, 158, and 159, respectively and a light chain variable domain comprising complementarity determining regions (CDR1, CDR2, and CDR3) consisting of amino acid sequences set forth in SEQ ID NOs: 161, 162, and 163, respectively;

(o) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 171, 172, and 173, respectively;

(p) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 177, 178, and 179, respectively;

(q) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 182, 183, and 184, respectively;

(r) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 187, 188, and 189, respectively;

(s) an antibody comprising a heavy chain variable domain comprising complementarity determining regions (CDR1, CDR2, and CDR3) consisting of amino acid sequences set forth in SEQ ID NOs: 167, 168, and 169, respectively and a light chain variable domain comprising complementarity determining regions (CDR1, CDR2, and CDR3) consisting of amino acid sequences set forth in SEQ ID NOs: 192, 193, and 194, respectively;

(t) an antibody comprising a heavy chain variable domain comprising complementarity determining regions (CDR1, CDR2, and CDR3) consisting of amino acid sequences set forth in SEQ ID NOs: 197, 198, and 199, respectively and a light chain variable domain comprising complementarity determining regions (CDR1, CDR2, and CDR3) consisting of amino acid sequences set forth in SEQ ID NOs: 201, 202, and 203, respectively;

(u) an antibody comprising a heavy chain variable domain comprising complementarity determining regions (CDR1, CDR2, and CDR3) consisting of amino acid sequences set forth in SEQ ID NOs: 207, 208, and 209, respectively and a light chain variable domain comprising complementarity determining regions (CDR1, CDR2, and CDR3) consisting of amino acid sequences set forth in SEQ ID NOs: 211, 212, and 213, respectively;

(v) an antibody comprising a heavy chain variable domain comprising complementarity determining regions (CDR1, CDR2, and CDR3) consisting of amino acid sequences set forth in SEQ ID NOs: 217, 218, and 219, respectively and a light chain variable domain comprising complementarity determining regions (CDR1, CDR2, and CDR3) consisting of amino acid sequences set forth in SEQ ID NOs: 221, 222, and 223, respectively;

(w) an antibody comprising a heavy chain variable domain comprising complementarity determining regions (CDR1, CDR2, and CDR3) consisting of amino acid sequences set forth in SEQ ID NOs: 227, 228, and 229, respectively and a light chain variable domain comprising complementarity determining regions (CDR1, CDR2, and CDR3) consisting of amino acid sequences set forth in SEQ ID NOs: 231, 232, and 233, respectively;

(x) an antibody comprising a heavy chain variable domain comprising complementarity determining regions (CDR1, CDR2, and CDR3) consisting of amino acid sequences set forth in SEQ ID NOs: 237, 238, and 239, respectively and a light chain variable domain comprising complementarity determining regions (CDR1, CDR2, and CDR3) consisting of amino acid sequences set forth in SEQ ID NOs: 241, 242, and 243, respectively;

(y) an antibody comprising a heavy chain variable domain comprising complementarity determining regions (CDR1, CDR2, and CDR3) consisting of amino acid sequences set forth in SEQ ID NOs: 247, 248, and 249, respectively and a light chain variable domain comprising complementarity determining regions (CDR1, CDR2, and CDR3) consisting of amino acid sequences set forth in SEQ ID NOs: 251, 252, and 253, respectively;

(z) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 280, 281, and 282, respectively;

(aa) an antibody comprising a heavy chain variable domain comprising complementarity determining regions (CDR1, CDR2, and CDR3) consisting of amino acid sequences set forth in SEQ ID NOs: 276, 277, and 278, respectively and a light chain variable domain comprising complementarity determining regions (CDR1, CDR2, and CDR3) consisting of amino acid sequences set forth in SEQ ID NOs: 286, 287, and 288, respectively;

(ab) an antibody comprising a heavy chain variable domain comprising complementarity determining regions (CDR1, CDR2, and CDR3) consisting of amino acid sequences set forth in SEQ ID NOs: 291, 292, and 293, respectively and a light chain variable domain comprising complementarity determining regions (CDR1, CDR2, and CDR3) consisting of amino acid sequences set forth in SEQ ID NOs: 295, 296, and 297, respectively;

(ac) an antibody comprising a heavy chain variable domain comprising complementarity determining regions (CDR1, CDR2, and CDR3) consisting of amino acid sequences set forth in SEQ ID NOs: 301, 302, and 303, respectively and a light chain variable domain comprising complementarity determining regions (CDR1, CDR2, and CDR3) consisting of amino acid sequences set forth in SEQ ID NOs: 305, 306, and 307, respectively;

(ad) an antibody comprising a heavy chain variable domain comprising complementarity determining regions (CDR1, CDR2, and CDR3) consisting of amino acid sequences set forth in SEQ ID NOs: 311, 312, and 313, respectively and a light chain variable domain comprising complementarity determining regions (CDR1, CDR2, and CDR3) consisting of amino acid sequences set forth in SEQ ID NOs: 315, 316, and 317, respectively;

(ae) an antibody comprising a heavy chain variable domain comprising complementarity determining regions (CDR1, CDR2, and CDR3) consisting of amino acid sequences set forth in SEQ ID NOs: 321, 322, and 323, respectively and a light chain variable domain comprising complementarity determining regions (CDR1, CDR2, and CDR3) consisting of amino acid sequences set forth in SEQ ID NOs: 325, 326, and 327, respectively;

(af) an antibody comprising a heavy chain variable domain comprising complementarity determining regions (CDR1, CDR2, and CDR3) consisting of amino acid sequences set forth in SEQ ID NOs: 331, 332, and 333, respectively and a light chain variable domain comprising complementarity determining regions (CDR1, CDR2, and CDR3) consisting of amino acid sequences set forth in SEQ ID NOs: 335, 336, and 337, respectively;

(ag) an antibody comprising a heavy chain variable domain comprising complementarity determining regions (CDR1, CDR2, and CDR3) consisting of amino acid sequences set forth in SEQ ID NOs: 341, 342, and 343, respectively and a light chain variable domain comprising complementarity determining regions (CDR1, CDR2, and CDR3) consisting of amino acid sequences set forth in SEQ ID NOs: 345, 346, and 347, respectively;

(ah) an antibody comprising a heavy chain variable domain comprising complementarity determining regions (CDR1, CDR2, and CDR3) consisting of amino acid sequences set forth in SEQ ID NOs: 351, 352, and 353, respectively and a light chain variable domain comprising complementarity determining regions (CDR1, CDR2, and CDR3) consisting of amino acid sequences set forth in SEQ ID NOs: 354, 355, and 356, respectively;

(ai) an antibody comprising a heavy chain variable domain comprising complementarity determining regions (CDR1, CDR2, and CDR3) consisting of amino acid sequences set forth in SEQ ID NOs: 351, 352, and 357, respectively and a light chain variable domain comprising complementarity determining regions (CDR1, CDR2, and CDR3) consisting of amino acid sequences set forth in SEQ ID NOs: 354, 355, and 356, respectively;

(aj) an antibody comprising a heavy chain variable domain comprising complementarity determining regions (CDR1, CDR2, and CDR3) consisting of amino acid sequences set forth in SEQ ID NOs: 373, 374, and 375, respectively and a light chain variable domain comprising complementarity determining regions (CDR1, CDR2, and CDR3) consisting of amino acid sequences set forth in SEQ ID NOs: 377, 378, and 379, respectively;

(ak) an antibody comprising a heavy chain variable domain comprising complementarity determining regions (CDR1, CDR2, and CDR3) consisting of amino acid sequences set forth in SEQ ID NOs: 383, 384, and 385, respectively and a light chain variable domain comprising complementarity determining regions (CDR1, CDR2, and CDR3) consisting of amino acid sequences set forth in SEQ ID NOs: 387, 388, and 389, respectively;

(al) an antibody comprising a heavy chain variable domain comprising complementarity determining regions (CDR1, CDR2, and CDR3) consisting of amino acid sequences set forth in SEQ ID NOs: 393, 394, and 395, respectively and a light chain variable domain comprising complementarity determining regions (CDR1, CDR2, and CDR3) consisting of amino acid sequences set forth in SEQ ID NOs: 387, 388, and 389, respectively;

(am) an antibody comprising a heavy chain variable domain comprising complementarity determining regions (CDR1, CDR2, and CDR3) consisting of amino acid sequences set forth in SEQ ID NOs: 398, 399, and 400, respectively and a light chain variable domain comprising complementarity determining regions (CDR1, CDR2, and CDR3) consisting of amino acid sequences set forth in SEQ ID NOs: 402, 403, and 404, respectively;

(an) an antibody comprising a heavy chain variable domain comprising complementarity determining regions (CDR1, CDR2, and CDR3) consisting of amino acid sequences set forth in SEQ ID NOs: 408, 409, respectively and 410 and a light chain variable domain comprising a light chain variable domain comprising complementarity determining regions (CDR1, CDR2, and CDR3) consisting of amino acid sequences set forth in SEQ ID NOs: 412, 413, and 414, respectively; and (ao) an antibody comprising a heavy chain variable domain comprising complementarity determining regions (CDR1, CDR2, and CDR3) consisting of amino acid sequences set forth in SEQ ID NOs: 418, 419, and 420, respectively and a light chain variable domain comprising a light chain variable domain comprising complementarity determining regions (CDR1, CDR2, and CDR3) consisting of amino acid sequences set forth in SEQ ID NOs: 422, 423, and 424, respectively.

19. The method according to claim 2, wherein the antibody or a fragment thereof is conjugated to an antitumor agent.

* * * * *

SEQUENCE LISTING

<160> NUMBER OF SEQ ID NOS: 432

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1

```
cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat       471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa       615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa       663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga       711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat       759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag       807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa       855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag       903
Lys Pro Val Cys Gly Thr Thr Tyr Lys Val Leu Lys Glu Ile Val Glu
        225                 230                 235
```

-continued

```
cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa     1863
Ala Ser Tyr Asn Gln Ser Phe Ser Ser Gln Pro His Gln Val Glu Gln
        545                 550                 555
```

-continued

```
aca gag ctt cag caa gaa cag ctt caa aca gtg gtt ggc act tac cat     1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct     1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat     2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685

cca cga ggt cgt gga ggg ccc cca aga ccc aac aga ggg atg ccg caa     2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca    2349
Met Asn Thr Gln Gln Val Asn
        705

aaaacacact ggccagtgta ccataatatg ttaccagaag agttattatc tatttgttct   2409

ccctttcagg aaacttattg taaagggact gttttcatcc cataaagaca ggactacaat   2469

tgtcagcttt ctattacctg gatatggaag gaaactattt ttactctgca tgttctgtcc   2529

taagcgtcat cttgagcctt gcacatgata ctcagattcc tcacccttgc ttaggagtaa   2589

aacaatatac tttacagggt gataataatc tccatagtta tttgaagtgg cttgaaaaag   2649

gcaagattga cttttatgac attggataaa atctacaaat cagccctcga gttattcaat   2709

gataactgac aaactaaatt atttccctag aaaggaagat gaaaggagtg gagtgtggtt   2769

tggcagaaca actgcatttc acagcttttc cagttaaatt ggagcactga acgttcagat   2829

gcataccaaa ttatgcatgg gtcctaatca cacatataag gctggctacc agctttgaca   2889

cagcactgtt catctggcca aacaactgtg gttaaaaaca catgtaaaat gctttttaac   2949

agctgatact gtataagaca aagccaagat gcaaaattag gctttgattg gcacttttg    3009

aaaaatatgc aacaaatatg ggatgtaatc cggatggccg cttctgtact taatgtgaaa   3069

tatttagata cctttttgaa cacttaacag tttctttgag acaatgactt ttgtaaggat   3129

tggtactatc tatcattcct tatgacatgt acattgtctg tcactaatcc ttggattttg   3189

ctgtattgtc acctaaattg gtacaggtac tgatgaaaat ctctagtgga taatcataac   3249

actctcggtc acatgttttt ccttcagctt gaaagctttt ttttaaaagg aaaagatacc   3309

aaatgcctgc tgctaccacc cttttcaatt gctatctttt gaaaggcacc agtatgtgtt   3369

ttagattgat ttccctgttt cagggaaatc acggacagta gtttcagttc tgatggtata   3429

agcaaaacaa ataaaacgtt tataaaagtt gtatcttgaa acactggtgt tcaacagcta   3489
```

```
gcagcttatg tgattcaccc catgccacgt tagtgtcaca aattttatgg tttatctcca   3549
gcaacatttc tctagtactt gcacttatta tcttttgtct aatttaacct taactgaatt   3609
ctccgtttct cctggaggca tttatattca gtgataattc cttcccttag atgcataggg   3669
agagtctcta aatttgatgg aaatggacac ttgagtagtg acttagcctt atgtactctg   3729
ttggaatttg tgctagcagt ttgagcacta gttctgtgtg cctaggaagt taatgctgct   3789
tattgtctca ttctgacttc atggagaatt aatcccacct ttaagcaaag gctactaagt   3849
taatggtatt ttctgtgcag aaattaaatt ttattttcag catttagccc aggaattctt   3909
ccagtaggtg ctcagctatt taaaaacaaa actattctca aacattcatc attagacaac   3969
tggagttttt gctggttttg taacctacca aaatggatag gctgttgaac attccacatt   4029
caaaagtttt gtagggtggt gggaaatggg ggatcttcaa tgtttatttt aaaataaaat   4089
aaaataagtt cttgactttt ctcatgtgtg gttgtggtac atcatattgg aagggttaac   4149
ctgttacttt ggcaaatgag tatttttttg ctagcacctc cccttgcgtg ctttaaatga   4209
catctgcctg ggatgtacca caaccatatg ttacctgtat cttaggggaa tggataaaat   4269
atttgtggtt tactgggtaa tccctagatg atgtatgctt gcagtcctat ataaaactaa   4329
atttgctatc tgtgtagaaa ataatttcat gacatttaca atcaggactg aagtaagttc   4389
ttcacacagt gacctctgaa tcagtttcag agaagggatg ggggagaaaa tgccttctag   4449
gttttgaact tctatgcatt agtgcagatg ttgtgaatgt gtaaaggtgt tcatagtttg   4509
actgtttcta tgtatgtttt ttcaaagaat tgttcctttt tttgaactat aatttttctt   4569
tttttggtta ttttaccatc acagtttaaa tgtatatctt ttatgtctct actcagacca   4629
tatttttaaa ggggtgcctc attatggggc agagaacttt tcaataagtc tcattaagat   4689
ctgaatcttg gttctaagca ttctgtataa tatgtgattg cttgtcctag ctgcagaagg   4749
ccttttgttt ggtcaaatgc atattttagc agagtttcaa ggaaatgatt gtcacacatg   4809
tcactgtagc ctcttggtgt agcaagctca catacaaaat acttttgtat atgcataata   4869
taaatcatct catgtggata tgaaacttct tttttaaaac ttaaaaaggt agaatgttat   4929
tgattacctt gattagggca gttttatttc cagatcctaa taattcctaa aaaatatgga   4989
aaagtttttt ttcaatcatt gtaccttgat attaaaacaa atatccttta agtatttcta   5049
atcagttagc ttctacagtt cttttgtctc cttttatatg cagctcttac gtgggagact   5109
tttccactta aaggagacat agaatgtgtg cttattctca gaaggttcat taactgaggt   5169
gatgagttaa caactagttg agcagtcagc ttcctaagtg ttttaggaca tttgttcatt   5229
atattttccg tcatataact agaggaagtg gaatgcagat aagtgccgaa ttcaaaccct   5289
tcattttatg tttaagctcc tgaatctgca ttccacttgg gttgttttta agcattctaa   5349
attttagttg attataagtt agatttcaca gaatcagtat tgcccttgat cttgtccttt   5409
ttatggagtt aacggggagg aagacccctc aggaaaacga aagtaaattg ttaaggctca   5469
tcttcatacc tttttccatt ttgaatccta caaaaatact gcaaaagact agtgaatgtt   5529
taaaattaca ctagattaaa taatatgaaa gtc                                5562
```

<210> SEQ ID NO 2
<211> LENGTH: 709
<212> TYPE: PRT
<213> ORGANISM: Homo sapiens

<400> SEQUENCE: 2

Met Pro Ser Ala Thr Ser His Ser Gly Ser Gly Ser Lys Ser Ser Gly

-continued

```
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430
```

```
Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705


<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3

cagagggctg ctggctggct aagtccctcc cgctcccggc tctcgcctca ctaggagcgg     60

ctctcggtgc agcgggacag ggcgaagcgg cctgcgccca cggagcgcgc gacactgccc    120

ggaagggacc gccacccttg ccccctcagc tgcccactcg tgatttccag cggcctccgc    180

gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30
```

-continued

```
gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
```

-continued

```
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460

cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa     1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat     1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct     1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat     2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat     2199
```

-continued

```
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc           2294
Pro Arg Gly Asn Ile Leu Trp Trp
            690

ttctgttctg gccttggaag agctgttaat agtctgcatg ttaggaatac atttatcctt   2354

tccagacttg ttgctaggga ttaaatgaaa tgctctgttt ctaaaactta atcttggacc   2414

caaattttaa tttttgaatg atttaatttt ccctgttact atataaactg tcttgaaaac   2474

tagaacatat tctcttctca gaaaaagtgt tttccaact gaaaattatt tttcaggtcc    2534

taaaacctgc taaatgtttt taggaagtac ttactgaaac atttttgtaa gacatttttg   2594

gaatgagatt gaacatttat ataaatttat tattcctctt tcattttttt gaaacatgcc   2654

tattatattt tagggccaga caccctttaa tggccggata agccatagtt aacatttaga   2714

gaaccattta gaagtgatag aactaatgga atttgcaatg ccttttggac ctctattagt   2774

gatataaata tcaagttatt tctgactttt aaacaaaact cccaaattcc taacttattg   2834

agctatactt aaaaaaaatt acaggtttag agagtttttt gtttttcttt tactgttgga   2894

aaactacttc ccattttggc aggaagttaa cctatttaac aattagagct agcatttcat   2954

gtagtctgaa attctaaatg gttctctgat ttgagggagg ttaaacatca aacaggtttc   3014

ctctattggc cataacatgt ataaaatgtg tgttaaggag gaattacaac gtactttgat   3074

ttgaatacta gtagaaactg gccaggaaaa aggtacattt ttctaaaaat taatggatca   3134

cttgggaatt actgacttga ctagaagtat caaaggatgt ttgcatgtga atgtgggtta   3194

tgttctttcc caccttgtag catattcgat gaaagttgag ttaactgata gctaaaaatc   3254

tgttttaaca gcatgtaaaa agttatttta tctgttaaaa gtcattatac agttttgaat   3314

gttatgtagt ttctttttaa cagtttaggt aataaggtct gttttcattc tggtgctttt   3374

attaattttg atagtatgat gttacttact actgaaatgt aagctagagt gtacactaga   3434

atgtaagctc catgagagca ggtaccttgt ctgtcttctc tgctgtatct attcccaacg   3494

cttgatgatg gtgcctggca catagtaggc actcaataaa tatttgttga atgaatgaa    3553


<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95
```

-continued

```
Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
```

```
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690


<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5

gtcacaaata acttggagtt tgcaaaagaa ttacagagga gtttc atg gca tta agt      57
                                                  Met Ala Leu Ser
                                                      1

caa gat att cag aaa aca ata aag aag act gca cgt cgg gag cag ctt       105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc       153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg       201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg       249
Lys Gln Gly Leu Asn Gly Val Pro Ile Leu Ser Glu Glu Glu Leu Ser
        55                  60                  65

ttg ttg gat gaa ttc tac aaa tta gca gac cct gaa cgg gac atg agc       297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac       345
Leu Arg Leu Asn Glu Gln Tyr Glu His Ala Ser Ile His Leu Trp Asp
85                  90                  95                  100

ttg ctg gaa gga aag gaa aag tct gta tgt gga aca acc tat aaa gca       393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc       441
```

-continued

```
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca      489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca      537
Ala Pro Thr Val Glu Asp Gln Val Ala Glu Ala Glu Pro Glu Pro Ala
    150                 155                 160

gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag      633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag      681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg      729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag      777
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275

cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc     1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa     1305
Asn Met Asn Ala Pro Val Pro Pro Val Asn Glu Pro Glu Thr Leu Lys
405                 410                 415                 420

caa caa aat cag tac cag gcc agt tat aac cag agc ttt tct agt cag     1353
Gln Gln Asn Gln Tyr Gln Ala Ser Tyr Asn Gln Ser Phe Ser Ser Gln
                425                 430                 435
```

```
cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582

gaaaaaaaaa aaaaaaaaaa aaa                                           1605


<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320
```

```
Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445


<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175
```

-continued

```
aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
```

-continued

```
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334

gaaactattt ttattctgca tgttcttcct aagcgtcatc ttgagccttg cacatgatac   2394

tcagattcct caccccttgct taggagtaaa acataataca ctttacaggg tgatatctcc   2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634

ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814
```

```
gggctttgat tggcactttt tgaaaaatat gcaacaaata tgggatgtaa tctggatggc   2874

cgcttctgta cttaatgtga agtatttaga taccttttg aacacttaac agtttcttct    2934

gacaatgact tttgtaagga ttggtactat ctatcattcc ttataatgta cattgtctgt   2994

cactaatcct cagatcttgc tgtattgtca cctaaattgg tacaggtact gatgaaaata   3054

tctaatggat aatcataaca ctcttggtca catgttttc ctgcagcctg aaggttttta    3114

aaagaaaaag atatcaaatg cctgctgcta ccaccctttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654

atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agttttttgt agggtggtgg ggaagggggg gtgtcttcaa   3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074

tggggaatag ataaaatatt cgtggtttat tgggtaatcc ctagatgtgt atgcttacaa   4134

tcctatatat aaaactaaat                                               4154
```

```
<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125
```

-continued

```
Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
```

```
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140
```

-continued

```
atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460
```

-continued

```
caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga         2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat   2169

gtaggttaca tgttaggaat acatttatca ttaccagact tgttgctagg gattaaatga   2229

aatgctctgt ttctaaaact tctcttgaac ccaaatttaa tttttgaat gactttccct    2289

gttactatat aaattgtctt gaaaactaga acatttctcc tcctcagaaa aagtgttttt   2349

ccaactgcaa attatttttc aggtcctaaa acctgctaaa tgtttttagg aagtacttac   2409

tgaaacattt ttgtaagaca tttttggaat gagattgaac atttatataa atttattatt   2469

attcctcttt catttttgaa catgcatatt atattttagg gtcagaaatc ctttaatggc   2529

caaataagcc atagttacat ttagagaacc atttagaagt gatagaacta actgaaattt   2589

caatgccttt ggatcattaa tagcgatata aatttcaaat tgtttctgac ttttaaataa   2649
```

-continued

```
aacatccaaa atcctaacta acttcctgaa ctatatttaa aaattacagg tttaaggagt   2709
ttctggtttt ttttctctta ccataggaaa actgtttcct gtttggccag gaagtcaacc   2769
tgtgtaataa ttagaagtag catttcatat gatctgaagt tctaaatggt tctctgattt   2829
aagggaagtt aaattgaata ggtttcctct agttattggc cataacatgt ataaaatgta   2889
tattaaggag gaatacaaag tactttgatt tcaatgctag tagaaactgg ccagcaaaaa   2949
ggtgcatttt atttttaaat taatggatca cttgggaatt actgacttga agtatcaaag   3009
gatatttgca tgtgaatgtg ggttatgttc tttctcacct tgtagcatat tctatgaaag   3069
ttgagttgac tggtagctaa aaatctgttt taacagcatg taaaaagtta ttttatctgt   3129
tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa aatatttccc ttcgagaagg agtggaatgt ggtttggcag aacaactgca   4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagatacctt   4449
tttgaacact taacagtttc ttctgacaat gacttttgta aggattggta ctatctatca   4509
ttccttataa tgtacattgt ctgtcactaa tcctcagatc ttgctgtatt gtcacctaaa   4569
ttggtacagg tactgatgaa aatatctaat ggataatcat aacactcttg gtcacatgtt   4629
tttcctgcag cctgaaggtt tttaaaagaa aaagatatca aatgcctgct gctaccaccc   4689
ttttaaattg ctatcttttg aaaagcacca gtatgtgttt tagattgatt tccctatttt   4749
agggaaatga cagacagtag tttcagttct gatggtataa gcaaaacaaa taaaacatgt   4809
ttataaaagt tgtatcttga aacactggtg ttcaacagct agcagcttat gtggttcacc   4869
ccatgcattg ttagtgtttc agattttatg gttatctcca gcagctgttt ctgtagtact   4929
tgcatttatc                                                          4939
```

```
<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380
```

-continued

```
Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700


<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30
```

```
ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350
```

```
act ccg gtg gct cag gca gat ccc ctt gtg aga aga cag cga gtc cag      1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca      1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
```

-continued

```
            660                 665                 670

tat cag cgg gga tgc cgc aaa tga acactcagca agtgaattaa tctgattcac    2070
Tyr Gln Arg Gly Cys Arg Lys
        675

aggattatgt ttaaacgcca aaaacacact ggccagtgta ccataatatg ttaccagaag   2130

agttattatc tatttgttct ccctttcagg aaacttattg taaagggact gttttcatcc   2190

cataaagaca ggactacaat tgtcagcttt atattacctg gatatggaag gaaactattt   2250

ttattctgca tgttcttcct aagcgtcatc ttgagccttg cacatgatac tcagattcct   2310

caccccttgct taggagtaaa acataataca ctttacaggg tgatatctcc atagttattt   2370

gaagtggctt ggaaaaagca agattaactt ctgacattgg ataaaaatca acaaatcagc   2430

cctagagtta ttcaaatggt aattgacaaa aactaaaata tttcccttcg agaaggagtg   2490

gaatgtggtt tggcagaaca actgcatttc acagcttttc cggttaaatt ggagcactaa   2550

acgtttagat gcataccaaa ttatgcatgg gcccttaata taaaaggctg gctaccagct   2610

ttgacacagc actattcatc ctctggccaa acaactgtgg ttaaacaaca catgtaaatt   2670

gctttttaac agctgatact ataataagac aaagccaaaa tgcaaaaatt gggctttgat   2730

tggcactttt tgaaaaatat gcaacaaata tgggatgtaa tctggatggc cgcttctgta   2790

cttaatgtga agtatttaga taccttttttg aacacttaac agtttcttct gacaatgact  2850

tttgtaagga ttggtactat ctatcattcc ttataatgta cattgtctgt cactaatcct   2910

cagatcttgc tgtattgtca cctaaattgg tacaggtact gatgaaaata tctaatggat   2970

aatcataaca ctcttggtca catgtttttc ctgcagcctg aaggttttta aaagaaaaag   3030

atatcaaatg cctgctgcta ccaccctttt aaattgctat cttttgaaaa gcaccagtat   3090

gtgttttaga ttgatttccc tattttaggg aaatgacaga cagtagtttc agttctgatg   3150

gtataagcaa aacaaataaa acatgtttat aaaagttgta tcttgaaaca ctggtgttca   3210

acagctagca gcttatgtgg ttcaccccat gcattgttag tgtttcagat tttatggtta   3270

tctccagcag ctgtttctgt agtacttgca tttatc                             3306


<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125
```

-continued

```
Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540
```

```
Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675


<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
```

-continued

```
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg       576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc       624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac       672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca       720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc       768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca       816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca       864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat       912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag       960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag      1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg      1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag      1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca      1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag      1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag      1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480
```

-continued tta aat aca gac cag act aca gcg tca tca tcc ctt ccg gct gct tct 1488
Leu Asn Thr Asp Gln Thr Thr Ala Ser Ser Ser Leu Pro Ala Ala Ser
485 490 495 cag cct cag gta ttc cag gct ggg aca agc aaa cca tta cat agc agt 1536
Gln Pro Gln Val Phe Gln Ala Gly Thr Ser Lys Pro Leu His Ser Ser
500 505 510 gga atc aat gta aat gca gct cca ttc caa tcc atg caa acg gtg ttc 1584
Gly Ile Asn Val Asn Ala Ala Pro Phe Gln Ser Met Gln Thr Val Phe
515 520 525 aat atg aat gcc cca gtt cct cct gtt aat gaa cca gaa act ttg aaa 1632
Asn Met Asn Ala Pro Val Pro Pro Val Asn Glu Pro Glu Thr Leu Lys
530 535 540 caa caa aat cag tac cag gcc agt tat aac cag agc ttt tct agt cag 1680
Gln Gln Asn Gln Tyr Gln Ala Ser Tyr Asn Gln Ser Phe Ser Ser Gln
545 550 555 560 cct cac caa gta gaa caa aca gac ctt cag caa gaa cag ctt caa aca 1728
Pro His Gln Val Glu Gln Thr Asp Leu Gln Gln Glu Gln Leu Gln Thr
565 570 575 gtg gtt ggc act tac cat ggt tcc cag gac cag ccc cac caa gtg act 1776
Val Val Gly Thr Tyr His Gly Ser Gln Asp Gln Pro His Gln Val Thr
580 585 590 ggt aac cat cag cag cct ccc cag cag aac act gga ttt cca cgt agc 1824
Gly Asn His Gln Gln Pro Pro Gln Gln Asn Thr Gly Phe Pro Arg Ser
595 600 605 agt cag ccc tat tac aat agt cgt ggt gtg tct cgt ggt ggt tcc cgt 1872
Ser Gln Pro Tyr Tyr Asn Ser Arg Gly Val Ser Arg Gly Gly Ser Arg
610 615 620 ggt gct aga ggc tta atg aat gga tac agg ggc cct gcc aat gga ttc 1920
Gly Ala Arg Gly Leu Met Asn Gly Tyr Arg Gly Pro Ala Asn Gly Phe
625 630 635 640 aga gga gga tat gat ggt tac cgc cct tca ttc tct aac act cca aac 1968
Arg Gly Gly Tyr Asp Gly Tyr Arg Pro Ser Phe Ser Asn Thr Pro Asn
645 650 655 agt ggt tat aca cag tct cag ttc agt gct ccc cgg gac tac tct ggc 2016
Ser Gly Tyr Thr Gln Ser Gln Phe Ser Ala Pro Arg Asp Tyr Ser Gly
660 665 670 tat cag cgg gat gga tat cag cag aat ttc aag cga ggc tct ggg cag 2064
Tyr Gln Arg Asp Gly Tyr Gln Gln Asn Phe Lys Arg Gly Ser Gly Gln
675 680 685 agt gga cca cgg gga gcc cca cga ggt cgt gga ggg ccc cca aga ccc 2112
Ser Gly Pro Arg Gly Ala Pro Arg Gly Arg Gly Gly Pro Pro Arg Pro
690 695 700 aac aga ggg atg ccg caa atg aac act cag caa gtg aat taa 2154
Asn Arg Gly Met Pro Gln Met Asn Thr Gln Gln Val Asn
705 710 715 tctgattcac aggattatgt ttaaacgcca aaaacacact ggccagtgta ccataatatg 2214 ttaccagaag agttattatc tatttggact gttttcatcc cataaagaca ggactacaat 2274 tgtcagc 2281

<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1 5 10 15

Pro Pro Pro Pro Ser Gly Ser Ser Gly Ser Glu Ala Ala Ala Ala Ala
20 25 30

```
Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445
```

-continued

```
Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc      111
                        Met Pro Ser Ala Thr Ser His Ser Gly Ser
                        1               5                   10

ggc agc aag tcg tcc gga ccg cca ccg ccg tcg ggt tcc tcc ggg aat      159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc      207
Glu Ala Gly Ala Gly Ala Ala Ala Pro Ala Ser Gln His Pro Met Thr
            30                  35                  40

ggc acc ggg gct gtc cag acc gag gcc atg aag cag att ctc ggg gtg      255
Gly Thr Gly Ala Val Gln Thr Glu Ala Met Lys Gln Ile Leu Gly Val
        45                  50                  55
```

-continued

```
atc gac aag aaa ctt cgg aac ctg gag aag aaa aag ggc aag ctt gat      303
Ile Asp Lys Lys Leu Arg Asn Leu Glu Lys Lys Lys Gly Lys Leu Asp
    60                  65                  70

gat tat cag gaa cga atg aac aaa ggg gaa agg ctt aat caa gat cag      351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt      399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag      447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa      495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg      543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg      591
Asp Lys Leu Gly Asp Asp Glu Val Arg Thr Asp Leu Lys Gln Gly Leu
155                 160                 165                 170

aat gga gtg cca ata ttg tct gaa gag gag ttg tcg ttg tta gat gag      639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat      687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga      735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att      783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac      831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt      879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act      927
Glu Asp Gln Ala Ala Glu Ala Glu Pro Glu Pro Val Glu Glu Tyr Thr
            270                 275                 280

gaa caa aat gag gtt gaa tca aca gag tat gta aat aga caa ttt atg      975
Glu Gln Asn Glu Val Glu Ser Thr Glu Tyr Val Asn Arg Gln Phe Met
        285                 290                 295

gca gaa aca cag ttc agc agt ggt gaa aag gag cag gta gat gat tgg     1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag     1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct     1119
Ala Ala Ser Pro Ser Val Pro Glu Pro His Ser Leu Thr Pro Val Ala
                335                 340                 345

caa gcc gat ccc ctc gtg aga aga cag cga gta cag gac ctt atg gca     1167
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt     1215
Gln Met Gln Gly Pro Tyr Asn Phe Ile Gln Asp Ser Met Leu Asp Phe
```

```
        365                 370                 375

gaa aac cag aca ctt gat cct gcc att gta tct gca cag ccg atg aat      1263
Glu Asn Gln Thr Leu Asp Pro Ala Ile Val Ser Ala Gln Pro Met Asn
    380                 385                 390

cca gca cag aac atg gac ata ccc cag ctg gtt tgc cct cca gtt cat      1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa      1359
Ser Glu Ser Arg Leu Ala Gln Pro Asn Gln Val Ser Val Gln Pro Glu
                415                 420                 425

gct aca cag gtt cct ttg gtt tca tcc aca agt gag gga tat aca gca      1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa      1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac      1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg      1551
Gln Thr Thr Ala Ser Ser Ser Leu Pro Ala Ala Ser Gln Pro Gln Val
475                 480                 485                 490

ttc cag gct ggg aca agc aaa cct tta cat agc agt gga atc aat gta      1599
Phe Gln Ala Gly Thr Ser Lys Pro Leu His Ser Ser Gly Ile Asn Val
                495                 500                 505

aat gca gct cca ttc caa tcc atg caa acg gta ttc aat atg aat gcc      1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag      1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta      1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act      1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag      1839
Tyr His Gly Ser Gln Asp Gln Pro His Gln Val Thr Gly Asn His Gln
                575                 580                 585

cag cct cct cag cag aac act gga ttt cca cgt agc aat cag ccc tat      1887
Gln Pro Pro Gln Gln Asn Thr Gly Phe Pro Arg Ser Asn Gln Pro Tyr
            590                 595                 600

tac aac agt cgt ggt gtg tct cgt gga ggt tcc cgt ggt gct aga ggc      1935
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat      1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat      2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg      2079
Thr Gln Ser Gln Phe Ser Ala Pro Arg Asp Tyr Ser Gly Tyr Gln Arg
                655                 660                 665

gat gga tat cag cag aat ttc aag cga ggc tct ggg cag agt gga cca      2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg      2175
```

```
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888

tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                 3386


<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125
```

-continued

```
Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
```

```
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705


<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17

atg gag ggc aag ctc gat gat tac caa gag cga atg aac aaa gga gaa       48
Met Glu Gly Lys Leu Asp Asp Tyr Gln Glu Arg Met Asn Lys Gly Glu
1               5                   10                  15

agg ctt aat cag gat cag ctg gat gct gtg tct aag tac cag gaa gtc       96
Arg Leu Asn Gln Asp Gln Leu Asp Ala Val Ser Lys Tyr Gln Glu Val
            20                  25                  30

aca aat aac ttg gag ttt gcg aaa gaa ttg cag agg agt ttc atg gcg      144
Thr Asn Asn Leu Glu Phe Ala Lys Glu Leu Gln Arg Ser Phe Met Ala
        35                  40                  45

ttg agt cag gat att cag aaa aca ata aag aag acg gca cgt cgg gag      192
Leu Ser Gln Asp Ile Gln Lys Thr Ile Lys Lys Thr Ala Arg Arg Glu
    50                  55                  60

cag ctt atg aga gaa gaa gct gaa cag aaa cgt tta aaa act gta ctt      240
Gln Leu Met Arg Glu Glu Ala Glu Gln Lys Arg Leu Lys Thr Val Leu
65                  70                  75                  80

gag ctg cag tat gtt ttg gac aaa ttg gga gat gaa gaa gtg cga act      288
Glu Leu Gln Tyr Val Leu Asp Lys Leu Gly Asp Glu Glu Val Arg Thr
                85                  90                  95

gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110

ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125

atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140
```

-continued

```
tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160

aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255

cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380

gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460
```

-continued

```
aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575

aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337

gaagatggaa ggactggagt gtggtttggc agaacaactg catttcacag cttttcctat   2397

taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817

tctctcatgg ataaacctaa cactcttcgt cacatgtttt tcctgcagcc tgaaggtttt   2877

taaaaggaaa agatatcaaa tgcctgctgc taccaccctt ttaaattgct atcttttgaa   2937
```

-continued

```
aagcaccagt atgtgttttt agattgattt ccctatttta gggaaatgac agtcagtagt   2997

ttcagttctg atggtataag caaagcaaat aaaacgtgtt tataaaagtt gtatcttgaa   3057

acactggtgt tcaacagcta gcagcttctg tggttcaccc cctgccttgt tagtgttacc   3117

catttatggt tatctccagc agcaatttct cta                                3150


<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335
```

```
Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635


<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
```

-continued

```
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335
```

-continued

```
cca gag ccc cac tct ttg act cca gtg gct cag tca gat cca ctt gtg      1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat      1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat      1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat      1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc      1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg      1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag      1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt      1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat      1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac      1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg      2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca      2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct      2146
Phe Ser Asn Thr Pro Asn Ser Gly Tyr Ser Gln Ser Gln Phe Thr Ala
                645                 650                 655
```

```
ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag     2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact         2342
Gln Val Asn
705

ggccagtgta ccataatatg ttaccagaag agttattatc tatttgttct ccctttcagg   2402

aaacttattg taaagggact gttttcatcc cataaagaca ggactgcaat tgtcagcttt   2462

acattacctg gatatggaag gaaactattt ttattctgca tgttctgtcc taagcgtcat   2522

cttgagcctt gcacacaata caatactcag attcctcacc cttgcttagg agtaaaacat   2582

tatatactta tggggtgata atatctccat agttagttga agtggcttgg aaaaaaaatg   2642

caagattgaa tttttgacct tggataaaat ctacaatcag ccctagaact attcagtggt   2702

aattgacaaa gttaaagcat tttctttgaa aggaagatgg aaggagtgga gtgtggttta   2762

gcaaaactgc atttcatagc tttcccatta aattggagca ccgacagatt aaaagcatac   2822

caaattatgc atgggtcctt actcacacaa gtgaggctgg ctaccagcct tgacatagca   2882

ctcactagtc ttctggccaa acgactgtga ttaaaacaca tgtaaattgc tctttagtag   2942

tggatactgt gtaagacaaa gccaaattgc aaatcaggct ttgattggct cttctggaaa   3002

atatgcatca aatatggggg ataatctgga tgggctgctg ctgtgctcaa tgtgaactat   3062

ttagatacct ttggaacact taacagtttc tctgaacaat gacttacatg gggattggtc   3122

ctgtttgtca ttcctcacca taattgcatt gtcatcacta atccttggat cttgctgtat   3182

tgttactcaa attggtaata ggtactgatg gaaatcgcta atggatggat aatcataaca   3242

cttttggtca catgttttct cctgcagcct gaaagttctt aaagaaaaag atatcaaatg   3302

cctgctgcta ccaccctttt aaattgctat ctttagaaaa gcaccggtat gtgttttaga   3362

ttcatttccc tgttttaggg aaatgacagg cagtagtttc agttctgatg gcaaaacaaa   3422

taaaaacatg tttctaaaag ttgtatcttg aaacactggt gttcaacagc tagcagctaa   3482

agtaattcaa cccatgcatt gctagtgtca cagcctttgg ttatgtctag tagctgtttc   3542

tgaagtattt tcatttatct tttgtcaaat ttaaccctgt ttgaattctc tcctttcctc   3602

aaggagacac ttatgttcaa agtgttgatt ctttgcctta ggtgcataga gagtagacag   3662

tttggagatg gaaaggttag cagtgactta gccatatgtt ctgtgttgga atttgtgcta   3722

gcagtttgag cactagctct gcgtgcctat gaactgaatg ctgcttgtcc cattccattt   3782

tatgtcatgg agaaataatt ccacttggta acacaaaggc taagttaatg ttattttctg   3842

tacagaaatt aaattttact tttagccttt tgtaaacttt tttttttttt ttccaagccg   3902

gtatcagcta ctcaaaacaa ttctcagata ttcatcatta gacaactgga gtttttgctg   3962

gttttgtagc ctactaaaac tgctgaggct gttgaacatt ccacattcaa aagttttgta   4022

gggtggtgga taatggggaa gcttcaatgt ttattttaaa ataaataaaa taagttcttg   4082

acttttctca tgtgtggtta tggtacatca tattggaagg gttatctgtt tacttttgcc   4142

aagactattt tgccagcacc tacacttgtg tgctttaaaa gacaactacc tgggatgtac   4202
```

```
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg atttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tctttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggttttggta   5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attacccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
agtcaagaga cctgtattcc agtgactcct gttttgttta agcattagca agatctgtct   6002
ggggaaactg gatagggcag ttttcttcca tgtttagttt ttgtctcaac atttggaagc   6062
tattgaaggt tttaaaatgg tgtgtattgt tttttttgg gggggggtg gccagaatag   6122
tgggtcatct aataaaactg ccatttaaaa gatcaaaaaa aaaaaaaaaa aaaaaaaaa    6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30
```

```
Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445
```

```
Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
```

```
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360
```

-continued

```
atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680
```

```
gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt          2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat tttctttgaa aggaagatgg   2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882

tgtaaattgc tctttagtag tggatactgt gtaagacaaa gccaaattgc aaatcaggct   2942

ttgattggct cttctggaaa atatgcatca aatatggggg ataatctgga tgggctgctg   3002

ctgtgctcaa tgtgaactat ttagatacct ttggaacact taacagtttc tctgaacaat   3062

gacttacatg gggattggtc ctgtttgtca ttcctcacca taattgcatt gtcatcacta   3122

atccttggat cttgctgtat tgttactcaa attggtaata ggtactgatg gaaatcgcta   3182

atggatggat aatcataaca cttttggtca catgttttct cctgcagcct gaaagttctt   3242

aaagaaaaag atatcaaatg cctgctgcta ccaccctttt aaattgctat ctttagaaaa   3302

gcaccggtat gtgttttaga ttcatttccc tgttttaggg aaatgacagg cagtagtttc   3362

agttctgatg gcaaaacaaa taaaaacatg tttctaaaag ttgtatcttg aaacactggt   3422

gttcaacagc tagcagctaa agtaattcaa cccatgcatt gctagtgtca cagcctttgg   3482

ttatgtctag tagctgtttc tgaagtattt tcatttatct tttgtcaaat ttaaccctgt   3542

ttgaattctc tcctttcctc aaggagacac ttatgttcaa agtgttgatt ctttgcctta   3602

ggtgcataga gagtagacag tttggagatg gaaaggttag cagtgactta gccatatgtt   3662

ctgtgttgga atttgtgcta gcagtttgag cactagctct gcgtgcctat gaactgaatg   3722

ctgcttgtcc cattccattt tatgtcatgg agaaataatt ccacttggta acacaaaggc   3782

taagttaatg ttattttctg tacagaaatt aaattttact tttagccttt tgtaaacttt   3842

tttttttttt ttccaagccg gtatcagcta ctcaaaacaa ttctcagata ttcatcatta   3902

gacaactgga gtttttgctg gttttgtagc ctactaaaac tgctgaggct gttgaacatt   3962

ccacattcaa aagttttgta gggtggtgga taatggggaa gcttcaatgt ttattttaaa   4022

ataaataaaa taagttcttg acttttctca tgtgtggtta tggtacatca tattggaagg   4082

gttatctgtt tacttttgcc aagactattt tgccagcacc tacacttgtg tgctttaaaa   4142

gacaactacc tgggatgtac cacaaccata tgttaattgt attttattgg gatggataaa   4202

atgtttgtgg tttattggat aatccctaga tggtgtgtta cgtgtgtaga atataatttt   4262

atgatagtaa gaaagcaaaa ttgaagaaaa taagtttagt attgaatttg agttctgaag   4322

tgaattcagg gaatgtctca cgtttcgggc ttctacccaa agtgtagggc agaaggtgta   4382
```

```
aaagttgttt gtagtttgac ttgtttattt tttaagttgc ttattccttt caacagcaac   4442
atatcattag ctgtcattct accattgcag ttctagtgag ttttaacgtc tgcattcaag   4502
actgttttaa aagcaacctc actggacaga gaactgctaa agtcttttcc ttaagatctg   4562
agtctttgtt actcagtatc ttctataata tgcaaatgct tgtctagagg cagaagacct   4622
tttgtttggt caagtgtgta ttttaccaga gtacagggaa ctgatggtcc tacatgtctc   4682
ttagtgtagt aagactataa aatcttttgt acatgcacaa ttcacagtat gtttagatac   4742
cacgtgtata atgccccccc ctcccccagg tagcatgcca ttgatgactt tttgcttagg   4802
gccattttat taccagggcc ttaatattcc taaaaagatg atttttttc atcctttctc   4862
ctcttttgat cattgtatct tgatattaaa aacatgacct tccaatgatt gtagtaaatt   4922
aacttctata gttcttttgt ctctatatgt attcatatat atgctattgt atagagactt   4982
caaggagaca tggagatgca tgcttattct caggttcatt cactaaggtg cttggcagac   5042
aaccagtttc taagtgcaga atgtagttaa gcagcttcat atatgtgcca ggcaatttgt   5102
tttgttaaat tttcatctac ttaaggaaat agggtattgt agcttaggct gatcataccc   5162
ttcatttcaa ccttaagctc tcaacctgca tccatccgac ttgagctatt aagtacttta   5222
gttttatcga gtataagtta acagaaaaag taaattaagc tttgccttta ctattttgaa   5282
tttatataca ttctggaaaa acttagaaac tgttgtatat ttcattagat taaattatat   5342
gaaaatgtga ttgtttatag caaagcctgt gagttgcata caccctaagg aaaactcctt   5402
aagtgctcct tgaagagaga agaaacaatt ctgggtctgg tctttttaag aacaaagcta   5462
gactactgta tgttagcact gtacattaat agtctgttgt gaagcttgag cagtttcctg   5522
catagccttg atccttcacc gttggcattg aaaatagcag tatccctgat gtacttaaaa   5582
cttaaagtca ggttttggta tatttatttg taagtcttaa tttcctctaa atactatatc   5642
tctttagcga gacaacctga aatttattag cacatttggg tatctcttgc ttggcattat   5702
ggccagtgtt aactattcag tggtgaaaaa attacccctc aagacactgg agtgacccca   5762
gatgtgtgta gtaagtggca tggttcaact gtgtggttaa tgataaatat atgacttagt   5822
cggtatgatc tggaaagact tgattgaaag ataattcagc tgacataagg atgagtgagg   5882
agtggcaaac tggataaaag agtcaagaga cctgtattcc agtgactcct gttttgttta   5942
agcattagca agatctgtct ggggaaactg gatagggcag ttttcttcca tgtttagttt   6002
ttgtctcaac atttggaagc tattgaaggt tttaaaatgg tgtgtattgt ttttttttgg   6062
gggggggtg gccagaatag tgggtcatct aataaaactg ccatttaaaa gatcaaaaaa   6122
aaaaaaaaaa aaaaaaaaa                                               6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60
```

-continued

```
Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480
```

```
Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75
```

-continued

```
tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                 100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag acg ctt gat cct gcc att gta     1275
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg     1323
Ser Ala Gln Pro Met Asn Pro Thr Gln Asn Met Asp Met Pro Gln Leu
```

-continued

```
380                 385                 390                 395

gtt tgc cct cag gtt cat tct gaa tct aga ctt gcc caa tct aat caa     1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca     1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct     1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca     1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct     1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac     1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg     1659
Ser Ser Gly Ile Asn Val Asn Ala Ala Pro Phe Gln Ser Met Gln Thr
            495                 500                 505

gtg ttc aat atg aat gct cca gtc cct cct gct aat gaa cca gaa acg     1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc     1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg     1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa     1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca     1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg     1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat     1995
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act     2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac     2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct     2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca     2187
Gly Gln Ser Gly Pro Arg Gly Ala Pro Arg Gly Arg Gly Gly Pro Pro
        670                 675                 680

aga ccc aac aga ggg atg ccg caa atg aac act cag caa gtg aat taa     2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg   2295
```

```
ttaccagaag agttattatc tatttgttct ccctttcagg aaacttattg taaagggact   2355
gttttcatcc cataaagaca ggactgcaat tgtcagcttt acattacctg gatatggaag   2415
gaaactattt ttattctgca tgttctgtcc taagcgtcat cttgagcctt gcacacaata   2475
caatactcag attcctcacc cttgcttagg agtaaaacat tatatactta tggggtgata   2535
atatctccat agttagttga agtggcttgg aaaaaaaatg caagattgaa tttttgacct   2595
tggataaaat ctacaatcag ccctagaact attcagtggt aattgacaaa gttaaagcat   2655
tttctttgaa aggaagatgg aaggagtgga gtgtggttta gcaaaactgc atttcatagc   2715
tttcccatta aattggagca ccgacagatt aaaagcatac caaattatgc atgggtcctt   2775
actcacacaa gtgaggctgg ctaccagcct tgacatagca ctcactagtc ttctggccaa   2835
acgactgtga ttaaaacaca tgtaaattgc tctttagtag tggatactgt gtaagacaaa   2895
gccaaattgc aaatcaggct ttgattggct cttctggaaa atatgcatca aatatggggg   2955
ataatctgga tgggctgctg ctgtgctcaa tgtgaactat ttagatacct ttggaacact   3015
taacagtttc tctgaacaat gacttacatg ggattggtc ctgtttgtca ttcctcacca   3075
taattgcatt gtcatcacta atccttggat cttgctgtat tgttactcaa attggtaata   3135
ggtactgatg gaaatcgcta atggatggat aatcataaca cttttggtca catgttttct   3195
cctgcagcct gaaagttctt aaagaaaaag atatcaaatg cctgctgcta ccaccctttt   3255
aaattgctat ctttagaaaa gcaccggtat gtgttttaga ttcatttccc tgttttaggg   3315
aaatgacagg cagtagtttc agttctgatg gcaaaacaaa taaaaacatg tttctaaaag   3375
ttgtatcttg aaacactggt gttcaacagc tagcagctaa agtaattcaa cccatgcatt   3435
gctagtgtca cagcctttgg ttatgtctag tagctgtttc tgaagtattt tcatttatct   3495
tttgtcaaat ttaaccctgt ttgaattctc tcctttcctc aaggagacac ttatgttcaa   3555
agtgttgatt ctttgcctta ggtgcataga gagtagacag tttggagatg gaaaggttag   3615
cagtgactta gccatatgtt ctgtgttgga atttgtgcta gcagtttgag cactagctct   3675
gcgtgcctat gaactgaatg ctgcttgtcc cattccattt tatgtcatgg agaaataatt   3735
ccacttggta acacaaaggc taagttaatg ttattttctg tacagaaatt aaattttact   3795
tttagccttt tgtaaacttt tttttttttt ttccaagccg gtatcagcta ctcaaaacaa   3855
ttctcagata ttcatcatta gacaactgga gtttttgctg gttttgtagc ctactaaaac   3915
tgctgaggct gttgaacatt ccacattcaa aagttttgta gggtggtgga taatggggaa   3975
gcttcaatgt ttattttaaa ataaataaaa taagttcttg acttttctca tgtgtggtta   4035
tggtacatca tattggaagg gttatctgtt tacttttgcc aagactattt tgccagcacc   4095
tacacttgtg tgctttaaaa gacaactacc tgggatgtac cacaaccata tgttaattgt   4155
attttattgg gatggataaa atgtttgtgg tttattggat aatccctaga tggtgtgtta   4215
cgtgtgtaga atataatttt atgatagtaa gaaagcaaaa ttgaagaaaa taagtttagt   4275
attgaatttg agttctgaag tgaattcagg gaatgtctca cgtttcgggc ttctacccaa   4335
agtgtagggc agaaggtgta aaagttgttt gtagtttgac ttgtttattt tttaagttgc   4395
ttattccttt caacagcaac atatcattag ctgtcattct accattgcag ttctagtgag   4455
ttttaacgtc tgcattcaag actgttttaa aagcaacctc actggacaga gaactgctaa   4515
agtcttttcc ttaagatctg agtctttgtt actcagtatc ttctataata tgcaaatgct   4575
tgtctagagg cagaagacct tttgtttggt caagtgtgta ttttaccaga gtacagggaa   4635
```

-continued

```
ctgatggtcc tacatgtctc ttagtgtagt aagactataa aatcttttgt acatgcacaa   4695

ttcacagtat gtttagatac cacgtgtata atgccccccc ctcccccagg tagcatgcca   4755

ttgatgactt tttgcttagg gccattttat taccagggcc ttaatattcc taaaaagatg   4815

atttttttc atcctttctc ctcttttgat cattgtatct tgatattaaa aacatgacct   4875

tccaatgatt gtagtaaatt aacttctata gttcttttgt ctctatatgt attcatatat   4935

atgctattgt atagagactt caaggagaca tggagatgca tgcttattct caggttcatt   4995

cactaaggtg cttggcagac aaccagtttc taagtgcaga atgtagttaa gcagcttcat   5055

atatgtgcca ggcaatttgt tttgttaaat tttcatctac ttaaggaaat agggtattgt   5115

agcttaggct gatcataccc ttcatttcaa ccttaagctc tcaacctgca tccatccgac   5175

ttgagctatt aagtacttta gttttatcga gtataagtta acagaaaaag taaattaagc   5235

tttgccttta ctattttgaa tttatataca ttctggaaaa acttagaaac tgttgtatat   5295

ttcattagat taaattatat gaaaatgtga ttgtttatag caaagcctgt gagttgcata   5355

caccctaagg aaaactcctt aagtgctcct tgaagagaga agaaacaatt ctgggtctgg   5415

tctttttaag aacaaagcta gactactgta tgttagcact gtacattaat agtctgttgt   5475

gaagcttgag cagtttcctg catagccttg atccttcacc gttggcattg aaaatagcag   5535

tatccctgat gtacttaaaa cttaaagtca ggttttggta tatttatttg taagtcttaa   5595

tttcctctaa atactatatc tctttagcga gacaacctga aatttattag cacatttggg   5655

tatctcttgc ttggcattat ggccagtgtt aactattcag tggtgaaaaa attacccctc   5715

aagacactgg agtgacccca gatgtgtgta gtaagtggca tggttcaact gtgtggttaa   5775

tgataaatat atgacttagt cggtatgatc tggaaagact tgattgaaag ataattcagc   5835

tgacataagg atgagtgagg agtggcaaac tggataaaag agtcaagaga cctgtattcc   5895

agtgactcct gttttgttta agcattagca agatctgtct ggggaaactg gatagggcag   5955

ttttcttcca tgtttagttt ttgtctcaac atttggaagc tattgaaggt tttaaaatgg   6015

tgtgtattgt tttttttgg gggggggtg gccagaatag tgggtcatct aataaaactg   6075

ccatttaaaa gatcaaaaaa aaaaaaaaaa aaaaaaaaa                          6114
```

```
<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110
```

```
Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
```

```
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695


<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca       562
Ser Phe Met Ala Leu Ser Gln Asp Ile Gln Lys Thr Ile Lys Lys Thr
```

```
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
```

```
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat     2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag     2297
Ile Leu Trp Trp
    690

aactgttcat agtccgcatg taggttacat gttaggaata catttatctt ttccagactt   2357

gttgctaaag attaaatgaa atgctctgtt tctaaaattt catcttgaat ccaaatttta   2417

atttttgaat gactttccct gctgttgtct tcaaaatcag aacattttct ctgcctcaga   2477

aaagcgtttt tccaactgga aatttatttt tcaggtctta aaacctgcta aatgttttta   2537

ggaagtacct actgaaactt tttgtaagac atttttggaa cgagcttgaa catttatata   2597

aatttattac cctctttgat tttgaaaca tgcatattat atttaggctg agaagccctt   2657
```

-continued caaatggcca gataagccac agttttagct agagaaccat ttagaattga cataactaat 2717 ctaaacttga acacttttag gaccaatgtt agtgttctaa ataccaacat atttctgatg 2777 tttaaacaga tctcccaaat tcttaggacc ttgatgtcat taaaatttag aatgacaagc 2837 ttaagaggct ttagtttcat ttgtttttca agtaatgaaa aataatttct tacatgggca 2897 gatagttaat ttgttgaaca attacaggta gcatttcatg taatctgatg ttctaaatgg 2957 ttctcttatt gaaggaggtt aaagaattag gtttcttaca gtttttggct ggccatgaca 3017 tgtataaaat gtatattaag gaggaattat aaagtacttt aatttgaatg ctagtggcaa 3077 ttgatcatta agaaagtact ttaaagcaaa aggttaatgg gtcatctggg aaaaatactg 3137 aagtatcaaa ggtatttgca tgtgaatgtg ggttatgttc ttctatccca ccttgtagca 3197 tattctatga aagttgagtt aaatgatagc taaaatatct gtttcaacag catgtaaaaa 3257 gttattttaa ctgttacaag tcattataca attttgaatg ttctgtagtt tctttttaac 3317 agtttaggta caaaggtctg ttttcattct ggtgcttttt attaattttg atagtatgat 3377 gtcacttcct attgaaatgt aagctagcgt gtaccttaga atgtgagctc catgagagca 3437 ggtaccttgt ttgtcttcac tgctgtatct attcccaacg cctcatgaca gtgcctggca 3497 catagtaggc actcaataaa tacttgttga atgaatgaaa aaaaaaaaaa a 3548

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1 5 10 15

Pro Pro Pro Pro Ser Gly Ser Ser Gly Ser Glu Ala Ala Ala Gly Ala
20 25 30

Ala Ala Pro Ala Ser Gln His Pro Ala Thr Gly Thr Gly Ala Val Gln
35 40 45

Thr Glu Ala Met Lys Gln Ile Leu Gly Val Ile Asp Lys Lys Leu Arg
50 55 60

Asn Leu Glu Lys Lys Lys Gly Lys Leu Asp Asp Tyr Gln Glu Arg Met
65 70 75 80

Asn Lys Gly Glu Arg Leu Asn Gln Asp Gln Leu Asp Ala Val Ser Lys
85 90 95

Tyr Gln Glu Val Thr Asn Asn Leu Glu Phe Ala Lys Glu Leu Gln Arg
100 105 110

Ser Phe Met Ala Leu Ser Gln Asp Ile Gln Lys Thr Ile Lys Lys Thr
115 120 125

Ala Arg Arg Glu Gln Leu Met Arg Glu Glu Ala Glu Gln Lys Arg Leu
130 135 140

Lys Thr Val Leu Glu Leu Gln Tyr Val Leu Asp Lys Leu Gly Asp Asp
145 150 155 160

Asp Val Arg Thr Asp Leu Lys Gln Gly Leu Ser Gly Val Pro Ile Leu
165 170 175

Ser Glu Glu Glu Leu Ser Leu Leu Asp Glu Phe Tyr Lys Leu Val Asp
180 185 190

Pro Glu Arg Asp Met Ser Leu Arg Leu Asn Glu Gln Tyr Glu His Ala
195 200 205

Ser Ile His Leu Trp Asp Leu Leu Glu Gly Lys Glu Lys Pro Val Cys
210 215 220

```
Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640
```

-continued

```
Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag       747
Tyr Lys Leu Val Asp Pro Glu Arg Asp Met Ser Leu Arg Leu Asn Glu
        190                 195                 200
```

-continued

```
cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc     1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct     1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa     1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag     1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat     1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca     1707
Ala Ala Pro Phe Gln Ser Met Gln Thr Val Phe Asn Met Asn Ala Pro
        510                 515                 520
```

-continued

```
gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc        2237
Ala Pro Arg Gly Asn Ile Leu Trp Trp
    685                 690

ttctgttctg gccttggaag aactgttcat agtccgcatg taggttacat gttaggaata   2297

catttatctt ttccagactt gttgctaaag attaaatgaa atgctctgtt tctaaaattt   2357

catcttgaat ccaaatttta atttttgaat gactttccct gctgttgtct tcaaaatcag   2417

aacattttct ctgcctcaga aaagcgtttt tccaactgga aatttatttt tcaggtctta   2477

aaacctgcta aatgttttta ggaagtacct actgaaactt tttgtaagac atttttggaa   2537

cgagcttgaa catttatata aatttattac cctctttgat ttttgaaaca tgcatattat   2597

atttaggctg agaagccctt caaatggcca gataagccac agttttagct agagaaccat   2657

ttagaattga cataactaat ctaaacttga acacttttag gaccaatgtt agtgttctaa   2717

ataccaacat atttctgatg tttaaacaga tctcccaaat tcttaggacc ttgatgtcat   2777

taaaatttag aatgacaagc ttaagaggct ttagtttcat ttgtttttca agtaatgaaa   2837

aataatttct tacatgggca gatagttaat ttgttgaaca attacaggta gcatttcatg   2897

taatctgatg ttctaaatgg ttctcttatt gaaggaggtt aaagaattag gtttcttaca   2957

gtttttggct ggccatgaca tgtataaaat gtatattaag gaggaattat aaagtacttt   3017

aatttgaatg ctagtggcaa ttgatcatta agaaagtact ttaaagcaaa aggttaatgg   3077

gtcatctggg aaaaatactg aagtatcaaa ggtatttgca tgtgaatgtg ggttatgttc   3137

ttctatccca ccttgtagca tattctatga aagttgagtt aaatgatagc taaaatatct   3197

gtttcaacag catgtaaaaa gttattttaa ctgttacaag tcattataca atttgaatg    3257
```

-continued

```
ttctgtagtt tctttttaac agtttaggta caaaggtctg ttttcattct ggtgcttttt   3317

attaattttg atagtatgat gtcacttcct attgaaatgt aagctagcgt gtaccttaga   3377

atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                        3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
```

-continued

```
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)
```

<400> SEQUENCE: 29

```
atg ccc tcg gct acc aac ggc acc atg gcg agc agc agc ggg aag gcg       48
Met Pro Ser Ala Thr Asn Gly Thr Met Ala Ser Ser Ser Gly Lys Ala
1               5                   10                  15

ggc ccg ggc ggc aac gag cag gcc ccg gcg gcg gca gcg gcg gcc ccg       96
Gly Pro Gly Gly Asn Glu Gln Ala Pro Ala Ala Ala Ala Ala Ala Pro
            20                  25                  30

cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45

cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60

aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80

cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95

aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
            100                 105                 110

agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125

ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140

ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160

ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175

aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190

aac atg agg ttg aat gag cag tat gag caa gca tct gtt cac ctg tgg      624
Asn Met Arg Leu Asn Glu Gln Tyr Glu Gln Ala Ser Val His Leu Trp
        195                 200                 205

gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220

gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225                 230                 235                 240

agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255

ccc aca cct gca gta gaa gac act gta gca gaa gct gag cct gat cca      816
Pro Thr Pro Ala Val Glu Asp Thr Val Ala Glu Ala Glu Pro Asp Pro
            260                 265                 270

gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275                 280                 285

aac aga caa ttc atg gca gag act cag ttc agc agt agt gag aag gaa      912
Asn Arg Gln Phe Met Ala Glu Thr Gln Phe Ser Ser Ser Glu Lys Glu
    290                 295                 300
```

-continued

```
cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta     1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac     1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct     1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415

cct gtg caa cca gaa gct acg cag gtt ccc ttg gtt tca tct aca agt     1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca     1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg     1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca     1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc     1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta     1536
Ser Gly Ile Asn Val Asn Ala Ala Pro Phe Gln Ser Met Gln Thr Val
            500                 505                 510

ttc aac atg aat gca cct gtt cct cct gtt aat gag cca gaa gcc ctt     1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat     1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag     1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg     1728
Thr Val Val Gly Thr Tyr His Gly Ser Pro Asp Gln Thr His Gln Val
                565                 570                 575

gca gga aac cac cag caa cct ccc cag cag aat act gga ttt cca cgc     1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca     1824
Asn Ser Gln Pro Tyr Tyr Asn Ser Arg Gly Val Ser Arg Gly Gly Ser
        595                 600                 605

cgt ggg act cgt gga ttg atg aat ggt tac agg gga cct gca aat gga     1872
Arg Gly Thr Arg Gly Leu Met Asn Gly Tyr Arg Gly Pro Ala Asn Gly
    610                 615                 620
```

```
ttt aga gga gga tat gat ggc tac cgt cct tca ttt tcc aac act ccg      1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca      1968
Asn Ser Gly Tyr Thr Gln Pro Gln Phe Asn Ala Pro Arg Asp Tyr Ser
            645                 650                 655

aac tac cag cgg gat gga tat cag cag aac ttc aaa cgt ggt tct gga      2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga      2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa          2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270
```

-continued

```
Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Gly Pro Pro Arg
        675                 680                 685
```

```
Pro Asn Arg Gly Met Pro Gln Met Asn Ala Gln Gln Val Asn
    690                 695                 700


<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31

aattaaccct cactaaaggg                                                  20


<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32

taatacgact cactatagg                                                   19


<210> SEQ ID NO 33
<211> LENGTH: 18
<212> TYPE: DNA
<213> ORGANISM: Artificial Sequence
<220> FEATURE:
<223> OTHER INFORMATION: Synthetic primer

<400> SEQUENCE: 33

aaggtttgaa tggagtgc                                                    18


<210> SEQ ID NO 34
<211> LENGTH: 18
<212> TYPE: DNA
<213> ORGANISM: Artificial Sequence
<220> FEATURE:
<223> OTHER INFORMATION: Synthetic primer

<400> SEQUENCE: 34

tgctcctttt caccactg                                                    18


<210> SEQ ID NO 35
<211> LENGTH: 18
<212> TYPE: DNA
<213> ORGANISM: Artificial Sequence
<220> FEATURE:
<223> OTHER INFORMATION: Synthetic primer

<400> SEQUENCE: 35

gggctgcttt taactctg                                                    18


<210> SEQ ID NO 36
<211> LENGTH: 18
<212> TYPE: DNA
<213> ORGANISM: Artificial Sequence
<220> FEATURE:
<223> OTHER INFORMATION: Synthetic primer

<400> SEQUENCE: 36

ccaggaaatg agcttgac                                                    18


<210> SEQ ID NO 37
<211> LENGTH: 5
<212> TYPE: PRT
```

<213> ORGANISM: Gallus gallus

<400> SEQUENCE: 37

Ser Tyr Gln Met Asn
1 5

<210> SEQ ID NO 38
<211> LENGTH: 17
<212> TYPE: PRT
<213> ORGANISM: Gallus gallus

<400> SEQUENCE: 38

Ala Ile Asn Lys Phe Gly Asn Ser Thr Gly His Gly Ala Ala Val Lys
1 5 10 15

Gly

<210> SEQ ID NO 39
<211> LENGTH: 19
<212> TYPE: PRT
<213> ORGANISM: Gallus gallus

<400> SEQUENCE: 39

His Ala Tyr Gly Tyr Cys Gly Ser Gly Thr Trp Cys Ala Ala Gly Glu
1 5 10 15

Ile Asp Ala

<210> SEQ ID NO 40
<211> LENGTH: 128
<212> TYPE: PRT
<213> ORGANISM: Gallus gallus

<400> SEQUENCE: 40

Ala Val Thr Leu Asp Glu Ser Gly Gly Gly Leu Gln Met Ser Arg Gly
1 5 10 15

Gly Leu Ser Leu Val Cys Lys Ala Ser Gly Phe Asp Phe Ser Ser Tyr
20 25 30

Gln Met Asn Trp Ile Arg Gln Ala Pro Gly Lys Gly Leu Glu Phe Val
35 40 45

Ala Ala Ile Asn Lys Phe Gly Asn Ser Thr Gly His Gly Ala Ala Val
50 55 60

Lys Gly Arg Val Thr Ile Ser Arg Asp Asn Gly Gln Ser Thr Val Arg
65 70 75 80

Leu Gln Leu Asn Asn Leu Arg Ala Glu Asp Thr Ala Ile Tyr Phe Cys
85 90 95

Thr Lys His Ala Tyr Gly Tyr Cys Gly Ser Gly Thr Trp Cys Ala Ala
100 105 110

Gly Glu Ile Asp Ala Trp Gly His Gly Thr Glu Val Ile Val Ser Ser
115 120 125

<210> SEQ ID NO 41
<211> LENGTH: 9
<212> TYPE: PRT
<213> ORGANISM: Gallus gallus

<400> SEQUENCE: 41

Ser Gly Gly Gly Ser Tyr Ser Tyr Gly
1 5

<210> SEQ ID NO 42
<211> LENGTH: 7

<212> TYPE: PRT
<213> ORGANISM: Gallus gallus

<400> SEQUENCE: 42

Asn Asn Lys Arg Pro Ser Asp
1               5

<210> SEQ ID NO 43
<211> LENGTH: 10
<212> TYPE: PRT
<213> ORGANISM: Gallus gallus

<400> SEQUENCE: 43

Ser Gly Asp Ser Thr Asp Thr Ala Val Phe
1               5                   10

<210> SEQ ID NO 44
<211> LENGTH: 108
<212> TYPE: PRT
<213> ORGANISM: Gallus gallus

<400> SEQUENCE: 44

Gln Ala Ala Ser Thr Gln Pro Ser Ser Val Ser Ala Asn Pro Gly Glu
1               5                   10                  15

Thr Val Glu Ile Thr Cys Ser Gly Gly Gly Ser Tyr Ser Tyr Gly Trp
            20                  25                  30

Phe Gln Gln Lys Ser Pro Gly Ser Ala Pro Val Thr Val Ile Tyr Tyr
        35                  40                  45

Asn Asn Lys Arg Pro Ser Asp Ile Pro Ser Arg Phe Ser Gly Ser Lys
    50                  55                  60

Ser Gly Ser Thr Gly Thr Leu Thr Ile Thr Gly Val Gln Ala Asp Asp
65                  70                  75                  80

Glu Ala Val Tyr Tyr Cys Gly Ser Gly Asp Ser Thr Asp Thr Ala Val
                85                  90                  95

Phe Gly Ala Gly Thr Thr Leu Thr Val Leu Gly Gln
            100                 105

<210> SEQ ID NO 45
<211> LENGTH: 384
<212> TYPE: DNA
<213> ORGANISM: Gallus gallus

<400> SEQUENCE: 45
gcggtgacgt tggacgagtc cgggggcggc ctccagatgt ccagaggagg gctcagcctc     60
gtctgcaagg cctccgggtt cgacttcagc agctatcaga tgaactggat ccgacaggca    120
cccggcaaag ggctggagtt cgtcgctgct attaacaaat ttgggaatag tacgggtcat    180
ggggcggcag tgaagggccg tgtcaccatc tcgagggaca acgggcagag cacagtgagg    240
ctgcagctga acaacctcag ggctgaggac accgccatct acttctgcac aaaacatgcc    300
tacggttatt gtggtagtgg tacttggtgt gctgctggtg agatcgacgc atggggccac    360
gggaccgaag tcatcgtctc ctcc                                           384

<210> SEQ ID NO 46
<211> LENGTH: 324
<212> TYPE: DNA
<213> ORGANISM: Gallus gallus

<400> SEQUENCE: 46
caggcagcta gcactcagcc gtcctcggtg tcagcgaacc cgggagagac cgtcgagatc     60

-continued

```
acctgctccg gggtggcag ctatagctat ggctggttcc agcagaagtc tcctggcagt    120

gcccctgtca ctgtgatcta ttacaacaac aagagaccct cggacatccc ttcacgattc    180

tccggttcca aatccggctc cacgggcaca ttaaccatca ctggggtcca agccgacgac    240

gaggctgtct attactgtgg gagtggagac agcactgata ctgctgtatt gggggccggg    300

acaaccctga ccgtcctagg ccag                                          324


<210> SEQ ID NO 47
<211> LENGTH: 4
<212> TYPE: PRT
<213> ORGANISM: Gallus gallus

<400> SEQUENCE: 47

Phe Asp Met Gly
1


<210> SEQ ID NO 48
<211> LENGTH: 17
<212> TYPE: PRT
<213> ORGANISM: Gallus gallus

<400> SEQUENCE: 48

Gln Ile Asn Asp Ala Gly Ser Arg Thr Trp Tyr Ala Thr Ala Val Lys
1               5                   10                  15

Gly


<210> SEQ ID NO 49
<211> LENGTH: 12
<212> TYPE: PRT
<213> ORGANISM: Gallus gallus

<400> SEQUENCE: 49

Gly Ser Gly Tyr Val Gly Ala Gly Ala Ile Asp Ala
1               5                   10


<210> SEQ ID NO 50
<211> LENGTH: 120
<212> TYPE: PRT
<213> ORGANISM: Gallus gallus

<400> SEQUENCE: 50

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
            20                  25                  30

Asp Met Gly Trp Val Arg Gln Ala Pro Gly Lys Gly Leu Glu Phe Val
        35                  40                  45

Ala Gln Ile Asn Asp Ala Gly Ser Arg Thr Trp Tyr Ala Thr Ala Val
    50                  55                  60

Lys Gly Arg Ala Thr Ile Ser Arg Asp Asn Gly Gln Thr Thr Val Arg
65                  70                  75                  80

Leu Gln Leu Asn Asn Leu Arg Ala Glu Asp Thr Gly Thr Tyr Tyr Cys
                85                  90                  95

Thr Arg Gly Ser Gly Tyr Val Gly Ala Gly Ala Ile Asp Ala Trp Gly
            100                 105                 110

His Gly Thr Glu Val Ile Val Ser
        115                 120
```

<210> SEQ ID NO 51
<211> LENGTH: 8
<212> TYPE: PRT
<213> ORGANISM: Gallus gallus

<400> SEQUENCE: 51

Ser Gly Gly Ser Gly Tyr Tyr Gly
1               5

<210> SEQ ID NO 52
<211> LENGTH: 7
<212> TYPE: PRT
<213> ORGANISM: Gallus gallus

<400> SEQUENCE: 52

Asn Asp Lys Arg Pro Ser Asp
1               5

<210> SEQ ID NO 53
<211> LENGTH: 10
<212> TYPE: PRT
<213> ORGANISM: Gallus gallus

<400> SEQUENCE: 53

Arg Tyr Asp Ser Thr Asp Ser Gly Ile Phe
1               5                   10

<210> SEQ ID NO 54
<211> LENGTH: 105
<212> TYPE: PRT
<213> ORGANISM: Gallus gallus

<400> SEQUENCE: 54

Ala Ala Leu Thr Gln Pro Ser Ser Val Ser Ala Asn Pro Gly Glu Thr
1               5                   10                  15

Val Lys Ile Thr Cys Ser Gly Gly Ser Gly Tyr Tyr Gly Trp Tyr Gln
            20                  25                  30

Gln Gln Lys Ser Pro Gly Ser Ala Pro Val Thr Val Ile Tyr Gln Asn
        35                  40                  45

Asp Lys Arg Pro Ser Asp Ile Pro Ser Arg Phe Ser Gly Ser Gly Ser
    50                  55                  60

Gly Ser Thr Asn Thr Leu Thr Ile Thr Gly Val Gln Ala Glu Asp Glu
65                  70                  75                  80

Ala Val Tyr Phe Cys Gly Arg Tyr Asp Ser Thr Asp Ser Gly Ile Phe
                85                  90                  95

Gly Ala Gly Thr Thr Leu Thr Val Leu
            100                 105

<210> SEQ ID NO 55
<211> LENGTH: 363
<212> TYPE: DNA
<213> ORGANISM: Gallus gallus

<400> SEQUENCE: 55
gccgccgtga cgttggacga gtccgggggc ggcctccaga cgcccggagg agggctcagc 60
ctcgtctgca aggcctccgg gttcaccttc agcagtttcg acatgggttg ggtgcgacag 120
gcgcctggca aggggctgga attcgtcgct caaattaatg atgctggtag taggacatgg 180
tacgcgacag cggtgaaggg ccgtgccacc atctcgaggg acaacgggca gaccacagtg 240
aggctgcagc tgaacaacct cagggctgag gacaccggca cctactactg caccagaggt 300
agtggttatg ttggtgctgg tgcgatcgac gcatggggcc acgggaccga agtcatcgtg 360
tcg 363

<210> SEQ ID NO 56
<211> LENGTH: 315
<212> TYPE: DNA
<213> ORGANISM: Gallus gallus

<400> SEQUENCE: 56
gccgcgctga ctcagccgtc ctcggtgtca gcaaacccag gagaaaccgt caagatcacc 60
tgctccgggg gtagtggcta ctatggctgg taccagcagc agaagtctcc tggcagtgcc 120
cctgtcactg tgatctatca aaacgacaag agaccctcgg acatcccttc acgattctcc 180
ggttctggat caggctccac aaacacatta accatcactg ggtccaagc cgaggacgag 240 gctgtctatt tctgtggtcg ttacgacagc actgatagtg gtatatttgg ggccgggaca 300
accctgaccg tccta 315

<210> SEQ ID NO 57
<211> LENGTH: 5
<212> TYPE: PRT
<213> ORGANISM: Gallus gallus

<400> SEQUENCE: 57

Gly Tyr Asp Met Leu
1               5

<210> SEQ ID NO 58
<211> LENGTH: 17
<212> TYPE: PRT
<213> ORGANISM: Gallus gallus

<400> SEQUENCE: 58

Gly Ile Gly Ser Thr Gly Gly Gly Thr Asp Tyr Gly Ala Ala Val Lys
1               5                   10                  15

Gly

<210> SEQ ID NO 59
<211> LENGTH: 19
<212> TYPE: PRT
<213> ORGANISM: Gallus gallus

<400> SEQUENCE: 59

Val Ala Gly Gly Cys Asn Ser Gly Tyr Cys Arg Asp Ser Pro Gly Ser
1               5                   10                  15

Ile Asp Ala

<210> SEQ ID NO 60
<211> LENGTH: 127
<212> TYPE: PRT
<213> ORGANISM: Gallus gallus

<400> SEQUENCE: 60

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Asp Met Leu Trp Val Arg Gln Ala Pro Gly Lys Gly Leu Glu Trp Val
        35                  40                  45

Ala Gly Ile Gly Ser Thr Gly Gly Gly Thr Asp Tyr Gly Ala Ala Val

```
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Val Ala Gly Gly Cys Asn Ser Gly Tyr Cys Arg Asp Ser Pro
            100                 105                 110

Gly Ser Ile Asp Ala Trp Gly His Gly Thr Glu Val Ile Val Ser
        115                 120                 125


<210> SEQ ID NO 61
<211> LENGTH: 10
<212> TYPE: PRT
<213> ORGANISM: Gallus gallus

<400> SEQUENCE: 61

Ser Gly Gly Gly Ser Arg Asn Tyr Tyr Gly
1               5                   10


<210> SEQ ID NO 62
<211> LENGTH: 7
<212> TYPE: PRT
<213> ORGANISM: Gallus gallus

<400> SEQUENCE: 62

Asp Asp Gln Arg Pro Ser Asn
1               5


<210> SEQ ID NO 63
<211> LENGTH: 11
<212> TYPE: PRT
<213> ORGANISM: Gallus gallus

<400> SEQUENCE: 63

Ser Ala Asp Ser Asn Thr Tyr Glu Gly Ser Phe
1               5                   10


<210> SEQ ID NO 64
<211> LENGTH: 107
<212> TYPE: PRT
<213> ORGANISM: Gallus gallus

<400> SEQUENCE: 64

Ala Val Thr Gln Gln Pro Ala Ser Val Ser Ala Asn Pro Gly Glu Thr
1               5                   10                  15

Val Lys Ile Thr Cys Ser Gly Gly Gly Ser Arg Asn Tyr Tyr Gly Trp
            20                  25                  30

Tyr Gln Gln Lys Ser Pro Gly Ser Val Pro Val Thr Val Ile Tyr Tyr
        35                  40                  45

Asp Asp Gln Arg Pro Ser Asn Ile Pro Ser Arg Phe Ser Gly Ala Leu
    50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

Ser Phe Gly Ala Gly Thr Thr Leu Thr Val Leu
            100                 105


<210> SEQ ID NO 65
<211> LENGTH: 384
```

<212> TYPE: DNA
<213> ORGANISM: Gallus gallus

<400> SEQUENCE: 65
gccgccgtga cgttggacga gtccgggggc ggcctccaga cgcccggagg agcgctcagc 60
ctcgtctgca aggcctccgg gttcaccttc agtggttatg acatgctctg ggtgcgacag 120
gcgcccggca aggggctgga gtgggtcgct ggtattggca gcactggtgg tggcacagac 180
tatggggcgg cggtgaaggg ccgtgccacc atctcgaggg acaacgggca gagcacagtg 240
aggctgcagc tgaacaacct cagggctgag gacaccgcca cctactactg cgccaaagtt 300
gctggtggtt gtaatagtgg ttattgtcgg gactctcccg gtagcatcga cgcatggggc 360
cacgggaccg aagtcatcgt gtcg 384

<210> SEQ ID NO 66
<211> LENGTH: 321
<212> TYPE: DNA
<213> ORGANISM: Gallus gallus

<400> SEQUENCE: 66
gcagtgactc agcagccggc ctcggtgtca gcaaacccag gagaaaccgt caagatcacc 60
tgctccgggg gtggtagtag gaactactat ggctggtacc agcagaagtc tcctggcagt 120
gtccctgtca ctgtgatcta ctatgatgat cagagaccct cgaacatccc ttcacgattc 180
tccggtgccc tatccggctc cacaagcaca ttaaccatca ctggggtcca agccgacgac 240
gaggctgtct atttctgtgg gagtgcagac agcaacacct atgagggtag ctttggggcc 300
gggacaaccc tgaccgtcct a 321

<210> SEQ ID NO 67
<211> LENGTH: 5
<212> TYPE: PRT
<213> ORGANISM: Mus musculus

<400> SEQUENCE: 67

Asp Tyr Asn Met Asp
1 5

<210> SEQ ID NO 68
<211> LENGTH: 17
<212> TYPE: PRT
<213> ORGANISM: Mus musculus

<400> SEQUENCE: 68

Asp Ile Asn Pro Asn Tyr Asp Ser Thr Ser Tyr Asn Gln Lys Phe Lys
1 5 10 15

Gly

<210> SEQ ID NO 69
<211> LENGTH: 11
<212> TYPE: PRT
<213> ORGANISM: Mus musculus

<400> SEQUENCE: 69

Ser Arg Ser Tyr Asp Tyr Glu Gly Phe Ala Tyr
1 5 10

<210> SEQ ID NO 70
<211> LENGTH: 148
<212> TYPE: PRT
<213> ORGANISM: Mus musculus

<400> SEQUENCE: 70

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 71
<211> LENGTH: 11
<212> TYPE: PRT
<213> ORGANISM: Mus musculus

<400> SEQUENCE: 71

Leu Ser Ile Val Asn Arg Tyr His Tyr Met Ser
1               5                   10

<210> SEQ ID NO 72
<211> LENGTH: 6
<212> TYPE: PRT
<213> ORGANISM: Mus musculus

<400> SEQUENCE: 72

Glu Ala Ser Ile Thr Lys
1               5

<210> SEQ ID NO 73
<211> LENGTH: 9
<212> TYPE: PRT
<213> ORGANISM: Mus musculus

<400> SEQUENCE: 73

Gln His Asn Arg Gly Ser Phe Leu Pro
1               5

<210> SEQ ID NO 74
<211> LENGTH: 105
<212> TYPE: PRT
<213> ORGANISM: Mus musculus

<400> SEQUENCE: 74

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

-continued

```
Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Arg Ser Asn
            100                 105
```

<210> SEQ ID NO 75
<211> LENGTH: 444
<212> TYPE: DNA
<213> ORGANISM: Mus musculus

<400> SEQUENCE: 75

```
atggaatgga gcggggtctt tatctttctc ctgtcaggaa ctgcaggtgt cctctctgag      60

gtccagctgc atcagtttgg agctgagctg gtgaagcctg gggcttcagt gaagatatcc     120

tgcaaggctt ctggctacac attcactgac tacaacatgg actgggtgaa gcagagccat     180

ggaaagagcc ttgagtggat tggagatatt aatcctaact atgatagtac tagctacaac     240

cagaagttca agggaaaggc cacattgact gtagacaagt cctccagcac agcctacatg     300

gagctccgca gcctgacatc tgaggacact gcagtctatt actgtgcaag atcgaggagc     360

tatgattacg aaggatttgc ttactggggc caagggactc tggtcactgt ctctgcagcc     420

aaaacaacac ccccatcagt ctat                                            444
```

<210> SEQ ID NO 76
<211> LENGTH: 317
<212> TYPE: DNA
<213> ORGANISM: Mus musculus

<400> SEQUENCE: 76

```
ggactcttct gctctgtgga gagatgtcac tatcaactgc aatccagtca gaatcttttg      60

agtattgtaa accggtatca ctacatgtcc ggaaaccctc ctaaactcct ggtctatcct     120

gcactgctta tctatgaggc atccattaca aaatcctgtg tccctgatcg gttcacacga     180

agtggatctg ggacaaactt cactctcacc attaattttg tgcatgctga tgacctaatt     240

ttttattact gtcaacacaa tcgtggcagc tttctcccct caagttcggt gcaggtacca     300

agaaggagat caaacaa                                                    317
```

<210> SEQ ID NO 77
<211> LENGTH: 5
<212> TYPE: PRT
<213> ORGANISM: Mus musculus

<400> SEQUENCE: 77

```
Asp Tyr Tyr Met Ser
1               5
```

<210> SEQ ID NO 78
<211> LENGTH: 17
<212> TYPE: PRT
<213> ORGANISM: Mus musculus

<400> SEQUENCE: 78

```
Arg Asn Lys Ala Asn Gly Tyr Thr Thr Glu Tyr Ser Ala Ser Val Lys
1               5                   10                  15

Gly


<210> SEQ ID NO 79
<211> LENGTH: 9
<212> TYPE: PRT
<213> ORGANISM: Mus musculus

<400> SEQUENCE: 79

Ala Arg Ala Asn Trp Ala Phe Asp Tyr
1               5


<210> SEQ ID NO 80
<211> LENGTH: 109
<212> TYPE: PRT
<213> ORGANISM: Mus musculus

<400> SEQUENCE: 80

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105


<210> SEQ ID NO 81
<211> LENGTH: 11
<212> TYPE: PRT
<213> ORGANISM: Mus musculus

<400> SEQUENCE: 81

Arg Ala Ser Gln Ser Ile Ser Asn Tyr Leu His
1               5                   10


<210> SEQ ID NO 82
<211> LENGTH: 7
<212> TYPE: PRT
<213> ORGANISM: Mus musculus

<400> SEQUENCE: 82

Tyr Ala Ser Gln Ser Ile Ser
1               5


<210> SEQ ID NO 83
<211> LENGTH: 7
<212> TYPE: PRT
<213> ORGANISM: Mus musculus

<400> SEQUENCE: 83

Tyr Ala Ser Gln Ser Ile Ser
1               5
```

<210> SEQ ID NO 84
<211> LENGTH: 94
<212> TYPE: PRT
<213> ORGANISM: Mus musculus

<400> SEQUENCE: 84

```
Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90
```

<210> SEQ ID NO 85
<211> LENGTH: 329
<212> TYPE: DNA
<213> ORGANISM: Mus musculus

<400> SEQUENCE: 85

```
ggccgcgtgc tagcctgggg gtctctgaga ctctcctgtg cacttctggg ttcaccttca      60

ctgattacta catgagctgg gtccgccagc ctccaggaaa ggcacttgag tggttgggtt     120

ttattagaaa caaagctaat ggttacacaa cagagtacag tgcatctgtg aagggtcggt     180

tcaccatctc cagagataat tcccaaagca tcctctatct tcaaatgaac accctgagag     240

ctgaggacag tgccacttat tactgtgcaa gggctaactg ggcctttgac tactggggcc     300

aagggaccac ggtcaccgtc tcctcaaaa                                       329
```

<210> SEQ ID NO 86
<211> LENGTH: 284
<212> TYPE: DNA
<213> ORGANISM: Mus musculus

<400> SEQUENCE: 86

```
tcaggagata gagtcagtct ttcctgcagg gccagtcaaa gtattagcaa ctacctacac      60

tggtatcaac aaaaatcaca tgagtctcca aggcttctca tcaagtatgc ttcccagtcc     120

atctctggga tcccctccag gttcagtggc agtggatcag ggacagattt cactctcagt     180

atcaacagtg tggagactga agattttgga atgtatttct gtcaacagag taacagctgg     240

ccgtacacgt tcggaggagg taccaagctg gagatcaaac agaa                      284
```

<210> SEQ ID NO 87
<211> LENGTH: 5
<212> TYPE: PRT
<213> ORGANISM: Mus musculus

<400> SEQUENCE: 87

```
Asn Tyr Leu Ile Val
1               5
```

<210> SEQ ID NO 88
<211> LENGTH: 17
<212> TYPE: PRT
<213> ORGANISM: Mus musculus

<400> SEQUENCE: 88

Val Ile Ser Pro Gly Ser Gly Gly Thr Asn Tyr Asn Glu Lys Phe Lys
1               5                   10                  15

Gly

<210> SEQ ID NO 89
<211> LENGTH: 11
<212> TYPE: PRT
<213> ORGANISM: Mus musculus

<400> SEQUENCE: 89

Glu Lys Ile Tyr Asp Asp Tyr Tyr Glu Gly Tyr
1               5                   10

<210> SEQ ID NO 90
<211> LENGTH: 118
<212> TYPE: PRT
<213> ORGANISM: Mus musculus

<400> SEQUENCE: 90

Ala Ala Glu Leu Val Arg Pro Gly Thr Ser Val Lys Val Ser Cys Lys
1               5                   10                  15

Ala Ser Gly Tyr Ala Phe Thr Asn Tyr Leu Ile Val Trp Ile Lys Gln
            20                  25                  30

Arg Pro Gly Gln Gly Leu Glu Trp Ile Gly Val Ile Ser Pro Gly Ser
        35                  40                  45

Gly Gly Thr Asn Tyr Asn Glu Lys Phe Lys Gly Lys Ala Ile Leu Thr
    50                  55                  60

Ala Asp Lys Ser Ser Ser Thr Ala Tyr Met Gln Leu Ser Ser Leu Thr
65                  70                  75                  80

Ser Asp Glu Phe Ala Val Tyr Phe Cys Ala Arg Glu Lys Ile Tyr Asp
                85                  90                  95

Asp Tyr Tyr Glu Gly Tyr Phe Asp Val Trp Gly Ala Gly Pro Arg His
            100                 105                 110

Leu Leu Ala Ser Leu Ser
        115

<210> SEQ ID NO 91
<211> LENGTH: 15
<212> TYPE: PRT
<213> ORGANISM: Mus musculus

<400> SEQUENCE: 91

Thr Ile Ser Cys Ser Ala Ser Leu Gly Ile Gly Asn Tyr Leu Asn
1               5                   10                  15

<210> SEQ ID NO 92
<211> LENGTH: 7
<212> TYPE: PRT
<213> ORGANISM: Mus musculus

<400> SEQUENCE: 92

Thr Ser Asn Leu His Ser Gly
1               5

<210> SEQ ID NO 93
<211> LENGTH: 9
<212> TYPE: PRT
<213> ORGANISM: Mus musculus

<400> SEQUENCE: 93

His Tyr Ser Lys Leu Pro Leu Thr Phe
1               5

<210> SEQ ID NO 94
<211> LENGTH: 107
<212> TYPE: PRT
<213> ORGANISM: Mus musculus

<400> SEQUENCE: 94

Gly Thr Arg Cys Asp Ile Arg Leu Thr Gln Thr Thr Ser Ser Leu Ser
1               5                   10                  15

Ala Ser Leu Gly Asp Arg Val Thr Ile Ser Cys Ser Ala Ser Leu Gly
            20                  25                  30

Ile Gly Asn Tyr Leu Asn Trp Tyr Gln Gln Lys Pro Asp Gly Thr Val
        35                  40                  45

Lys Leu Leu Ile Tyr Tyr Thr Ser Asn Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln His Tyr Ser
                85                  90                  95

Lys Leu Pro Leu Thr Phe Gly Ala Gly Pro Ser
            100                 105

<210> SEQ ID NO 95
<211> LENGTH: 354
<212> TYPE: DNA
<213> ORGANISM: Mus musculus

<400> SEQUENCE: 95
gcagctgagc tggtaaggcc tgggacttca gtgaaggtgt cctgcaaggc ttctggatac 60
gccttcacta attacttgat agtgtggata aagcagaggc ctggacaggg ccttgagtgg 120
attggggtga ttagtcctgg aagtggtggt actaactaca atgagaagtt caagggcaag 180
gcaatactga ctgcagacaa atcctccagc actgcctaca tgcagctcag cagcctgaca 240
tctgatgagt ttgcggtgta tttctgtgca agagagaaaa tctatgatga ttactacgag 300
gggtacttcg atgtctgggg cgcaggacca cgtcaccttc tagcatctct gtca 354

<210> SEQ ID NO 96
<211> LENGTH: 321
<212> TYPE: DNA
<213> ORGANISM: Mus musculus

<400> SEQUENCE: 96
ggtaccagat gtgatatccg gttgacacag actacatcct ccctgtctgc ctctctggga 60
gacagagtca ccatcagttg cagtgcaagt ctgggcattg gcaattattt aaactggtat 120
cagcagaaac cagatggaac tgttaaactc ctgatctatt acacatcaaa tttacactca 180
ggagtcccat caaggttcag tggcagtggg tctgggacag attattctct caccatcagc 240
aacctggaac ctgaagatat tgccacttac tattgtcagc actatagtaa gcttccgctc 300
acgttcggtg ctggaccaag c 321

<210> SEQ ID NO 97
<211> LENGTH: 5
<212> TYPE: PRT
<213> ORGANISM: Mus musculus

<400> SEQUENCE: 97

Asp Tyr Asn Met Tyr
1               5

<210> SEQ ID NO 98
<211> LENGTH: 17
<212> TYPE: PRT
<213> ORGANISM: Mus musculus

<400> SEQUENCE: 98

Tyr Ile Tyr Pro Gly Asn Gly Gly Thr Asn Tyr Asn Gln Lys Phe Lys
1               5                   10                  15

Gly

<210> SEQ ID NO 99
<211> LENGTH: 11
<212> TYPE: PRT
<213> ORGANISM: Mus musculus

<400> SEQUENCE: 99

Asp Tyr Asp Asp Gly Gly Tyr Ala Met Asp Tyr
1               5                   10

<210> SEQ ID NO 100
<211> LENGTH: 113
<212> TYPE: PRT
<213> ORGANISM: Mus musculus

<400> SEQUENCE: 100

Gly Ala Glu Leu Val Arg Ser Gly Ala Ser Val Lys Met Ser Cys Lys
1               5                   10                  15

Ala Ser Gly Tyr Ser Phe Thr Asp Tyr Asn Met Tyr Trp Val Lys Gln
            20                  25                  30

Thr Pro Gly Gln Gly Leu Glu Trp Ile Gly Tyr Ile Tyr Pro Gly Asn
        35                  40                  45

Gly Gly Thr Asn Tyr Asn Gln Lys Phe Lys Gly Lys Ala Thr Leu Thr
    50                  55                  60

Ala Asp Thr Ser Ser Ser Thr Ala Tyr Met Gln Ile Ser Ser Leu Thr
65                  70                  75                  80

Ser Glu Asp Ser Ala Val Tyr Phe Cys Ala Arg Asp Tyr Asp Asp Gly
                85                  90                  95

Gly Tyr Ala Met Asp Tyr Trp Gly Gln Gly Thr Thr Val Thr Val Ser
            100                 105                 110

Ser

<210> SEQ ID NO 101
<211> LENGTH: 15
<212> TYPE: PRT
<213> ORGANISM: Mus musculus

<400> SEQUENCE: 101

Ser Val Gly Glu Thr Val Thr Ile Thr Cys Arg Ala Ser Gly Asn
1               5                   10                  15

<210> SEQ ID NO 102
<211> LENGTH: 7
<212> TYPE: PRT
<213> ORGANISM: Mus musculus

<400> SEQUENCE: 102

Asn Ala Lys Thr Leu Ala Asp
1 5

<210> SEQ ID NO 103
<211> LENGTH: 9
<212> TYPE: PRT
<213> ORGANISM: Mus musculus

<400> SEQUENCE: 103

Gln His Phe Trp Asn Ile Pro Trp Thr
1 5

<210> SEQ ID NO 104
<211> LENGTH: 117
<212> TYPE: PRT
<213> ORGANISM: Mus musculus

<400> SEQUENCE: 104

Leu Leu Leu Trp Leu Thr Gly Ala Arg Cys Asp Ile Gln Met Thr Gln
1 5 10 15

Ser Pro Ala Ser Leu Ser Ala Ser Val Gly Glu Thr Val Thr Ile Thr
20 25 30

Cys Arg Ala Ser Gly Asn Ile His Asn Tyr Leu Thr Trp Tyr Gln Gln
35 40 45

Lys Gln Gly Lys Ser Pro Gln Leu Leu Val Tyr Asn Ala Lys Thr Leu
50 55 60

Ala Asp Gly Val Pro Ser Arg Phe Ser Gly Ser Gly Ser Gly Thr Gln
65 70 75 80

Tyr Ser Leu Lys Ile Asn Arg Leu Gln Pro Glu Asp Phe Gly Ser Tyr
85 90 95

Tyr Cys Gln His Phe Trp Asn Ile Pro Trp Thr Phe Gly Gly Gly Thr
100 105 110

Lys Leu Asn Ser Arg
115

<210> SEQ ID NO 105
<211> LENGTH: 339
<212> TYPE: DNA
<213> ORGANISM: Mus musculus

<400> SEQUENCE: 105
ggggctgagc tggtgaggtc tggggcctca gtgaagatgt cctgcaaggc ttctggctac 60
tcatttaccg attacaatat gtattgggta aaacagacac ctggacaggg cctggaatgg 120
attggatata tttatcctgg aaatggtggt actaactaca atcagaagtt caagggcaag 180
gccacattga ctgcagacac atcctccagc acagcctaca tgcagatcag cagcctgaca 240
tctgaagact ctgcggtcta tttctgtgca agagactatg atgacggggg gtatgctatg 300
gactactggg gccaagggac cacggtcacg gtctcctca 339

<210> SEQ ID NO 106
<211> LENGTH: 351
<212> TYPE: DNA
<213> ORGANISM: Mus musculus

<400> SEQUENCE: 106
ctgctgctgt ggcttacagg tgccagatgt gacatccaga tgactcagtc tccagcctcc 60
ctatctgcat ctgtgggaga aactgtcacc atcacatgtc gagcaagtgg gaatattcac 120

```
aattatttaa catggtatca gcagaaacag ggaaaatctc ctcagctcct ggtctataat    180

gcaaaaacct tagcagatgg tgtgccatca aggttcagtg gcagtggatc aggaacacaa    240

tattctctca agatcaatag actgcagcct gaagattttg ggagttatta ctgtcaacat    300

ttttggaata ttccgtggac gttcggtgga ggcaccaagc tgaatagccg c             351
```

```
<210> SEQ ID NO 107
<211> LENGTH: 5
<212> TYPE: PRT
<213> ORGANISM: Mus musculus

<400> SEQUENCE: 107

Asp His Ser Ile His
1               5


<210> SEQ ID NO 108
<211> LENGTH: 17
<212> TYPE: PRT
<213> ORGANISM: Mus musculus

<400> SEQUENCE: 108

Tyr Ile Ser Pro Gly Asn Gly Asn Ile Lys Tyr Asn Glu Lys Phe Lys
1               5                   10                  15

Gly


<210> SEQ ID NO 109
<211> LENGTH: 12
<212> TYPE: PRT
<213> ORGANISM: Mus musculus

<400> SEQUENCE: 109

Ser Leu Gly Arg Gly Gly Pro Tyr Tyr Phe Asp Tyr
1               5                   10


<210> SEQ ID NO 110
<211> LENGTH: 114
<212> TYPE: PRT
<213> ORGANISM: Mus musculus

<400> SEQUENCE: 110

Asp Ala Glu Leu Val Lys Pro Gly Ala Ser Val Lys Ile Ser Cys Lys
1               5                   10                  15

Ala Ser Gly Tyr Thr Phe Thr Asp His Ser Ile His Trp Val Gln Gln
            20                  25                  30

Lys Pro Glu Gln Gly Leu Glu Trp Ile Gly Tyr Ile Ser Pro Gly Asn
        35                  40                  45

Gly Asn Ile Lys Tyr Asn Glu Lys Phe Lys Gly Lys Ala Thr Leu Thr
    50                  55                  60

Ala Asp Lys Ser Ser Ser Thr Ala Tyr Met Gln Leu Asn Ser Leu Thr
65                  70                  75                  80

Ser Glu Asp Ser Ala Val Tyr Phe Cys Lys Arg Ser Leu Gly Arg Gly
                85                  90                  95

Gly Pro Tyr Tyr Phe Asp Tyr Trp Gly Gln Gly Thr Thr Val Thr Val
            100                 105                 110

Ser Ser


<210> SEQ ID NO 111
<211> LENGTH: 16
<212> TYPE: PRT
<213> ORGANISM: Mus musculus
```

<400> SEQUENCE: 111

Arg Ser Ser Lys Ser Leu Leu His Ser Asn Gly Asn Thr Tyr Leu Tyr
1 5 10 15

<210> SEQ ID NO 112
<211> LENGTH: 7
<212> TYPE: PRT
<213> ORGANISM: Mus musculus

<400> SEQUENCE: 112

Arg Met Ser Asn Leu Ala Ser
1 5

<210> SEQ ID NO 113
<211> LENGTH: 9
<212> TYPE: PRT
<213> ORGANISM: Mus musculus

<400> SEQUENCE: 113

Met Gln His Arg Glu Tyr Pro Val Thr
1 5

<210> SEQ ID NO 114
<211> LENGTH: 108
<212> TYPE: PRT
<213> ORGANISM: Mus musculus

<400> SEQUENCE: 114

Asp Ile Val Leu Thr Gln Ala Ala Pro Ser Leu Pro Val Thr Pro Gly
1 5 10 15

Glu Ser Val Ser Ile Ser Cys Arg Ser Ser Lys Ser Leu Leu His Ser
20 25 30

Asn Gly Asn Thr Tyr Leu Tyr Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Arg Glu Tyr Pro Val Thr Phe Gly Ser Gly Pro Asn
100 105

<210> SEQ ID NO 115
<211> LENGTH: 342
<212> TYPE: DNA
<213> ORGANISM: Mus musculus

<400> SEQUENCE: 115
gacgctgagt tggtgaaacc cggggcttca gtgaagatat cgtgcaaggc ttctggctac 60
accttcactg accattctat tcactgggtg cagcagaagc ctgaacaggg cctggaatgg 120
attggatata tttctcccgg aaatggtaat attaagtaca atgagaaatt caagggcaag 180
gccacactga ctgcagacaa atcctccagc actgcctaca tgcagctcaa cagcctgaca 240
tctgaggatt ctgcagtgta tttctgtaaa agatctctgg gacgtggggg cccgtactac 300
tttgactact ggggccaagg gaccacggtc accgtctcct ca 342

<210> SEQ ID NO 116

```
<211> LENGTH: 323
<212> TYPE: DNA
<213> ORGANISM: Mus musculus

<400> SEQUENCE: 116

atattgtgct gactcaggct gcaccctctc tacctgtcac tcctggagag tcagtatcca     60

tctcctgcag gtctagtaag agtctcctgc atagtaatgg caacacttac ttgtattggt    120

tcctgcagag gccaggccag tctcctcagc tcctgatata tcggatgtcc aaccttgcct    180

caggagtccc agacaggttc agtggcagtg ggtcaggaac tgctttcaca ctgagaatca    240

gtagagtgga ggctgaggat gtgggtgttt attactgtat gcaacatcga gaatatccgg    300

tcacgttcgg ttctggacca aac                                            323


<210> SEQ ID NO 117
<211> LENGTH: 5
<212> TYPE: PRT
<213> ORGANISM: Mus musculus

<400> SEQUENCE: 117

Ser Tyr Trp Ile Glu
1               5


<210> SEQ ID NO 118
<211> LENGTH: 17
<212> TYPE: PRT
<213> ORGANISM: Mus musculus

<400> SEQUENCE: 118

Glu Ile Leu Pro Gly Ser Gly Ser Thr Asn Tyr Asn Glu Lys Phe Lys
1               5                   10                  15

Gly


<210> SEQ ID NO 119
<211> LENGTH: 11
<212> TYPE: PRT
<213> ORGANISM: Mus musculus

<400> SEQUENCE: 119

Tyr Tyr Trp Tyr Phe Asp Val Trp Ala Gln Asp
1               5                   10


<210> SEQ ID NO 120
<211> LENGTH: 111
<212> TYPE: PRT
<213> ORGANISM: Mus musculus

<400> SEQUENCE: 120

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95
```

Ala Ser Tyr Tyr Trp Tyr Phe Asp Val Trp Ala Gln Asp His Val
            100                 105                 110

<210> SEQ ID NO 121
<211> LENGTH: 15
<212> TYPE: PRT
<213> ORGANISM: Mus musculus

<400> SEQUENCE: 121

Ser Ser Lys Asn Leu Leu His Ser Asn Gly Ile Thr Tyr Leu Tyr
1               5                   10                  15

<210> SEQ ID NO 122
<211> LENGTH: 7
<212> TYPE: PRT
<213> ORGANISM: Mus musculus

<400> SEQUENCE: 122

Arg Val Ser Asn Leu Ala Ser
1               5

<210> SEQ ID NO 123
<211> LENGTH: 9
<212> TYPE: PRT
<213> ORGANISM: Mus musculus

<400> SEQUENCE: 123

Ala Gln Leu Leu Glu Leu Pro Tyr Thr
1               5

<210> SEQ ID NO 124
<211> LENGTH: 109
<212> TYPE: PRT
<213> ORGANISM: Mus musculus

<400> SEQUENCE: 124

Ile Val Met Thr Gln Ala Ala Phe Ser Asn Pro Val Thr Leu Gly Thr
1               5                   10                  15

Ser Ala Ser Ile Ser Cys Arg Ser Ser Lys Asn Leu Leu His Ser Asn
            20                  25                  30

Gly Ile Thr Tyr Leu Tyr Trp Tyr Leu Gln Arg Pro Gly Gln Ser Pro
        35                  40                  45

Gln Leu Leu Ile Tyr Arg Val Ser Asn Leu Ala Ser Gly Val Pro Asn
    50                  55                  60

Arg Phe Ser Gly Ser Glu Ser Gly Thr Asp Phe Thr Leu Arg Ile Ser
65                  70                  75                  80

Arg Val Glu Ala Glu Asp Val Gly Val Tyr Tyr Cys Ala Gln Leu Leu
                85                  90                  95

Glu Leu Pro Tyr Thr Ser Glu Gly Thr Lys Arg Trp Glu
            100                 105

<210> SEQ ID NO 125
<211> LENGTH: 333
<212> TYPE: DNA
<213> ORGANISM: Mus musculus

<400> SEQUENCE: 125
caggttcagc tgcagcagtc tggagctgag ctgatgaagc ctggggcctc agtgaagata     60
tcctgcaagg ctactggcta cacattcagt agctactgga tagagtgggt aaagcagagg    120
cctggacatg gccttgagtg gattggagag attttacctg gaagtggtag tactaactac    180

```
aatgagaagt tcaagggcaa ggccacattc actgcagata catcctccaa cacagcctac    240

atgcaactca gcagcctgac atctgaggac tctgccgtct attactgtgc aagttactac    300

tggtacttcg atgtctgggc gcaggaccac gta                                 333
```

<210> SEQ ID NO 126
<211> LENGTH: 327
<212> TYPE: DNA
<213> ORGANISM: Mus musculus

<400> SEQUENCE: 126

```
attgtgatga cgcaggctgc cttctccaat ccagtcactc ttggaacatc agcttccatc     60

tcctgcaggt ctagtaagaa tctcctacat agtaatggca tcacttattt gtattggtat    120

ctgcagaggc caggccagtc tcctcagctc ctgatatatc gggtgtccaa tctggcctca    180

ggagtcccaa acaggttcag tggcagtgag tcaggaactg atttcacact gagaatcagc    240

agagtggagg ctgaggatgt gggtgtttat tactgtgctc aactgctaga actcccgtac    300

acgtcggagg ggaccaagcg ctgggag                                        327
```

<210> SEQ ID NO 127
<211> LENGTH: 5
<212> TYPE: PRT
<213> ORGANISM: Mus musculus

<400> SEQUENCE: 127

```
Ser Phe Gly Met His
1               5
```

<210> SEQ ID NO 128
<211> LENGTH: 17
<212> TYPE: PRT
<213> ORGANISM: Mus musculus

<400> SEQUENCE: 128

```
Tyr Ile Ser Ser Gly Ser Ser Thr Ile Tyr Tyr Ala Asp Thr Val Lys
1               5                   10                  15

Gly
```

<210> SEQ ID NO 129
<211> LENGTH: 11
<212> TYPE: PRT
<213> ORGANISM: Mus musculus

<400> SEQUENCE: 129

```
Ile Gly Thr Thr Thr Gly Pro Arg His His Phe
1               5                   10
```

<210> SEQ ID NO 130
<211> LENGTH: 113
<212> TYPE: PRT
<213> ORGANISM: Mus musculus

<400> SEQUENCE: 130

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
```

```
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Ser Thr Ile Gly Thr Thr Thr Gly Pro Arg His His Phe Thr Leu
            100                 105                 110

Arg


<210> SEQ ID NO 131
<211> LENGTH: 339
<212> TYPE: DNA
<213> ORGANISM: Mus musculus

<400> SEQUENCE: 131

gatgtgcagc tggtggagtc tgggggaggc ttagtgcagc ctggagggtc ccggaaactc      60

tcctgtgcag cctctggatt cactttcagt agctttggaa tgcactgggt tcgtcaggct     120

ccagagaagg ggctggagtg ggtcgcatac attagtagtg gcagtagtac catctactat     180

gcagacacag tgaagggccg attcaccatc tccagagaca atcccaagaa caccctgttc     240

ctgcaaatga ccagtctaag gtctgaggac acggccatgt attactgtgc aagtactata     300

ggtacgacta ctgggccaag gcaccacttc acgctccgc                            339


<210> SEQ ID NO 132
<211> LENGTH: 5
<212> TYPE: PRT
<213> ORGANISM: Mus musculus

<400> SEQUENCE: 132

Ser Tyr Asp Met Ser
1               5


<210> SEQ ID NO 133
<211> LENGTH: 17
<212> TYPE: PRT
<213> ORGANISM: Mus musculus

<400> SEQUENCE: 133

Tyr Ile Ser Ser Gly Ala Gly Ser Thr Tyr Tyr Pro Asp Thr Val Lys
1               5                   10                  15

Gly


<210> SEQ ID NO 134
<211> LENGTH: 11
<212> TYPE: PRT
<213> ORGANISM: Mus musculus

<400> SEQUENCE: 134

His Phe Tyr Arg Phe Asp Tyr Trp Gly Gln Gly
1               5                   10


<210> SEQ ID NO 135
<211> LENGTH: 109
<212> TYPE: PRT
<213> ORGANISM: Mus musculus

<400> SEQUENCE: 135

Gly Gly Gly Leu Val Lys Pro Gly Gly Ser Leu Lys Leu Ser Cys Ala
1               5                   10                  15
```

```
Ala Ser Gly Phe Ala Phe Ser Ser Tyr Asp Met Ser Trp Ile Arg Gln
            20                  25                  30

Thr Pro Glu Lys Arg Leu Glu Trp Val Ala Tyr Ile Ser Ser Gly Ala
        35                  40                  45

Gly Ser Thr Tyr Tyr Pro Asp Thr Val Lys Gly Arg Phe Thr Val Ser
    50                  55                  60

Arg Asp Asn Ala Lys Asn Thr Leu Tyr Leu Gln Met Ser Ser Leu Lys
65                  70                  75                  80

Ser Glu Asp Thr Ala Met Tyr Tyr Cys Ala Arg His Phe Tyr Arg Phe
                85                  90                  95

Asp Tyr Trp Gly Gln Gly Thr Thr Val Thr Val Ser Ser
            100                 105


<210> SEQ ID NO 136
<211> LENGTH: 15
<212> TYPE: PRT
<213> ORGANISM: Mus musculus

<400> SEQUENCE: 136

Ser Ala Gly Asp Arg Ile Thr Ile Thr Cys Lys Ala Ser Gln Ser
1               5                   10                  15


<210> SEQ ID NO 137
<211> LENGTH: 7
<212> TYPE: PRT
<213> ORGANISM: Mus musculus

<400> SEQUENCE: 137

Tyr Ala Ser Asn Arg Tyr Thr
1               5


<210> SEQ ID NO 138
<211> LENGTH: 9
<212> TYPE: PRT
<213> ORGANISM: Mus musculus

<400> SEQUENCE: 138

Gln Gln Asp Asp Arg Phe Pro Leu Thr
1               5


<210> SEQ ID NO 139
<211> LENGTH: 113
<212> TYPE: PRT
<213> ORGANISM: Mus musculus

<400> SEQUENCE: 139

Leu Leu Leu Cys Val Ser Gly Ala Pro Gly Ser Ile Val Met Thr Gln
1               5                   10                  15

Thr Pro Lys Phe Leu Leu Val Ser Ala Gly Asp Arg Ile Thr Ile Thr
            20                  25                  30

Cys Lys Ala Ser Gln Ser Val Ser Asn Asp Val Ala Trp Tyr Gln Gln
        35                  40                  45

Lys Pro Gly Gln Ser Pro Lys Leu Leu Ile Tyr Tyr Ala Ser Asn Arg
    50                  55                  60

Tyr Thr Gly Val Pro Asp Arg Phe Thr Gly Ser Gly Tyr Gly Thr Asp
65                  70                  75                  80

Phe Thr Phe Thr Ile Ser Thr Val Gln Ala Glu Asp Leu Ala Val Tyr
                85                  90                  95

Phe Cys Gln Gln Asp Asp Arg Phe Pro Leu Thr Phe Gly Ala Gly Pro
            100                 105                 110
```

Ser

<210> SEQ ID NO 140
<211> LENGTH: 327
<212> TYPE: DNA
<213> ORGANISM: Mus musculus

<400> SEQUENCE: 140
gggggaggct tagtgaagcc tggagggtcc ctgaaactct cctgtgcagc ctctggattc 60
gctttcagta gctatgacat gtcttggatt cgccagactc cggagaagag gctggaatgg 120
gtcgcataca ttagcagtgg tgctggtagc acctactatc cagacactgt gaaaggccga 180
ttcaccgtct ccagagacaa tgccaagaac accctgtatc tgcaaatgag cagtctgaag 240
tctgaggaca cagccatgta ttactgtgca agacatttct accgctttga ctactggggc 300
caagggacca cggtcaccgt ctcctca 327

<210> SEQ ID NO 141
<211> LENGTH: 339
<212> TYPE: DNA
<213> ORGANISM: Mus musculus

<400> SEQUENCE: 141
ctactgctct gtgtgtctgg tgctcctggg agtattgtga tgacccagac tcccaaattc 60
ctgcttgtat cagcaggaga caggattacc atcacctgca aggccagtca gagtgtgagt 120
aatgatgtag cttggtacca acagaagcca gggcagtctc ctaaactact gatatactat 180
gcatccaatc gctacactgg agtccctgat cgcttcactg gcagtggata tgggacggat 240
ttcactttca ccatcagcac tgtgcaggct gaagacctgg cagtttattt ctgtcagcag 300
gatgataggt ttcctctcac gttcggtgct ggaccaagc 339

<210> SEQ ID NO 142
<211> LENGTH: 5
<212> TYPE: PRT
<213> ORGANISM: Mus musculus

<400> SEQUENCE: 142

Asn Tyr Gly Met Asn
1 5

<210> SEQ ID NO 143
<211> LENGTH: 17
<212> TYPE: PRT
<213> ORGANISM: Mus musculus

<400> SEQUENCE: 143

Trp Ile Asn Thr Tyr Thr Gly Glu Pro Thr Tyr Ala Asp Asp Phe Lys
1 5 10 15

Gly

<210> SEQ ID NO 144
<211> LENGTH: 11
<212> TYPE: PRT
<213> ORGANISM: Mus musculus

<400> SEQUENCE: 144

Gly Ala Trp Phe Ala Tyr Trp Ala Lys Asp Ser
1 5 10

<210> SEQ ID NO 145
<211> LENGTH: 112
<212> TYPE: PRT
<213> ORGANISM: Mus musculus

<400> SEQUENCE: 145

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Gly Ala Trp Phe Ala Tyr Trp Ala Lys Asp Ser Ser Arg His
            100                 105                 110
```

<210> SEQ ID NO 146
<211> LENGTH: 15
<212> TYPE: PRT
<213> ORGANISM: Mus musculus

<400> SEQUENCE: 146

```
Ser Ile Thr Cys Lys Ala Ser Gln Asp Val Gly Thr Ala Val Ala
1               5                   10                  15
```

<210> SEQ ID NO 147
<211> LENGTH: 7
<212> TYPE: PRT
<213> ORGANISM: Mus musculus

<400> SEQUENCE: 147

```
Trp Ala Ser Thr Arg His Thr
1               5
```

<210> SEQ ID NO 148
<211> LENGTH: 9
<212> TYPE: PRT
<213> ORGANISM: Mus musculus

<400> SEQUENCE: 148

```
Gln Gln Tyr Ser Ser Tyr Pro Leu Thr
1               5
```

<210> SEQ ID NO 149
<211> LENGTH: 107
<212> TYPE: PRT
<213> ORGANISM: Mus musculus

<400> SEQUENCE: 149

```
Gly Val Glu Gly Asp Ile Val Met Thr Gln Ser His Lys Phe Met Ser
1               5                   10                  15

Thr Ser Val Gly Asp Arg Val Ser Ile Thr Cys Lys Ala Ser Gln Asp
            20                  25                  30

Val Gly Thr Ala Val Ala Trp Tyr Gln Gln Lys Pro Gly Gln Ser Pro
        35                  40                  45

Lys Leu Leu Ile Tyr Trp Ala Ser Thr Arg His Thr Gly Val Pro Asp
```

-continued

```
    50                  55                  60

Arg Phe Thr Gly Ser Gly Ser Gly Thr Asp Phe Thr Leu Thr Ile Ser
65                  70                  75                  80

Asn Val Gln Ser Glu Asp Leu Ala Asp Tyr Phe Cys Gln Gln Tyr Ser
                85                  90                  95

Ser Tyr Pro Leu Thr Phe Gly Ala Gly Pro Ser
            100                 105


<210> SEQ ID NO 150
<211> LENGTH: 336
<212> TYPE: DNA
<213> ORGANISM: Mus musculus

<400> SEQUENCE: 150

cagatccagt tggtgcagtc tggacctgag ctgaagaagc ctggagagac agtcaagatc      60

tcctgcaagg cttctgggta taccttcaca aactatggaa tgaactgggt gaagcaggct     120

ccaggaaagg gtttaaagtg gatgggctgg ataaacacct acactggaga gccaacatat     180

gctgatgact tcaagggacg gtttgccttc tctttggaaa cctctgccag cactgcctat     240

ttgcagatca acaacctcaa aaatgaggac acggctacat atttctgtgc aactggggcc     300

tggtttgctt actgggccaa ggactcttca cgccac                               336


<210> SEQ ID NO 151
<211> LENGTH: 333
<212> TYPE: DNA
<213> ORGANISM: Mus musculus

<400> SEQUENCE: 151

ataatatcca gaggacaaat tgttctcacc cagtctccag caatcatgtc tgcatctcca      60

ggggagaagg tcaccatgac ctgcagtgcc agctcaagtg taagttacat gcactggtac     120

cagcagaagt caggcacctc ccccaaaaga tggatttatg acacatccaa actggcttct     180

ggagtccctg ctcgcttcag tggcagtggg tctgggacct cttactctct cacaatcagc     240

agcatggagg ctgaagatgc tgccacttat tactgccagc agtggagtag taacccaccc     300

atctcacgtt cggtgctgga ccaagcgagc tgc                                  333


<210> SEQ ID NO 152
<211> LENGTH: 15
<212> TYPE: PRT
<213> ORGANISM: Mus musculus

<400> SEQUENCE: 152

Val Thr Met Thr Cys Ser Ala Ser Ser Ser Val Ser Tyr Met His
1               5                   10                  15


<210> SEQ ID NO 153
<211> LENGTH: 7
<212> TYPE: PRT
<213> ORGANISM: Mus musculus

<400> SEQUENCE: 153

Asp Thr Ser Lys Leu Ala Ser
1               5


<210> SEQ ID NO 154
<211> LENGTH: 9
<212> TYPE: PRT
<213> ORGANISM: Mus musculus
```

<400> SEQUENCE: 154

Gln Gln Trp Ser Ser Asn Pro Pro Ile
1 5

<210> SEQ ID NO 155
<211> LENGTH: 111
<212> TYPE: PRT
<213> ORGANISM: Mus musculus

<400> SEQUENCE: 155

Ile Ile Ser Arg Gly Gln Ile Val Leu Thr Gln Ser Pro Ala Ile Met
1 5 10 15

Ser Ala Ser Pro Gly Glu Lys Val Thr Met Thr Cys Ser Ala Ser Ser
20 25 30

Ser Val Ser Tyr Met His Trp Tyr Gln Gln Lys Ser Gly Thr Ser Pro
35 40 45

Lys Arg Trp Ile Tyr Asp Thr Ser Lys Leu Ala Ser Gly Val Pro Ala
50 55 60

Arg Phe Ser Gly Ser Gly Ser Gly Thr Ser Tyr Ser Leu Thr Ile Ser
65 70 75 80

Ser Met Glu Ala Glu Asp Ala Ala Thr Tyr Tyr Cys Gln Gln Trp Ser
85 90 95

Ser Asn Pro Pro Ile Ser Arg Ser Val Leu Asp Gln Ala Ser Cys
100 105 110

<210> SEQ ID NO 156
<211> LENGTH: 321
<212> TYPE: DNA
<213> ORGANISM: Mus musculus

<400> SEQUENCE: 156
ggtgttgaag gagacattgt gatgacccag tctcacaaat tcatgtccac atcagtagga 60
gacagggtca gcatcacctg caaggccagt caggatgtgg gtactgctgt agcctggtat 120
caacagaaac cagggcaatc tcctaaacta ctgatttact gggcatccac ccggcacact 180
ggagtccctg atcgcttcac aggcagtgga tctgggacag atttcactct caccattagc 240
aatgtgcagt ctgaagactt ggcagattat ttctgtcagc aatatagcag ctatcctctc 300
acgttcggtg ctggaccaag c 321

<210> SEQ ID NO 157
<211> LENGTH: 5
<212> TYPE: PRT
<213> ORGANISM: Mus musculus

<400> SEQUENCE: 157

Asp Phe Trp Met Asn
1 5

<210> SEQ ID NO 158
<211> LENGTH: 19
<212> TYPE: PRT
<213> ORGANISM: Mus musculus

<400> SEQUENCE: 158

Glu Ile Arg Leu Lys Ser Asn Asn Tyr Ala Thr His Tyr Ala Glu Ser
1 5 10 15

Val Lys Gly

<210> SEQ ID NO 159
<211> LENGTH: 13
<212> TYPE: PRT
<213> ORGANISM: Mus musculus

<400> SEQUENCE: 159

Leu Phe Tyr Tyr Tyr Asp Gly Thr Ser Gly Phe Ala Tyr
1 5 10

<210> SEQ ID NO 160
<211> LENGTH: 118
<212> TYPE: PRT
<213> ORGANISM: Mus musculus

<400> SEQUENCE: 160

Gly Gly Gly Leu Val Gln Pro Gly Gly Ser Met Lys Val Ser Cys Val
1 5 10 15

Ala Ser Gly Phe Ser Phe Ile Asp Phe Trp Met Asn Trp Val Arg Gln
20 25 30

Ser Pro Glu Lys Gly Leu Glu Trp Val Ala Glu Ile Arg Leu Lys Ser
35 40 45

Asn Asn Tyr Ala Thr His Tyr Ala Glu Ser Val Lys Gly Arg Phe Thr
50 55 60

Ile Ser Arg Asp Asp Ser Lys Ser Ser Val Tyr Leu Gln Met Asn Asn
65 70 75 80

Leu Arg Pro Glu Asp Thr Gly Ile Tyr Tyr Cys Thr Ser Leu Phe Tyr
85 90 95

Tyr Tyr Asp Gly Thr Ser Gly Phe Ala Tyr Trp Gly Gln Gly Thr Thr
100 105 110

Val Thr Val Leu Leu Lys
115

<210> SEQ ID NO 161
<211> LENGTH: 17
<212> TYPE: PRT
<213> ORGANISM: Mus musculus

<400> SEQUENCE: 161

Lys Ser Ser Gln Ser Leu Leu Asn Ser Gly Asp Gln Lys Asn Tyr Leu
1 5 10 15

Thr

<210> SEQ ID NO 162
<211> LENGTH: 7
<212> TYPE: PRT
<213> ORGANISM: Mus musculus

<400> SEQUENCE: 162

Trp Ala Ser Thr Arg Glu Ser
1 5

<210> SEQ ID NO 163
<211> LENGTH: 9
<212> TYPE: PRT
<213> ORGANISM: Mus musculus

<400> SEQUENCE: 163

Gln Asn Asp Tyr Asp Tyr Pro Leu Thr
1 5

<210> SEQ ID NO 164

<211> LENGTH: 109
<212> TYPE: PRT
<213> ORGANISM: Mus musculus

<400> SEQUENCE: 164

Asp Ile Val Met Thr Gln Ser Pro Ser Ser Leu Thr Val Thr Ala Gly
1 5 10 15

Glu Lys Val Thr Met His Cys Lys Ser Ser Gln Ser Leu Leu Asn Ser
20 25 30

Gly Asp Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Asp Tyr Pro Leu Thr Phe Gly Ala Gly Pro Ser
100 105

<210> SEQ ID NO 165
<211> LENGTH: 354
<212> TYPE: DNA
<213> ORGANISM: Mus musculus

<400> SEQUENCE: 165
ggaggaggct tggtgcaacc tggaggatcc atgaaagtct cctgtgttgc ctctggattc 60
tctttcattg acttttggat gaactgggtc cgccagtctc cagagaaggg gcttgagtgg 120
gttgctgaaa ttagattgaa atctaataat tatgcaacac attatgcgga gtctgtgaaa 180
gggaggttca ccatctcaag agatgattcc aaaagtagtg tctacctgca aatgaacaac 240
ttaagacctg aagacactgg catttattac tgtaccagcc tcttttatta ctatgatggt 300
acttcggggt ttgcttactg gggccaaggg accacggtca ccgttctcct caaa 354

<210> SEQ ID NO 166
<211> LENGTH: 327
<212> TYPE: DNA
<213> ORGANISM: Mus musculus

<400> SEQUENCE: 166
gacattgtga tgacacagtc tccgtcctcc ctgactgtga cagcaggaga gaaggtcact 60
atgcactgca agtccagtca gagtctttta aacagtggag atcaaaagaa ctacttgacc 120
tggtaccagc agaaaccagg acagcctcct aaactgttga tctactgggc atccactcgg 180
gaatctgggg tccctgatcg cttcacaggc agtggatctg gaacagattt cactctcacc 240
atcagcagtg tgcaggctga agacctggca gtttattact gtcagaatga ttatgattat 300
ccgctcacgt tcggtgctgg accaagc 327

<210> SEQ ID NO 167
<211> LENGTH: 5
<212> TYPE: PRT
<213> ORGANISM: Mus musculus

<400> SEQUENCE: 167

Asp Tyr Asn Met Asp
1 5

<210> SEQ ID NO 168
<211> LENGTH: 17
<212> TYPE: PRT
<213> ORGANISM: Mus musculus

<400> SEQUENCE: 168

Asp Ile Asn Pro Asn Tyr Asp Ser Thr Ser Tyr Asn Gln Lys Phe Lys
1               5                   10                  15

Gly

<210> SEQ ID NO 169
<211> LENGTH: 11
<212> TYPE: PRT
<213> ORGANISM: Mus musculus

<400> SEQUENCE: 169

Ser Arg Ser Tyr Asp Tyr Glu Gly Phe Ala Tyr
1               5                   10

<210> SEQ ID NO 170
<211> LENGTH: 148
<212> TYPE: PRT
<213> ORGANISM: Mus musculus

<400> SEQUENCE: 170

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 171
<211> LENGTH: 11
<212> TYPE: PRT
<213> ORGANISM: Mus musculus

<400> SEQUENCE: 171

Arg Ala Ser Gly Asn Ile His Asn Tyr Leu Ala
1               5                   10

<210> SEQ ID NO 172
<211> LENGTH: 7
<212> TYPE: PRT
<213> ORGANISM: Mus musculus

<400> SEQUENCE: 172

```
Asn Ala Lys Thr Leu Ala Asp
1               5


<210> SEQ ID NO 173
<211> LENGTH: 8
<212> TYPE: PRT
<213> ORGANISM: Mus musculus

<400> SEQUENCE: 173

Gln His Phe Trp Ser Thr Leu Thr
1               5


<210> SEQ ID NO 174
<211> LENGTH: 139
<212> TYPE: PRT
<213> ORGANISM: Mus musculus

<400> SEQUENCE: 174

Met Ser Val Leu Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
    130                 135


<210> SEQ ID NO 175
<211> LENGTH: 444
<212> TYPE: DNA
<213> ORGANISM: Mus musculus

<400> SEQUENCE: 175

atggaatgga gcggggtctt tatctttctc ctgtcaggaa ctgcaggtgt cctctctgag      60

gtccagctgc atcagtttgg agctgagctg gtgaagcctg gggcttcagt gaagatatcc     120

tgcaaggctt ctggctacac attcactgac tacaacatgg actgggtgaa gcagagccat     180

ggaaagagcc ttgagtggat tggagatatt aatcctaact atgatagtac tagctacaac     240

cagaagttca agggaaaggc cacattgact gtagacaagt cctccagcac agcctacatg     300

gagctccgca gcctgacatc tgaggacact gcagtctatt actgtgcaag atcgaggagc     360

tatgattacg aaggatttgc ttactggggc caagggactc tggtcactgt ctctgcagcc     420

aaaacaacac ccccatcagt ctat                                            444


<210> SEQ ID NO 176
<211> LENGTH: 444
<212> TYPE: DNA
<213> ORGANISM: Mus musculus
```

<400> SEQUENCE: 176
atggaatgga gcggggtctt tatctttctc ctgtcaggaa ctgcaggtgt cctctctgag 60
gtccagctgc atcagtttgg agctgagctg gtgaagcctg gggcttcagt gaagatatcc 120
tgcaaggctt ctggctacac attcactgac tacaacatgg actgggtgaa gcagagccat 180
ggaaagagcc ttgagtggat tggagatatt aatcctaact atgatagtac tagctacaac 240
cagaagttca agggaaaggc cacattgact gtagacaagt cctccagcac agcctacatg 300
gagctccgca gcctgacatc tgaggacact gcagtctatt actgtgcaag atcgaggagc 360
tatgattacg aaggatttgc ttactggggc caagggactc tggtcactgt ctctgcagcc 420
aaaacaacac ccccatcagt ctat 444

<210> SEQ ID NO 177
<211> LENGTH: 11
<212> TYPE: PRT
<213> ORGANISM: Mus musculus

<400> SEQUENCE: 177

Leu Trp Ser Val Asn Gln Lys Asn Tyr Leu Ser
1 5 10

<210> SEQ ID NO 178
<211> LENGTH: 7
<212> TYPE: PRT
<213> ORGANISM: Mus musculus

<400> SEQUENCE: 178

Gly Ala Ser Ile Arg Glu Ser
1 5

<210> SEQ ID NO 179
<211> LENGTH: 9
<212> TYPE: PRT
<213> ORGANISM: Mus musculus

<400> SEQUENCE: 179

Gln His Asn His Gly Ser Phe Leu Pro
1 5

<210> SEQ ID NO 180
<211> LENGTH: 132
<212> TYPE: PRT
<213> ORGANISM: Mus musculus

<400> SEQUENCE: 180

Ala Val Leu Arg Cys Ser Arg Gly Leu Leu Val Ile Trp Ile Ser Asp
1 5 10 15

Ile Gln Leu Thr Gln Ser Pro Ser Ser Leu Ala Val Thr Ala Gly Glu
20 25 30

Lys Val Thr Met Ser Cys Lys Ser Ser Gln Ser Leu Leu Trp Ser Val
35 40 45

Asn Gln Lys Asn Tyr Leu Ser Trp Tyr Gln Gln Lys Gln Arg Gln Pro
50 55 60

Pro Lys Leu Leu Ile Tyr Gly Ala Ser Ile Arg Glu Ser Trp Val Pro
65 70 75 80

Asp Arg Phe Thr Gly Ser Gly Ser Gly Thr Asp Phe Thr Leu Thr Ile
85 90 95

Ser Asn Val His Ala Glu Asp Leu Ala Val Tyr Tyr Cys Gln His Asn

```
            100                 105                 110

His Gly Ser Phe Leu Pro Ser Arg Ser Glu Gln Val Pro Ser Trp Arg
        115                 120                 125

Ser Asn Asn Arg
    130
```

<210> SEQ ID NO 181
<211> LENGTH: 398
<212> TYPE: DNA
<213> ORGANISM: Mus musculus

<400> SEQUENCE: 181

```
gcggtcctgc ggtgctctag aggactacta gtcatatgga tttccgatat ccagctgacc     60

cagtctccat cctccctggc tgtgacagca ggagagaagg tcactatgag ctgcaagtcc    120

agtcagagtc ttttgtggag tgtaaaccag aagaactact tgtcctggta ccagcagaaa    180

caaaggcagc ctcctaaact gcttatctat ggggcatcca ttagagaatc ttgggtccct    240

gatcggttca caggaagtgg atctgggaca gacttcactc tcaccattag caatgtgcat    300

gctgaagacc tagcagttta ttactgtcaa cacaatcatg gcagctttct cccctcacgt    360

tcggagcagg taccaagctg gagatcaaac aatcggat                            398
```

<210> SEQ ID NO 182
<211> LENGTH: 11
<212> TYPE: PRT
<213> ORGANISM: Mus musculus

<400> SEQUENCE: 182

```
Arg Ala Ser Gly Asn Ile His Asn Tyr Leu Ala
1               5                   10
```

<210> SEQ ID NO 183
<211> LENGTH: 7
<212> TYPE: PRT
<213> ORGANISM: Mus musculus

<400> SEQUENCE: 183

```
Asn Ala Lys Thr Leu Ala Asp
1               5
```

<210> SEQ ID NO 184
<211> LENGTH: 9
<212> TYPE: PRT
<213> ORGANISM: Mus musculus

<400> SEQUENCE: 184

```
Gln His Phe Trp Ser Thr Leu Thr Phe
1               5
```

<210> SEQ ID NO 185
<211> LENGTH: 117
<212> TYPE: PRT
<213> ORGANISM: Mus musculus

<400> SEQUENCE: 185

```
Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
            20                  25                  30

Ala Ser Gly Asn Ile His Asn Tyr Leu Ala Trp Tyr Gln Gln Lys Gln
        35                  40                  45
```

Gly Lys Ser Pro Gln Leu Leu Val Tyr Asn Ala Lys Thr Leu Ala Asp
    50                  55                  60

Gly Val Pro Ser Arg Phe Ser Gly Ser Gly Ser Gly Thr Gln Tyr Ser
65                  70                  75                  80

Leu Lys Ile Asn Ser Leu Gln Pro Glu Asp Phe Gly Ser Tyr Tyr Cys
                85                  90                  95

Gln His Phe Trp Ser Thr Leu Thr Phe Gly Gly Gly Thr Lys Leu Glu
            100                 105                 110

Ile Lys Gln Ser Asp
        115

<210> SEQ ID NO 186
<211> LENGTH: 353
<212> TYPE: DNA
<213> ORGANISM: Mus musculus

<400> SEQUENCE: 186
gaggactact agtcatatgg attccgatat ccagctgacc cagtctccag cctccctatc     60
tgcatctgtg ggagaaactg tcaccatcac atgtcgagca agtgggaata ttcacaatta    120
tttagcatgg tatcagcaga aacagggaaa atctcctcag ctcctggtct ataatgcaaa    180
aaccttagca gatggtgtgc catcaaggtt cagtggcagt ggatcaggaa cacaatattc    240
tctcaagatc aacagcctgc agcctgaaga ttttgggagt tattactgtc aacatttttg    300
gagtacgctc acgttcggag gtggtaccaa gctggagatc aaacaatcgg atc           353

<210> SEQ ID NO 187
<211> LENGTH: 11
<212> TYPE: PRT
<213> ORGANISM: Mus musculus

<400> SEQUENCE: 187

Arg Ala Ser Gln Ser Ile Ser Asn Tyr Leu His
1               5                   10

<210> SEQ ID NO 188
<211> LENGTH: 7
<212> TYPE: PRT
<213> ORGANISM: Mus musculus

<400> SEQUENCE: 188

Tyr Ala Ser Gln Ser Ile Ser
1               5

<210> SEQ ID NO 189
<211> LENGTH: 9
<212> TYPE: PRT
<213> ORGANISM: Mus musculus

<400> SEQUENCE: 189

Gln Gln Ser Asn Ser Trp Pro Tyr Thr
1               5

<210> SEQ ID NO 190
<211> LENGTH: 94
<212> TYPE: PRT
<213> ORGANISM: Mus musculus

<400> SEQUENCE: 190

Ser Gly Asp Arg Val Ser Leu Ser Cys Arg Ala Ser Gln Ser Ile Ser
1               5                   10                  15

```
Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Ala Gly Thr Lys Leu Glu Ile Lys Gln
                85                  90


<210> SEQ ID NO 191
<211> LENGTH: 283
<212> TYPE: DNA
<213> ORGANISM: Mus musculus

<400> SEQUENCE: 191

tcaggagata gagtcagtct ttcctgcagg gccagtcaaa gtattagcaa ctacctacac      60

tggtatcaac aaaaatcaca tgagtctcca aggcttctca tcaagtatgc ttcccagtcc     120

atctctggga tcccctccag gttcagtggc agtggatcag ggacagattt cactctcagt     180

atcaacagtg tggagactga agattttgga atgtatttct gtcaacagag taacagctgg     240

ccgtacacgt tcggtgcagg taccaagctg gagatcaaac aga                       283


<210> SEQ ID NO 192
<211> LENGTH: 11
<212> TYPE: PRT
<213> ORGANISM: Mus musculus

<400> SEQUENCE: 192

Leu Ser Ile Val Asn Arg Tyr His Tyr Met Ser
1               5                   10


<210> SEQ ID NO 193
<211> LENGTH: 6
<212> TYPE: PRT
<213> ORGANISM: Mus musculus

<400> SEQUENCE: 193

Glu Ala Ser Ile Thr Lys
1               5


<210> SEQ ID NO 194
<211> LENGTH: 9
<212> TYPE: PRT
<213> ORGANISM: Mus musculus

<400> SEQUENCE: 194

Gln His Asn Arg Gly Ser Phe Leu Pro
1               5


<210> SEQ ID NO 195
<211> LENGTH: 105
<212> TYPE: PRT
<213> ORGANISM: Mus musculus

<400> SEQUENCE: 195

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
```

```
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Arg Ser Asn
            100                 105


<210> SEQ ID NO 196
<211> LENGTH: 317
<212> TYPE: DNA
<213> ORGANISM: Mus musculus

<400> SEQUENCE: 196

ggactcttct gctctgtgga gagatgtcac tatcaactgc aatccagtca gaatcttttg      60

agtattgtaa accggtatca ctacatgtcc ggaaaccctc ctaaactcct ggtctatcct     120

gcactgctta tctatgaggc atccattaca aaatcctgtg tccctgatcg gttcacacga     180

agtggatctg ggacaaactt cactctcacc attaattttg tgcatgctga tgacctaatt     240

ttttattact gtcaacacaa tcgtggcagc tttctcccct caagttcggt gcaggtacca     300

agaaggagat caaacaa                                                    317


<210> SEQ ID NO 197
<211> LENGTH: 5
<212> TYPE: PRT
<213> ORGANISM: Mus musculus

<400> SEQUENCE: 197

Gly Tyr Thr Met Asn
1               5


<210> SEQ ID NO 198
<211> LENGTH: 16
<212> TYPE: PRT
<213> ORGANISM: Mus musculus

<400> SEQUENCE: 198

Asn Pro Tyr Asn Gly Gly Thr Ser Tyr Asn Gln Lys Phe Lys Gly Lys
1               5                   10                  15


<210> SEQ ID NO 199
<211> LENGTH: 9
<212> TYPE: PRT
<213> ORGANISM: Mus musculus

<400> SEQUENCE: 199

Trp Gly Val Trp Ser Ala Met Asp Tyr
1               5


<210> SEQ ID NO 200
<211> LENGTH: 100
<212> TYPE: PRT
<213> ORGANISM: Mus musculus

<400> SEQUENCE: 200

Asp Ile Leu Gln Ala Ser Gly Tyr Ser Phe Thr Gly Tyr Thr Met Asn
```

```
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100


<210> SEQ ID NO 201
<211> LENGTH: 11
<212> TYPE: PRT
<213> ORGANISM: Mus musculus

<400> SEQUENCE: 201

Lys Ala Ser Gln Asn Val Arg Thr Ala Val Ala
1               5                   10


<210> SEQ ID NO 202
<211> LENGTH: 7
<212> TYPE: PRT
<213> ORGANISM: Mus musculus

<400> SEQUENCE: 202

Leu Ala Ser Asn Arg Asp Thr
1               5


<210> SEQ ID NO 203
<211> LENGTH: 9
<212> TYPE: PRT
<213> ORGANISM: Mus musculus

<400> SEQUENCE: 203

Leu Gln His Cys Asn Tyr Pro Asn Glu
1               5


<210> SEQ ID NO 204
<211> LENGTH: 90
<212> TYPE: PRT
<213> ORGANISM: Mus musculus

<400> SEQUENCE: 204

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90
```

<210> SEQ ID NO 205
<211> LENGTH: 301
<212> TYPE: DNA
<213> ORGANISM: Mus musculus

<400> SEQUENCE: 205
gatatcctgc aggcttctgg ttactcattc actggctaca ccatgaactg ggtgaagcag 60
agccatggaa agaaccttga gtggattgga cttattaatc cttacaatgg tggtactagc 120
tacaaccaga agttcaaggg caaggccaca ttaactgtag acaagtcatc cagcacagcc 180
tacatggagc tcctcagtct gacatctgag gactctgcag tctattactg tgcaagatgg 240
ggggtatggt cggctatgga ctactggggc caagggacca cggtcaccgt ctcctcaaaa 300
a 301

<210> SEQ ID NO 206
<211> LENGTH: 290
<212> TYPE: DNA
<213> ORGANISM: Mus musculus

<400> SEQUENCE: 206
gacagggtca gcatcacctg caaggccagt caaaatgttc gtactgctgt agcctggtat 60
caacagaaac cacggcagtc tcctaaagca ctgatttact tggcatccaa ccgggacact 120
ggactccctg atcgcttccc aggcagggga tctgggacag atttcactct caacattacc 180
aatgtgcaat ctgaagacct ggaagattat ttctgtctgc aacattgtaa ttatcctaac 240
gagttcagag gttgtaccaa ggtgccaatc taaagaacaa acaccccctg 290

<210> SEQ ID NO 207
<211> LENGTH: 5
<212> TYPE: PRT
<213> ORGANISM: Mus musculus

<400> SEQUENCE: 207

Ser Tyr Trp Met Gln
1 5

<210> SEQ ID NO 208
<211> LENGTH: 17
<212> TYPE: PRT
<213> ORGANISM: Mus musculus

<400> SEQUENCE: 208

Ala Ile Tyr Pro Gly Asp Gly Asp Thr Arg Tyr Thr Gln Lys Phe Lys
1 5 10 15

Gly

<210> SEQ ID NO 209
<211> LENGTH: 11
<212> TYPE: PRT
<213> ORGANISM: Mus musculus

<400> SEQUENCE: 209

Ala Arg Gly Glu Tyr Gly Asn Tyr Phe Ala Tyr
1 5 10

<210> SEQ ID NO 210
<211> LENGTH: 116
<212> TYPE: PRT
<213> ORGANISM: Mus musculus

<400> SEQUENCE: 210

Leu Gln Glu Ser Gly Ala Glu Leu Ala Arg Pro Gly Ala Ser Val Lys
1 5 10 15

Leu Ser Cys Lys Ala Ser Gly Tyr Thr Phe Thr Ser Tyr Trp Met Gln
20 25 30

Trp Val Lys Gln Arg Pro Gly Gln Gly Leu Glu Trp Ile Gly Ala Ile
35 40 45

Tyr Pro Gly Asp Gly Asp Thr Arg Tyr Thr Gln Lys Phe Lys Gly Lys
50 55 60

Ala Thr Leu Thr Ala Asp Lys Ser Ser Ser Thr Ala Tyr Met Gln Leu
65 70 75 80

Ser Ser Leu Ala Ser Glu Asp Ser Ala Val Tyr Tyr Cys Ala Arg Gly
85 90 95

Glu Tyr Gly Asn Tyr Phe Ala Tyr Trp Gly Gln Gly Thr Thr Val Thr
100 105 110

Val Ser Ser Asn
115

<210> SEQ ID NO 211
<211> LENGTH: 11
<212> TYPE: PRT
<213> ORGANISM: Mus musculus

<400> SEQUENCE: 211

Lys Ala Ser Gln Asp Ile Asn Ser Tyr Leu Ser
1 5 10

<210> SEQ ID NO 212
<211> LENGTH: 7
<212> TYPE: PRT
<213> ORGANISM: Mus musculus

<400> SEQUENCE: 212

Arg Ala Asn Arg Leu Val Asp
1 5

<210> SEQ ID NO 213
<211> LENGTH: 9
<212> TYPE: PRT
<213> ORGANISM: Mus musculus

<400> SEQUENCE: 213

Leu Gln Tyr Asp Glu Phe Pro Leu Thr
1 5

<210> SEQ ID NO 214
<211> LENGTH: 100
<212> TYPE: PRT
<213> ORGANISM: Mus musculus

<400> SEQUENCE: 214

Thr Ser Asp Ala Ser Leu Gly Glu Arg Val Thr Ile Thr Cys Lys Ala
1 5 10 15

Ser Gln Asp Ile Asn Ser Tyr Leu Ser Trp Phe Gln Gln Lys Pro Gly
20 25 30

Lys Ser Pro Lys Thr Leu Ile Tyr Arg Ala Asn Arg Leu Val Asp Gly
35 40 45

Val Pro Ser Arg Phe Ser Gly Ser Gly Ser Gly Gln Asp Tyr Ser Leu
50 55 60

-continued

Thr Ile Ser Ser Leu Glu Tyr Glu Asp Met Gly Ile Tyr Tyr Cys Leu
65 70 75 80

Gln Tyr Asp Glu Phe Pro Leu Thr Phe Gly Gly Gly Thr Lys Leu Glu
85 90 95

Ile Lys Gln Lys
100

<210> SEQ ID NO 215
<211> LENGTH: 352
<212> TYPE: DNA
<213> ORGANISM: Mus musculus

<400> SEQUENCE: 215
aactgcagga gtctggggct gagctggcaa gacctggggc ttcagtgaag ttgtcctgca 60
aggcttctgg ctacaccttt actagctact ggatgcagtg ggtaaaacag aggcctggac 120
agggtctgga atggattggg gctatttatc ctggagatgg tgatactagg tacactcaga 180
agttcaaggg caaggccaca ttgactgcag ataaatcctc cagcacagcc tacatgcaac 240
tcagcagctt ggcatctgag gactctgcgg tctattactg tgcaagaggg gagtatggta 300
actattttgc ttactggggc caagggacca cggtcaccgt ctcctcaaat cg 352

<210> SEQ ID NO 216
<211> LENGTH: 302
<212> TYPE: DNA
<213> ORGANISM: Mus musculus

<400> SEQUENCE: 216
ggacatcgga tgcatctcta ggagagagag tcactatcac ttgcaaggcg agtcaggaca 60
ttaatagcta tttaagctgg ttccagcaga aaccagggaa atctcctaag accctgatct 120
atcgtgcaaa cagattggta gatggggtcc catcaaggtt cagtggcagt ggatctgggc 180
aagattattc tctcaccatc agcagcctgg agtatgaaga tatgggaatt tattattgtc 240
tacagtatga tgagtttccg ctcacgttcg gaggaggtac caagctggag atcaaacaaa 300
aa 302

<210> SEQ ID NO 217
<211> LENGTH: 5
<212> TYPE: PRT
<213> ORGANISM: Mus musculus

<400> SEQUENCE: 217

Asp Thr Tyr Met His
1 5

<210> SEQ ID NO 218
<211> LENGTH: 17
<212> TYPE: PRT
<213> ORGANISM: Mus musculus

<400> SEQUENCE: 218

Arg Ile Asp Pro Ala Asn Gly Asn Thr Lys Tyr Asp Pro Lys Phe Gln
1 5 10 15

Gly

<210> SEQ ID NO 219
<211> LENGTH: 14
<212> TYPE: PRT
<213> ORGANISM: Mus musculus

<400> SEQUENCE: 219

Ala Arg Pro Ile His Tyr Tyr Tyr Gly Ser Ser Leu Ala Tyr
1 5 10

<210> SEQ ID NO 220
<211> LENGTH: 108
<212> TYPE: PRT
<213> ORGANISM: Mus musculus

<400> SEQUENCE: 220

Ala Trp Leu Ser Gln Leu Ser Cys Thr Ala Ser Gly Phe Asn Ile Lys
1 5 10 15

Asp Thr Tyr Met His Trp Val Lys Gln Arg Pro Glu Gln Gly Leu Glu
20 25 30

Trp Ile Gly Arg Ile Asp Pro Ala Asn Gly Asn Thr Lys Tyr Asp Pro
35 40 45

Lys Phe Gln Gly Lys Ala Thr Ile Thr Ala Asp Thr Ser Ser Asn Thr
50 55 60

Ala Tyr Leu Gln Leu Ser Ser Leu Thr Ser Glu Asp Thr Ala Val Tyr
65 70 75 80

Tyr Cys Ala Arg Pro Ile His Tyr Tyr Tyr Gly Ser Ser Leu Ala Tyr
85 90 95

Trp Gly Gln Gly Thr Thr Val Thr Val Ser Ser Lys
100 105

<210> SEQ ID NO 221
<211> LENGTH: 11
<212> TYPE: PRT
<213> ORGANISM: Mus musculus

<400> SEQUENCE: 221

Ser Val Asp Ser Tyr Gly Asn Ser Phe Met His
1 5 10

<210> SEQ ID NO 222
<211> LENGTH: 7
<212> TYPE: PRT
<213> ORGANISM: Mus musculus

<400> SEQUENCE: 222

Arg Ala Ser Asn Leu Glu Ser
1 5

<210> SEQ ID NO 223
<211> LENGTH: 9
<212> TYPE: PRT
<213> ORGANISM: Mus musculus

<400> SEQUENCE: 223

Gln Gln Ser Asn Glu Asp Pro Gly Arg
1 5

<210> SEQ ID NO 224
<211> LENGTH: 104
<212> TYPE: PRT
<213> ORGANISM: Mus musculus

<400> SEQUENCE: 224

Glu Phe His Ala Val Ser Leu Gly Gln Arg Ala Thr Ile Ser Cys Arg
1 5 10 15

Ala Ser Glu Ser Val Asp Ser Tyr Gly Asn Ser Phe Met His Trp Tyr

```
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100


<210> SEQ ID NO 225
<211> LENGTH: 326
<212> TYPE: DNA
<213> ORGANISM: Mus musculus

<400> SEQUENCE: 225

gcatggctca gtcagttgtc ctgcacagct tctggcttca acattaaaga cacctatatg      60

cactgggtga agcagaggcc tgaacagggc ctggagtgga ttggaaggat tgatcctgcg     120

aatggtaata ctaaatatga cccgaagttc cagggcaagg ccactataac agcagacaca     180

tcctccaaca cagcctacct gcagctcagc agcctgacat ctgaggacac tgccgtctat     240

tactgtgcta gaccgattca ttattactac ggtagtagcc ttgcttactg gggccaaggg     300

accacggtca ccgtctcctc aaaaaa                                          326


<210> SEQ ID NO 226
<211> LENGTH: 313
<212> TYPE: DNA
<213> ORGANISM: Mus musculus

<400> SEQUENCE: 226

gagtttcatg ctgtgtctct agggcagagg gccaccatat cctgcagagc cagtgaaagt      60

gttgatagtt atggcaatag ttttatgcac tggtaccagc agaaaccagg acagccaccc     120

aaactcctca tctatcgtgc atccaaccta gaatctggga tccctgccag gttcagtggc     180

agtgggtcta ggacagactt caccctcacc attaatcctg tggaggctga tgatgttgca     240

acctattact gtcagcaaag taatgaggat cctggacgtt cggaggtggt accaagctgg     300

agatcaaaca aaa                                                        313


<210> SEQ ID NO 227
<211> LENGTH: 5
<212> TYPE: PRT
<213> ORGANISM: Mus musculus

<400> SEQUENCE: 227

Asp Tyr Tyr Met Ser
1               5


<210> SEQ ID NO 228
<211> LENGTH: 17
<212> TYPE: PRT
<213> ORGANISM: Mus musculus

<400> SEQUENCE: 228

Arg Asn Lys Ala Asn Gly Tyr Thr Thr Glu Tyr Ser Ala Ser Val Lys
1               5                   10                  15
```

Gly

<210> SEQ ID NO 229
<211> LENGTH: 9
<212> TYPE: PRT
<213> ORGANISM: Mus musculus

<400> SEQUENCE: 229

Ala Arg Ala Asn Trp Ala Phe Asp Tyr
1 5

<210> SEQ ID NO 230
<211> LENGTH: 109
<212> TYPE: PRT
<213> ORGANISM: Mus musculus

<400> SEQUENCE: 230

Pro Arg Ala Ser Leu Gly Val Ser Glu Thr Leu Leu Cys Thr Ser Gly
1 5 10 15

Phe Thr Phe Thr Asp Tyr Tyr Met Ser Trp Val Arg Gln Pro Pro Gly
20 25 30

Lys Ala Leu Glu Trp Leu Gly Phe Ile Arg Asn Lys Ala Asn Gly Tyr
35 40 45

Thr Thr Glu Tyr Ser Ala Ser Val Lys Gly Arg Phe Thr Ile Ser Arg
50 55 60

Asp Asn Ser Gln Ser Ile Leu Tyr Leu Gln Met Asn Thr Leu Arg Ala
65 70 75 80

Glu Asp Ser Ala Thr Tyr Tyr Cys Ala Arg Ala Asn Trp Ala Phe Asp
85 90 95

Tyr Trp Gly Gln Gly Thr Thr Val Thr Val Ser Ser Lys
100 105

<210> SEQ ID NO 231
<211> LENGTH: 11
<212> TYPE: PRT
<213> ORGANISM: Mus musculus

<400> SEQUENCE: 231

Arg Ala Ser Gln Ser Ile Ser Asn Tyr Leu His
1 5 10

<210> SEQ ID NO 232
<211> LENGTH: 7
<212> TYPE: PRT
<213> ORGANISM: Mus musculus

<400> SEQUENCE: 232

Tyr Ala Ser Gln Ser Ile Ser
1 5

<210> SEQ ID NO 233
<211> LENGTH: 9
<212> TYPE: PRT
<213> ORGANISM: Mus musculus

<400> SEQUENCE: 233

Gln Gln Ser Asn Ser Trp Pro Tyr Thr
1 5

<210> SEQ ID NO 234
<211> LENGTH: 94
<212> TYPE: PRT

<213> ORGANISM: Mus musculus

<400> SEQUENCE: 234

Ser Gly Asp Arg Val Ser Leu Ser Cys Arg Ala Ser Gln Ser Ile Ser
1 5 10 15

Asn Tyr Leu His Trp Tyr Gln Gln Lys Ser His Glu Ser Pro Arg Leu
20 25 30

Leu Ile Lys Tyr Ala Ser Gln Ser Ile Ser Gly Ile Pro Ser Arg Phe
35 40 45

Ser Gly Ser Gly Ser Gly Thr Asp Phe Thr Leu Ser Ile Asn Ser Val
50 55 60

Glu Thr Glu Asp Phe Gly Met Tyr Phe Cys Gln Gln Ser Asn Ser Trp
65 70 75 80

Pro Tyr Thr Phe Gly Gly Gly Thr Lys Leu Glu Ile Lys Gln
85 90

<210> SEQ ID NO 235
<211> LENGTH: 329
<212> TYPE: DNA
<213> ORGANISM: Mus musculus

<400> SEQUENCE: 235
ggccgcgtgc tagcctgggg gtctctgaga ctctcctgtg cacttctggg ttcaccttca 60
ctgattacta catgagctgg gtccgccagc ctccaggaaa ggcacttgag tggttgggtt 120
ttattagaaa caaagctaat ggttacacaa cagagtacag tgcatctgtg aagggtcggt 180
tcaccatctc cagagataat tcccaaagca tcctctatct tcaaatgaac accctgagag 240
ctgaggacag tgccacttat tactgtgcaa gggctaactg ggcctttgac tactggggcc 300
aagggaccac ggtcaccgtc tcctcaaaa 329

<210> SEQ ID NO 236
<211> LENGTH: 284
<212> TYPE: DNA
<213> ORGANISM: Mus musculus

<400> SEQUENCE: 236
tcaggagata gagtcagtct ttcctgcagg gccagtcaaa gtattagcaa ctacctacac 60
tggtatcaac aaaaatcaca tgagtctcca aggcttctca tcaagtatgc ttcccagtcc 120
atctctggga tcccctccag gttcagtggc agtggatcag ggacagattt cactctcagt 180
atcaacagtg tggagactga agattttgga atgtatttct gtcaacagag taacagctgg 240
ccgtacacgt tcggaggagg taccaagctg gagatcaaac agaa 284

<210> SEQ ID NO 237
<211> LENGTH: 5
<212> TYPE: PRT
<213> ORGANISM: Mus musculus

<400> SEQUENCE: 237

Asp Tyr Tyr Met Ser
1 5

<210> SEQ ID NO 238
<211> LENGTH: 17
<212> TYPE: PRT
<213> ORGANISM: Mus musculus

<400> SEQUENCE: 238

Arg Asn Lys Ala Asn Gly Tyr Thr Thr Glu Tyr Ser Ala Ser Val Lys
1 5 10 15

Gly

<210> SEQ ID NO 239
<211> LENGTH: 12
<212> TYPE: PRT
<213> ORGANISM: Mus musculus

<400> SEQUENCE: 239

Ala Arg Ala Pro Leu Leu Tyr Tyr Ala Met Asp Tyr
1 5 10

<210> SEQ ID NO 240
<211> LENGTH: 111
<212> TYPE: PRT
<213> ORGANISM: Mus musculus

<400> SEQUENCE: 240

Pro Ala Cys Leu Pro Gly Gly Ser Leu Arg Leu Ser Cys Ala Thr Ser
1 5 10 15

Gly Phe Thr Phe Thr Asp Tyr Tyr Met Ser Trp Val Arg Gln Pro Pro
20 25 30

Gly Lys Ala Leu Glu Trp Leu Gly Phe Ile Arg Asn Lys Ala Asn Gly
35 40 45

Tyr Thr Thr Glu Tyr Ser Ala Ser Val Lys Gly Arg Phe Thr Ile Ser
50 55 60

Arg Asp Asn Ser Gln Ser Ile Leu Tyr Leu Gln Met Asn Thr Leu Arg
65 70 75 80

Ala Glu Asp Ser Ala Thr Tyr Tyr Cys Ala Arg Ala Pro Leu Leu Tyr
85 90 95

Tyr Ala Met Asp Tyr Trp Gly Gln Gly Thr Thr Val Thr Val Ser
100 105 110

<210> SEQ ID NO 241
<211> LENGTH: 11
<212> TYPE: PRT
<213> ORGANISM: Mus musculus

<400> SEQUENCE: 241

Asn Val Ser Thr Ser Gly Tyr Ser Tyr Met His
1 5 10

<210> SEQ ID NO 242
<211> LENGTH: 7
<212> TYPE: PRT
<213> ORGANISM: Mus musculus

<400> SEQUENCE: 242

Leu Val Ser Asn Leu Glu Ser
1 5

<210> SEQ ID NO 243
<211> LENGTH: 8
<212> TYPE: PRT
<213> ORGANISM: Mus musculus

<400> SEQUENCE: 243

Gln His Ile Arg Glu Leu Thr Arg
1 5

<210> SEQ ID NO 244
<211> LENGTH: 102
<212> TYPE: PRT
<213> ORGANISM: Mus musculus

<400> SEQUENCE: 244

Arg Leu Pro Phe Tyr Ser Leu Glu Gln Arg Ala Thr Ile Ser Tyr Arg
1 5 10 15

Ala Ser Lys Asn Val Ser Thr Ser Gly Tyr Ser Tyr Met His Trp Asn
20 25 30

Gln Gln Lys Pro Gly Gln Pro Pro Lys Leu Leu Ile Tyr Leu Val Ser
35 40 45

Asn Leu Glu Ser Gly Val Pro Ala Arg Phe Ser Gly Ser Gly Ser Gly
50 55 60

Thr Asp Phe Thr Leu Asn Ile His Pro Val Glu Glu Glu Asp Ala Ala
65 70 75 80

Thr Tyr Tyr Cys Gln His Ile Arg Glu Leu Thr Arg Ser Glu Leu Val
85 90 95

Pro Ser Trp Lys Ser Asn
100

<210> SEQ ID NO 245
<211> LENGTH: 340
<212> TYPE: DNA
<213> ORGANISM: Mus musculus

<400> SEQUENCE: 245
ccggcctgct tgcctggtgg ttctctgaga ctctcctgtg caacttctgg gttcaccttc 60
actgattact acatgagctg ggtccgccag cctccaggaa aggcacttga gtggttgggt 120
tttattagaa acaaagctaa tggttacaca acagagtaca gtgcatctgt gaagggtcgg 180
ttcaccatct ccagagataa ttcccaaagc atcctctatc ttcaaatgaa caccctgaga 240
gctgaggaca gtgccactta ttactgtgca agagcccctc tactttacta tgctatggac 300
tactggggcc aagggaccac ggtcaccgtc tcctaaatta 340

<210> SEQ ID NO 246
<211> LENGTH: 306
<212> TYPE: DNA
<213> ORGANISM: Mus musculus

<400> SEQUENCE: 246
cgccttcctt tctattctct ggagcagagg gccaccatct catacagggc cagcaaaaat 60
gtcagtacat ctggctatag ttatatgcac tggaaccaac agaaaccagg acagccaccc 120
aaactcctca tctatcttgt atccaaccta gaatctgggg tccctgccag gttcagtggc 180
agtgggtctg ggacagactt caccctcaac atccatcctg tggaggagga ggatgctgca 240
acctattact gtcagcacat tagggagctt acacgttcgg agctggtacc aagctggaaa 300
tcaaac 306

<210> SEQ ID NO 247
<211> LENGTH: 5
<212> TYPE: PRT
<213> ORGANISM: Mus musculus

<400> SEQUENCE: 247

Ser Tyr Trp Met His
1 5

<210> SEQ ID NO 248
<211> LENGTH: 17
<212> TYPE: PRT
<213> ORGANISM: Mus musculus

<400> SEQUENCE: 248

Met Ile Asp Pro Ser Asn Ser Glu Thr Arg Leu Asn Gln Lys Phe Lys
1 5 10 15

Asp

<210> SEQ ID NO 249
<211> LENGTH: 12
<212> TYPE: PRT
<213> ORGANISM: Mus musculus

<400> SEQUENCE: 249

Ala Arg Gly Leu Arg His Tyr Trp Tyr Phe Asp Val
1 5 10

<210> SEQ ID NO 250
<211> LENGTH: 101
<212> TYPE: PRT
<213> ORGANISM: Mus musculus

<400> SEQUENCE: 250

Val Ser Cys Lys Ala Ser Gly Tyr Thr Phe Thr Ser Tyr Trp Met His
1 5 10 15

Trp Val Lys Gln Arg Pro Gly Gln Gly Leu Glu Trp Ile Gly Met Ile
20 25 30

Asp Pro Ser Asn Ser Glu Thr Arg Leu Asn Gln Lys Phe Lys Asp Lys
35 40 45

Ala Thr Leu Asn Val Asp Lys Ser Ser Asn Thr Ala Tyr Met Gln Leu
50 55 60

Ser Ser Leu Thr Ser Glu Asp Ser Ala Val Tyr Tyr Cys Ala Arg Gly
65 70 75 80

Leu Arg His Tyr Trp Tyr Phe Asp Val Trp Gly Gln Gly Thr Thr Val
85 90 95

Thr Val Ser Ser Lys
100

<210> SEQ ID NO 251
<211> LENGTH: 11
<212> TYPE: PRT
<213> ORGANISM: Mus musculus

<400> SEQUENCE: 251

Ser Val Ser Thr Ser Gly Tyr Ser Tyr Met His
1 5 10

<210> SEQ ID NO 252
<211> LENGTH: 7
<212> TYPE: PRT
<213> ORGANISM: Mus musculus

<400> SEQUENCE: 252

Leu Val Ser Asn Leu Glu Ser
1 5

<210> SEQ ID NO 253
<211> LENGTH: 9
<212> TYPE: PRT

<213> ORGANISM: Mus musculus

<400> SEQUENCE: 253

Gln His Ile Arg Glu Leu Thr Arg Ser
1 5

<210> SEQ ID NO 254
<211> LENGTH: 99
<212> TYPE: PRT
<213> ORGANISM: Mus musculus

<400> SEQUENCE: 254

Thr Ile Leu Trp Arg Glu Gly Pro Phe Ser Tyr Arg Ala Ser Lys Ser
1 5 10 15

Val Ser Thr Ser Gly Tyr Ser Tyr Met His Trp Asn Gln Gln Lys Pro
20 25 30

Gly Gln Pro Pro Arg Leu Leu Ile Tyr Leu Val Ser Asn Leu Glu Ser
35 40 45

Gly Val Pro Ala Arg Phe Ser Gly Ser Gly Ser Gly Thr Asp Phe Thr
50 55 60

Leu Asn Ile His Pro Val Glu Glu Glu Asp Ala Ala Thr Tyr Tyr Cys
65 70 75 80

Gln His Ile Arg Glu Leu Thr Arg Ser Glu Glu Val Pro Ser Trp Arg
85 90 95

Ser Asn Lys

<210> SEQ ID NO 255
<211> LENGTH: 304
<212> TYPE: DNA
<213> ORGANISM: Mus musculus

<400> SEQUENCE: 255
gtgtcctgca aggcttcagg ctataccttc accagctact ggatgcactg ggtgaaacag 60
aggcctggac aaggccttga gtggattggc atgattgatc cttccaatag tgaaactagg 120
ttaaatcaga agttcaagga caaggccaca ttgaatgtag acaaatcctc caacacagcc 180
tacatgcagc tcagcagcct gacatctgag gactctgcag tctattactg tgcaagaggg 240
ttacgccact actggtactt cgatgtctgg ggccaaggga ccacggtcac cgtctcctca 300
aaaa 304

<210> SEQ ID NO 256
<211> LENGTH: 298
<212> TYPE: DNA
<213> ORGANISM: Mus musculus

<400> SEQUENCE: 256
actattctct ggagagaggg ccccttctca tacagggcca gcaaaagtgt cagtacatct 60
ggctatagtt atatgcactg gaaccaacag aaaccaggac agccacccag actcctcatc 120
tatcttgtat ccaacctaga atctggggtc cctgccaggt tcagtggcag tgggtctggg 180
acagacttca ccctcaacat ccatcctgtg gaggaggagg atgctgcaac ctattactgt 240
cagcacatta gggagcttac acgttcggag gaggtaccaa gctggagatc aaacaaaa 298

<210> SEQ ID NO 257
<211> LENGTH: 22
<212> TYPE: DNA
<213> ORGANISM: Artificial Sequence
<220> FEATURE:

<223> OTHER INFORMATION: Synthetic primer

<400> SEQUENCE: 257
aggtsharct gcagsagtcw gg 22

<210> SEQ ID NO 258
<211> LENGTH: 34
<212> TYPE: DNA
<213> ORGANISM: Artificial Sequence
<220> FEATURE:
<223> OTHER INFORMATION: Synthetic primer

<400> SEQUENCE: 258
tgaggagacg gtgaccgtgg tcccttggcc ccag 34

<210> SEQ ID NO 259
<211> LENGTH: 27
<212> TYPE: DNA
<213> ORGANISM: Artificial Sequence
<220> FEATURE:
<223> OTHER INFORMATION: Synthetic primer

<400> SEQUENCE: 259
tccgatatcc agctgaccca gtctcca 27

<210> SEQ ID NO 260
<211> LENGTH: 31
<212> TYPE: DNA
<213> ORGANISM: Artificial Sequence
<220> FEATURE:
<223> OTHER INFORMATION: Synthetic primer

<400> SEQUENCE: 260
gtttgatctc cagcttggta cchscdccga a 31

<210> SEQ ID NO 261
<211> LENGTH: 15
<212> TYPE: DNA
<213> ORGANISM: Artificial Sequence
<220> FEATURE:
<223> OTHER INFORMATION: Synthetic primer

<400> SEQUENCE: 261
agtcacgacg ttgta 15

<210> SEQ ID NO 262
<211> LENGTH: 17
<212> TYPE: DNA
<213> ORGANISM: Artificial Sequence
<220> FEATURE:
<223> OTHER INFORMATION: Synthetic primer

<400> SEQUENCE: 262
caggaaacag ctatgac 17

<210> SEQ ID NO 263
<211> LENGTH: 240
<212> TYPE: DNA
<213> ORGANISM: Gallus gallus

<400> SEQUENCE: 263
accatgagcc cactcgtctc ctccctcctg ctcctggccg ccctgccagg tgagggcgct 60
gtggggctct atggggctct atggggtctc agcggggctc tgcgggctca atgggggcca 120
aagggggggt ctgcgggctc tatgggggggg tcaacggggg gtctcacggg gggccggctc 180
cgcgaggccg tgtggcggcg gctccgtcag cgctttctgt ccttccccac agggcgcgcc 240

<210> SEQ ID NO 264
<211> LENGTH: 330
<212> TYPE: PRT
<213> ORGANISM: Homo sapiens

<400> SEQUENCE: 264

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 265
<211> LENGTH: 106
<212> TYPE: PRT
<213> ORGANISM: Homo sapiens

<400> SEQUENCE: 265

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 266
<211> LENGTH: 63
<212> TYPE: PRT
<213> ORGANISM: Homo sapiens

<400> SEQUENCE: 266

Glu Glu Tyr Thr Glu Gln Ser Glu Val Glu Ser Thr Glu Tyr Val Asn
1 5 10 15

Arg Gln Phe Met Ala Glu Thr Gln Phe Thr Ser Gly Glu Lys Glu Gln
20 25 30

Val Asp Glu Trp Thr Val Glu Thr Val Glu Val Val Asn Ser Leu Gln
35 40 45

Gln Gln Pro Gln Ala Ala Ser Pro Ser Val Pro Glu Pro His Ser
50 55 60

<210> SEQ ID NO 267
<211> LENGTH: 12
<212> TYPE: PRT
<213> ORGANISM: Homo sapiens

<400> SEQUENCE: 267

Gln Gln Pro Gln Ala Ala Ser Pro Ser Val Pro Glu
1 5 10

<210> SEQ ID NO 268
<211> LENGTH: 12
<212> TYPE: PRT
<213> ORGANISM: Homo sapiens

<400> SEQUENCE: 268

Phe Thr Ser Gly Glu Lys Glu Gln Val Asp Glu Trp
1 5 10

<210> SEQ ID NO 269
<211> LENGTH: 18
<212> TYPE: PRT
<213> ORGANISM: Homo sapiens

<400> SEQUENCE: 269

Pro Pro Val Asn Glu Pro Glu Thr Leu Lys Gln Gln Asn Gln Tyr Gln
1 5 10 15

Ala Ser

<210> SEQ ID NO 270
<211> LENGTH: 25
<212> TYPE: PRT
<213> ORGANISM: Homo sapiens

<400> SEQUENCE: 270

Gln Ile Leu Gly Val Ile Asp Lys Lys Leu Arg Asn Leu Glu Lys Lys
1 5 10 15

Lys Gly Lys Leu Asp Asp Tyr Gln Glu
20 25

<210> SEQ ID NO 271
<211> LENGTH: 14
<212> TYPE: PRT
<213> ORGANISM: Homo sapiens

<400> SEQUENCE: 271

Arg Asn Leu Glu Lys Lys Lys Gly Lys Leu Asp Asp Tyr Gln
1 5 10

<210> SEQ ID NO 272
<211> LENGTH: 23
<212> TYPE: PRT
<213> ORGANISM: Homo sapiens

<400> SEQUENCE: 272

Pro Arg Gly Arg Gly Gly Pro Pro Arg Pro Asn Arg Gly Met Pro Gln
1 5 10 15

Met Asn Thr Gln Gln Val Asn
20

<210> SEQ ID NO 273
<211> LENGTH: 58
<212> TYPE: PRT
<213> ORGANISM: Homo sapiens

<400> SEQUENCE: 273

Val Phe Gln Ser Asn Tyr Phe Asp Ser Thr His Asn His Gln Asn Gly
1 5 10 15

Leu Cys Glu Glu Glu Glu Ala Ala Ser Ala Pro Ala Val Glu Asp Gln
20 25 30

Val Pro Glu Ala Glu Pro Glu Pro Ala Glu Glu Tyr Thr Glu Gln Ser
35 40 45

Glu Val Glu Ser Thr Glu Tyr Val Asn Arg
50 55

<210> SEQ ID NO 274
<211> LENGTH: 15
<212> TYPE: PRT
<213> ORGANISM: Homo sapiens

<400> SEQUENCE: 274

Tyr Thr Glu Gln Ser Glu Val Glu Ser Thr Glu Tyr Val Asn Arg
1 5 10 15

<210> SEQ ID NO 275
<211> LENGTH: 11
<212> TYPE: PRT
<213> ORGANISM: Homo sapiens

<400> SEQUENCE: 275

Ser Glu Val Glu Ser Thr Glu Tyr Val Asn Arg 1 5 10

<210> SEQ ID NO 276
<211> LENGTH: 5
<212> TYPE: PRT
<213> ORGANISM: Mus musculus

<400> SEQUENCE: 276

Ser Tyr Gly Met Ser
1 5

<210> SEQ ID NO 277
<211> LENGTH: 14
<212> TYPE: PRT
<213> ORGANISM: Mus musculus

<400> SEQUENCE: 277

Trp Val Arg Gln Thr Pro Glu Lys Arg Leu Glu Trp Val Ala
1 5 10

<210> SEQ ID NO 278
<211> LENGTH: 11
<212> TYPE: PRT
<213> ORGANISM: Mus musculus

<400> SEQUENCE: 278

Leu Ala Ser Tyr Tyr Phe Asp Tyr Trp Gly Gln
1 5 10

<210> SEQ ID NO 279
<211> LENGTH: 110
<212> TYPE: PRT
<213> ORGANISM: Mus musculus

<400> SEQUENCE: 279

Gly Gly Gly Leu Val Lys Pro Gly Gly Ser Leu Lys Leu Ser Cys Ala
1 5 10 15

Ala Ser Gly Phe Thr Phe Ser Ser Tyr Gly Met Ser Trp Val Arg Gln
20 25 30

Thr Pro Glu Lys Arg Leu Glu Trp Val Ala Thr Ile Ser Ser Gly Gly
35 40 45

Ser Tyr Thr Tyr Tyr Pro Asp Ser Val Lys Gly Arg Phe Thr Ile Ser
50 55 60

Arg Asp Asn Ala Lys Asn Thr Leu Tyr Leu Gln Met Ser Ser Leu Arg
65 70 75 80

Ser Glu Asp Thr Ala Met Tyr Tyr Cys Ala Ser Leu Ala Ser Tyr Tyr
85 90 95

Phe Asp Tyr Trp Gly Gln Gly Thr Thr Leu Thr Val Ser Ser
100 105 110

<210> SEQ ID NO 280
<211> LENGTH: 15
<212> TYPE: PRT
<213> ORGANISM: Mus musculus

<400> SEQUENCE: 280

Thr Met Thr Cys Gln Ala Ser Gln Gly Thr Ser Ile Asn Leu Asn
1 5 10 15

<210> SEQ ID NO 281
<211> LENGTH: 7
<212> TYPE: PRT

<213> ORGANISM: Mus musculus

<400> SEQUENCE: 281

Gly Ala Ser Ser Leu Glu Asp
1 5

<210> SEQ ID NO 282
<211> LENGTH: 11
<212> TYPE: PRT
<213> ORGANISM: Mus musculus

<400> SEQUENCE: 282

Leu Gln His Ser Tyr Leu Pro Pro Leu Thr Phe
1 5 10

<210> SEQ ID NO 283
<211> LENGTH: 113
<212> TYPE: PRT
<213> ORGANISM: Mus musculus

<400> SEQUENCE: 283

Gly Ala Arg Cys Asp Val Gln Met Ile Gln Ser Pro Ser Ser Leu Ser
1 5 10 15

Ala Ser Leu Gly Asp Ile Val Thr Met Thr Cys Gln Ala Ser Gln Gly
20 25 30

Thr Ser Ile Asn Leu Asn Trp Phe Gln Gln Lys Pro Gly Lys Ala Pro
35 40 45

Lys Leu Leu Ile Tyr Gly Ala Ser Ser Leu Glu Asp Gly Val Pro Ser
50 55 60

Arg Phe Ser Gly Ser Cys Phe Gly Thr Asp Phe Thr Leu Thr Ile Ser
65 70 75 80

Ser Leu Glu Asp Glu Asp Met Ala Thr Tyr Phe Cys Leu Gln His Ser
85 90 95

Tyr Leu Pro Pro Leu Thr Phe Gly Ala Gly Thr Lys Leu Glu Leu Lys
100 105 110

Arg

<210> SEQ ID NO 284
<211> LENGTH: 330
<212> TYPE: DNA
<213> ORGANISM: Mus musculus

<400> SEQUENCE: 284
gggggaggct tagtgaagcc tggagggtcc ctgaaactct cctgtgcagc ctctggattc 60
actttcagta gctatggcat gtcttgggtt cgccagactc cggagaagag gctggagtgg 120
gtcgcaacca ttagtagtgg tggtagttac acctactatc cagacagtgt gaagggtcga 180
ttcaccatct ccagagacaa tgccaagaac accctgtacc tgcaaatgag cagtctgagg 240
tctgaggaca cggccatgta ttactgtgca agcctggcct cctactactt tgactactgg 300
ggccaaggca ccactctcac agtctcctca 330

<210> SEQ ID NO 285
<211> LENGTH: 339
<212> TYPE: DNA
<213> ORGANISM: Mus musculus

<400> SEQUENCE: 285
ggtgccagat gtgatgtcca gatgattcag tctccatcct ccctgtctgc atctttggga 60

-continued

```
gacatagtca ccatgacttg ccaggcaagt cagggcacta gcattaattt aaactggttt    120

cagcaaaaac cagggaaagc tcctaagctc ctgatctatg gtgcaagcag cttggaagat    180

ggggtcccat caaggttcag tggcagttgt tttgggacag atttcactct caccatcagc    240

agcctggagg atgaagatat ggcaacttat ttctgtctac agcatagtta tctccctccg    300

ctcacgttcg gtgctgggac caagctggag ctgaaacgt                          339


<210> SEQ ID NO 286
<211> LENGTH: 11
<212> TYPE: PRT
<213> ORGANISM: Mus musculus

<400> SEQUENCE: 286

Lys Ser Ser Gln Ser Leu Leu Tyr Ser Ser Asn
1               5                   10


<210> SEQ ID NO 287
<211> LENGTH: 7
<212> TYPE: PRT
<213> ORGANISM: Mus musculus

<400> SEQUENCE: 287

Trp Ala Ser Thr Arg Glu Ser
1               5


<210> SEQ ID NO 288
<211> LENGTH: 9
<212> TYPE: PRT
<213> ORGANISM: Mus musculus

<400> SEQUENCE: 288

Gln Gln Tyr Tyr Ser Tyr Pro Phe Thr
1               5


<210> SEQ ID NO 289
<211> LENGTH: 115
<212> TYPE: PRT
<213> ORGANISM: Mus musculus

<400> SEQUENCE: 289

Gly Val Ile Val Met Ser Gln Ser Pro Ser Ser Leu Ala Val Ser Leu
1               5                   10                  15

Gly Glu Lys Val Thr Met Ser Cys Lys Ser Ser Gln Ser Leu Leu Tyr
            20                  25                  30

Ser Ser Asn Gln Lys Asn Tyr Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Lys Ala Glu Asp Leu Ala Val Tyr Tyr Cys Gln
                85                  90                  95

Gln Tyr Tyr Ser Tyr Pro Phe Thr Phe Gly Ser Gly Thr Lys Leu Glu
            100                 105                 110

Ile Lys Arg
        115


<210> SEQ ID NO 290
<211> LENGTH: 345
<212> TYPE: DNA
```

<213> ORGANISM: Mus musculus

<400> SEQUENCE: 290

```
ggggtcattg tgatgtcaca gtctccatcc tccctagctg tgtcacttgg agagaaggtt     60
actatgagct gcaagtccag tcagagcctt ttatatagta gcaatcaaaa gaactacttg    120
gcctggtacc agcagaaacc agggcagtct cctaaactgc tgatttactg ggcatccact    180
agggaatctg gggtccctga tcgcttcaca ggcagtggat ctgggacaga tttcactctc    240
accatcagca gtgtgaaggc tgaagacctg gcagtttatt actgtcagca atattatagc    300
tatccattca cgttcggctc ggggacaaag ttggaaataa aacgt                    345
```

<210> SEQ ID NO 291
<211> LENGTH: 5
<212> TYPE: PRT
<213> ORGANISM: Mus musculus

<400> SEQUENCE: 291

```
Thr Tyr Asp Leu His
1               5
```

<210> SEQ ID NO 292
<211> LENGTH: 16
<212> TYPE: PRT
<213> ORGANISM: Mus musculus

<400> SEQUENCE: 292

```
Val Ile Trp Ser Gly Gly Ser Thr Asp Tyr Asn Ala Ala Phe Ile Ser
1               5                   10                  15
```

<210> SEQ ID NO 293
<211> LENGTH: 11
<212> TYPE: PRT
<213> ORGANISM: Mus musculus

<400> SEQUENCE: 293

```
Asn Tyr Gly Tyr Ser Ala Trp Phe Ala Tyr Trp
1               5                   10
```

<210> SEQ ID NO 294
<211> LENGTH: 111
<212> TYPE: PRT
<213> ORGANISM: Mus musculus

<400> SEQUENCE: 294

```
Gly Pro Gly Leu Val Gln Pro Ser Gln Ser Leu Ser Ile Thr Cys Thr
1               5                   10                  15

Val Ser Gly Phe Ser Leu Thr Thr Tyr Asp Leu His Trp Val Arg Gln
            20                  25                  30

Ser Pro Gly Lys Gly Leu Glu Trp Leu Gly Val Ile Trp Ser Gly Gly
        35                  40                  45

Ser Thr Asp Tyr Asn Ala Ala Phe Ile Ser Arg Leu Ser Ile Ser Lys
    50                  55                  60

Asp Asn Ser Lys Ser Gln Val Phe Phe Lys Met Asn Ser Leu Gln Ala
65                  70                  75                  80

Asn Asp Thr Ala Ile Tyr Tyr Cys Ala Arg Asn Tyr Gly Tyr Ser Ala
                85                  90                  95

Trp Phe Ala Tyr Trp Gly Gln Gly Thr Leu Val Thr Val Ser Ala
            100                 105                 110
```

<210> SEQ ID NO 295
<211> LENGTH: 15
<212> TYPE: PRT
<213> ORGANISM: Mus musculus

<400> SEQUENCE: 295

Ala Ser Ile Ser Cys Arg Ser Ser Gln Ser Ile Val His Ser Asn
1               5                   10                  15

<210> SEQ ID NO 296
<211> LENGTH: 7
<212> TYPE: PRT
<213> ORGANISM: Mus musculus

<400> SEQUENCE: 296

Lys Val Ser Asn Arg Phe Ser
1               5

<210> SEQ ID NO 297
<211> LENGTH: 9
<212> TYPE: PRT
<213> ORGANISM: Mus musculus

<400> SEQUENCE: 297

Phe Gln Gly Ser His Val Pro Leu Thr
1               5

<210> SEQ ID NO 298
<211> LENGTH: 118
<212> TYPE: PRT
<213> ORGANISM: Mus musculus

<400> SEQUENCE: 298

Pro Ala Ser Ser Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Leu Thr Phe Gly Ala Gly Thr
            100                 105                 110

Lys Leu Glu Leu Lys Arg
        115

<210> SEQ ID NO 299
<211> LENGTH: 333
<212> TYPE: DNA
<213> ORGANISM: Mus musculus

<400> SEQUENCE: 299
ggacctggcc tagtgcagcc ctcacagagc ctgtccatca cctgcacagt ctctggtttc 60
tcattgacta cctatgattt acactgggtt cgccagtctc caggaaaggg tctggagtgg 120
ctgggagtga tatggagtgg tggaagcaca gactataatg cagctttcat atccagactg 180
agcatcagca aggacaattc caagagccaa gttttcttta aaatgaacag tctgcaagct 240

-continued

```
aatgacacag ccatatatta ctgtgccaga aactacggct actccgcctg gtttgcttac    300

tggggccaag ggactctggt cactgtctct gca                                 333


<210> SEQ ID NO 300
<211> LENGTH: 354
<212> TYPE: DNA
<213> ORGANISM: Mus musculus

<400> SEQUENCE: 300

cctgcttcca gcagtgatgt tttgatgacc caaactccac tctccctgcc tgtcagtctt     60

ggagatcaag cctccatctc ttgcagatct agtcagagca ttgtacatag taatggaaac    120

acctatttag aatggtacct gcagaaacca ggccagtctc caaagctcct gatctacaaa    180

gtttccaacc gattttctgg ggtcccagac aggttcagtg gcagtggatc agggacagat    240

ttcacactca agatcagcag agtggaggct gaggatctgg gagtttatta ctgctttcaa    300

ggttcacatg ttccgctcac gttcggtgct gggaccaagc tggagctgaa acgt          354


<210> SEQ ID NO 301
<211> LENGTH: 5
<212> TYPE: PRT
<213> ORGANISM: Mus musculus

<400> SEQUENCE: 301

Ala Tyr Ser Met His
1               5


<210> SEQ ID NO 302
<211> LENGTH: 17
<212> TYPE: PRT
<213> ORGANISM: Mus musculus

<400> SEQUENCE: 302

Trp Ile Asn Thr Glu Thr Gly Glu Pro Thr Tyr Thr Asp Asp Phe Lys
1               5                   10                  15

Gly


<210> SEQ ID NO 303
<211> LENGTH: 11
<212> TYPE: PRT
<213> ORGANISM: Mus musculus

<400> SEQUENCE: 303

Arg Ile Tyr Tyr Phe Gly Arg Gly Gly Phe Asp
1               5                   10


<210> SEQ ID NO 304
<211> LENGTH: 114
<212> TYPE: PRT
<213> ORGANISM: Mus musculus

<400> SEQUENCE: 304

Gly Phe Glu Leu Lys Lys Pro Gly Glu Thr Val Lys Ile Ser Cys Lys
1               5                   10                  15

Ala Ser Gly Tyr Thr Phe Thr Ala Tyr Ser Met His Trp Val Lys Gln
            20                  25                  30

Thr Pro Gly Lys Gly Leu Lys Trp Leu Gly Trp Ile Asn Thr Glu Thr
        35                  40                  45

Gly Glu Pro Thr Tyr Thr Asp Asp Phe Lys Gly Arg Phe Thr Phe Ser
    50                  55                  60
```

Leu Glu Thr Ser Ala Arg Ile Ala Tyr Leu Gln Ile Asn Asp Leu Lys
65 70 75 80

Asn Glu Asp Thr Ala Thr Tyr Phe Cys Ala Arg Arg Ile Tyr Tyr Phe
85 90 95

Gly Arg Gly Gly Phe Asp Tyr Trp Gly Gln Gly Thr Thr Val Thr Val
100 105 110

Ser Ser

<210> SEQ ID NO 305
<211> LENGTH: 15
<212> TYPE: PRT
<213> ORGANISM: Mus musculus

<400> SEQUENCE: 305

Ser Ser Ile Ser Cys Arg Ser Ser Gln Ser Ile Val His Ser Asn
1 5 10 15

<210> SEQ ID NO 306
<211> LENGTH: 7
<212> TYPE: PRT
<213> ORGANISM: Mus musculus

<400> SEQUENCE: 306

Lys Val Ser Asn Arg Phe Ser
1 5

<210> SEQ ID NO 307
<211> LENGTH: 9
<212> TYPE: PRT
<213> ORGANISM: Mus musculus

<400> SEQUENCE: 307

Phe Gln Gly Ser His Val Pro Tyr Thr
1 5

<210> SEQ ID NO 308
<211> LENGTH: 118
<212> TYPE: PRT
<213> ORGANISM: Mus musculus

<400> SEQUENCE: 308

Pro Ala Ser Ser Ser Asp Val Leu Met Thr Gln Thr Pro Leu Ser Leu
1 5 10 15

Pro Val Arg Leu Gly Asp Gln Ser Ser Ile Ser Cys Arg Ser Ser Gln
20 25 30

Ser Ile Val His Ser Asn Gly Asn Thr Tyr Leu Glu Trp Tyr Leu Gln
35 40 45

Lys Pro Gly Gln Ser Pro Lys Leu Leu Ile Tyr Lys Val Ser Asn Arg
50 55 60

Phe Ser Gly Val Pro Asp Arg Phe Ser Gly Ser Gly Ser Gly Thr Asp
65 70 75 80

Phe Thr Leu Lys Ile Ser Arg Val Glu Pro Glu Asp Leu Gly Val Tyr
85 90 95

Tyr Cys Phe Gln Gly Ser His Val Pro Tyr Thr Ser Glu Gly Asp Gln
100 105 110

Ala Glu Ile Lys Leu Ala
115

<210> SEQ ID NO 309

-continued

<211> LENGTH: 342
<212> TYPE: DNA
<213> ORGANISM: Mus musculus

<400> SEQUENCE: 309
ggatttgagc tgaagaagcc tggagagaca gtcaagatct cctgcaaggc ttctggttat 60
accttcacag cctattcaat gcactgggtg aagcagactc caggaaaggg tttaaagtgg 120
ctgggctgga taaacactga gactggtgag ccaacatata cagatgactt caagggacgg 180
tttaccttct ctttggaaac ctctgccagg attgcctatt tgcagatcaa cgacctcaaa 240
aacgaggaca cggctacata tttctgtgct agaaggatct attacttcgg tagaggtggg 300
tttgactact ggggccaagg gaccacggtc accgtctcct ca 342

<210> SEQ ID NO 310
<211> LENGTH: 354
<212> TYPE: DNA
<213> ORGANISM: Mus musculus

<400> SEQUENCE: 310
cctgcttcca gcagtgatgt tttgatgacc caaactcctc tctccctgcc tgtccgtctt 60
ggagatcagt cctccatctc ttgcagatct agtcagtcca ttgtacatag taatggaaac 120
acctatttag aatggtacct gcagaaacca ggccagtctc caaagctcct gatctacaaa 180
gtttccaacc gattttctgg ggtcccagac aggttcagtg gcagtggatc agggacagat 240
ttcacactca agatcagcag agtggagcct gaggatctgg gagtttatta ctgctttcag 300
ggttcacatg ttccgtacac gtcggagggg gaccaagctg aaataaaatt ggcc 354

<210> SEQ ID NO 311
<211> LENGTH: 5
<212> TYPE: PRT
<213> ORGANISM: Mus musculus

<400> SEQUENCE: 311

Asn Ser Trp Phe Asn
1 5

<210> SEQ ID NO 312
<211> LENGTH: 19
<212> TYPE: PRT
<213> ORGANISM: Mus musculus

<400> SEQUENCE: 312

Glu Ile Arg Leu Thr Ser Asp Asn Tyr Ala Ile Tyr Tyr Ala Glu Ser
1 5 10 15

Val Lys Gly

<210> SEQ ID NO 313
<211> LENGTH: 11
<212> TYPE: PRT
<213> ORGANISM: Mus musculus

<400> SEQUENCE: 313

Pro Glu Thr Ala Arg Ala Thr Phe Ala Tyr Trp
1 5 10

<210> SEQ ID NO 314
<211> LENGTH: 114
<212> TYPE: PRT
<213> ORGANISM: Mus musculus

<400> SEQUENCE: 314

Gly Gly Gly Leu Val Gln Pro Gly Gly Ser Met Arg Leu Ser Cys Val
1               5                   10                  15

Ala Ser Gly Phe Thr Phe Ser Asn Ser Trp Phe Asn Trp Val Arg Gln
            20                  25                  30

Ser Pro Glu Lys Gly Leu Glu Trp Val Ala Glu Ile Arg Leu Thr Ser
        35                  40                  45

Asp Asn Tyr Ala Ile Tyr Tyr Ala Glu Ser Val Lys Gly Arg Phe Thr
    50                  55                  60

Ile Ser Arg Asp Asp Ser Lys Ser Ser Val Tyr Leu Gln Met Asn Asn
65                  70                  75                  80

Leu Arg Ala Glu Asp Thr Gly Ile Tyr Tyr Cys Thr Arg Pro Glu Thr
                85                  90                  95

Ala Arg Ala Thr Phe Ala Tyr Trp Gly Gln Gly Thr Thr Val Thr Val
            100                 105                 110

Ser Ser

<210> SEQ ID NO 315
<211> LENGTH: 15
<212> TYPE: PRT
<213> ORGANISM: Mus musculus

<400> SEQUENCE: 315

Ala Ser Ile Ser Cys Arg Ser Ser Gln Ser Ile Val His Ser Asn
1               5                   10                  15

<210> SEQ ID NO 316
<211> LENGTH: 7
<212> TYPE: PRT
<213> ORGANISM: Mus musculus

<400> SEQUENCE: 316

Lys Val Phe Asn Arg Phe Ser
1               5

<210> SEQ ID NO 317
<211> LENGTH: 9
<212> TYPE: PRT
<213> ORGANISM: Mus musculus

<400> SEQUENCE: 317

Phe Gln Gly Ser His Val Pro Arg Thr
1               5

<210> SEQ ID NO 318
<211> LENGTH: 118
<212> TYPE: PRT
<213> ORGANISM: Mus musculus

<400> SEQUENCE: 318

Pro Ala Ser Thr Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Val Leu Ile Tyr Lys Val Phe Asn Arg
    50                  55                  60

Phe Ser Gly Val Pro Asp Arg Phe Ser Gly Ser Gly Ser Gly Thr Asp

```
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Arg Thr Phe Gly Gly Gly Thr
            100                 105                 110

Lys Leu Asn Gln Thr Gly
        115


<210> SEQ ID NO 319
<211> LENGTH: 342
<212> TYPE: DNA
<213> ORGANISM: Mus musculus

<400> SEQUENCE: 319

ggaggaggct tggtgcaacc tggaggatct atgagactct cctgtgttgc ctctggattc      60

actttcagta actcctggtt taactgggtc cgccagtctc cagagaaggg gcttgagtgg     120

gttgctgaaa ttagattgac atctgataat tatgcaatat attatgcgga gtctgtgaaa     180

gggaggttca ccatctcaag agatgattcc aaaagcagtg tctatctgca aatgaacaac     240

ttaagagctg aagacactgg catttattac tgtaccaggc ctgagacagc tcgggctacg     300

tttgcttact ggggccaagg gaccacggtc acggtctcct ca                        342


<210> SEQ ID NO 320
<211> LENGTH: 354
<212> TYPE: DNA
<213> ORGANISM: Mus musculus

<400> SEQUENCE: 320

cctgcttcca ccagtgatgt tttgatgacc caaactccac tctccctgcc tgtcagtctt      60

ggagatcaag cctccatctc ttgcagatct agtcagagca ttgtacatag taatggaaac     120

acctatttag aatggtacct gcagaaacca ggccagtctc caaaggtctt gatctacaaa     180

gtttttaacc gattttctgg ggtcccagac aggttcagtg gcagtggatc agggacagat     240

ttcacactca agatcagcag agtggaggct gaggatctgg gagtttatta ctgctttcaa     300

ggttcacatg ttcctcggac gttcggtgga ggcaccaagc tgaatcagac gggc           354


<210> SEQ ID NO 321
<211> LENGTH: 5
<212> TYPE: PRT
<213> ORGANISM: Mus musculus

<400> SEQUENCE: 321

Ala Tyr Tyr Met His
1               5


<210> SEQ ID NO 322
<211> LENGTH: 17
<212> TYPE: PRT
<213> ORGANISM: Mus musculus

<400> SEQUENCE: 322

Arg Val Asn Pro Asn Asn Gly Gly Thr Thr Tyr Asn Gln Lys Phe Lys
1               5                   10                  15

Gly


<210> SEQ ID NO 323
<211> LENGTH: 11
<212> TYPE: PRT
```

<213> ORGANISM: Mus musculus

<400> SEQUENCE: 323

Arg Ile Tyr Tyr Gly Tyr Phe Asp Tyr Trp Gly
1 5 10

<210> SEQ ID NO 324
<211> LENGTH: 111
<212> TYPE: PRT
<213> ORGANISM: Mus musculus

<400> SEQUENCE: 324

Gly Pro Asp Leu Val Lys Pro Gly Ala Ser Val Lys Ile Ser Cys Lys
1 5 10 15

Ala Ser Gly Tyr Ser Phe Thr Ala Tyr Tyr Met His Trp Val Lys Gln
20 25 30

Ser His Gly Lys Ser Leu Glu Trp Ile Gly Arg Val Asn Pro Asn Asn
35 40 45

Gly Gly Thr Thr Tyr Asn Gln Lys Phe Lys Gly Lys Ala Ile Leu Thr
50 55 60

Val Asp Lys Ser Ser Ser Thr Ala Tyr Met Glu Leu Arg Ser Leu Thr
65 70 75 80

Phe Glu Asp Ser Ala Val Tyr Tyr Cys Ala Arg Arg Ile Tyr Tyr Gly
85 90 95

Tyr Phe Asp Tyr Trp Gly Gln Gly Thr Thr Val Thr Val Ser Ser
100 105 110

<210> SEQ ID NO 325
<211> LENGTH: 15
<212> TYPE: PRT
<213> ORGANISM: Mus musculus

<400> SEQUENCE: 325

Lys Ala Ser Gln Ser Val Asp Tyr Asp Gly Asp Ser Tyr Met Asn
1 5 10 15

<210> SEQ ID NO 326
<211> LENGTH: 7
<212> TYPE: PRT
<213> ORGANISM: Mus musculus

<400> SEQUENCE: 326

Val Ala Ser Asn Leu Glu Ser
1 5

<210> SEQ ID NO 327
<211> LENGTH: 9
<212> TYPE: PRT
<213> ORGANISM: Mus musculus

<400> SEQUENCE: 327

Gln Gln Ser Asn Glu Asp Pro Tyr Thr
1 5

<210> SEQ ID NO 328
<211> LENGTH: 104
<212> TYPE: PRT
<213> ORGANISM: Mus musculus

<400> SEQUENCE: 328

Ala Phe Phe Ala Val Ser Leu Gly Gln Arg Ala Thr Ile Ser Cys Lys
1 5 10 15

```
Ala Ser Gln Ser Val Asp Tyr Asp Gly Asp Ser Tyr Met Asn Trp Tyr
            20                  25                  30

Gln Gln Lys Pro Gly Gln Pro Pro Lys Leu Leu Ile Tyr Val Ala Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln Gln Ser Asn Glu Asp Pro Tyr Thr Phe Gly Gly
                85                  90                  95

Gly Thr Lys Leu Glu Ile Lys Gln
            100
```

<210> SEQ ID NO 329
<211> LENGTH: 333
<212> TYPE: DNA
<213> ORGANISM: Mus musculus

<400> SEQUENCE: 329

```
ggacctgacc tggtgaagcc tggggcttca gtgaagatat cctgcaaggc ttctggttac     60

tcattcactg cctactacat gcactgggtg aagcagagcc atggaaagag ccttgagtgg    120

attggacgtg ttaatcctaa caatggtggt actacctaca accagaagtt caagggcaag    180

gccatattaa ctgtagataa gtcatccagc acagcctaca tggagctccg cagcctgaca    240

tttgaggact ctgcggtcta ttactgtgca agaaggattt actacggcta ctttgactac    300

tggggccaag ggaccacggt caccgtctcc tca                                 333
```

<210> SEQ ID NO 330
<211> LENGTH: 312
<212> TYPE: DNA
<213> ORGANISM: Mus musculus

<400> SEQUENCE: 330

```
gcattctttg ctgtgtctct agggcagagg gccaccatct cctgcaaggc cagccaaagt     60

gttgattatg atggtgatag ttatatgaac tggtaccaac agaaaccagg acagccaccc    120

aaactcctca tctatgttgc atccaatctt gaatctgggg tcccagccag gttcagtggc    180

agtgggtctg ggacagactt caccctcaac atccatcctg tggaggagga ggatgctgca    240

acctattact gtcagcaaag taatgaggat ccgtacacgt tcggaggagg taccaagcta    300

gagatcaaac aa                                                        312
```

<210> SEQ ID NO 331
<211> LENGTH: 4
<212> TYPE: PRT
<213> ORGANISM: Mus musculus

<400> SEQUENCE: 331

```
Asp Ile Tyr Met
1
```

<210> SEQ ID NO 332
<211> LENGTH: 17
<212> TYPE: PRT
<213> ORGANISM: Mus musculus

<400> SEQUENCE: 332

```
Lys Ile Asp Pro Ala Asn Gly Asn Thr Lys Tyr Asp Pro Lys Phe Gln
```

1 5 10 15

Gly

<210> SEQ ID NO 333
<211> LENGTH: 11
<212> TYPE: PRT
<213> ORGANISM: Mus musculus

<400> SEQUENCE: 333

Thr Gly Asp Tyr Trp Gly Gln Gly Thr Thr Val
1 5 10

<210> SEQ ID NO 334
<211> LENGTH: 106
<212> TYPE: PRT
<213> ORGANISM: Mus musculus

<400> SEQUENCE: 334

Gly Ala Glu Leu Val Lys Pro Gly Ala Ser Val Lys Leu Ser Cys Thr
1 5 10 15

Ala Ser Gly Leu Asn Ile Arg Asp Ile Tyr Met His Trp Val Lys Gln
20 25 30

Arg Pro Glu Gln Gly Leu Glu Trp Ile Gly Lys Ile Asp Pro Ala Asn
35 40 45

Gly Asn Thr Lys Tyr Asp Pro Lys Phe Gln Gly Lys Ala Thr Ile Thr
50 55 60

Ala Asp Thr Ser Ser Asn Thr Ala Tyr Val Gln Leu Ser Ser Leu Thr
65 70 75 80

Ser Glu Asp Thr Ala Val Tyr Tyr Cys Ala Gly Thr Gly Asp Tyr Trp
85 90 95

Gly Gln Gly Thr Thr Val Thr Val Ser Ser
100 105

<210> SEQ ID NO 335
<211> LENGTH: 15
<212> TYPE: PRT
<213> ORGANISM: Mus musculus

<400> SEQUENCE: 335

Thr Met Ser Cys Lys Ser Ser Gln Ser Leu Leu Asn Ser Arg Thr
1 5 10 15

<210> SEQ ID NO 336
<211> LENGTH: 7
<212> TYPE: PRT
<213> ORGANISM: Mus musculus

<400> SEQUENCE: 336

Trp Ala Ser Thr Arg Glu Ser
1 5

<210> SEQ ID NO 337
<211> LENGTH: 9
<212> TYPE: PRT
<213> ORGANISM: Mus musculus

<400> SEQUENCE: 337

Arg Gln Ser Tyr Asn Leu Val Thr Phe
1 5

<210> SEQ ID NO 338

<211> LENGTH: 112
<212> TYPE: PRT
<213> ORGANISM: Mus musculus

<400> SEQUENCE: 338

```
Gly Thr Cys Gly Asp Ile Val Met Ser Gln Ser Pro Ser Ser Leu Ala
1               5                   10                  15

Val Ser Ala Gly Glu Lys Val Thr Met Ser Cys Lys Ser Ser Gln Ser
            20                  25                  30

Leu Leu Asn Ser Arg Thr Arg Lys Asn Tyr Leu Ala Trp Val Gln His
        35                  40                  45

Lys Pro Gly Gln Ser Pro Arg Leu Leu Ile Tyr Trp Ala Ser Thr Arg
    50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Arg Gln Ser Tyr Asn Leu Val Thr Phe Gly Ala Gly Pro Ser
            100                 105                 110
```

<210> SEQ ID NO 339
<211> LENGTH: 318
<212> TYPE: DNA
<213> ORGANISM: Mus musculus

<400> SEQUENCE: 339

```
ggggcagagc ttgtgaagcc aggggcctca gtcaagttgt cctgcacagc ttctggcctc     60

aacattagag acatttatat gcactgggtg aagcagaggc ctgaacaggg cctggagtgg    120

attggaaaga ttgatcctgc gaatggtaat actaaatatg acccgaagtt ccagggcaag    180

gccactataa cagcagacac atcctccaac actgcctatg tgcagctcag cagcctgaca    240

tctgaggaca ctgccgtcta ttactgtgct gggactggtg actactgggg ccaagggacc    300

acggtcaccg tctcctca                                                  318
```

<210> SEQ ID NO 340
<211> LENGTH: 336
<212> TYPE: DNA
<213> ORGANISM: Mus musculus

<400> SEQUENCE: 340

```
ggtacctgtg ggacattgt gatgtcacag tctccatcct ccctggctgt gtcagcagga     60

gagaaggtca ctatgagctg caaatccagt cagagtctgc tcaacagtag aacccgaaag    120

aactacttgg cttgggtcca gcacaaacca gggcagtctc ctagactact aatctactgg    180

gcatccacta gggaatctgg ggtccctgat cgcttcacag gcagtggatc tgggacagat    240

ttcactctca ccatcagcag tgtgcaggct gaggacctgg cagtttatta ctgcaggcaa    300

tcttataatc tggtcacgtt cggtgctgga ccaagc                              336
```

<210> SEQ ID NO 341
<211> LENGTH: 5
<212> TYPE: PRT
<213> ORGANISM: Mus musculus

<400> SEQUENCE: 341

```
Ser Tyr Val Met His
1               5
```

<210> SEQ ID NO 342
<211> LENGTH: 17
<212> TYPE: PRT
<213> ORGANISM: Mus musculus

<400> SEQUENCE: 342

Tyr Ile Asn Pro Tyr Asn Asp Gly Thr Lys Tyr Asn Glu Lys Phe Lys
1 5 10 15

Gly

<210> SEQ ID NO 343
<211> LENGTH: 11
<212> TYPE: PRT
<213> ORGANISM: Mus musculus

<400> SEQUENCE: 343

Arg Tyr Tyr Tyr Gly Ser Ser Gly Gly Tyr Phe
1 5 10

<210> SEQ ID NO 344
<211> LENGTH: 112
<212> TYPE: PRT
<213> ORGANISM: Mus musculus

<400> SEQUENCE: 344

Gly Pro Glu Leu Val Lys Pro Gly Ala Ser Val Lys Met Ser Cys Lys
1 5 10 15

Ala Ser Gly Tyr Thr Phe Thr Ser Tyr Val Met His Trp Val Lys Gln
20 25 30

Lys Pro Gly Gln Gly Leu Glu Trp Ile Gly Tyr Ile Asn Pro Tyr Asn
35 40 45

Asp Gly Thr Lys Tyr Asn Glu Lys Phe Lys Gly Lys Ala Thr Leu Thr
50 55 60

Ser Asp Lys Ser Ser Ser Thr Ala Tyr Met Glu Leu Ser Ser Leu Thr
65 70 75 80

Ser Glu Asp Ser Ala Val Tyr Tyr Cys Ala Arg Arg Tyr Tyr Tyr Gly
85 90 95

Ser Ser Gly Gly Tyr Phe Asp Val Trp Ala Gln Asp His Val Arg Thr
100 105 110

<210> SEQ ID NO 345
<211> LENGTH: 15
<212> TYPE: PRT
<213> ORGANISM: Mus musculus

<400> SEQUENCE: 345

Arg Ala Ser Lys Ser Ile Ser Lys Tyr Leu Ala Trp Tyr Gln Glu
1 5 10 15

<210> SEQ ID NO 346
<211> LENGTH: 7
<212> TYPE: PRT
<213> ORGANISM: Mus musculus

<400> SEQUENCE: 346

Ser Gly Ser Thr Leu Gln Ser
1 5

<210> SEQ ID NO 347
<211> LENGTH: 9
<212> TYPE: PRT
<213> ORGANISM: Mus musculus

<400> SEQUENCE: 347

Gln Gln His Asn Glu Tyr Pro Tyr Thr
1 5

<210> SEQ ID NO 348
<211> LENGTH: 108
<212> TYPE: PRT
<213> ORGANISM: Mus musculus

<400> SEQUENCE: 348

Asp Val Gln Ile Thr Gln Ser Pro Ser Tyr Leu Ala Ala Ser Pro Gly
1 5 10 15

Glu Thr Ile Thr Ile Asn Cys Arg Ala Ser Lys Ser Ile Ser Lys Tyr
20 25 30

Leu Ala Trp Tyr Gln Glu Lys Pro Gly Lys Thr Asn Lys Leu Leu Ile
35 40 45

Tyr Ser Gly Ser Thr Leu Gln Ser Gly Ile Pro Ser Arg Phe Ser Gly
50 55 60

Ser Gly Ser Gly Thr Asp Phe Thr Leu Thr Ile Ser Ser Leu Glu Pro
65 70 75 80

Glu Asp Phe Ala Met Tyr Tyr Cys Gln Gln His Asn Glu Tyr Pro Tyr
85 90 95

Thr Phe Gly Gly Gly Thr Lys Leu Glu Ile Lys Arg
100 105

<210> SEQ ID NO 349
<211> LENGTH: 336
<212> TYPE: DNA
<213> ORGANISM: Mus musculus

<400> SEQUENCE: 349
ggacctgagc tggtaaagcc tggggcttca gtgaagatgt cctgcaaggc ttctggatac 60
acattcacta gctatgttat gcactgggtg aagcagaagc ctgggcaggg ccttgagtgg 120
attggatata ttaatcctta caatgatggt actaagtaca atgagaagtt caaaggcaag 180
gccacactga cttcagacaa atcctccagc acagcctaca tggagctcag cagcctgacc 240
tctgaggact ctgcggtcta ttactgtgca aggaggtatt actacggtag tagcgggggg 300
tacttcgatg tctgggcgca ggaccacgta cgcacg 336

<210> SEQ ID NO 350
<211> LENGTH: 324
<212> TYPE: DNA
<213> ORGANISM: Mus musculus

<400> SEQUENCE: 350
gatgtccaga taacccagtc tccatcttat cttgctgcat ctcctggaga aaccattact 60
attaattgca gggcaagtaa gagcattagc aaatatttag cctggtatca agagaaacct 120
gggaaaacta ataagcttct tatctactct ggatccactt tgcaatctgg aattccatca 180
aggttcagtg gcagtggatc tggtacagat ttcactctca ccatcagtag cctggagcct 240
gaagattttg caatgtatta ctgtcaacag cataatgaat acccgtacac gttcggaggg 300
gggaccaagc tggaaataaa acgg 324

<210> SEQ ID NO 351
<211> LENGTH: 6
<212> TYPE: PRT

<213> ORGANISM: Oryctolagus cuniculus

<400> SEQUENCE: 351

Gly Ser Tyr Tyr Met Ser
1 5

<210> SEQ ID NO 352
<211> LENGTH: 17
<212> TYPE: PRT
<213> ORGANISM: Oryctolagus cuniculus

<400> SEQUENCE: 352

Tyr Ile Tyr Ile Gly Asp Gly Val Thr Ala Tyr Ala Asn Trp Ala Lys
1 5 10 15

Gly

<210> SEQ ID NO 353
<211> LENGTH: 4
<212> TYPE: PRT
<213> ORGANISM: Oryctolagus cuniculus

<400> SEQUENCE: 353

Gly Asn Lys Leu
1

<210> SEQ ID NO 354
<211> LENGTH: 11
<212> TYPE: PRT
<213> ORGANISM: Oryctolagus cuniculus

<400> SEQUENCE: 354

Gln Ala Ser Gln Ser Ile Ser Ser Tyr Leu Ala
1 5 10

<210> SEQ ID NO 355
<211> LENGTH: 7
<212> TYPE: PRT
<213> ORGANISM: Oryctolagus cuniculus

<400> SEQUENCE: 355

Asp Ala Ser Asn Leu Asp Ser
1 5

<210> SEQ ID NO 356
<211> LENGTH: 14
<212> TYPE: PRT
<213> ORGANISM: Oryctolagus cuniculus

<400> SEQUENCE: 356

Gln Cys Thr Ala Val Ser Ser Ala Thr Ile Tyr Gly Asn Ala
1 5 10

<210> SEQ ID NO 357
<211> LENGTH: 4
<212> TYPE: PRT
<213> ORGANISM: Artificial
<220> FEATURE:
<223> OTHER INFORMATION: humanized

<400> SEQUENCE: 357

Gly Asn Arg Leu
1

<210> SEQ ID NO 358

```
<211> LENGTH: 393
<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(57)
<220> FEATURE:
<221> NAME/KEY: CDS
<222> LOCATION: (58)..(393)

<400> SEQUENCE: 358

atggagactg ggctgcgctg gcttctcctg gtcgctgtgc tcaaaggtgt ccagtgt        57

cag tca ttg gag gag tcc ggg gga gac ctg gtc aag cct ggg gca tcc      105
Gln Ser Leu Glu Glu Ser Gly Gly Asp Leu Val Lys Pro Gly Ala Ser
1               5                   10                  15

ctg aca ctc acc tgc aca gcc tct gga ttc tcc ttc agt ggc agc tac      153
Leu Thr Leu Thr Cys Thr Ala Ser Gly Phe Ser Phe Ser Gly Ser Tyr
            20                  25                  30

tac atg tcc tgg gtc cgc cag gct cca ggg aag ggg ctg gag tgg atc      201
Tyr Met Ser Trp Val Arg Gln Ala Pro Gly Lys Gly Leu Glu Trp Ile
        35                  40                  45

gca tac att tat att ggt gac ggt gtc act gcc tac gcg aac tgg gcg      249
Ala Tyr Ile Tyr Ile Gly Asp Gly Val Thr Ala Tyr Ala Asn Trp Ala
    50                  55                  60

aaa ggc cga ttc acc atc tcc aag gcc tcg tcg acc acg gtg act cta      297
Lys Gly Arg Phe Thr Ile Ser Lys Ala Ser Ser Thr Thr Val Thr Leu
65                  70                  75                  80

caa atg acc agt ctg aca gcc gcg gac acg gcc acc tat ttc tgt gcg      345
Gln Met Thr Ser Leu Thr Ala Ala Asp Thr Ala Thr Tyr Phe Cys Ala
                85                  90                  95

agg ggt aat aag ttg tgg ggc cca ggc acc ctg gtc acc gtc tcc tca      393
Arg Gly Asn Lys Leu Trp Gly Pro Gly Thr Leu Val Thr Val Ser Ser
            100                 105                 110


<210> SEQ ID NO 359
<211> LENGTH: 112
<212> TYPE: PRT
<213> ORGANISM: Artificial
<220> FEATURE:
<223> OTHER INFORMATION: Synthetic Construct: humanized

<400> SEQUENCE: 359

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Ser Tyr
            20                  25                  30

Tyr Met Ser Trp Val Arg Gln Ala Pro Gly Lys Gly Leu Glu Trp Ile
        35                  40                  45

Ala Tyr Ile Tyr Ile Gly Asp Gly Val Thr Ala Tyr Ala Asn Trp Ala
    50                  55                  60

Lys Gly Arg Phe Thr Ile Ser Lys Ala Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Asn Lys Leu Trp Gly Pro Gly Thr Leu Val Thr Val Ser Ser
            100                 105                 110


<210> SEQ ID NO 360
<211> LENGTH: 402
<212> TYPE: DNA
```

```
<213> ORGANISM: Artificial
<220> FEATURE:
<223> OTHER INFORMATION: humanized
<220> FEATURE:
<221> NAME/KEY: signal_sequence
<222> LOCATION: (1)..(66)
<220> FEATURE:
<221> NAME/KEY: CDS
<222> LOCATION: (67)..(402)

<400> SEQUENCE: 360

atggacacga gggcccccac tcagctgctg gggctcctgc tgctctggct cccaggtgcc      60

agatgt gat gtt gtg atg acc cag act cca gcc tcc gtg gag gca gct       108
       Asp Val Val Met Thr Gln Thr Pro Ala Ser Val Glu Ala Ala
       1               5                   10

gtg gga ggc aca gtc acc atc aag tgc cag gcc agt cag agc att agt       156
Val Gly Gly Thr Val Thr Ile Lys Cys Gln Ala Ser Gln Ser Ile Ser
15                  20                  25                  30

agc tac tta gcc tgg tat cag cag aaa cca ggg cag cct ccc aag cgc       204
Ser Tyr Leu Ala Trp Tyr Gln Gln Lys Pro Gly Gln Pro Pro Lys Arg
                35                  40                  45

ctg atc tat gat gca tcc aat ctg gat tct ggg gtc cca tcg cgg ttc       252
Leu Ile Tyr Asp Ala Ser Asn Leu Asp Ser Gly Val Pro Ser Arg Phe
            50                  55                  60

aaa ggc agt gga tct ggg aca gac ttc act atc acc atc agc gac ctg       300
Lys Gly Ser Gly Ser Gly Thr Asp Phe Thr Ile Thr Ile Ser Asp Leu
        65                  70                  75

gag tgt gcc gat gct gcc act tac tac tgt caa tgc act gct gtt agt       348
Glu Cys Ala Asp Ala Ala Thr Tyr Tyr Cys Gln Cys Thr Ala Val Ser
    80                  85                  90

agt gct act att tat gga aat gct ttc ggc gga ggg acc gag gtg gtg       396
Ser Ala Thr Ile Tyr Gly Asn Ala Phe Gly Gly Gly Thr Glu Val Val
95                  100                 105                 110

gtc aaa                                                               402
Val Lys


<210> SEQ ID NO 361
<211> LENGTH: 112
<212> TYPE: PRT
<213> ORGANISM: Artificial
<220> FEATURE:
<223> OTHER INFORMATION: Synthetic Construct: humanized

<400> SEQUENCE: 361

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Arg Leu Ile
        35                  40                  45

Tyr Asp Ala Ser Asn Leu Asp Ser Gly Val Pro Ser Arg Phe Lys Gly
    50                  55                  60

Ser Gly Ser Gly Thr Asp Phe Thr Ile Thr Ile Ser Asp Leu Glu Cys
65                  70                  75                  80

Ala Asp Ala Ala Thr Tyr Tyr Cys Gln Cys Thr Ala Val Ser Ser Ala
                85                  90                  95

Thr Ile Tyr Gly Asn Ala Phe Gly Gly Gly Thr Glu Val Val Val Lys
            100                 105                 110


<210> SEQ ID NO 362
<211> LENGTH: 399
```

<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(57)
<220> FEATURE:
<221> NAME/KEY: CDS
<222> LOCATION: (58)..(399)

<400> SEQUENCE: 362

```
atggagttcg ggctgagctg ggtctttctg gtcgctatta tcaaaggtgt ccagtgt        57

cag gtg cag ttg gtc gag tcc ggg gga ggc ctg gtc aag cct ggg gga      105
Gln Val Gln Leu Val Glu Ser Gly Gly Gly Leu Val Lys Pro Gly Gly
1               5                   10                  15

tcc ctg aga ctc tct tgc gct gcc tct gga ttc tcc ttc agt ggc agc      153
Ser Leu Arg Leu Ser Cys Ala Ala Ser Gly Phe Ser Phe Ser Gly Ser
            20                  25                  30

tac tac atg tcc tgg gtc cgc cag gct cca ggg aag ggg ctg gag tgg      201
Tyr Tyr Met Ser Trp Val Arg Gln Ala Pro Gly Lys Gly Leu Glu Trp
        35                  40                  45

atc gca tac att tat att ggt gac ggt gtc act gcc tac gcg aac tgg      249
Ile Ala Tyr Ile Tyr Ile Gly Asp Gly Val Thr Ala Tyr Ala Asn Trp
    50                  55                  60

gcg aaa ggc cga ttc acc atc tcc aga gat aac gca aag aat agc ctg      297
Ala Lys Gly Arg Phe Thr Ile Ser Arg Asp Asn Ala Lys Asn Ser Leu
65                  70                  75                  80

tac cta caa atg aac agt ctg cgc gcc gag gac acg gcc gtt tat ttc      345
Tyr Leu Gln Met Asn Ser Leu Arg Ala Glu Asp Thr Ala Val Tyr Phe
                85                  90                  95

tgt gcg agg ggt aat agg ttg tgg ggc cag ggc acc ctg gtc acc gtc      393
Cys Ala Arg Gly Asn Arg Leu Trp Gly Gln Gly Thr Leu Val Thr Val
            100                 105                 110

tcc tca                                                              399
Ser Ser
```

<210> SEQ ID NO 363
<211> LENGTH: 114
<212> TYPE: PRT
<213> ORGANISM: Artificial
<220> FEATURE:
<223> OTHER INFORMATION: Synthetic Construct: humanized

<400> SEQUENCE: 363

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Gly Ser
            20                  25                  30

Tyr Tyr Met Ser Trp Val Arg Gln Ala Pro Gly Lys Gly Leu Glu Trp
        35                  40                  45

Ile Ala Tyr Ile Tyr Ile Gly Asp Gly Val Thr Ala Tyr Ala Asn Trp
    50                  55                  60

Ala Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Phe
                85                  90                  95

Cys Ala Arg Gly Asn Arg Leu Trp Gly Gln Gly Thr Leu Val Thr Val
            100                 105                 110

Ser Ser
```

<210> SEQ ID NO 364
<211> LENGTH: 402
<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(66)
<220> FEATURE:
<221> NAME/KEY: CDS
<222> LOCATION: (67)..(402)

<400> SEQUENCE: 364

```
atggacatga gggtgcccgc acagctgctg gggctcctgc tgctctggct ctctggtgcc      60

agatgt gat att cag atg acc cag agc cca agc tcc ctc agc gca gct       108
       Asp Ile Gln Met Thr Gln Ser Pro Ser Ser Leu Ser Ala Ala
       1               5                   10

gtg gga gac cgc gtc acc atc aag tgc cag gcc agt cag agc att agt      156
Val Gly Asp Arg Val Thr Ile Lys Cys Gln Ala Ser Gln Ser Ile Ser
15                  20                  25                  30

agc tac tta gcc tgg tat cag cag aaa cca ggg aag cct ccc aag cgc      204
Ser Tyr Leu Ala Trp Tyr Gln Gln Lys Pro Gly Lys Pro Pro Lys Arg
                35                  40                  45

ctg atc tat gat gca tcc aat ctg gat tct ggg gtc cca tcg cgg ttc      252
Leu Ile Tyr Asp Ala Ser Asn Leu Asp Ser Gly Val Pro Ser Arg Phe
            50                  55                  60

tcc ggc agt gga tct ggg aca gac ttc act ttt acc atc agc agc ctg      300
Ser Gly Ser Gly Ser Gly Thr Asp Phe Thr Phe Thr Ile Ser Ser Leu
        65                  70                  75

cag cct gag gat atc gcc act tac tac tgt caa tgc act gct gtt agt      348
Gln Pro Glu Asp Ile Ala Thr Tyr Tyr Cys Gln Cys Thr Ala Val Ser
    80                  85                  90

agt gct act att tat gga aat gct ttc ggc gga ggg acc aag gtg gag      396
Ser Ala Thr Ile Tyr Gly Asn Ala Phe Gly Gly Gly Thr Lys Val Glu
95                  100                 105                 110

atc aaa                                                              402
Ile Lys
```

<210> SEQ ID NO 365
<211> LENGTH: 112
<212> TYPE: PRT
<213> ORGANISM: Artificial
<220> FEATURE:
<223> OTHER INFORMATION: Synthetic Construct: humanized

<400> SEQUENCE: 365

```
Asp Ile Gln Met Thr Gln Ser Pro Ser Ser Leu Ser Ala Ala Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Pro Pro Lys Arg Leu Ile
        35                  40                  45

Tyr Asp Ala Ser Asn Leu Asp Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Cys Thr Ala Val Ser Ser Ala
                85                  90                  95

Thr Ile Tyr Gly Asn Ala Phe Gly Gly Gly Thr Lys Val Glu Ile Lys
            100                 105                 110
```

<210> SEQ ID NO 366
<211> LENGTH: 17
<212> TYPE: PRT
<213> ORGANISM: Artificial
<220> FEATURE:
<223> OTHER INFORMATION: humanized

<400> SEQUENCE: 366

```
Ile Ser Gln Ala Val His Ala Ala His Ala Glu Ile Asn Glu Ala Gly
1               5                   10                  15

Arg
```

<210> SEQ ID NO 367
<211> LENGTH: 399
<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(57)
<220> FEATURE:
<221> NAME/KEY: CDS
<222> LOCATION: (58)..(399)

<400> SEQUENCE: 367

```
atggagtttg ggctgagctg ggttttcctt gttgctattt taaaaggtgt ccagtgt        57

gag gtg cag ctc gtg gaa tcc gga ggc ggc ctc gtg cag cct ggc ggc      105
Glu Val Gln Leu Val Glu Ser Gly Gly Gly Leu Val Gln Pro Gly Gly
1               5                   10                  15

agc ctg agg ctc tcc tgc gcc gct tcc ggc ttc tcc ttc agc ggc agc      153
Ser Leu Arg Leu Ser Cys Ala Ala Ser Gly Phe Ser Phe Ser Gly Ser
            20                  25                  30

tac tac atg agc tgg gtg agg cag gct ccc gga aag ggc ctc gag tgg      201
Tyr Tyr Met Ser Trp Val Arg Gln Ala Pro Gly Lys Gly Leu Glu Trp
        35                  40                  45

att gcc tac att tac atc ggc gac ggc gtc acc gcc tac gct aac tgg      249
Ile Ala Tyr Ile Tyr Ile Gly Asp Gly Val Thr Ala Tyr Ala Asn Trp
    50                  55                  60

gcc aaa ggc agg ttc aca atc agc aag gat aac agc aag aat acc ctc      297
Ala Lys Gly Arg Phe Thr Ile Ser Lys Asp Asn Ser Lys Asn Thr Leu
65                  70                  75                  80

tac ctg cag atg aac tcc ctg agg gcc gaa gac aca gcc gtc tac ttt      345
Tyr Leu Gln Met Asn Ser Leu Arg Ala Glu Asp Thr Ala Val Tyr Phe
                85                  90                  95

tgc gct cgg ggc aac aaa ctg tgg ggc cct ggc aca ctg gtg aca gtg      393
Cys Ala Arg Gly Asn Lys Leu Trp Gly Pro Gly Thr Leu Val Thr Val
            100                 105                 110

agc tcc                                                              399
Ser Ser
```

<210> SEQ ID NO 368
<211> LENGTH: 114
<212> TYPE: PRT
<213> ORGANISM: Artificial
<220> FEATURE:
<223> OTHER INFORMATION: Synthetic Construct: humanized

<400> SEQUENCE: 368

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Ser
```

```
            20                  25                  30

Tyr Tyr Met Ser Trp Val Arg Gln Ala Pro Gly Lys Gly Leu Glu Trp
        35                  40                  45

Ile Ala Tyr Ile Tyr Ile Gly Asp Gly Val Thr Ala Tyr Ala Asn Trp
    50                  55                  60

Ala Lys Gly Arg Phe Thr Ile Ser Lys Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Gly Asn Lys Leu Trp Gly Pro Gly Thr Leu Val Thr Val
            100                 105                 110

Ser Ser


<210> SEQ ID NO 369
<211> LENGTH: 402
<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(66)
<220> FEATURE:
<221> NAME/KEY: CDS
<222> LOCATION: (67)..(402)

<400> SEQUENCE: 369

atggacatga gggtccccgc tcagctcctg gggctcctgc tactctggct ccgaggtgcc     60

agatgt gac atc cag atg acc cag agc ccc agc agc ctg agc gcc agc       108
       Asp Ile Gln Met Thr Gln Ser Pro Ser Ser Leu Ser Ala Ser
       1               5                   10

gtg ggc gac aga gtg acc atc aag tgc cag gcc agc cag agc atc agc      156
Val Gly Asp Arg Val Thr Ile Lys Cys Gln Ala Ser Gln Ser Ile Ser
15                  20                  25                  30

agc tac ctg gcc tgg tac cag cag aag ccc ggc aag gcc ccc aag aga      204
Ser Tyr Leu Ala Trp Tyr Gln Gln Lys Pro Gly Lys Ala Pro Lys Arg
                35                  40                  45

ctg atc tac gac gcc agc aac ctg gac agc ggc gtg ccc agc aga ttc      252
Leu Ile Tyr Asp Ala Ser Asn Leu Asp Ser Gly Val Pro Ser Arg Phe
            50                  55                  60

agc ggc agc ggc agc ggc acc gac ttc acc ttc acc atc agc agc ctg      300
Ser Gly Ser Gly Ser Gly Thr Asp Phe Thr Phe Thr Ile Ser Ser Leu
        65                  70                  75

cag ccc gag gac atc gcc acc tac tac tgc cag tgc acc gcc gtg agc      348
Gln Pro Glu Asp Ile Ala Thr Tyr Tyr Cys Gln Cys Thr Ala Val Ser
    80                  85                  90

agc gcc acc atc tac ggc aac gcc ttc ggc ggc ggc acc aag gtg gag      396
Ser Ala Thr Ile Tyr Gly Asn Ala Phe Gly Gly Gly Thr Lys Val Glu
95                  100                 105                 110

atc aag                                                              402
Ile Lys


<210> SEQ ID NO 370
<211> LENGTH: 112
<212> TYPE: PRT
<213> ORGANISM: Artificial
<220> FEATURE:
<223> OTHER INFORMATION: Synthetic Construct: humanized

<400> SEQUENCE: 370

Asp Ile Gln Met Thr Gln Ser Pro Ser Ser Leu Ser Ala Ser Val Gly
```

-continued

```
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Arg Leu Ile
        35                  40                  45

Tyr Asp Ala Ser Asn Leu Asp Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Cys Thr Ala Val Ser Ser Ala
                85                  90                  95

Thr Ile Tyr Gly Asn Ala Phe Gly Gly Gly Thr Lys Val Glu Ile Lys
            100                 105                 110


<210> SEQ ID NO 371
<211> LENGTH: 399
<212> TYPE: DNA
<213> ORGANISM: Artificial
<220> FEATURE:
<223> OTHER INFORMATION: humanized
<220> FEATURE:
<221> NAME/KEY: signal_sequence
<222> LOCATION: (1)..(57)
<220> FEATURE:
<221> NAME/KEY: CDS
<222> LOCATION: (58)..(399)

<400> SEQUENCE: 371

atggagtttg ggctgagctg ggttttcctt gttgctattt taaaaggtgt ccagtgt        57

gag gtg cag ctc gtg gaa tcc gga ggc ggc ctc gtg cag cct ggc ggc      105
Glu Val Gln Leu Val Glu Ser Gly Gly Gly Leu Val Gln Pro Gly Gly
1               5                   10                  15

agc ctg agg ctc tcc tgc gcc gct tcc ggc ttc tcc ttc agc ggc agc      153
Ser Leu Arg Leu Ser Cys Ala Ala Ser Gly Phe Ser Phe Ser Gly Ser
            20                  25                  30

tac tac atg agc tgg gtg agg cag gct ccc gga aag ggc ctc gag tgg      201
Tyr Tyr Met Ser Trp Val Arg Gln Ala Pro Gly Lys Gly Leu Glu Trp
        35                  40                  45

att gcc tac att tac atc ggc gac ggc gtc acc gcc tac gct aac tgg      249
Ile Ala Tyr Ile Tyr Ile Gly Asp Gly Val Thr Ala Tyr Ala Asn Trp
    50                  55                  60

gcc aaa ggc agg ttc aca atc agc agg gat aac agc aag aat acc ctc      297
Ala Lys Gly Arg Phe Thr Ile Ser Arg Asp Asn Ser Lys Asn Thr Leu
65                  70                  75                  80

tac ctg cag atg aac tcc ctg agg gcc gaa gac aca gcc gtc tac tac      345
Tyr Leu Gln Met Asn Ser Leu Arg Ala Glu Asp Thr Ala Val Tyr Tyr
                85                  90                  95

tgc gct cgg ggc aac aaa ctg tgg ggc cct ggc aca ctg gtg aca gtg      393
Cys Ala Arg Gly Asn Lys Leu Trp Gly Pro Gly Thr Leu Val Thr Val
            100                 105                 110

agc tcc                                                              399
Ser Ser


<210> SEQ ID NO 372
<211> LENGTH: 114
<212> TYPE: PRT
<213> ORGANISM: Artificial
<220> FEATURE:
<223> OTHER INFORMATION: Synthetic Construct: humanized

<400> SEQUENCE: 372
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Ser
            20                  25                  30

Tyr Tyr Met Ser Trp Val Arg Gln Ala Pro Gly Lys Gly Leu Glu Trp
        35                  40                  45

Ile Ala Tyr Ile Tyr Ile Gly Asp Gly Val Thr Ala Tyr Ala Asn Trp
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Asn Lys Leu Trp Gly Pro Gly Thr Leu Val Thr Val
            100                 105                 110

Ser Ser


<210> SEQ ID NO 373
<211> LENGTH: 5
<212> TYPE: PRT
<213> ORGANISM: Mus musculus

<400> SEQUENCE: 373

Gly Tyr Phe Met Asn
1               5


<210> SEQ ID NO 374
<211> LENGTH: 17
<212> TYPE: PRT
<213> ORGANISM: Mus musculus

<400> SEQUENCE: 374

Arg Ile Asn Pro Tyr Asn Gly Asp Thr Phe Tyr Asn Gln Lys Phe Lys
1               5                   10                  15

Gly


<210> SEQ ID NO 375
<211> LENGTH: 11
<212> TYPE: PRT
<213> ORGANISM: Mus musculus

<400> SEQUENCE: 375

Arg Ile His Tyr Tyr Tyr Gly Ser Ser Tyr Tyr
1               5                   10


<210> SEQ ID NO 376
<211> LENGTH: 113
<212> TYPE: PRT
<213> ORGANISM: Mus musculus

<400> SEQUENCE: 376

Gly Pro Glu Leu Val Lys Pro Gly Ala Ser Val Lys Ile Ser Cys Lys
1               5                   10                  15

Ala Ser Gly Tyr Ser Phe Thr Gly Tyr Phe Met Asn Trp Val Met Gln
            20                  25                  30

Ser His Gly Lys Ser Leu Glu Trp Ile Gly Arg Ile Asn Pro Tyr Asn
        35                  40                  45

Gly Asp Thr Phe Tyr Asn Gln Lys Phe Lys Gly Lys Ala Thr Leu Thr
    50                  55                  60

Val Asp Lys Ser Ser Ser Thr Ala His Met Glu Leu Arg Ser Leu Ala
```

```
65                  70                  75                  80

Ser Glu Asp Ser Ala Val Tyr Tyr Cys Ala Arg Arg Ile His Tyr Tyr
                85                  90                  95

Tyr Gly Ser Ser Tyr Tyr Ala Met Asp Tyr Trp Gly Gln Glu Pro His
            100                 105                 110

His


<210> SEQ ID NO 377
<211> LENGTH: 15
<212> TYPE: PRT
<213> ORGANISM: Mus musculus

<400> SEQUENCE: 377

Arg Ala Ser Lys Ser Ile Ser Lys Tyr Leu Ala Trp Tyr Gln Glu
1               5                   10                  15


<210> SEQ ID NO 378
<211> LENGTH: 7
<212> TYPE: PRT
<213> ORGANISM: Mus musculus

<400> SEQUENCE: 378

Ser Gly Ser Thr Leu Gln Ser
1               5


<210> SEQ ID NO 379
<211> LENGTH: 9
<212> TYPE: PRT
<213> ORGANISM: Mus musculus

<400> SEQUENCE: 379

Gln Gln His Asn Glu Tyr Pro Trp Thr
1               5


<210> SEQ ID NO 380
<211> LENGTH: 108
<212> TYPE: PRT
<213> ORGANISM: Mus musculus

<400> SEQUENCE: 380

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys Arg
            100                 105


<210> SEQ ID NO 381
<211> LENGTH: 339
<212> TYPE: DNA
<213> ORGANISM: Mus musculus

<400> SEQUENCE: 381
```

```
ggacctgagc tggtgaagcc tggggcttca gtgaagatat cctgcaaggc ttctggttac     60

tcatttactg gctactttat gaactgggtg atgcagagcc atggaaagag ccttgagtgg    120

attggacgta ttaatcctta caatggtgat actttctaca accagaagtt caagggcaag    180

gccacattga ctgtagacaa atcctctagc acagcccaca tggagctccg gagcctggca    240

tctgaggact ctgcagtcta ttattgtgca agacgcatcc attactacta cggtagtagc    300

tactatgcta tggactactg gggtcaagaa cctcatcac                            339


<210> SEQ ID NO 382
<211> LENGTH: 324
<212> TYPE: DNA
<213> ORGANISM: Mus musculus

<400> SEQUENCE: 382

gatgtccaga taacccagtc tccatcttat cttgctgcat ctcctggaga aaccattact     60

attaattgca gggcaagtaa gagcattagc aaatatttag cctggtatca agagaaacct    120

gggaaaacta ataagcttct tatctactct ggatccactt tgcaatctgg aattccatca    180

aggttcagtg gcagtggatc tggtacagat ttcactctca ccatcagtag cctggagcct    240

gaagattttg caatgtatta ctgtcaacag cataatgaat acccgtggac gttcggtgga    300

ggcaccaagc tggaaatcaa acgg                                            324


<210> SEQ ID NO 383
<211> LENGTH: 5
<212> TYPE: PRT
<213> ORGANISM: Mus musculus

<400> SEQUENCE: 383

Glu Tyr Ile Ile His
1               5


<210> SEQ ID NO 384
<211> LENGTH: 17
<212> TYPE: PRT
<213> ORGANISM: Mus musculus

<400> SEQUENCE: 384

Trp Phe Tyr Pro Gly Ser Gly Ser Ile Lys Tyr Asn Glu Lys Phe Lys
1               5                   10                  15

Asp


<210> SEQ ID NO 385
<211> LENGTH: 11
<212> TYPE: PRT
<213> ORGANISM: Mus musculus

<400> SEQUENCE: 385

His Glu Val Tyr Tyr Asp Tyr Asp Lys Ser Met
1               5                   10


<210> SEQ ID NO 386
<211> LENGTH: 113
<212> TYPE: PRT
<213> ORGANISM: Mus musculus

<400> SEQUENCE: 386

Gly Ala Gly Leu Val Lys Pro Gly Ala Ser Val Lys Leu Ser Cys Lys
1               5                   10                  15
```

Ala Ser Gly Tyr Thr Phe Thr Glu Tyr Ile Ile His Trp Val Lys Gln
20 25 30

Arg Ser Gly Gln Gly Leu Glu Trp Ile Gly Trp Phe Tyr Pro Gly Ser
35 40 45

Gly Ser Ile Lys Tyr Asn Glu Lys Phe Lys Asp Lys Ala Thr Leu Thr
50 55 60

Ala Asp Lys Ser Ser Ser Thr Val Tyr Met Glu Leu Ser Arg Leu Thr
65 70 75 80

Ser Glu Asp Ser Ala Val Tyr Phe Cys Ala Arg His Glu Val Tyr Tyr
85 90 95

Asp Tyr Asp Lys Ser Met Leu Trp Thr Thr Gly Val Lys Asn Leu Ile
100 105 110

Arg

<210> SEQ ID NO 387
<211> LENGTH: 15
<212> TYPE: PRT
<213> ORGANISM: Mus musculus

<400> SEQUENCE: 387

Leu Tyr Ser Ser Asn Gln Lys Asn Tyr Leu Ala Trp Tyr Gln Gln
1 5 10 15

<210> SEQ ID NO 388
<211> LENGTH: 7
<212> TYPE: PRT
<213> ORGANISM: Mus musculus

<400> SEQUENCE: 388

Trp Ala Ser Thr Arg Glu Ser
1 5

<210> SEQ ID NO 389
<211> LENGTH: 9
<212> TYPE: PRT
<213> ORGANISM: Mus musculus

<400> SEQUENCE: 389

Gln Gln Tyr Tyr Ser Tyr Pro Tyr Thr
1 5

<210> SEQ ID NO 390
<211> LENGTH: 108
<212> TYPE: PRT
<213> ORGANISM: Mus musculus

<400> SEQUENCE: 390

Ser Pro Ser Ser Leu Ala Val Ser Val Gly Glu Lys Val Thr Met Ser
1 5 10 15

Cys Lys Ser Ser Gln Ser Leu Leu Tyr Ser Ser Asn Gln Lys Asn Tyr
20 25 30

Leu Ala Trp Tyr Gln Gln Lys Pro Gly Gln Ser Pro Lys Leu Leu Ile
35 40 45

Tyr Trp Ala Ser Thr Arg Glu Ser Gly Val Pro Asp Arg Phe Thr Gly
50 55 60

Ser Gly Ser Gly Thr Asp Phe Thr Leu Thr Ile Ser Ser Val Lys Ala
65 70 75 80

Glu Asp Leu Ala Val Tyr Tyr Cys Gln Gln Tyr Tyr Ser Tyr Pro Tyr
85 90 95

Thr Phe Gly Gly Gly Thr Lys Leu Glu Ile Lys Arg
100 105

<210> SEQ ID NO 391
<211> LENGTH: 339
<212> TYPE: DNA
<213> ORGANISM: Mus musculus

<400> SEQUENCE: 391
ggagctgggc tggtgaaacc cggggcatca gtgaagctgt cctgcaaggc ttctggctac 60
accttcactg agtatattat acactgggta aagcagaggt ctggacaggg tcttgagtgg 120
attgggtggt tttaccctgg aagtggtagt ataaagtaca atgagaaatt caaggacaag 180
gccacattga ctgcggacaa atcctccagc acagtctata tggagcttag tagattgaca 240
tctgaagact ctgcggtcta tttctgtgca agacacgagg tctactatga ttacgacaag 300
tctatgctat ggactactgg ggtcaagaac ctcatccgc 339

<210> SEQ ID NO 392
<211> LENGTH: 324
<212> TYPE: DNA
<213> ORGANISM: Mus musculus

<400> SEQUENCE: 392
tctccatcct ccctagctgt gtcagttgga gagaaggtta ctatgagctg caagtccagt 60
cagagccttt tatatagtag caatcaaaag aactacttgg cctggtacca gcagaaacca 120
gggcagtctc ctaaactgct gatttactgg gcatccacta gggaatctgg ggtccctgat 180
cgcttcacag gcagtggatc tgggacagat ttcactctca ccatcagcag tgtgaaggct 240
gaagacctgg cagtttatta ctgtcagcaa tattatagct atccgtacac gttcggaggg 300
gggaccaagc tggaaataaa acgg 324

<210> SEQ ID NO 393
<211> LENGTH: 6
<212> TYPE: PRT
<213> ORGANISM: Mus musculus

<400> SEQUENCE: 393

Ser Gly Tyr Tyr Trp Asn
1 5

<210> SEQ ID NO 394
<211> LENGTH: 17
<212> TYPE: PRT
<213> ORGANISM: Mus musculus

<400> SEQUENCE: 394

Tyr Ile Ser Tyr Asp Gly Ser Asn Asn Tyr Asn Pro Ser Leu Lys Asn
1 5 10 15

Arg

<210> SEQ ID NO 395
<211> LENGTH: 11
<212> TYPE: PRT
<213> ORGANISM: Mus musculus

<400> SEQUENCE: 395

Gly Met Ala Trp Phe Ala Tyr Trp Ala Lys Asp
1 5 10

<210> SEQ ID NO 396
<211> LENGTH: 107
<212> TYPE: PRT
<213> ORGANISM: Mus musculus

<400> SEQUENCE: 396

```
Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Asn Trp Ile Arg
            20                  25                  30

Gln Phe Pro Gly Asn Lys Leu Glu Trp Met Gly Tyr Ile Ser Tyr Asp
        35                  40                  45

Gly Ser Asn Asn Tyr Asn Pro Ser Leu Lys Asn Arg Ile Ser Ile Thr
    50                  55                  60

Arg Asp Thr Ser Lys Asn Gln Phe Phe Leu Lys Leu Asn Ser Val Thr
65                  70                  75                  80

Thr Glu Asp Thr Ala Thr Tyr Tyr Cys Ala Thr Gly Met Ala Trp Phe
                85                  90                  95

Ala Tyr Trp Ala Lys Asp Ser Val Thr Pro Pro
            100                 105
```

<210> SEQ ID NO 397
<211> LENGTH: 321
<212> TYPE: DNA
<213> ORGANISM: Mus musculus

<400> SEQUENCE: 397

```
ggacctggcc tcgtgaaacc ttctcagtct ctgtctctca cctgctctgt cactggctac      60

tccatcacca gtggttatta ctggaactgg atccggcagt ttccaggaaa caaactggaa     120

tggatgggct acataagcta cgacggtagc aataactaca acccatctct caaaaatcga     180

atctccatca ctcgtgacac atctaagaac cagtttttcc tgaagttgaa ttctgtgact     240

actgaggaca cagctacata ttactgtgct actgggatgg cctggtttgc ttactgggcc     300

aaggactctg tcacgccgcc t                                               321
```

<210> SEQ ID NO 398
<211> LENGTH: 5
<212> TYPE: PRT
<213> ORGANISM: Mus musculus

<400> SEQUENCE: 398

```
Asn Tyr Leu Ile Glu
1               5
```

<210> SEQ ID NO 399
<211> LENGTH: 19
<212> TYPE: PRT
<213> ORGANISM: Mus musculus

<400> SEQUENCE: 399

```
Val Ile Asn Pro Lys Ser Gly Gly Thr Lys Tyr Asn Glu Lys Phe Arg
1               5                   10                  15

Gly Lys Ala
```

<210> SEQ ID NO 400
<211> LENGTH: 11
<212> TYPE: PRT
<213> ORGANISM: Mus musculus

<400> SEQUENCE: 400

Thr Gly Thr Asp Tyr Trp Gly Gln Gly Thr Thr
1 5 10

<210> SEQ ID NO 401
<211> LENGTH: 113
<212> TYPE: PRT
<213> ORGANISM: Mus musculus

<400> SEQUENCE: 401

Gly Ala Glu Leu Val Arg Pro Gly Thr Ser Val Lys Val Ser Cys Lys
1 5 10 15

Ala Ser Val Tyr Ala Phe Thr Asn Tyr Leu Ile Glu Trp Val Lys Gln
20 25 30

Arg Pro Gly Gln Gly Leu Glu Trp Ile Gly Val Ile Asn Pro Lys Ser
35 40 45

Gly Gly Thr Lys Tyr Asn Glu Lys Phe Arg Gly Lys Ala Thr Leu Thr
50 55 60

Ala Asp Lys Ser Ser Ser Thr Ala Tyr Met Gln Leu Ser Ser Leu Thr
65 70 75 80

Ser Gly Asp Ser Ala Val Tyr Phe Cys Ala Ile Thr Gly Thr Asp Tyr
85 90 95

Trp Gly Gln Gly Thr Thr Leu Thr Val Ser Ser Ala Lys Thr Thr Pro
100 105 110

Pro

<210> SEQ ID NO 402
<211> LENGTH: 10
<212> TYPE: PRT
<213> ORGANISM: Mus musculus

<400> SEQUENCE: 402

Val Thr Ile Ser Cys Ser Ala Ser Gln Gly
1 5 10

<210> SEQ ID NO 403
<211> LENGTH: 7
<212> TYPE: PRT
<213> ORGANISM: Mus musculus

<400> SEQUENCE: 403

Tyr Thr Ser Ser Leu Arg Ser
1 5

<210> SEQ ID NO 404
<211> LENGTH: 9
<212> TYPE: PRT
<213> ORGANISM: Mus musculus

<400> SEQUENCE: 404

Gln Gln Tyr Ser Lys Leu Pro Arg Thr
1 5

<210> SEQ ID NO 405
<211> LENGTH: 113
<212> TYPE: PRT
<213> ORGANISM: Mus musculus

<400> SEQUENCE: 405

Gln Gly Thr Arg Cys Asp Ile Gln Met Thr Gln Thr Thr Ser Ser Leu
1 5 10 15

```
Ser Ala Ser Leu Gly Asp Arg Val Thr Ile Ser Cys Ser Ala Ser Gln
            20                  25                  30

Gly Ile Asn Asn Tyr Leu Asn Trp Tyr Gln Gln Lys Pro Asp Gly Thr
        35                  40                  45

Val Lys Leu Leu Ile Tyr Tyr Thr Ser Ser Leu Arg Ser Gly Val Pro
    50                  55                  60

Ser Arg Phe Ser Gly Ser Gly Ser Gly Thr Asp Tyr Ser Leu Thr Ile
65                  70                  75                  80

Ser Asn Leu Glu Pro Glu Asp Val Ala Thr Tyr Tyr Cys Gln Gln Tyr
                85                  90                  95

Ser Lys Leu Pro Arg Thr Phe Gly Gly Gly Thr Lys Leu Glu Ile Lys
            100                 105                 110

Arg


<210> SEQ ID NO 406
<211> LENGTH: 339
<212> TYPE: DNA
<213> ORGANISM: Mus musculus

<400> SEQUENCE: 406

ggagctgagc tggtaaggcc tgggacttca gtgaaggtgt cctgcaaggc ttctgtatac      60

gccttcacta attacttgat agagtgggta aagcagaggc ctggacaggg ccttgagtgg     120

attggagtga ttaatcctaa aagtggtggt actaagtaca atgagaagtt caggggcaag     180

gcaacactga ctgcagacaa atcctccagc actgcctaca tgcagctcag cagcctgaca     240

tctggtgact ctgcggtcta tttctgtgca ataactggga cagactactg gggccaaggc     300

accactctca cagtctcctc agccaaaaca acacccccca                          339


<210> SEQ ID NO 407
<211> LENGTH: 339
<212> TYPE: DNA
<213> ORGANISM: Mus musculus

<400> SEQUENCE: 407

caaggtacca gatgtgatat ccagatgaca cagactacat cctccctgtc tgcctctctg      60

ggcgacagag tcaccatcag ttgcagtgca agtcagggca ttaacaatta tttaaactgg     120

tatcagcaaa aaccagatgg aactgttaaa ctcctgatct attacacatc aagtttacgc     180

tcaggagtcc catcaaggtt cagtggcagt gggtctggga cagattattc tctcaccatc     240

agcaacctgg aacctgaaga tgttgccact tactattgtc agcagtatag taagcttcct     300

cggacgttcg gtggcggcac caagctggaa atcaaacgg                           339


<210> SEQ ID NO 408
<211> LENGTH: 5
<212> TYPE: PRT
<213> ORGANISM: Mus musculus

<400> SEQUENCE: 408

Thr Asn Ala Met Asn
1               5


<210> SEQ ID NO 409
<211> LENGTH: 17
<212> TYPE: PRT
<213> ORGANISM: Mus musculus

<400> SEQUENCE: 409
```

```
Arg Ile Arg Ser Lys Ser Asn Asn Tyr Ala Thr Tyr Tyr Ala Asp Ser
1               5                   10                  15

Val


<210> SEQ ID NO 410
<211> LENGTH: 11
<212> TYPE: PRT
<213> ORGANISM: Mus musculus

<400> SEQUENCE: 410

Asp Trp Asp Gly Phe Leu Tyr Phe Asp Tyr Trp
1               5                   10


<210> SEQ ID NO 411
<211> LENGTH: 112
<212> TYPE: PRT
<213> ORGANISM: Mus musculus

<400> SEQUENCE: 411

Gly Gly Gly Leu Val Gln Pro Lys Gly Ser Leu Lys Leu Ser Cys Ala
1               5                   10                  15

Ala Ser Gly Phe Thr Phe Asn Thr Asn Ala Met Asn Trp Val Arg Gln
            20                  25                  30

Ala Pro Gly Lys Gly Leu Glu Trp Val Ala Arg Ile Arg Ser Lys Ser
        35                  40                  45

Asn Asn Tyr Ala Thr Tyr Tyr Ala Asp Ser Val Lys Asp Arg Phe Thr
    50                  55                  60

Ile Ser Arg Asp Asp Ser Gln Ser Met Leu Tyr Leu Gln Met Asn Asn
65                  70                  75                  80

Leu Lys Thr Glu Asp Thr Ala Met Tyr Tyr Cys Val Arg Asp Trp Asp
                85                  90                  95

Gly Phe Leu Tyr Phe Asp Tyr Trp Ala Lys His His Leu Thr Leu Phe
            100                 105                 110


<210> SEQ ID NO 412
<211> LENGTH: 15
<212> TYPE: PRT
<213> ORGANISM: Mus musculus

<400> SEQUENCE: 412

Ser Val Ser Thr Ser Gly Tyr Ser Tyr Met His Trp Asn Gln Gln
1               5                   10                  15


<210> SEQ ID NO 413
<211> LENGTH: 7
<212> TYPE: PRT
<213> ORGANISM: Mus musculus

<400> SEQUENCE: 413

Leu Val Ser Asn Leu Glu Ser
1               5


<210> SEQ ID NO 414
<211> LENGTH: 9
<212> TYPE: PRT
<213> ORGANISM: Mus musculus

<400> SEQUENCE: 414

Gln His Ile Arg Glu Leu Thr Arg Ser
1               5
```

<210> SEQ ID NO 415
<211> LENGTH: 104
<212> TYPE: PRT
<213> ORGANISM: Mus musculus

<400> SEQUENCE: 415

Thr Gln Ser Pro Ala Ser Leu Ala Val Ser Leu Gly Gln Arg Ala Thr
1 5 10 15

Ile Ser Tyr Arg Ala Ser Lys Ser Val Ser Thr Ser Gly Tyr Ser Tyr
20 25 30

Met His Trp Asn Gln Gln Lys Pro Gly Gln Pro Pro Arg Leu Leu Ile
35 40 45

Tyr Leu Val Ser Asn Leu Glu Ser Gly Val Pro Ala Arg Phe Ser Gly
50 55 60

Ser Gly Ser Gly Thr Asp Phe Thr Leu Asn Ile His Pro Val Glu Glu
65 70 75 80

Glu Asp Ala Ala Thr Tyr Tyr Cys Gln His Ile Arg Glu Leu Thr Arg
85 90 95

Ser Glu Gly Gly Pro Ser Trp Lys
100

<210> SEQ ID NO 416
<211> LENGTH: 336
<212> TYPE: DNA
<213> ORGANISM: Mus musculus

<400> SEQUENCE: 416
ggtggaggat tggtgcagcc taaagggtca ttgaaactct catgtgcagc ctctggattc 60
accttcaata ccaatgccat gaactgggtc cgccaggctc caggaaaggg tttggaatgg 120
gttgctcgca taagaagtaa aagtaataat tatgcaacat attatgccga ttcagtgaaa 180
gacaggttca ccatctccag agatgattca caaagcatgc tctatctgca aatgaacaac 240
ttgaaaactg aggacacagc catgtattac tgtgtgagag attgggatgg tttcctttac 300
tttgactact gggccaagca ccacttgacg ctattc 336

<210> SEQ ID NO 417
<211> LENGTH: 312
<212> TYPE: DNA
<213> ORGANISM: Mus musculus

<400> SEQUENCE: 417
acacagtctc ctgcttcctt agctgtatct ctggggcaga gggccaccat ctcatacagg 60
gccagcaaaa gtgtcagtac atctggctat agttatatgc actggaacca acagaaacca 120
ggacagccac ccagactcct catctatctt gtatccaacc tagaatctgg ggtccctgcc 180
aggttcagtg gcagtgggtc tgggacagac ttcaccctca acatccatcc tgtggaggag 240
gaggatgctg caacctatta ctgtcagcac attagggagc ttacacgttc ggagggggga 300
ccaagctgga aa 312

<210> SEQ ID NO 418
<211> LENGTH: 5
<212> TYPE: PRT
<213> ORGANISM: Mus musculus

<400> SEQUENCE: 418

Ser Tyr Trp Met His
1 5

<210> SEQ ID NO 419
<211> LENGTH: 17
<212> TYPE: PRT
<213> ORGANISM: Mus musculus

<400> SEQUENCE: 419

Met Ile Asp Pro Ser Asp Ser Glu Thr Arg Leu Asn Gln Lys Phe Lys
1 5 10 15

Asp

<210> SEQ ID NO 420
<211> LENGTH: 11
<212> TYPE: PRT
<213> ORGANISM: Mus musculus

<400> SEQUENCE: 420

Tyr Pro Asp Trp Ala Lys Ala His Ser Pro Leu
1 5 10

<210> SEQ ID NO 421
<211> LENGTH: 103
<212> TYPE: PRT
<213> ORGANISM: Mus musculus

<400> SEQUENCE: 421

Gly Pro Gln Leu Val Arg Pro Gly Ala Ser Val Lys Ile Ser Cys Lys
1 5 10 15

Ala Ser Gly Tyr Ser Phe Thr Ser Tyr Trp Met His Trp Val Lys Gln
20 25 30

Arg Pro Gly Gln Gly Leu Glu Trp Ile Gly Met Ile Asp Pro Ser Asp
35 40 45

Ser Glu Thr Arg Leu Asn Gln Lys Phe Lys Asp Lys Ala Thr Leu Thr
50 55 60

Val Asp Lys Ser Ser Ser Thr Ala Tyr Met Gln Leu Ser Ser Pro Thr
65 70 75 80

Ser Glu Asp Ser Ala Val Tyr Tyr Cys Ala Thr Tyr Pro Asp Trp Ala
85 90 95

Lys Ala His Ser Pro Leu Arg
100

<210> SEQ ID NO 422
<211> LENGTH: 15
<212> TYPE: PRT
<213> ORGANISM: Mus musculus

<400> SEQUENCE: 422

Leu Leu Tyr Lys Asp Gly Lys Thr Tyr Leu Asn Trp Phe Leu Gln
1 5 10 15

<210> SEQ ID NO 423
<211> LENGTH: 7
<212> TYPE: PRT
<213> ORGANISM: Mus musculus

<400> SEQUENCE: 423

Leu Met Ser Thr Arg Ala Ser
1 5

<210> SEQ ID NO 424
<211> LENGTH: 9
<212> TYPE: PRT

<213> ORGANISM: Mus musculus

<400> SEQUENCE: 424

Gln Gln Leu Val Glu Asp Pro Leu Thr
1               5

<210> SEQ ID NO 425
<211> LENGTH: 108
<212> TYPE: PRT
<213> ORGANISM: Mus musculus

<400> SEQUENCE: 425

Gln Asp Glu Leu Ser Asn Pro Val Thr Ser Gly Glu Ser Val Ser Ile
1               5                   10                  15

Ser Cys Arg Ser Ser Lys Ser Leu Leu Tyr Lys Asp Gly Lys Thr Tyr
            20                  25                  30

Leu Asn Trp Phe Leu Gln Arg Pro Gly Gln Ser Pro Gln Leu Leu Ile
        35                  40                  45

Tyr Leu Met Ser Thr Arg Ala Ser Gly Val Ser Asp Arg Phe Ser Gly
    50                  55                  60

Ser Gly Ser Gly Thr Asp Phe Thr Leu Glu Ile Ser Arg Val Lys Ala
65                  70                  75                  80

Glu Asp Val Gly Val Tyr Tyr Cys Gln Gln Leu Val Glu Asp Pro Leu
                85                  90                  95

Thr Phe Gly Ala Gly Thr Lys Leu Glu Leu Lys Arg
            100                 105

<210> SEQ ID NO 426
<211> LENGTH: 309
<212> TYPE: DNA
<213> ORGANISM: Mus musculus

<400> SEQUENCE: 426
gggcctcagc tggttaggcc tggggcttca gtgaagatat cctgcaaggc ttctggttac 60
tcattcacca gctactggat gcactgggtg aagcagaggc ctggacaagg tcttgagtgg 120
attggcatga ttgatccttc cgatagtgaa actaggttaa atcagaagtt caaggacaag 180
gccacattga ctgtagacaa atcctccagc acagcctaca tgcaactcag cagcccgaca 240
tctgaggact ctgcggtcta ttactgtgca acctacccgg actgggccaa ggcacactct 300
ccattacgt 309

<210> SEQ ID NO 427
<211> LENGTH: 324
<212> TYPE: DNA
<213> ORGANISM: Mus musculus

<400> SEQUENCE: 427
caggatgaac tctccaatcc tgtcacttct ggagaatcag tttccatctc ctgcaggtct 60
agtaagagtc tcctatataa ggatgggaag acatatttga attggtttct gcagagacca 120
ggacaatctc ctcagctcct gatctatttg atgtccaccc gtgcatcagg agtctcagac 180
cggtttagtg gcagtgggtc aggaacagat ttcaccctgg aaatcagtag agtgaaggct 240
gaggatgtgg gtgtgtatta ctgtcaacaa cttgtagagg atccgctcac gttcggtgct 300
gggaccaagc tggagctgaa acgg 324

<210> SEQ ID NO 428
<211> LENGTH: 18

```
<212> TYPE: PRT
<213> ORGANISM: Homo sapiens

<400> SEQUENCE: 428

Val Phe Asn Met Asn Ala Pro Val Pro Pro Val Asn Glu Pro Glu Thr
1               5                   10                  15

Leu Lys


<210> SEQ ID NO 429
<211> LENGTH: 16
<212> TYPE: PRT
<213> ORGANISM: Homo sapiens

<400> SEQUENCE: 429

Ala Glu Gln Lys Arg Leu Lys Thr Val Leu Glu Leu Gln Tyr Val Leu
1               5                   10                  15


<210> SEQ ID NO 430
<211> LENGTH: 16
<212> TYPE: PRT
<213> ORGANISM: Homo sapiens

<400> SEQUENCE: 430

Ala Thr Gln Val Pro Leu Val Ser Ser Thr Ser Glu Gly Tyr Thr Ala
1               5                   10                  15


<210> SEQ ID NO 431
<211> LENGTH: 16
<212> TYPE: PRT
<213> ORGANISM: Homo sapiens

<400> SEQUENCE: 431

Val Glu Arg Val Phe Gln Ser Asn Tyr Phe Asp Ser Thr His Asn His
1               5                   10                  15


<210> SEQ ID NO 432
<211> LENGTH: 16
<212> TYPE: PRT
<213> ORGANISM: Homo sapiens

<400> SEQUENCE: 432

Phe Gln Ser Met Gln Thr Val Phe Asn Met Asn Ala Pro Val Pro Pro
1               5                   10                  15
```